United States Patent
Hubbell et al.

(10) Patent No.: US 11,574,747 B2
(45) Date of Patent: Feb. 7, 2023

(54) METHODS OF TREATING CANCER WITH PLACENTA GROWTH FACTOR PEPTIDE LINKED TO IMMUNOTHERAPEUTIC ANTIBODIES

(71) Applicant: The University of Chicago, Chicago, IL (US)

(72) Inventors: Jeffrey A. Hubbell, Chicago, IL (US); Jun Ishihara, Chicago, IL (US); Ako Ishihara, Chicago, IL (US); Kazuto Fukunaga, Chicago, IL (US); Melody Swartz, Chicago, IL (US)

(73) Assignee: The University of Chicago, Chicago, IL (US)

( * ) Notice: Subject to any disclaimer, the term of this patent is extended or adjusted under 35 U.S.C. 154(b) by 112 days.

(21) Appl. No.: 16/606,539

(22) PCT Filed: Apr. 20, 2018

(86) PCT No.: PCT/US2018/028505
§ 371 (c)(1),
(2) Date: Oct. 18, 2019

(87) PCT Pub. No.: WO2018/195386
PCT Pub. Date: Oct. 25, 2018

(65) Prior Publication Data
US 2020/0123228 A1    Apr. 23, 2020

Related U.S. Application Data

(60) Provisional application No. 62/487,823, filed on Apr. 20, 2017.

(51) Int. Cl.
| | |
|---|---|
| A61P 35/00 | (2006.01) |
| A61K 9/00 | (2006.01) |
| A61K 38/18 | (2006.01) |
| A61K 39/395 | (2006.01) |
| C07K 14/475 | (2006.01) |
| A61K 39/00 | (2006.01) |
| G21F 5/12 | (2006.01) |
| G21F 7/005 | (2006.01) |
| A61K 38/19 | (2006.01) |
| A61K 38/36 | (2006.01) |
| A61K 45/06 | (2006.01) |
| C07K 14/52 | (2006.01) |
| C07K 14/755 | (2006.01) |
| C07K 16/28 | (2006.01) |
| G21F 5/14 | (2006.01) |

(52) U.S. Cl.
CPC .............. *G21F 5/12* (2013.01); *A61K 9/0019* (2013.01); *A61K 38/18* (2013.01); *A61K 38/195* (2013.01); *A61K 38/36* (2013.01); *A61K 39/3955* (2013.01); *A61K 45/06* (2013.01); *A61P 35/00* (2018.01); *C07K 14/475* (2013.01); *C07K 14/522* (2013.01); *C07K 14/755* (2013.01); *C07K 16/2818* (2013.01); *C07K 16/2827* (2013.01); *C07K 16/2878* (2013.01); *G21F 7/005* (2013.01); *A61K 2039/507* (2013.01); *A61K 2039/545* (2013.01); *C07K 2317/24* (2013.01); *C07K 2317/75* (2013.01); *C07K 2317/92* (2013.01); *C07K 2319/30* (2013.01); *C07K 2319/70* (2013.01); *G21F 5/14* (2013.01)

(58) Field of Classification Search
None
See application file for complete search history.

(56) References Cited

U.S. PATENT DOCUMENTS

| | | |
|---|---|---|
| 6,277,812 B1 | 8/2001 | Ruoslahti et al. |
| 2003/0099644 A1 | 5/2003 | Ahuja et al. |
| 2012/0052043 A1 | 3/2012 | Kungl |
| 2012/0289468 A1 | 11/2012 | Barnett et al. |
| 2014/0010832 A1 | 1/2014 | Hubbell et al. |

FOREIGN PATENT DOCUMENTS

| | | |
|---|---|---|
| JP | 2003532681 | 11/2003 |
| WO | WO 01/85192 | 11/2001 |
| WO | WO 2014/006082 | 1/2014 |
| WO | WO 2016/054107 | 4/2016 |
| WO | WO 2016/054555 | 4/2016 |
| WO | WO 2017/009842 | 1/2017 |

OTHER PUBLICATIONS

European Search Report issued in Corresponding European Application No. 18787963.0, dated Nov. 20, 2020.
Lu et al., "The extracellular matrix: A dynamic niche in cancer progression" *The Journal of Cell Biology* 2012, 196(4), 395-406.
Xiong et al. "Function of cancer cell-derived extracellular matrix in tumor progression" *Journal of Cancer Metastasis and Treatment* 2016, 2, 357-64.
Yonezawa et al., "Boosting Cancer Immunotherapy with Anti-CD137 Antibody Therapy" *Clinical Cancer Research* 2015, 21(14), 3113-3120.
Addi, et al., "Design and Use of Chimeric Proteins Containing a Collagen-Binding Domain for Wound Healing and Bone Regeneration," *Tissue Engineering Part B: Reviews*, 23(2): 163-182, 2016.
Beatty, et al., "CD40 Agonists Alter Tumor Stroma and Show Efficacy Against Pancreatic Carcinoma in Mice and Humans," *Science*, 331(6024):1612-1616, 2011.

(Continued)

*Primary Examiner* — Elly-Gerald Stoica
(74) *Attorney, Agent, or Firm* — Norton Rose Fulbright US LLP

(57) ABSTRACT

The methods and compositions described herein address the need in the art by providing compositions and methods for a therapy with an antibody that is specifically targeted to and/or retained intra- or peri-tumorally, limiting systemic exposure and reducing side-effects. Accordingly, aspects of the disclosure relate to a composition comprising an immunotherapeutic antibody operatively linked to an extracellular matrix (ECM)-affinity peptide. An ECM-affinity peptide is one that has affinity for an extracellular matrix protein.

13 Claims, 71 Drawing Sheets

Specification includes a Sequence Listing.

(56) References Cited

OTHER PUBLICATIONS

Briquez, et al., "Extracellular Matrix-Inspired Growth Factor Delivery Systems for Skin Wound Healing," *Advances in Wound Care*, 4(8): 479-489, 2015.

Camemolla, et al., "Enhancement of the Antitumor Properties of Interleukin-2 by Its Targeted Delivery to the Tumor Blood Vessel Extracellular Matrix," *Blood*, 99(5): 1659-1665, 2002.

Danhier, et al., "To Exploit the Tumor Microenvironment: Passive and Active Tumor Targeting of Nanocarriers for Anti-Cancer Drug Delivery," *Journal of Controlled Release*, 148(2): 35-146, 2010.

Ellmark, et al., "Tumor-Directed Immunotherapy Can Generate Tumor-Specific T Cell Responses Through Localized Costimulation," *Cancer Immunology, Immunotherapy*, 66: 1-7, 2017.

Fransen, et al., "Controlled Local Delivery of CTLA-4 Blocking Antibody Induces CDS+T-Cell-Dependent Tumor Eradication and Decreases Risk of Toxic Side Effects," *Clinical Cancer Research*, 19(19): 5381-5389, 2013.

International Search Report and Written Opinion Issued in Corresponding PCT Patent Application No. PCT/US2018/028505, dated Jul. 24, 2018.

Ishihara, et al., "Matrix-binding Checkpoint Immunotherapies Enhance Antitumor Efficacy and Reduce Adverse Events," *Science Translational Medicine*, 9(415): eaan0401, 2017.

Liang, et al., "A Collagen-Binding EGFR Antibody Fragment Targeting Tumors With a Collagen-Rich Extracellular Matrix," *Scientific Reports*, 6 (Article 18205), 2016.

Liang, et al., "A Collagen-Binding EGFR Single-Chain Fv Antibody Fragment for the Targeted Cancer Therapy," *Journal of Control Release*, 209, 101-109 (2015).

Luheshi, et al., "Transformation of the Tumour Microenvironment by a CD40 Agonist Antibody Correlates with Improved Responses to DL-L1 Blockade in a Mouse Orthotopic Pancreativ Tumour Model," *Oncotarget*, 7(14): 18508-18520, 2016.

Martino, et al., "Growth Factors Engineered for Super-Affinity to the Extracellular Matrix Enhance Tissue Healing," *Science*, 343: 885-888, 2014.

Spranger, et al., "Melanoma-Intrinsic Beta-Catenin Signalling Prevents Anti-Tumour Immunity," *Nature*, 523(7559): 231-235, 2015.

Xu, et al., "Proteolytic Exposure of a Cryptic Site Within Collagen Type IV is Required for Angiogenesis and Tumor Growth In Vivo," *The Journal of Cell Biology*, 154(5), 1069-1080, 2001.

Yasunaga, et al., "Cancer-Stroma Targeting Therapy by Cytotoxic Immunoconjugate Bound to the Collagen 4 Network in the Tumor Tissue," Bioconjugate Chemistry, 22(9): 1776-1783, 2011.

Cruz et al., "Interaction of the von Willebrand Factor (vWF) with Collagen" The Journal of Biological Chemistry 1995, 270(18), 10822-10827.

Machha et al., "The Von Willebrand Factor A 1-Collagen III Interaction is Independent of Conformation and Type 2 Von Willebrand Disease Phenotype" *J Mol Biol*. 2017, 429, 32-47.

Office Action issued in Corresponding Japanese Application No. 2019-557434, dated May 30, 2022 (English translation provided).

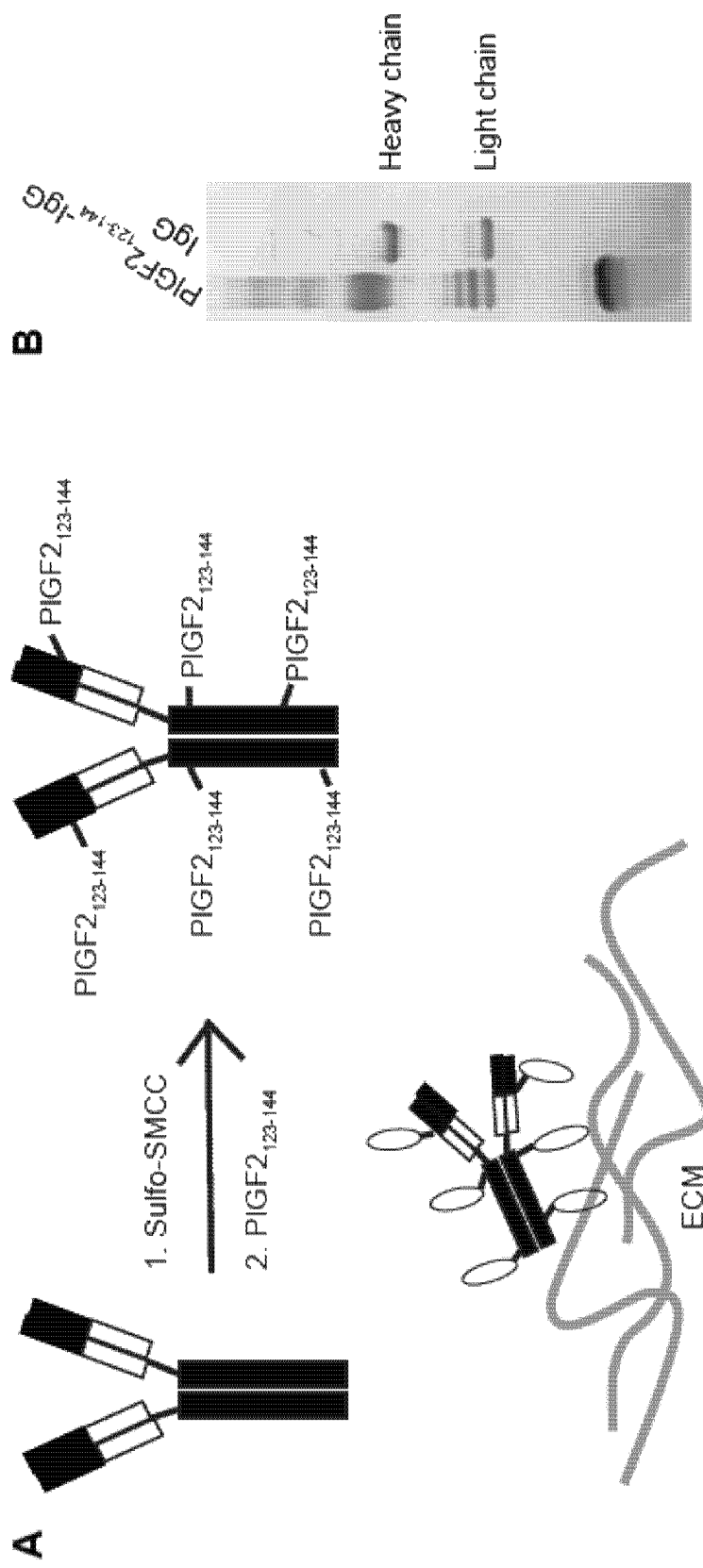
FIG. 1A-B

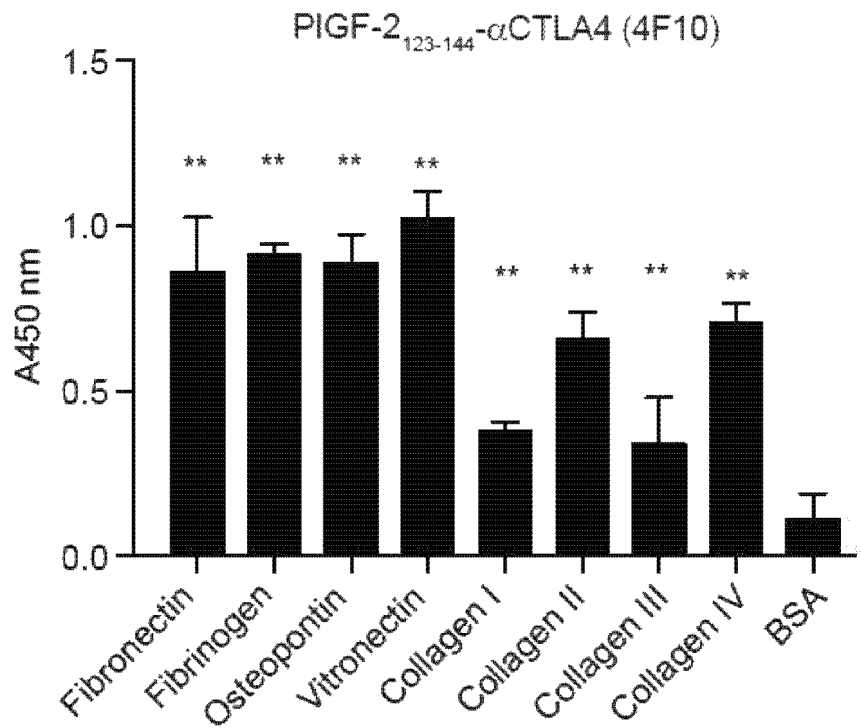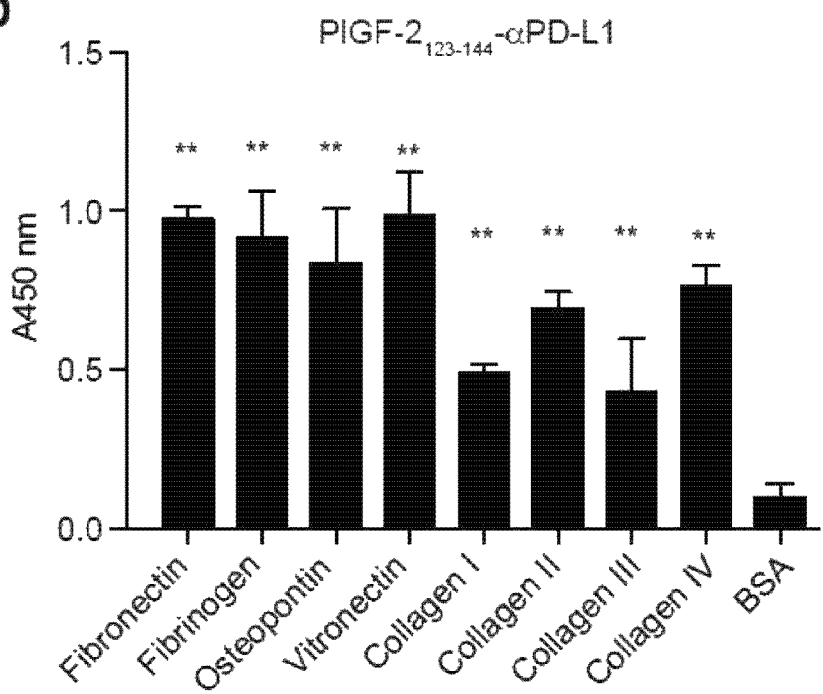
FIG. 1C-D

E
| Kd (nM) | Fibronectin | Collagen I | rmCTLA4 |
|---|---|---|---|
| PlGF-2$_{123-144}$-4F10 | 4.7 | 26.7 | $1.6 \times 10^{-1}$ |
| 4F10 | N.D. | N.D. | $1.0 \times 10^{-1}$ |
| Kd (nM) | Fibronectin | Collagen I | rmCTLA4 |
|---|---|---|---|
| PlGF-2$_{123-144}$-9H10 | $8.7 \times 10^{-1}$ | 1.3 | 5.7 |
| 9H10 | N.D. | N.D. | 15 |
| Kd (nM) | Fibronectin | Collagen I | rmPD-L1 |
|---|---|---|---|
| PlGF-2$_{123-144}$-αPD-L1 | 3.7 | 5.1 | $1.7 \times 10^{-1}$ |
| αPD-L1 | N.D. | N.D. | $9.5 \times 10^{-2}$ |
F
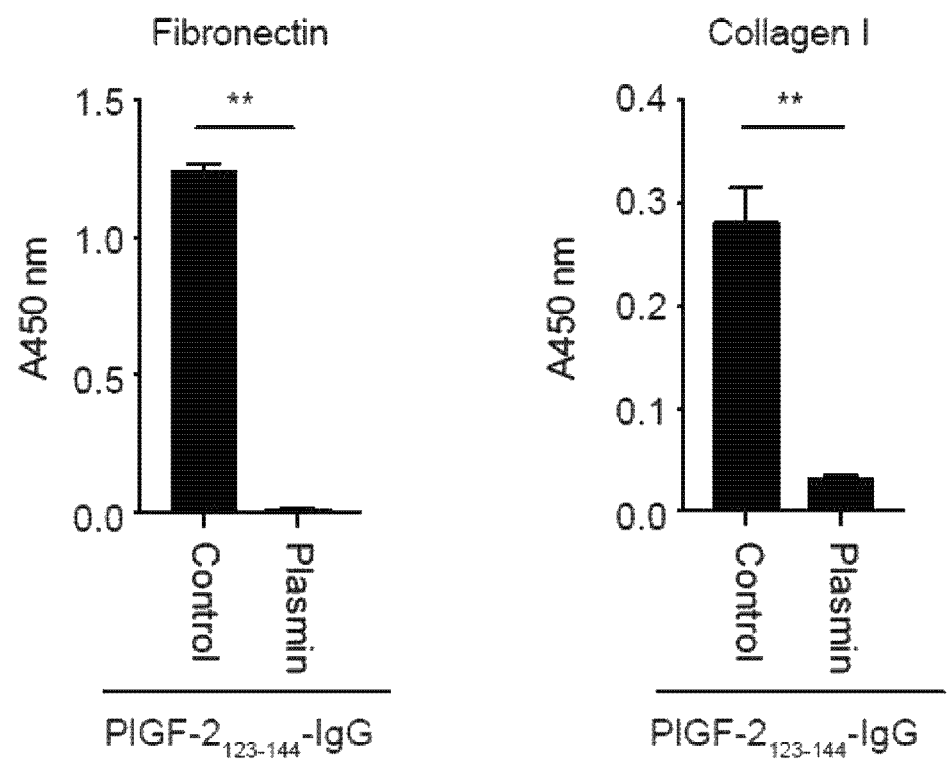
FIG. 1E-F

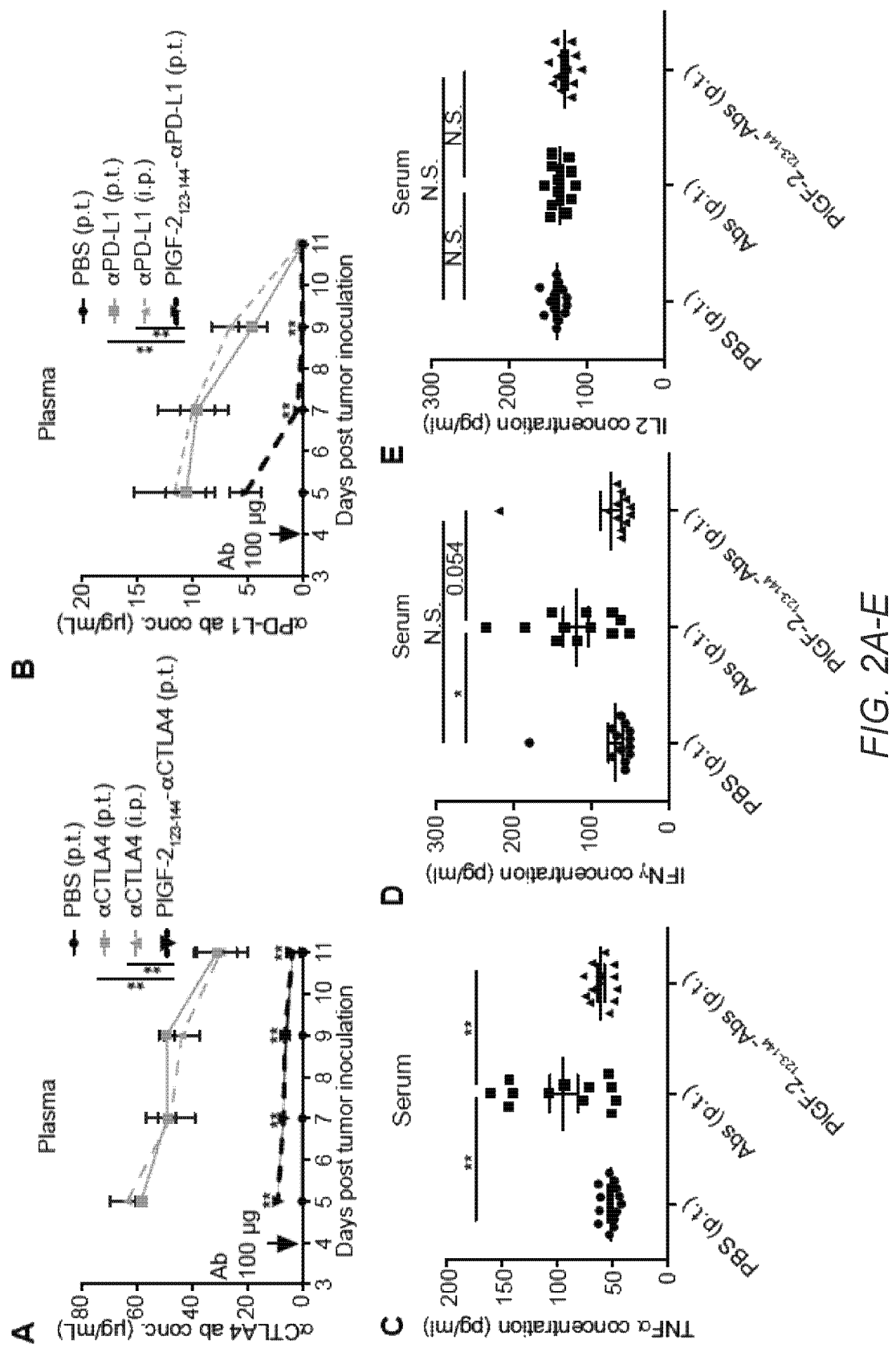
FIG. 2A-E

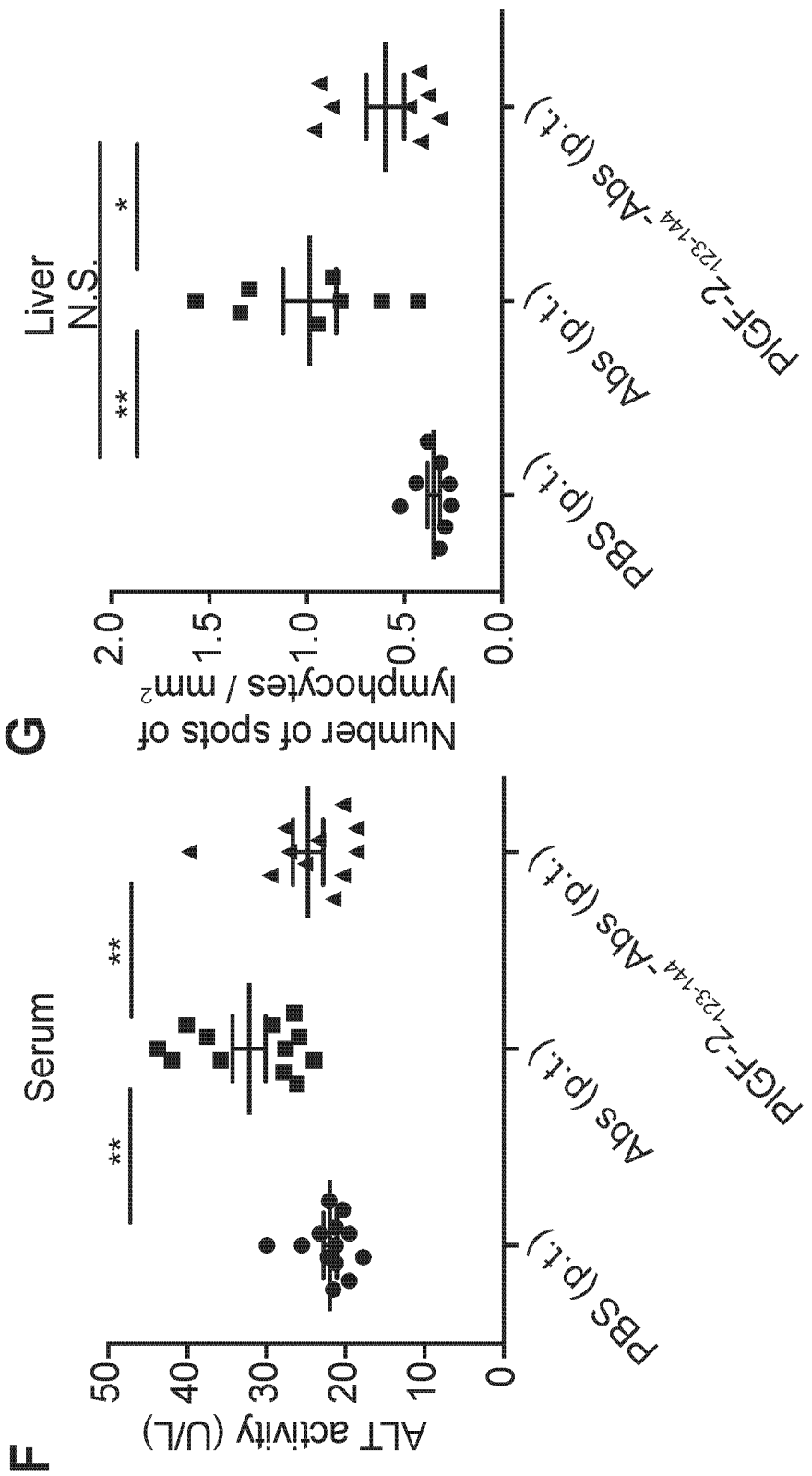
FIG. 2F-G

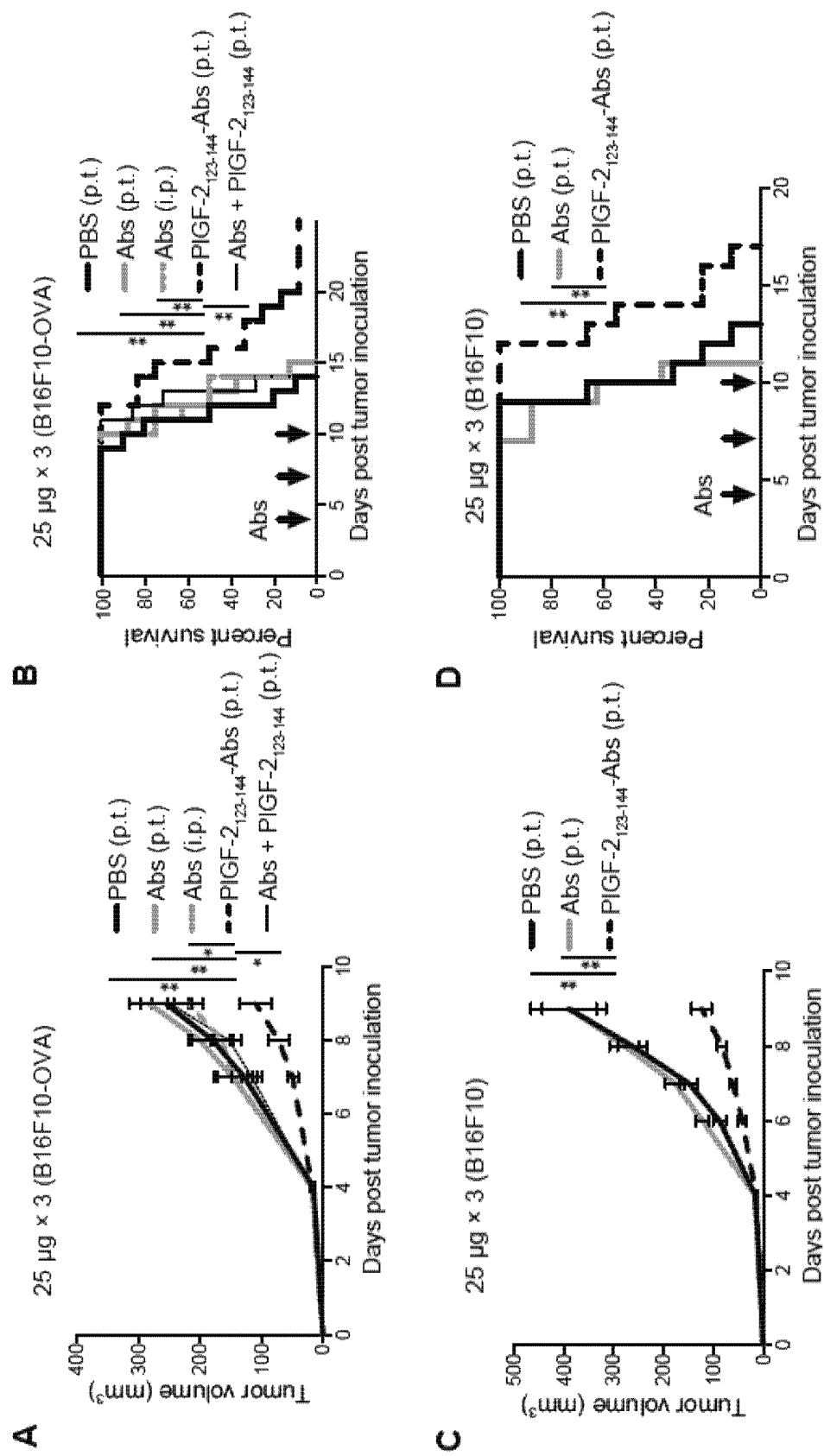
FIG. 3A-D

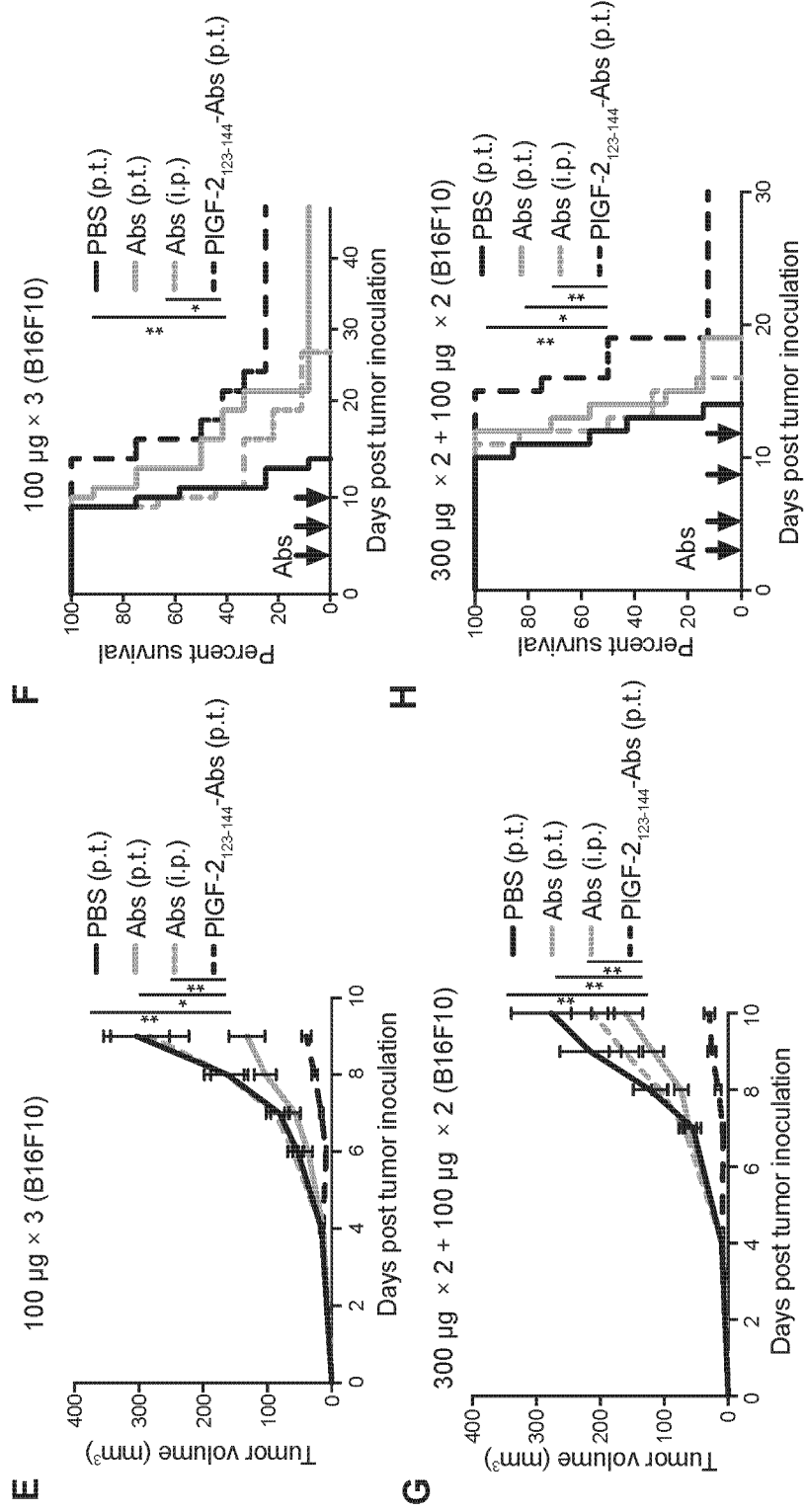
FIG. 3E-H

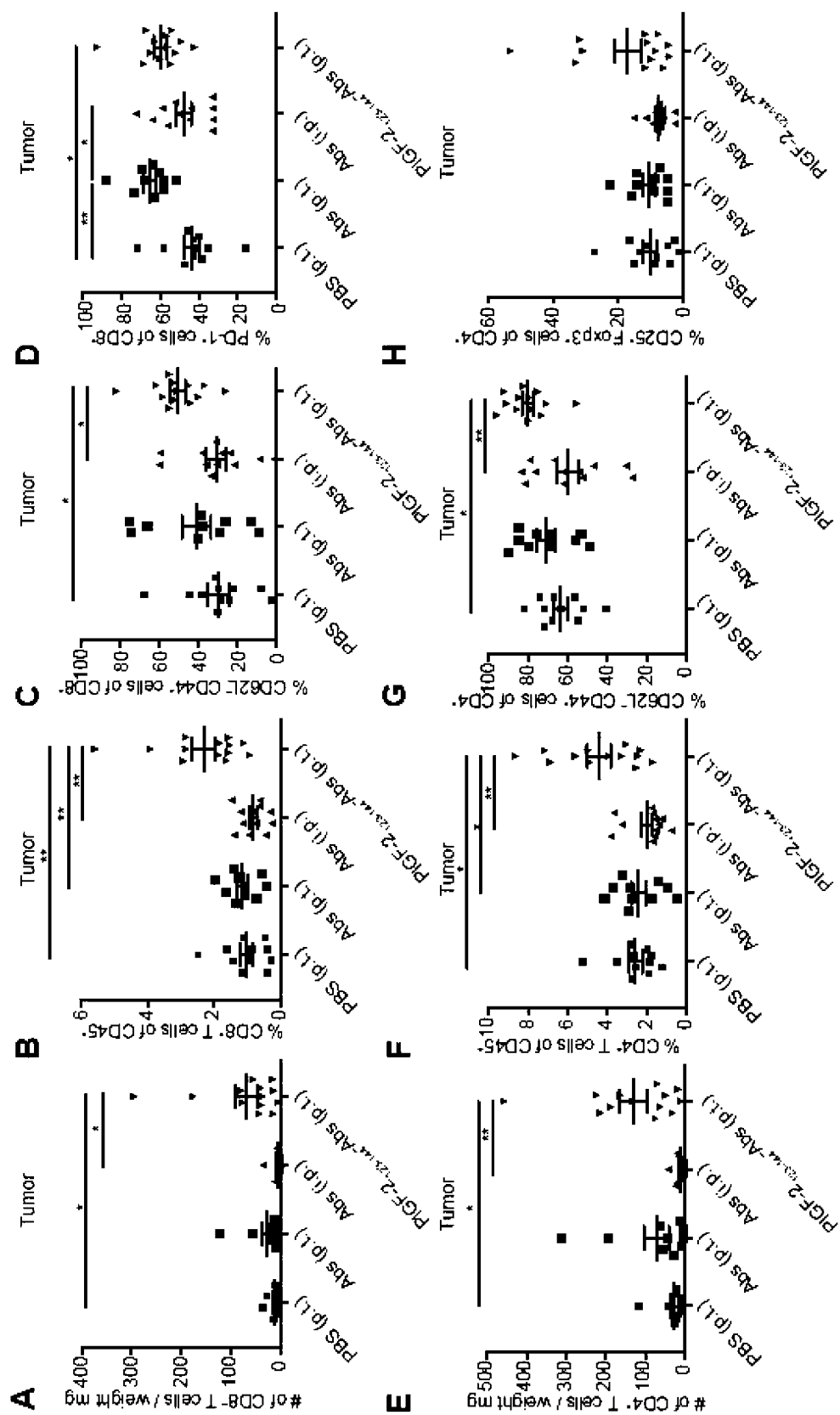
FIG. 4A-H

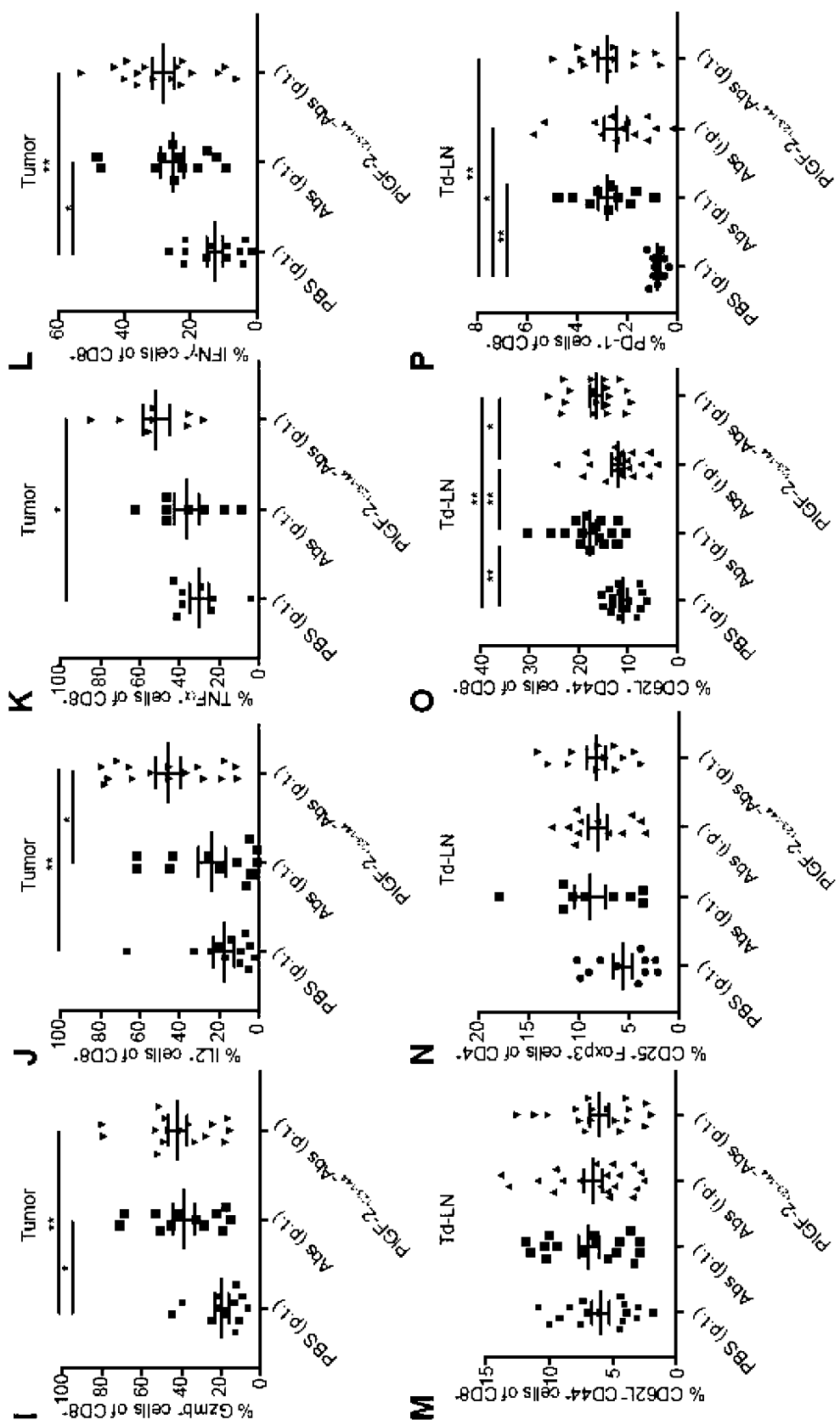
FIG. 4I-P

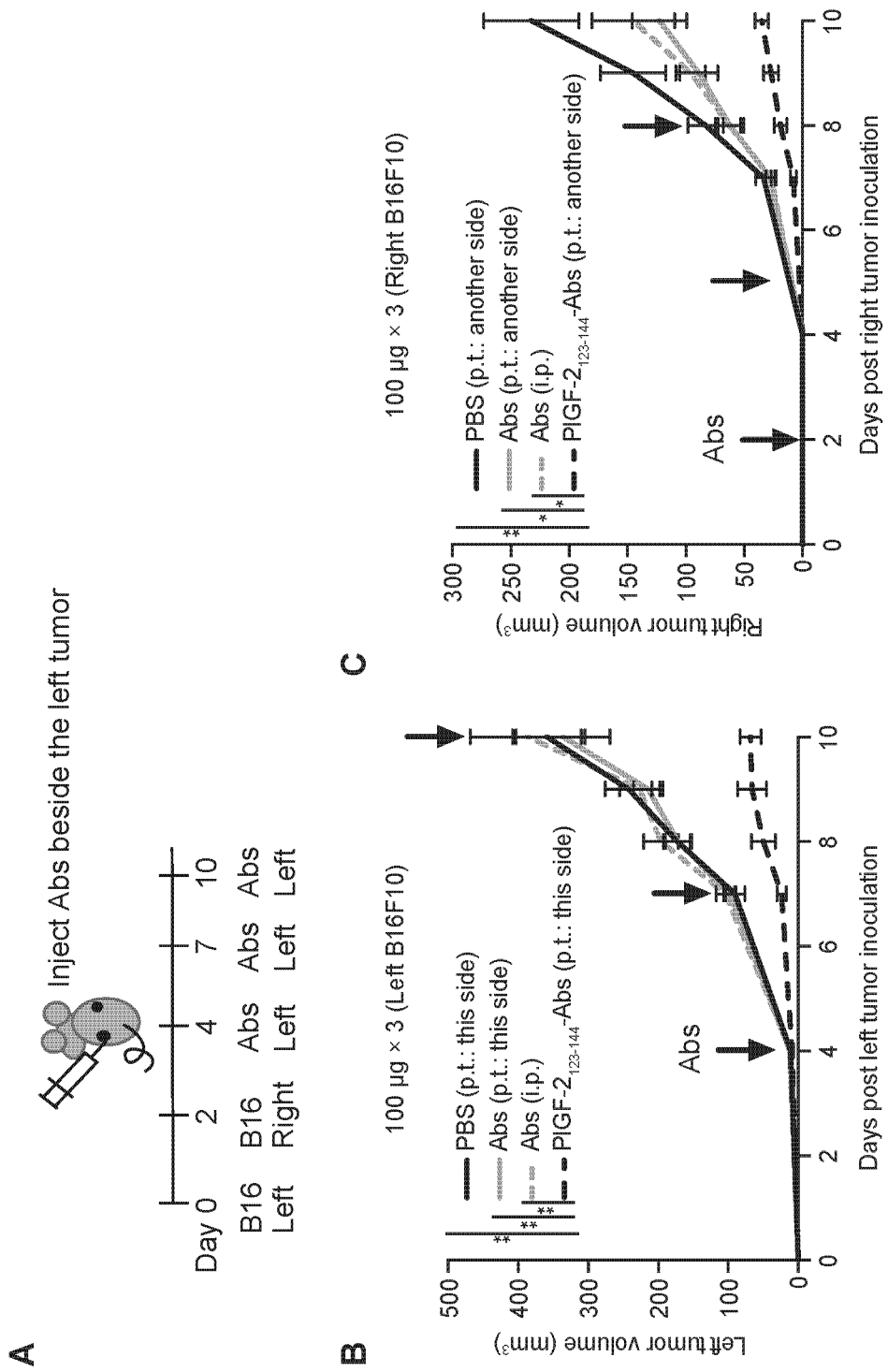
FIG. 5A-C

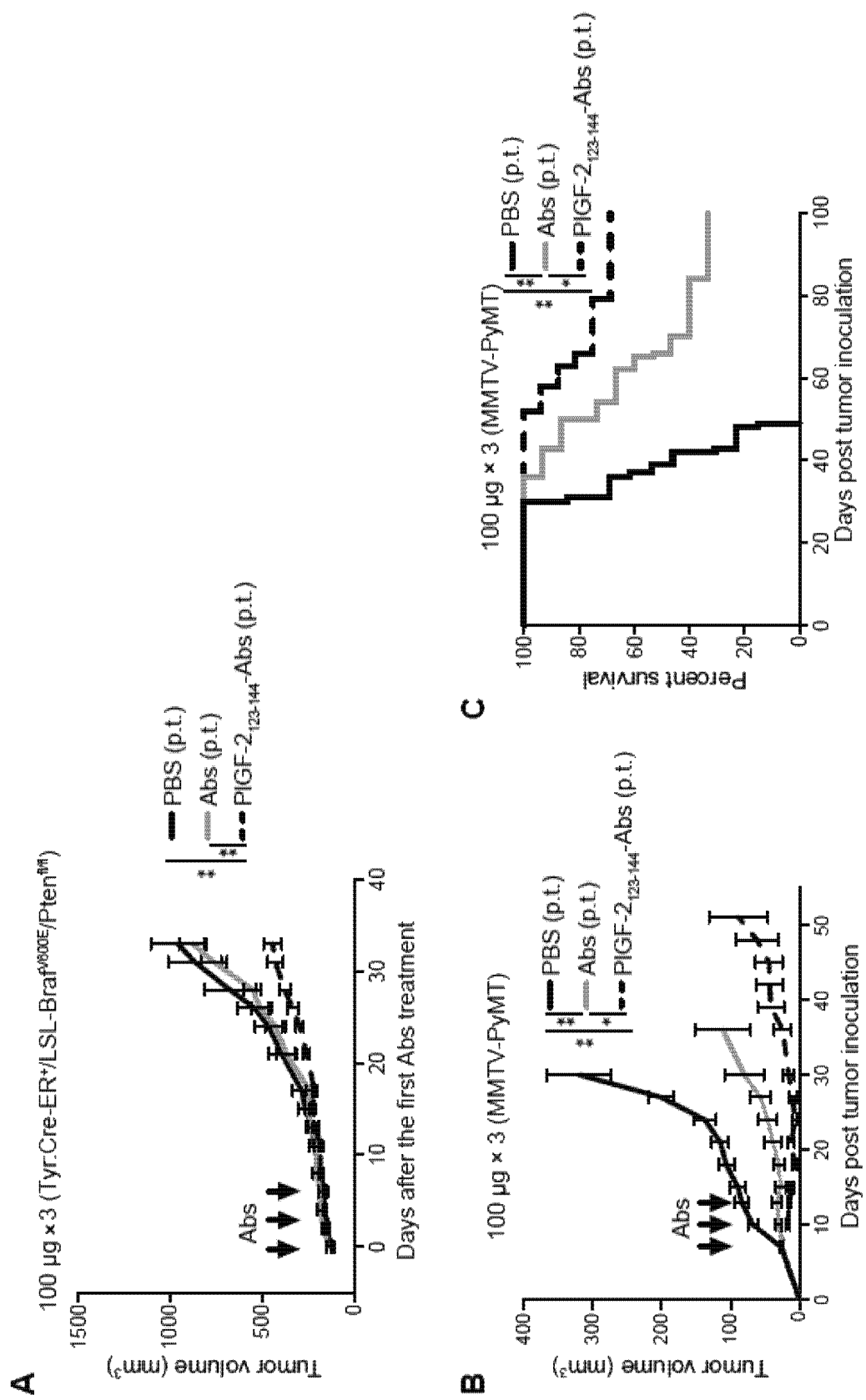
FIG. 6A-C

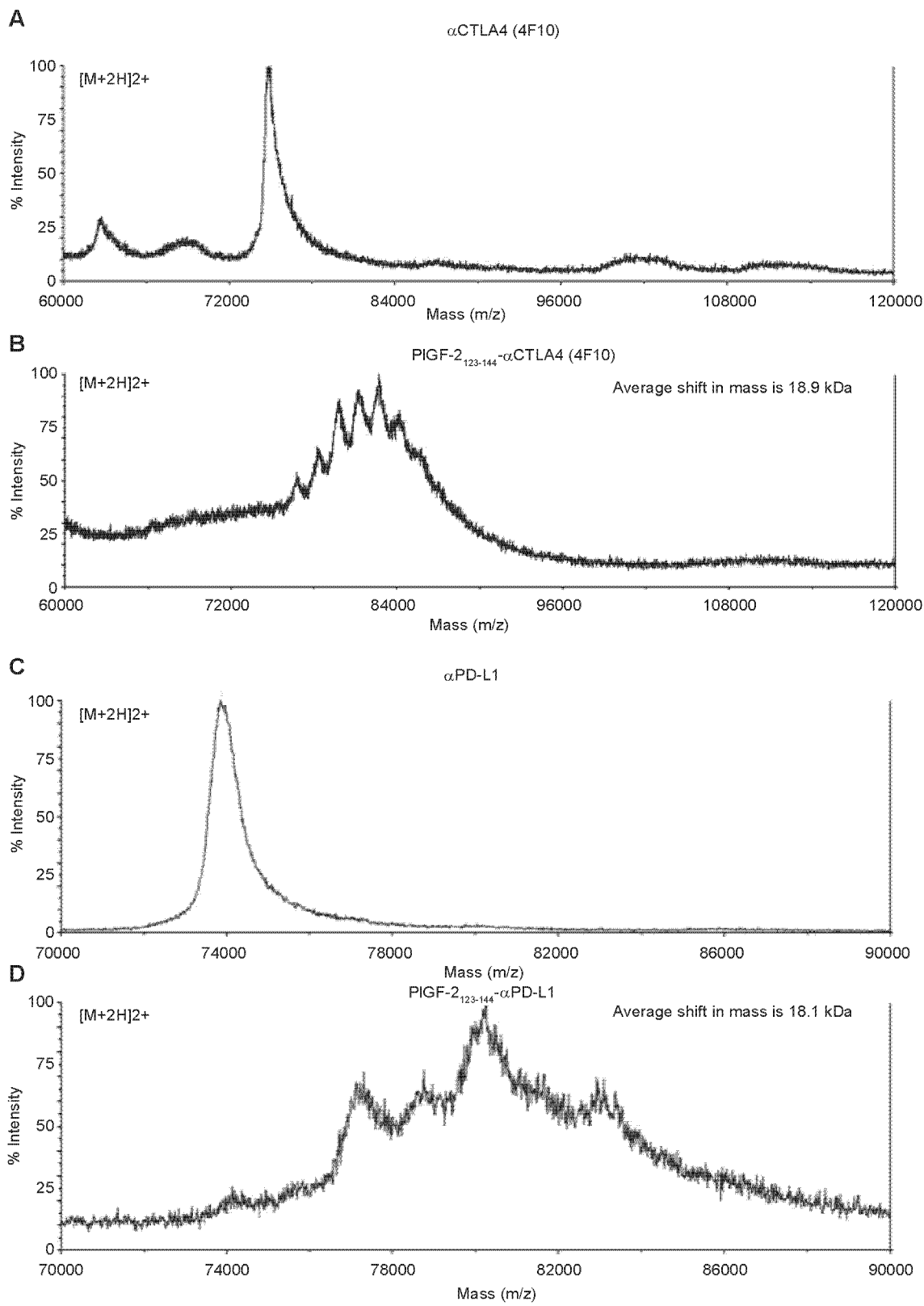
FIG. 7A-C

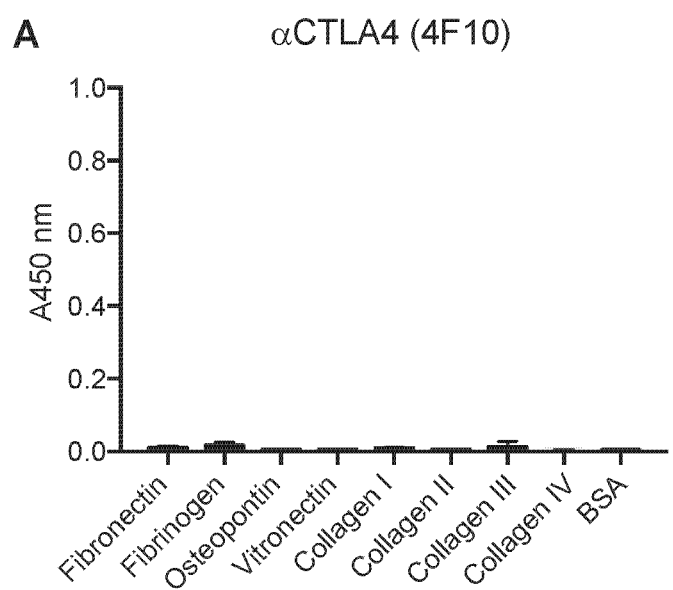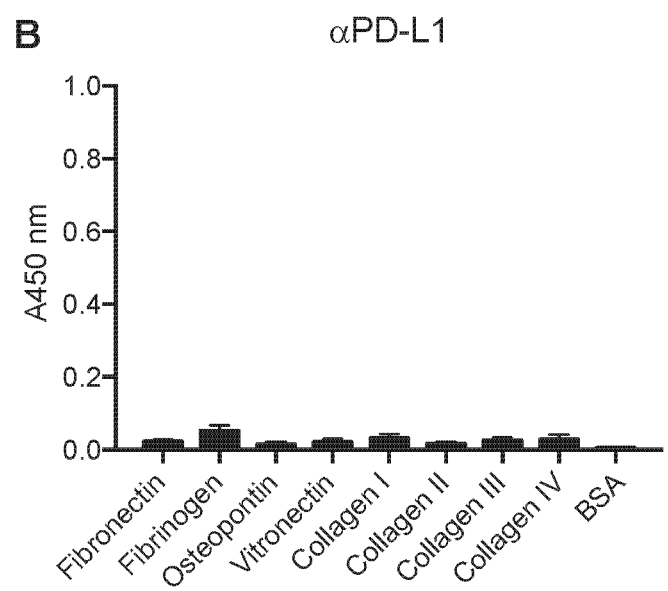
FIG. 8A-B

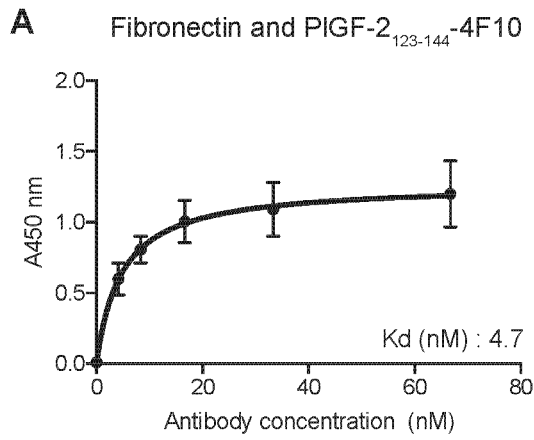
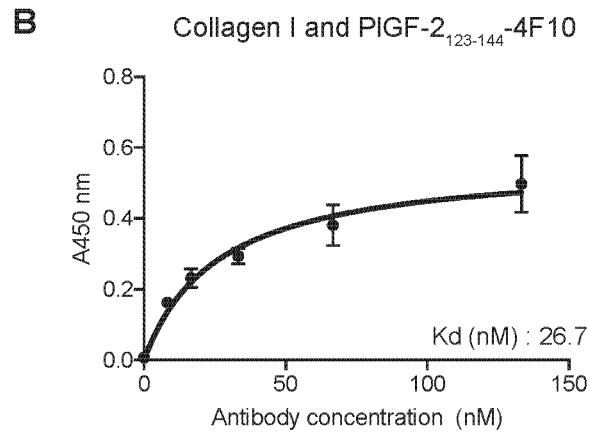
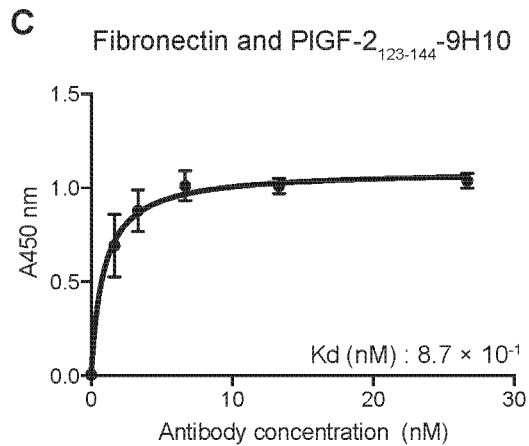
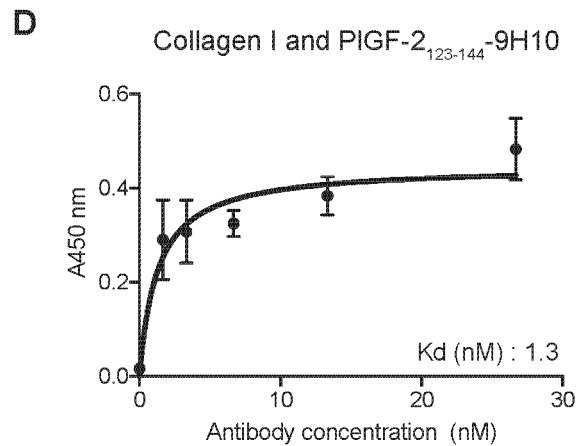
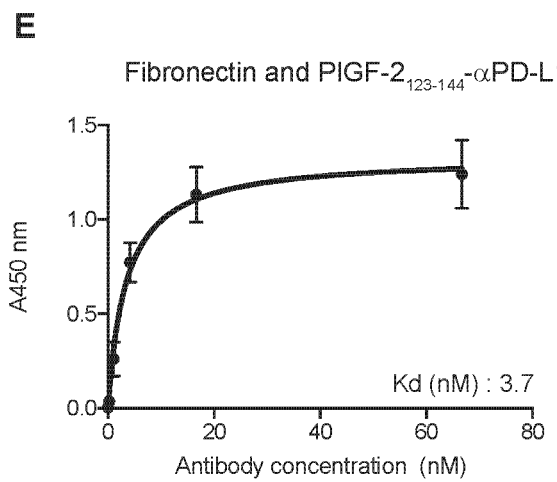
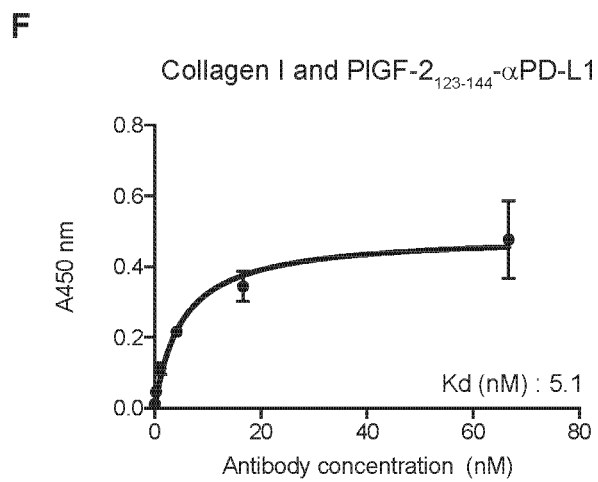
FIG. 9A-F

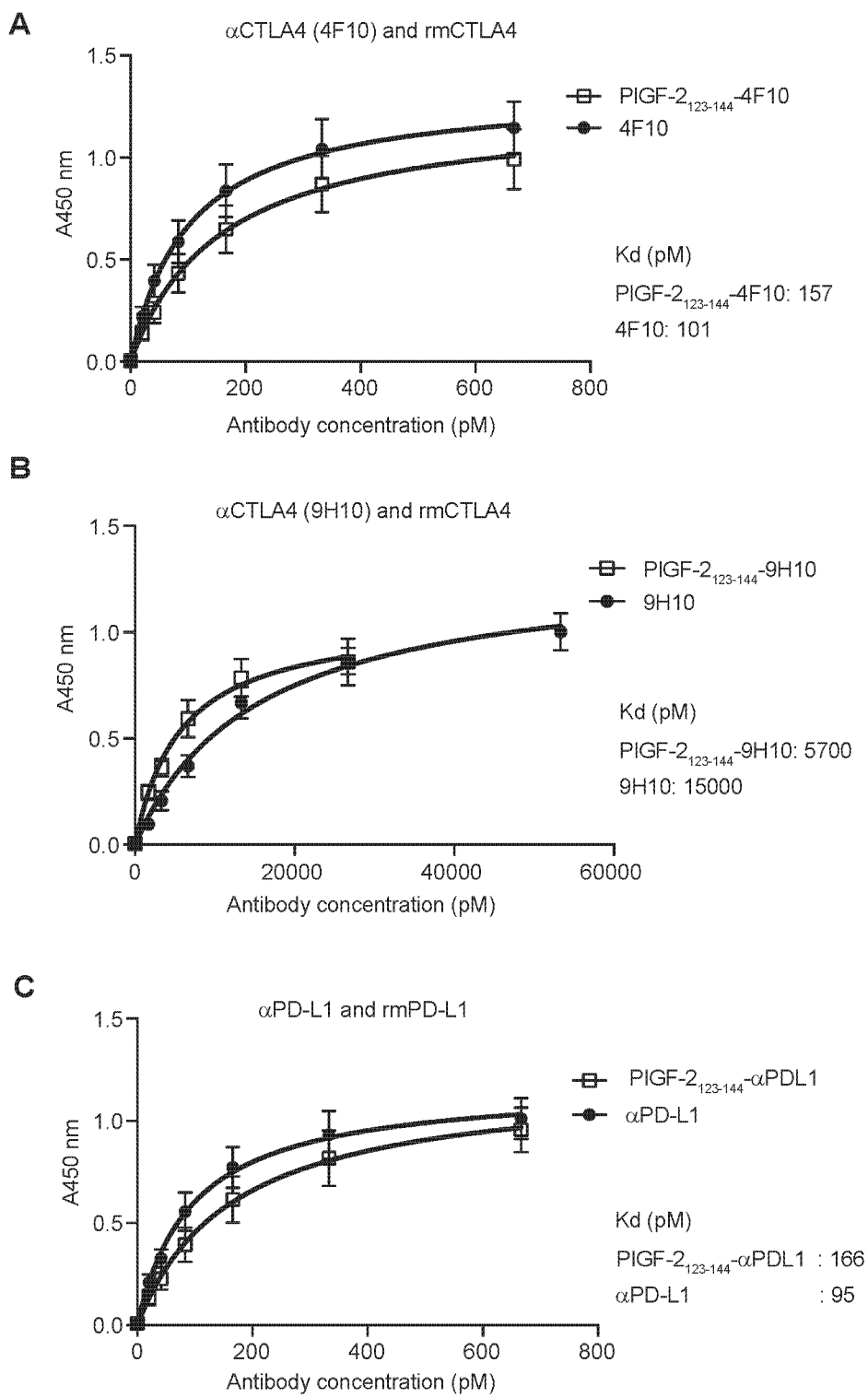
FIG. 10A-C

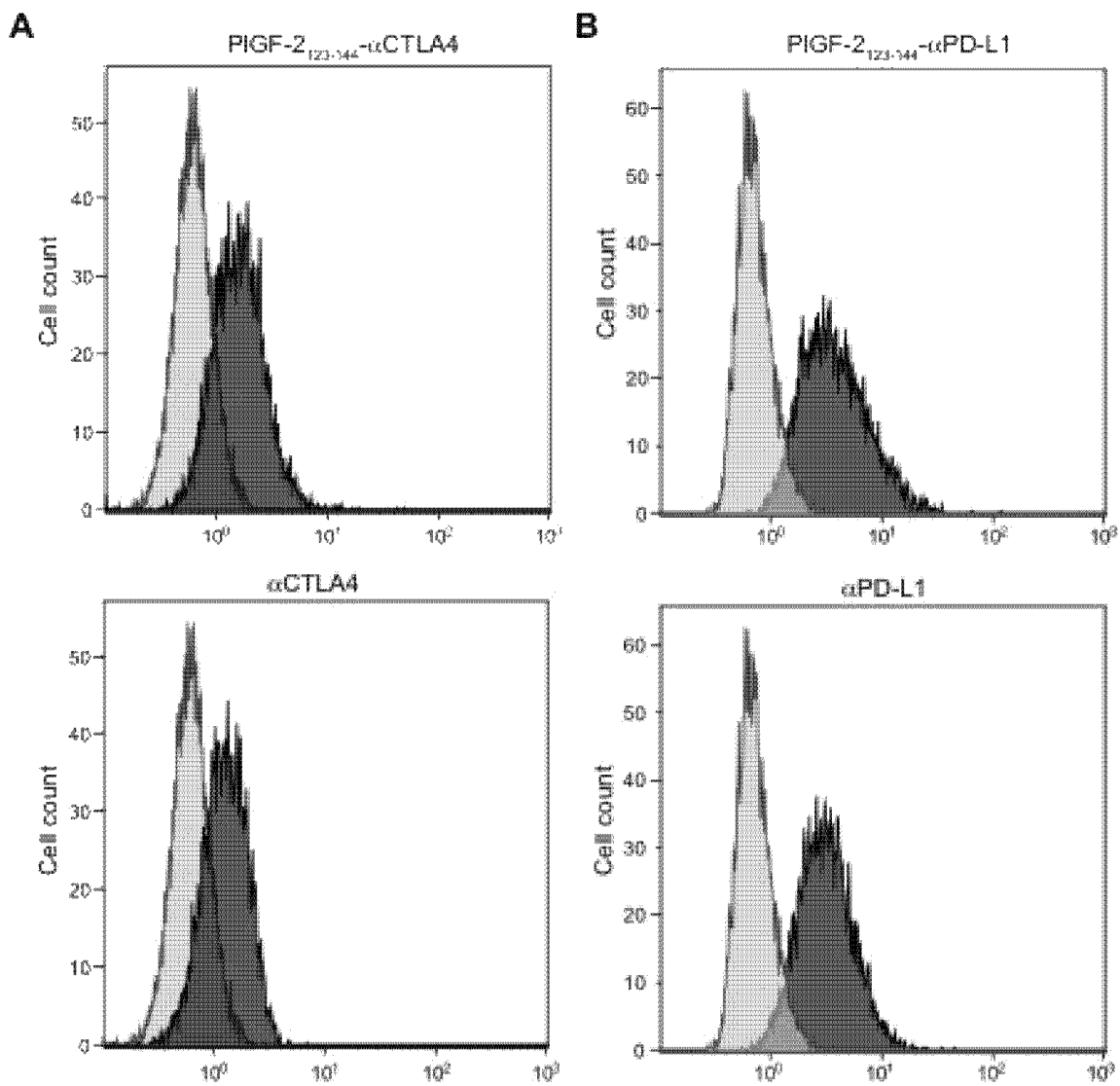
FIG. 11A-B

| $K_D$ (nM) | Collagen I | Collagen III | Binding target |
|---|---|---|---|
| CBD-αPD-L1 | 158 | 94.6 | 0.03 |
| αPD-L1 | N.D. | N.D. | 0.05 |
| CBD-αCTLA4 | 138 | 54.1 | 1.61 |
| αCTLA4 | N.D. | N.D. | 1.65 |
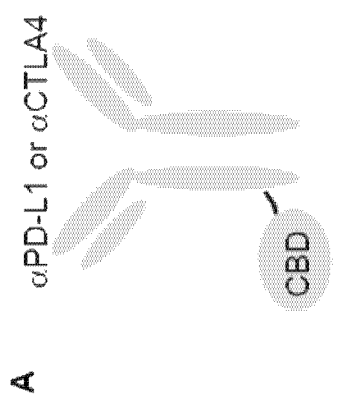
FIG. 28A-B

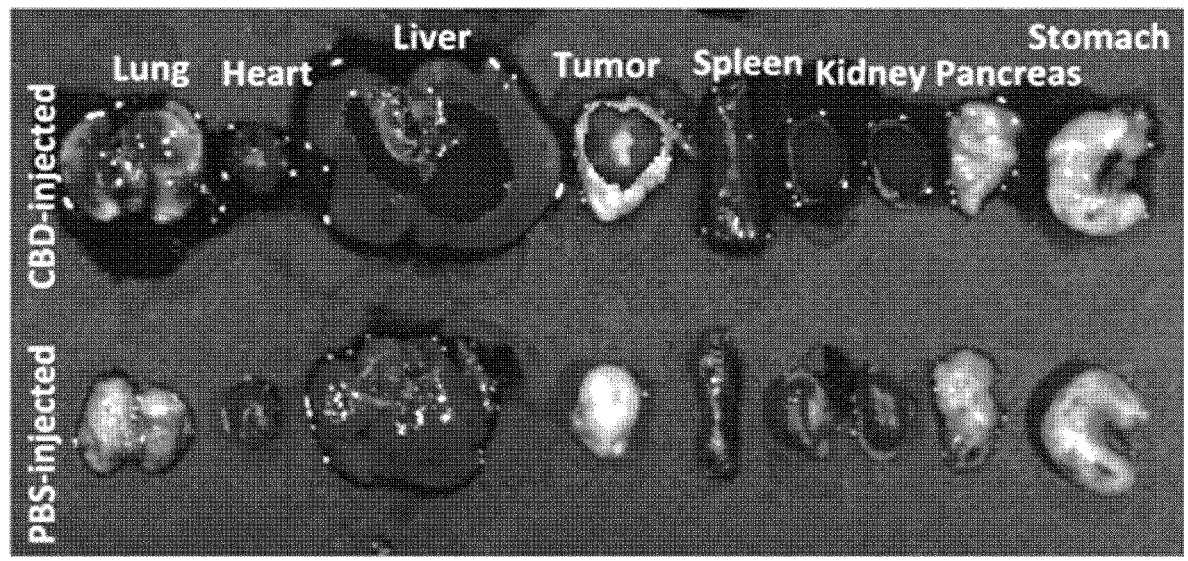
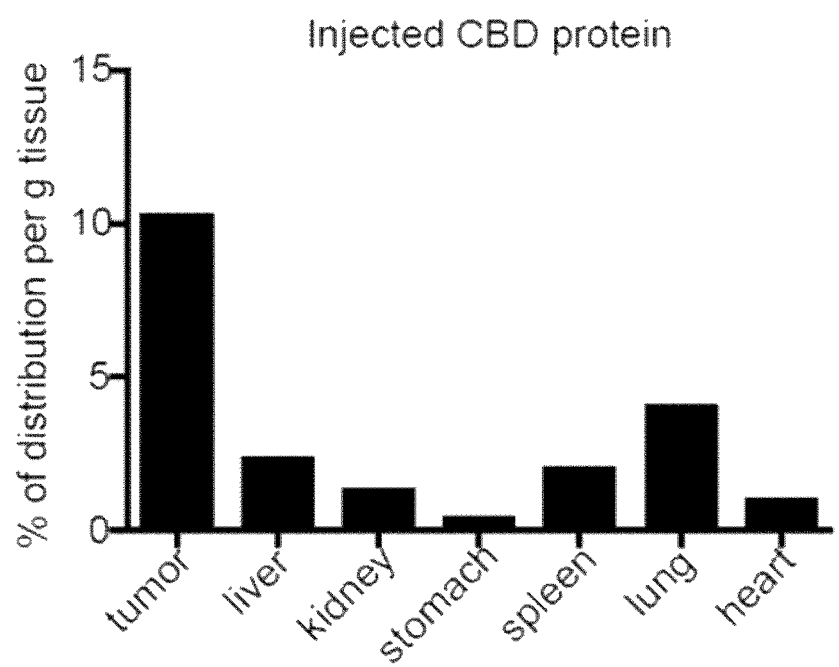
*FIG. 29A*

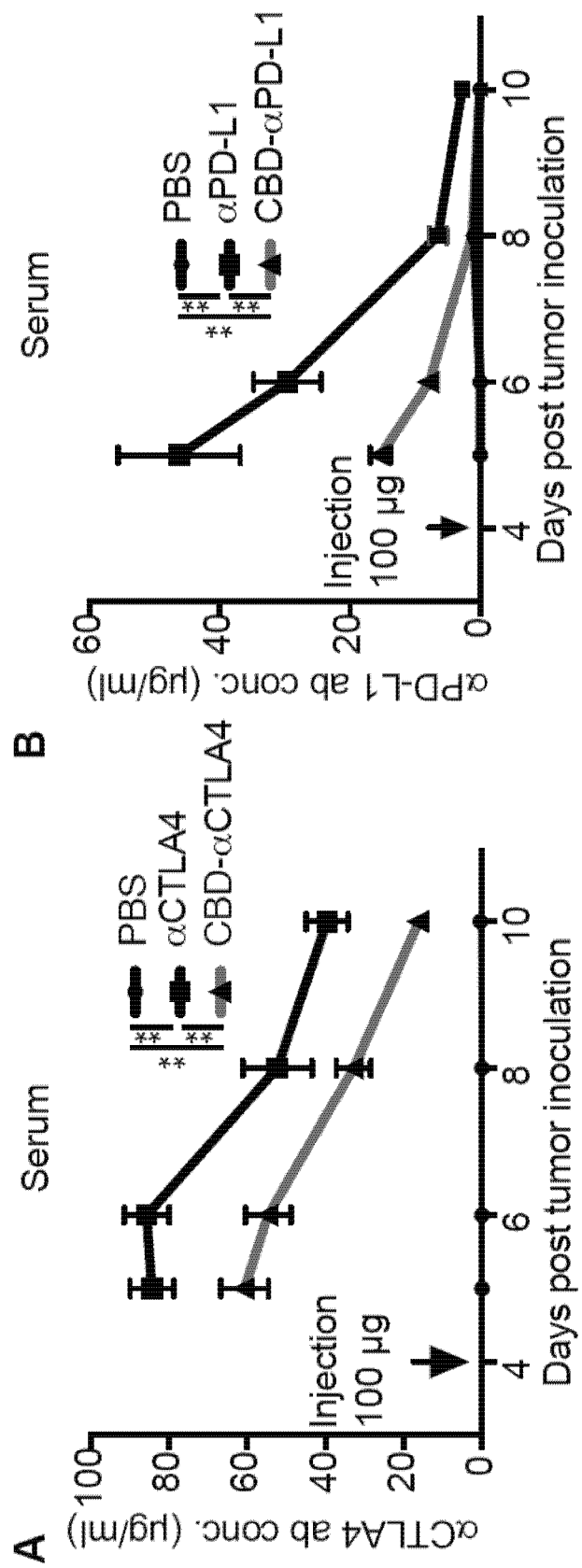
FIG. 30A-B

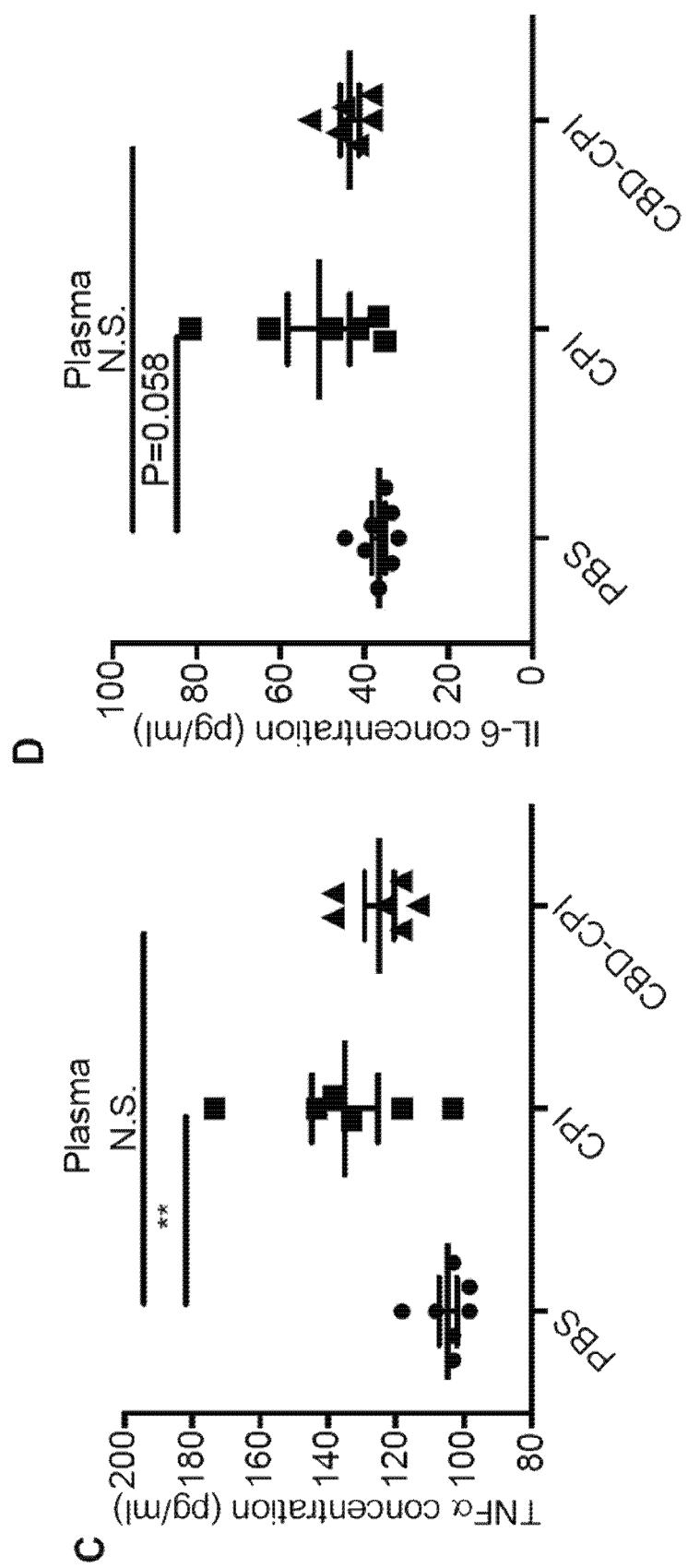
FIG. 30C-D

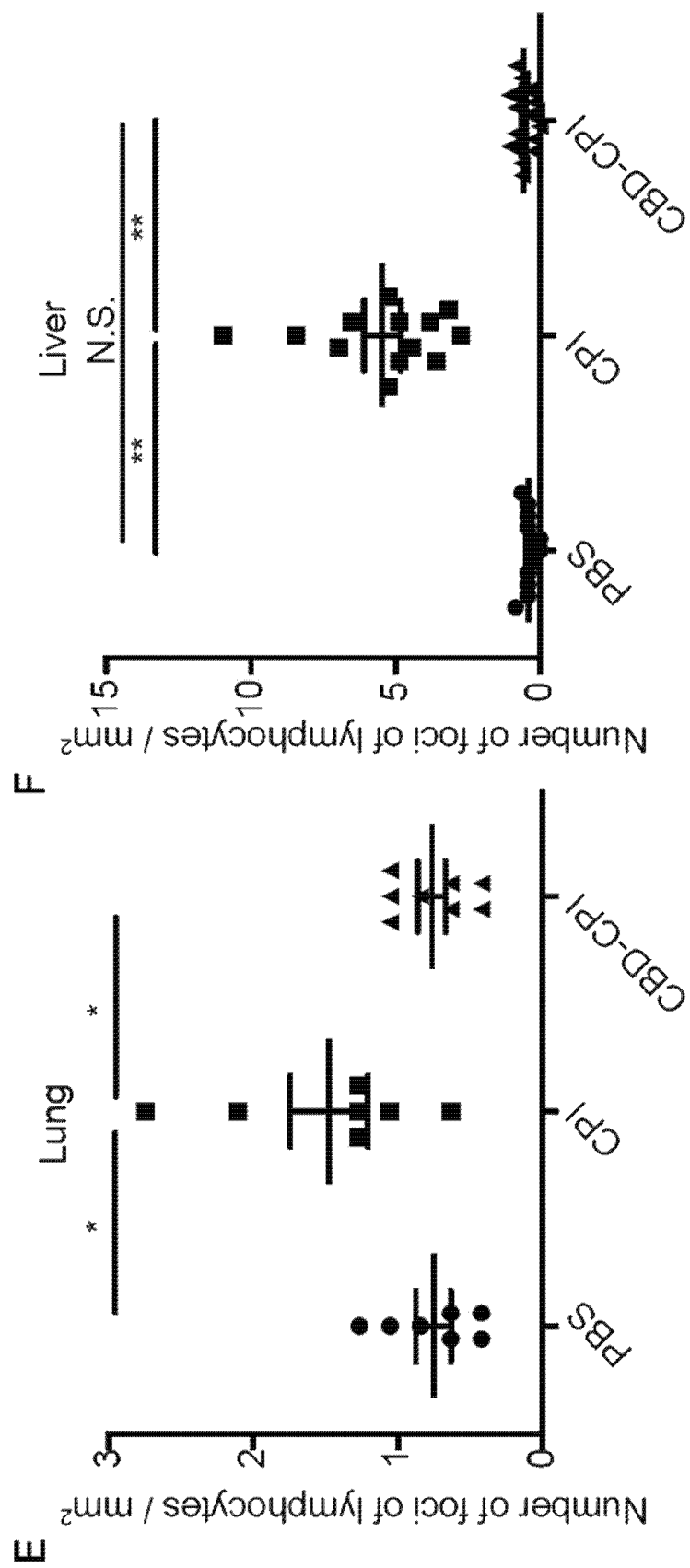
FIG. 30E-F

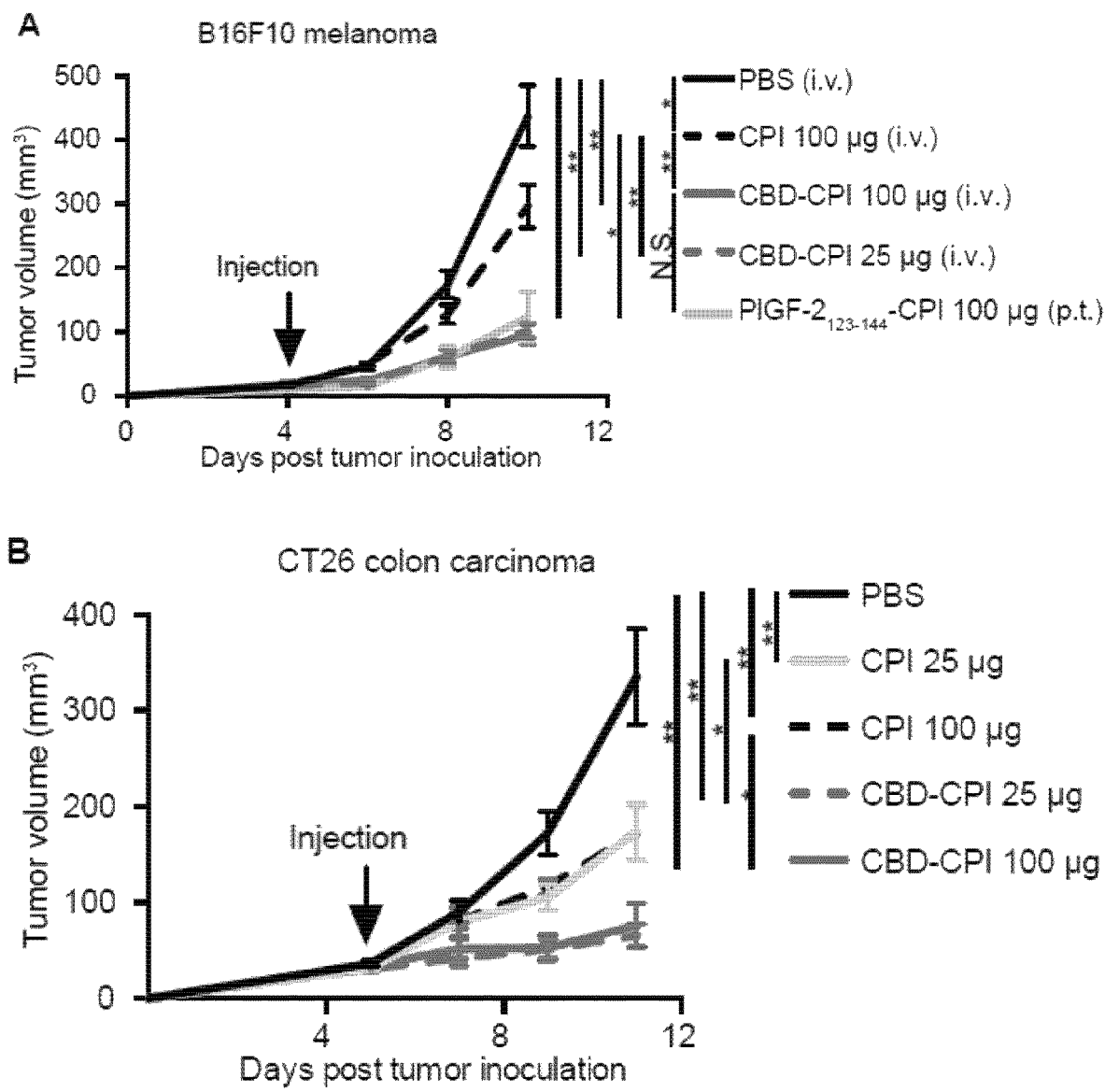
FIG. 31A-B

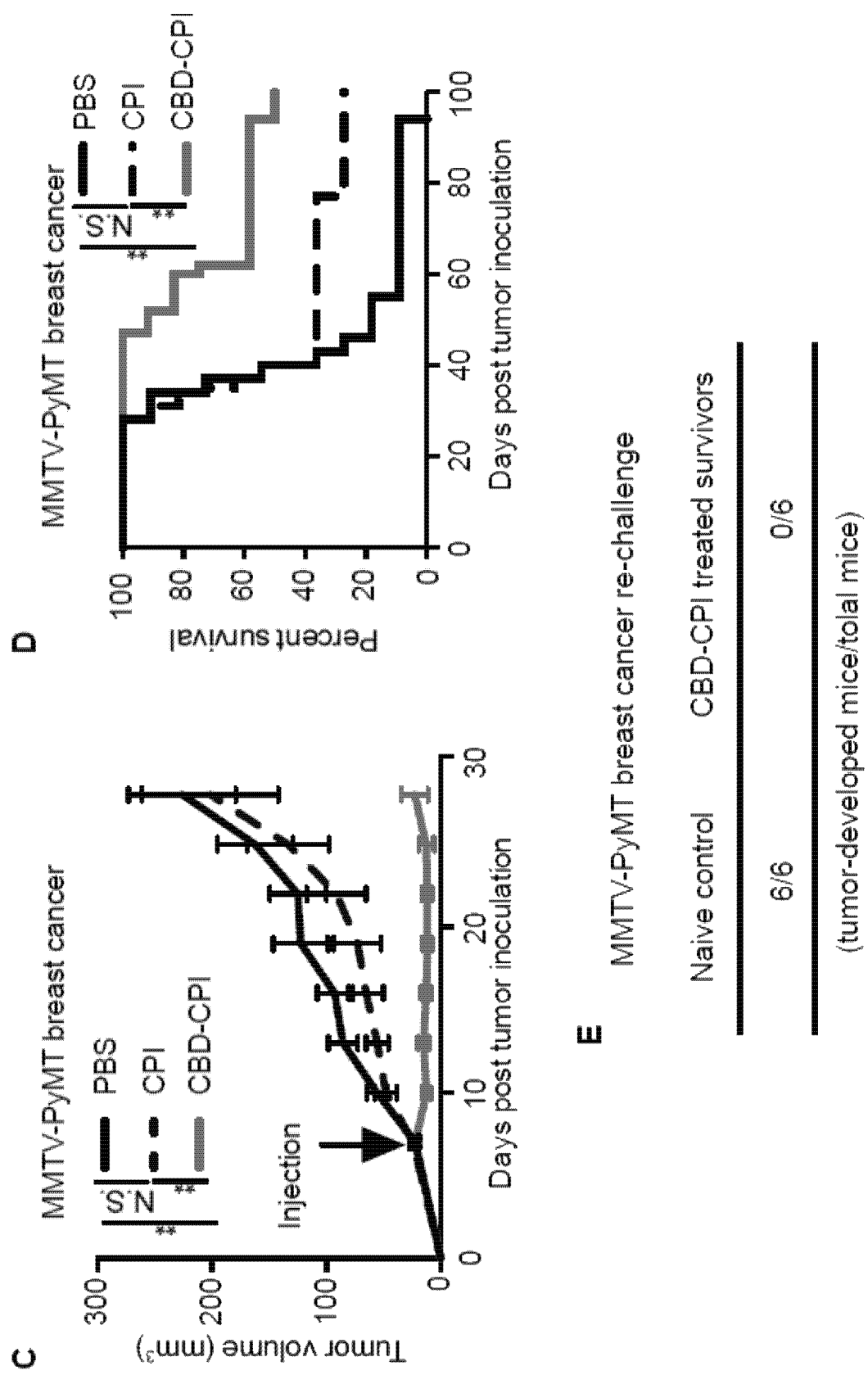
FIG. 31C-E

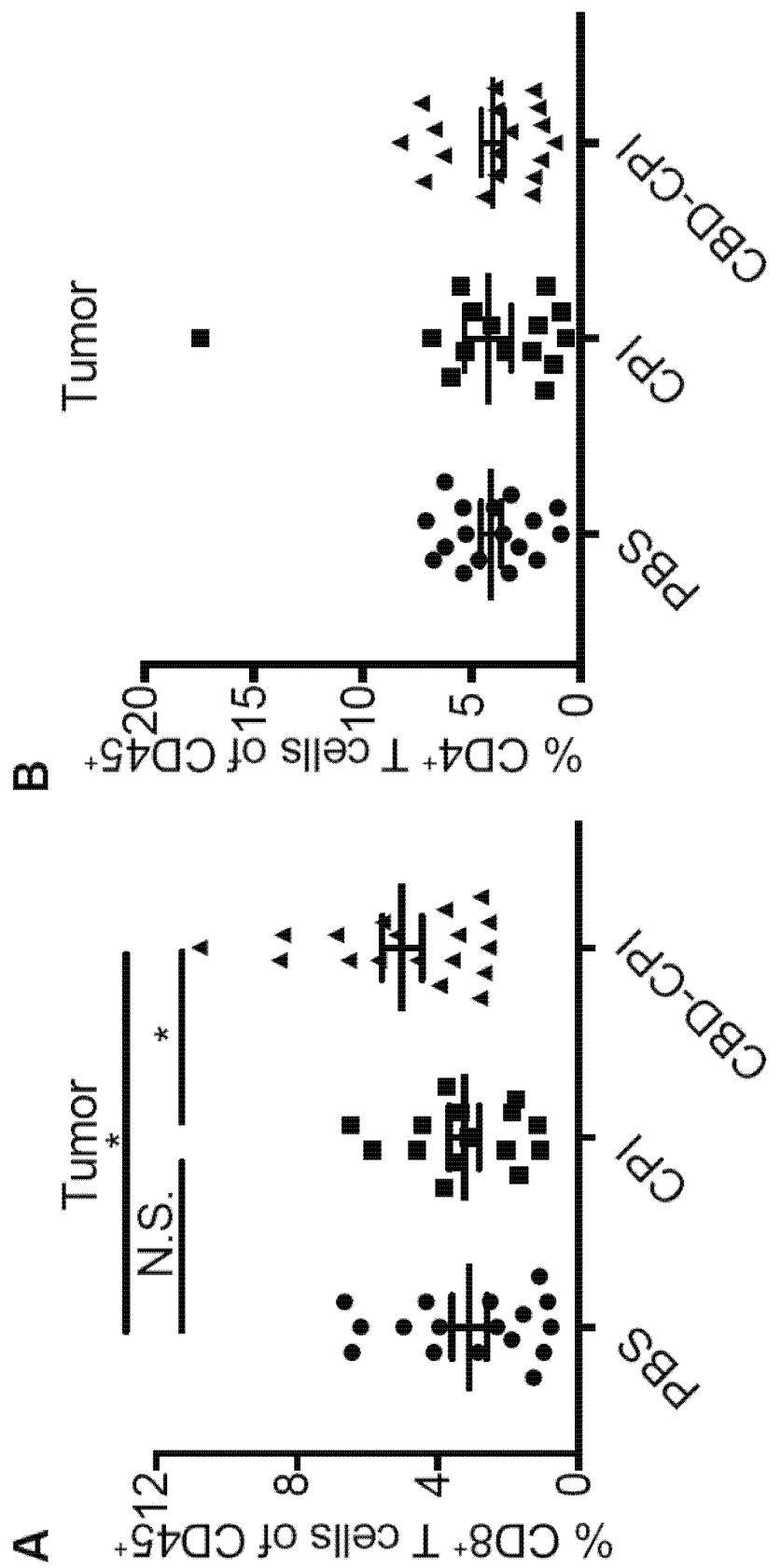
FIG 33A-B

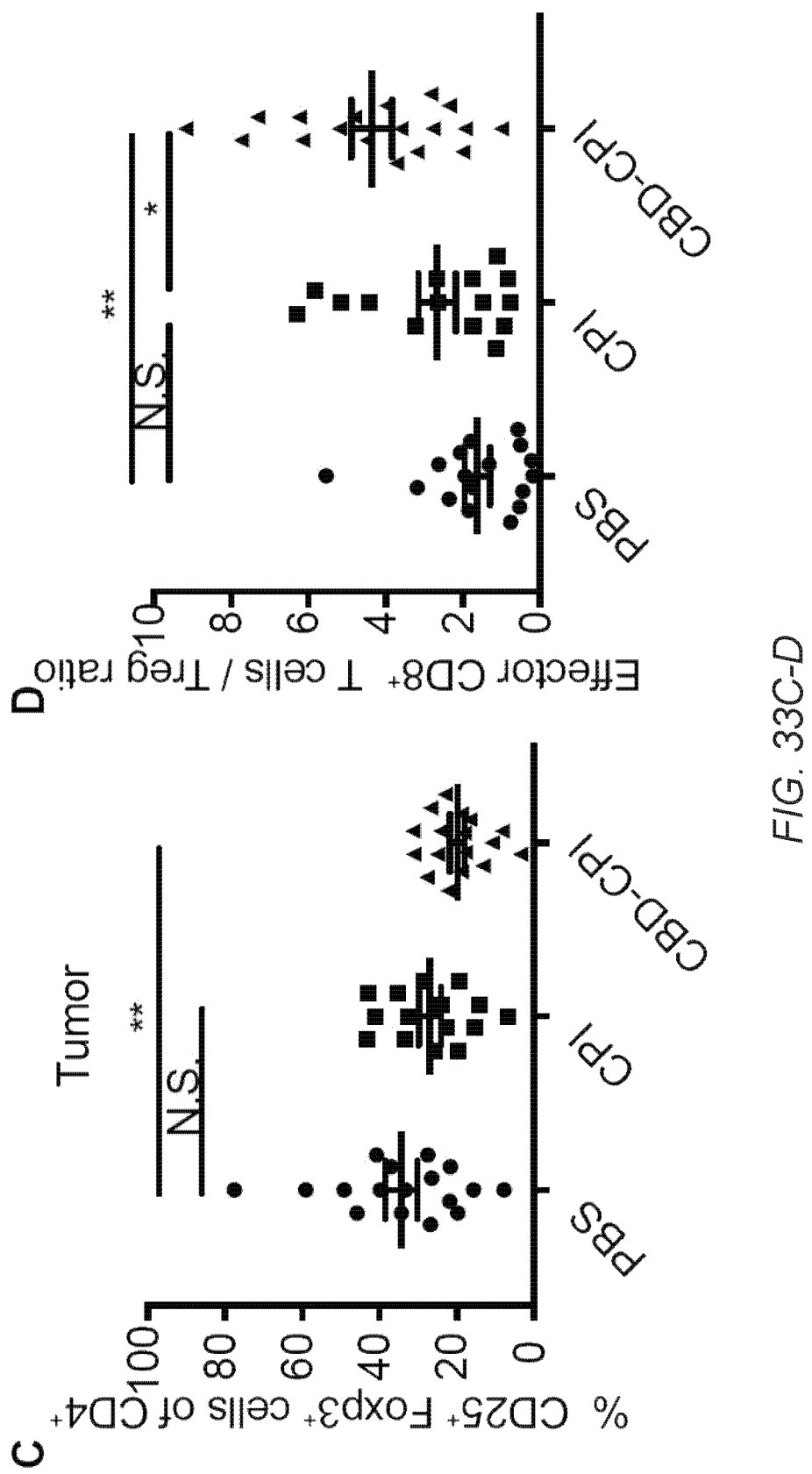
FIG. 33C-D

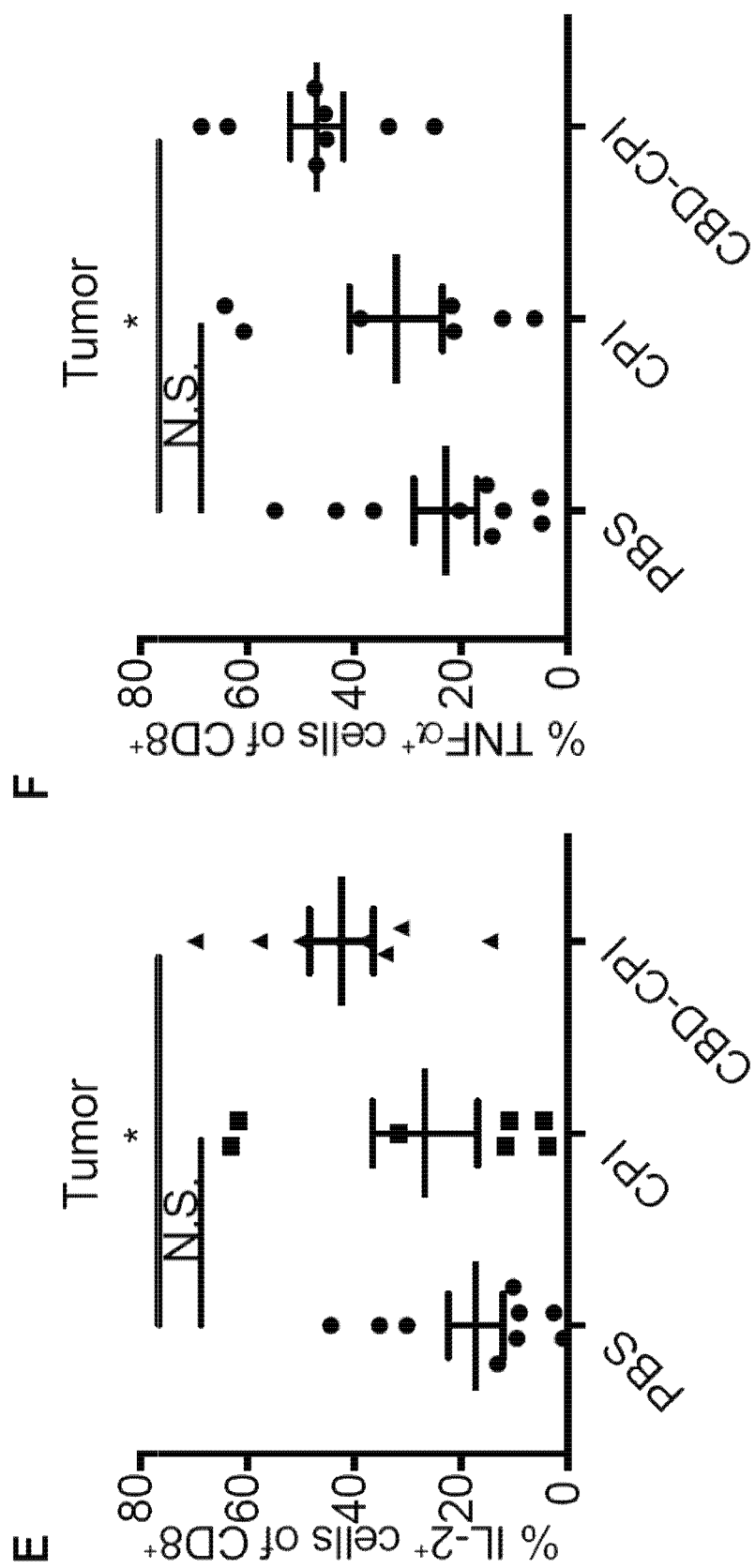
FIG. 33E-F

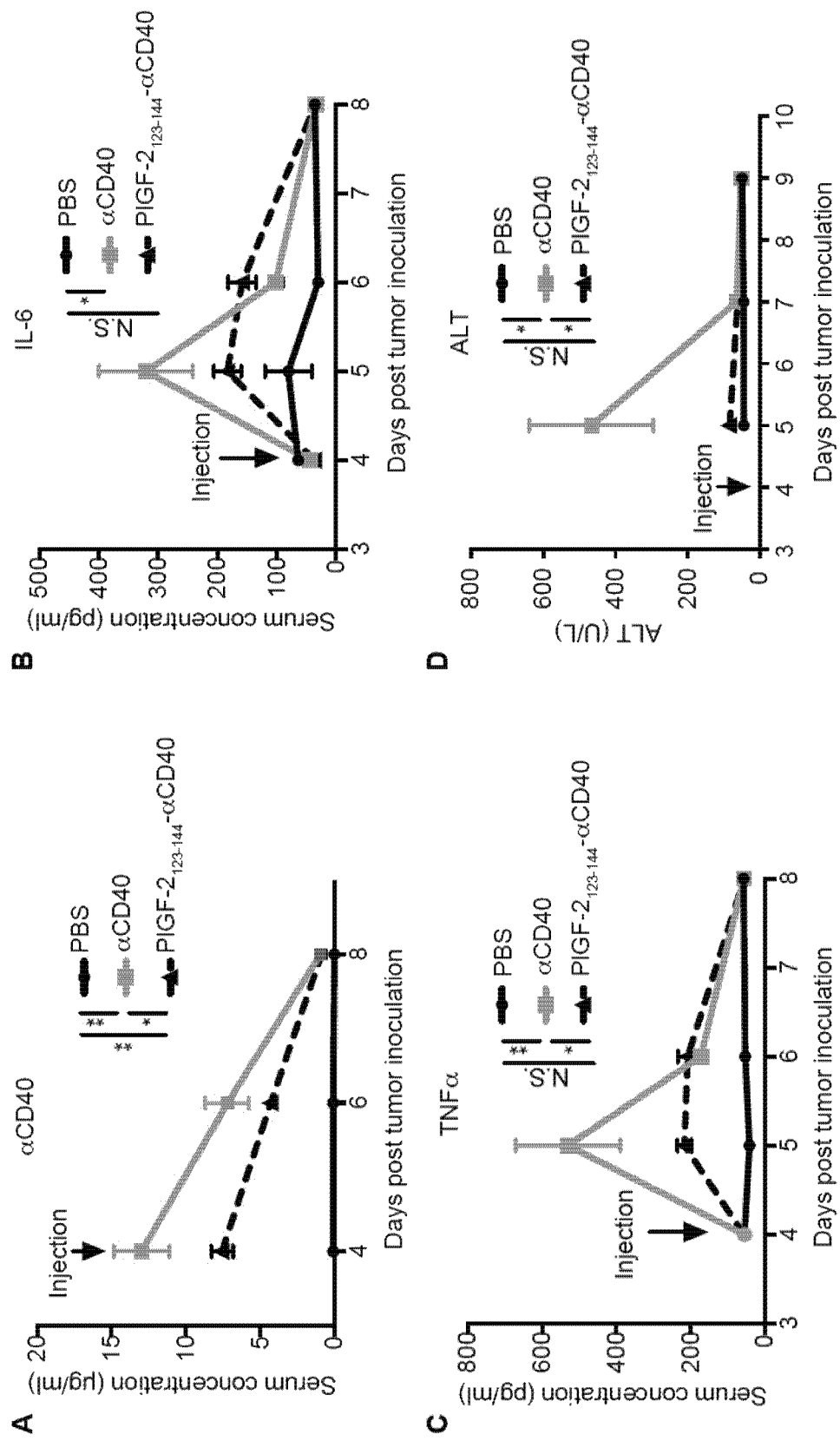
FIG. 35A-D

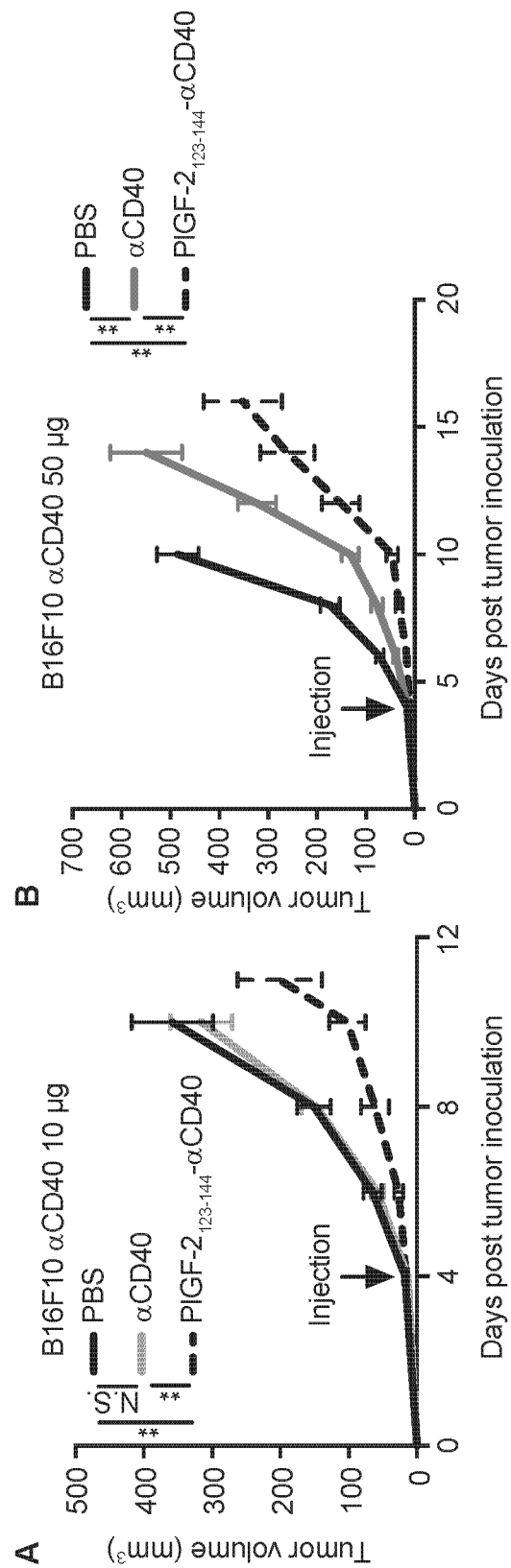
FIG. 37A-B

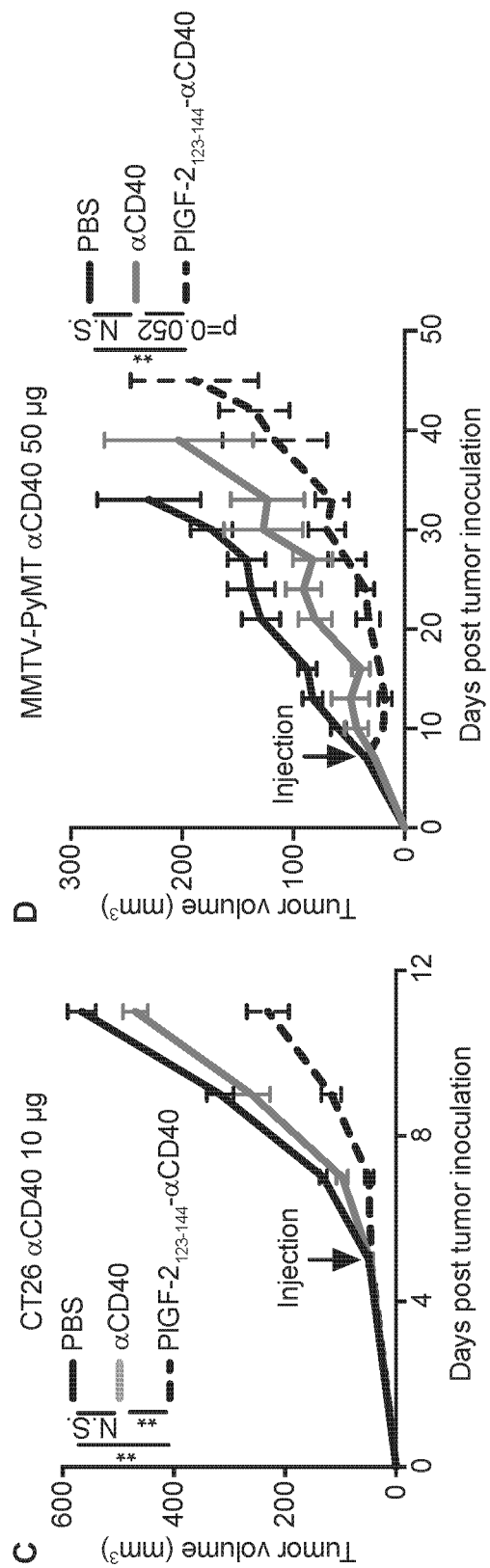
FIG. 37C-D

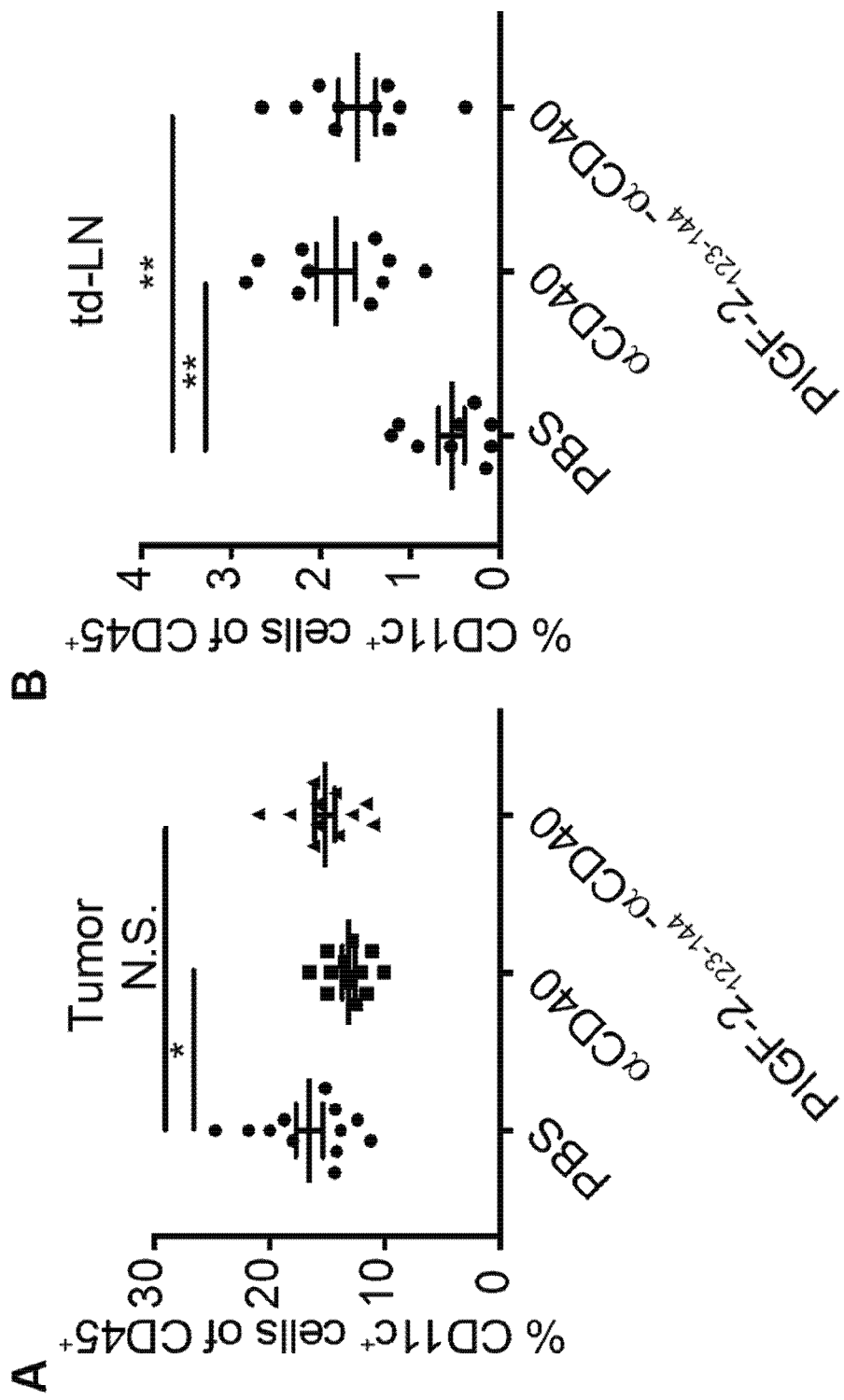
FIG. 38A-B

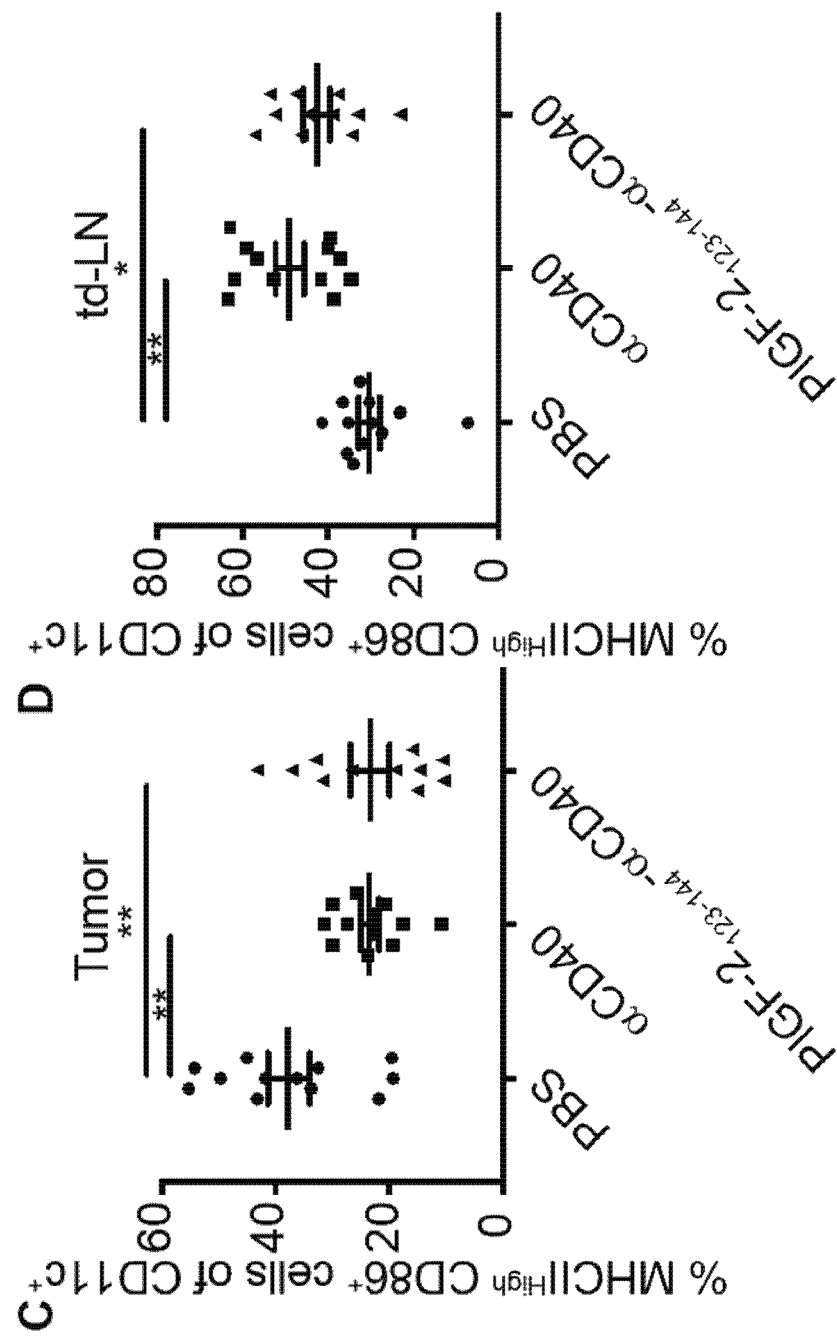
FIG. 38C-D

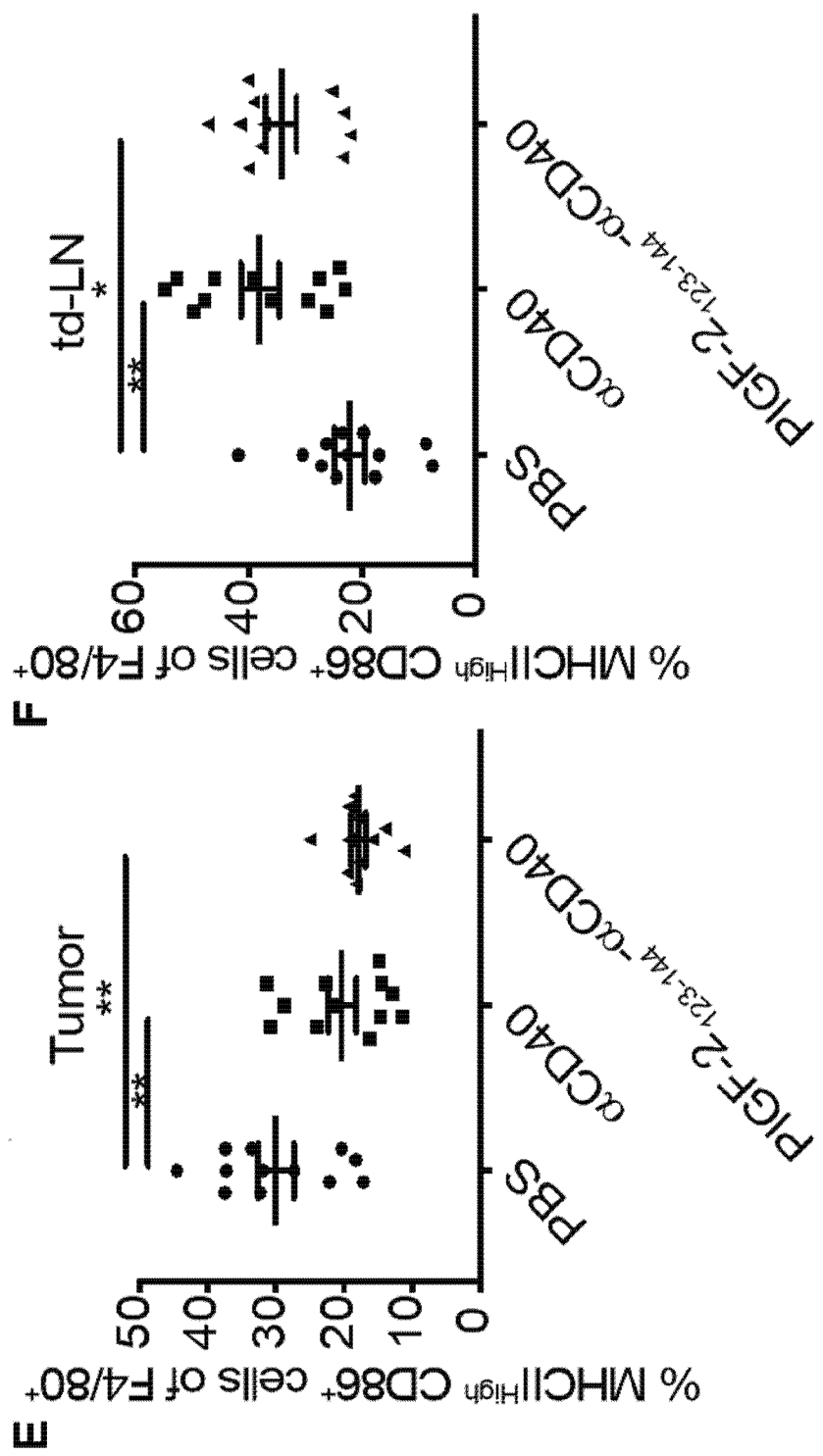
FIG. 38E-F

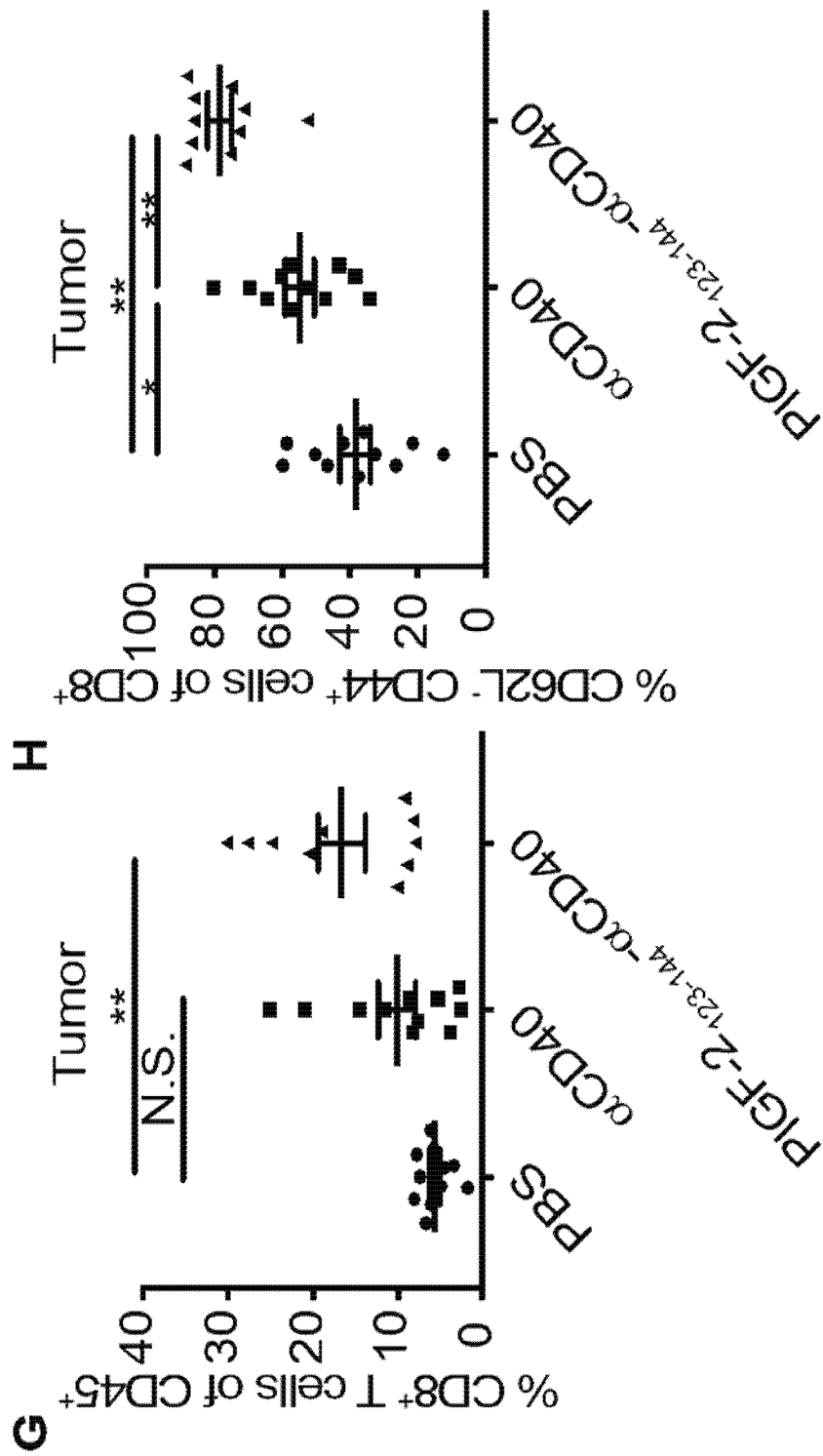
FIG. 38G-H

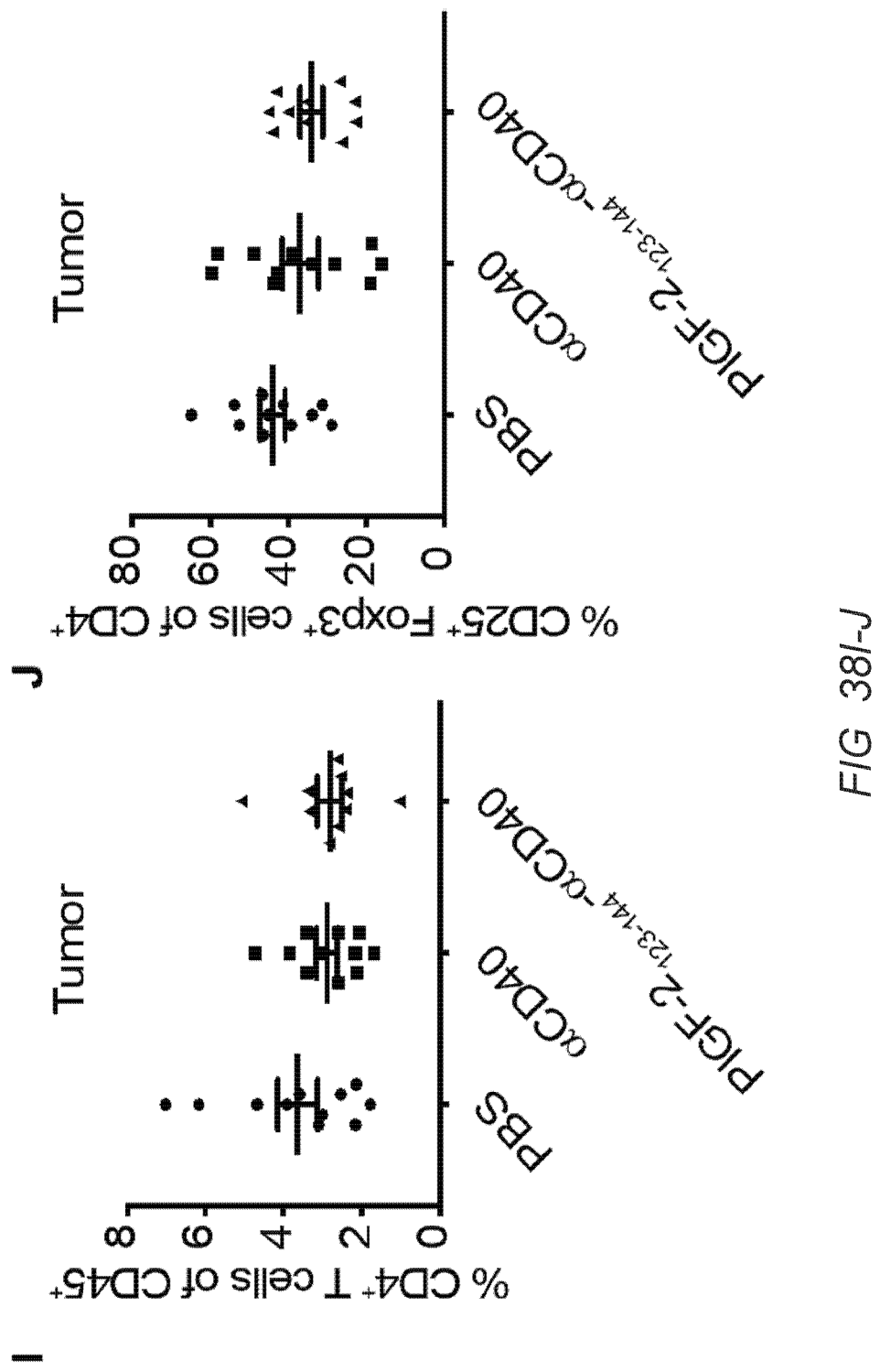
FIG 38I-J

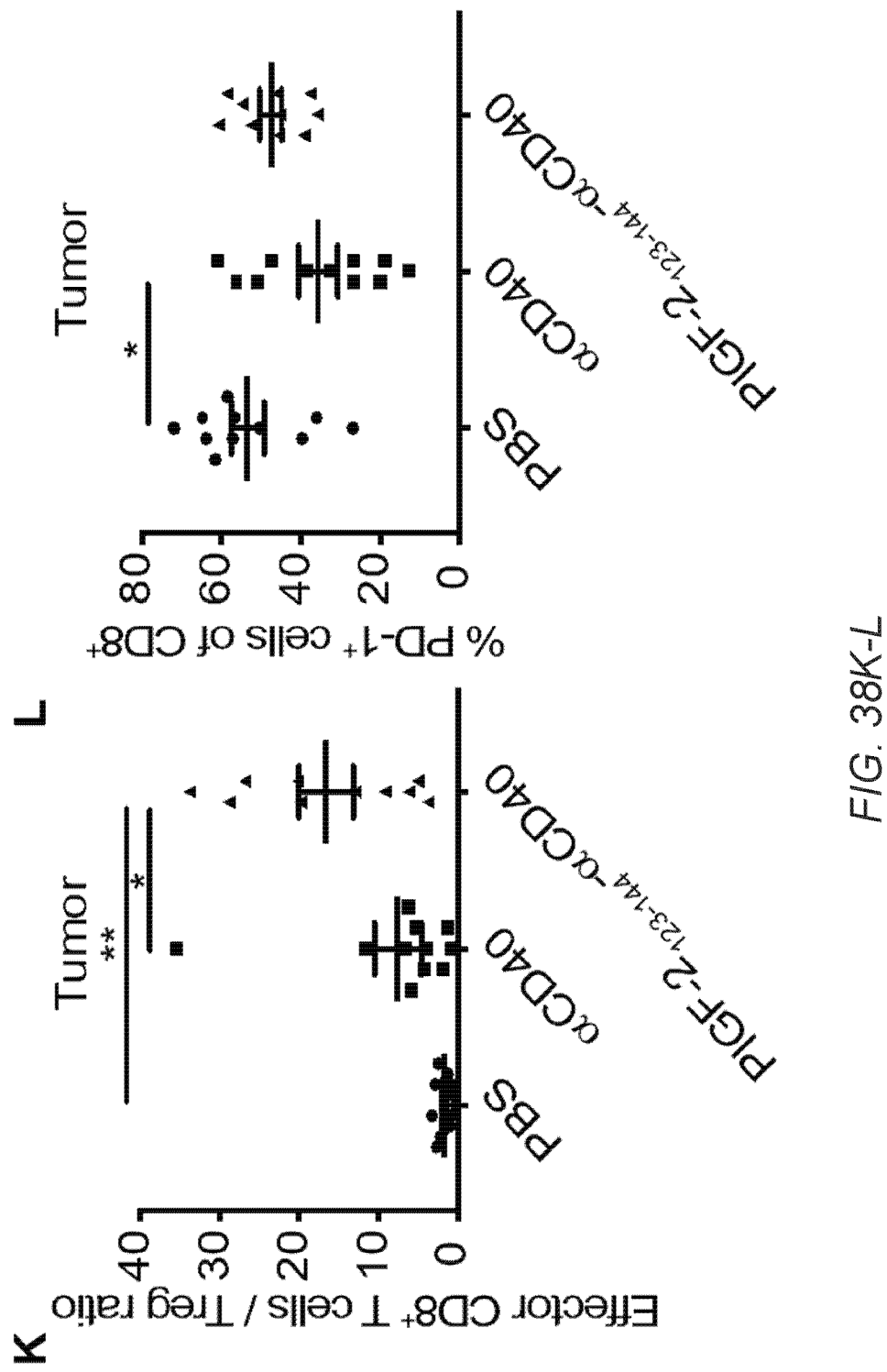
FIG. 38K-L

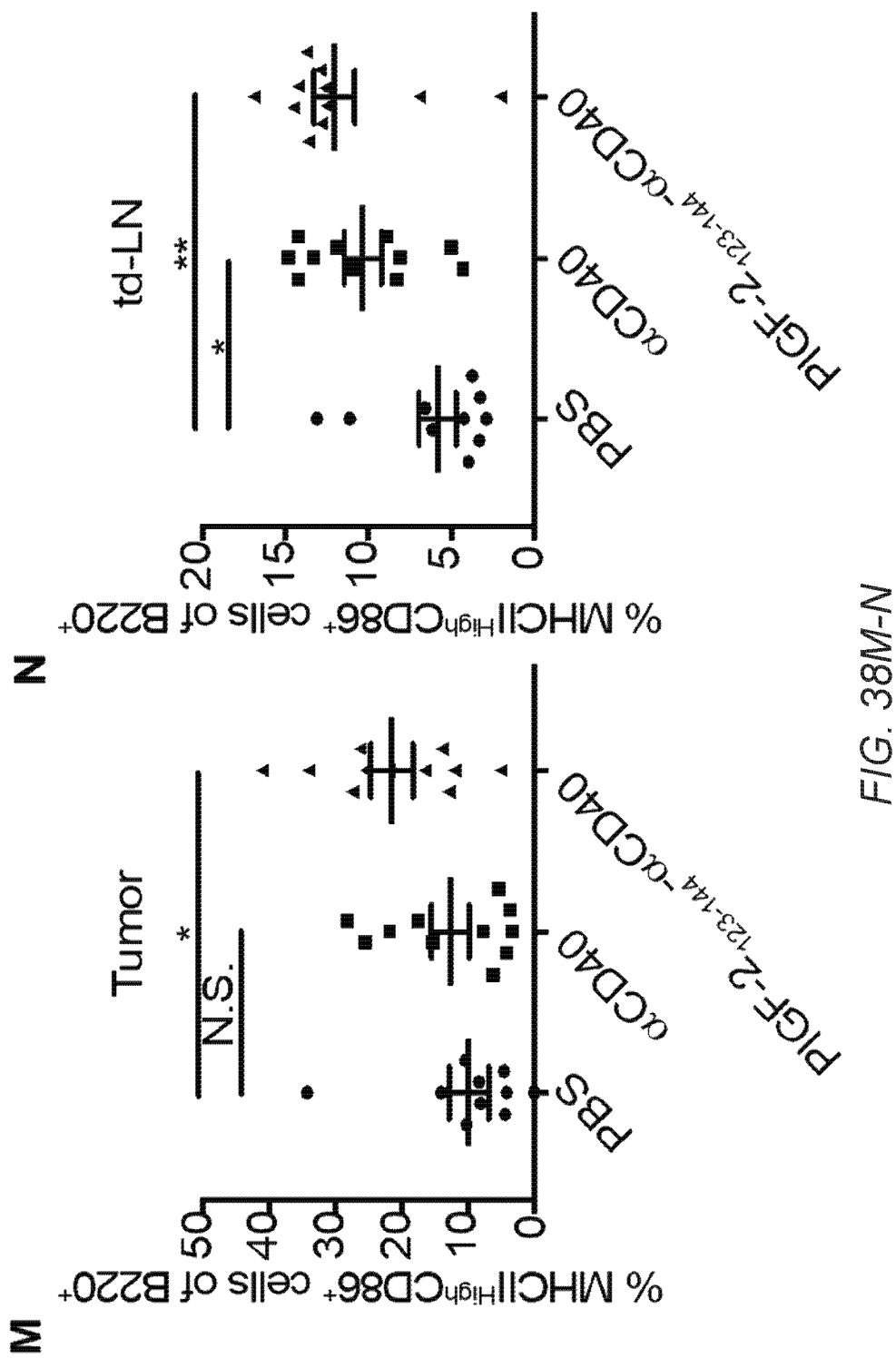
FIG. 38M-N

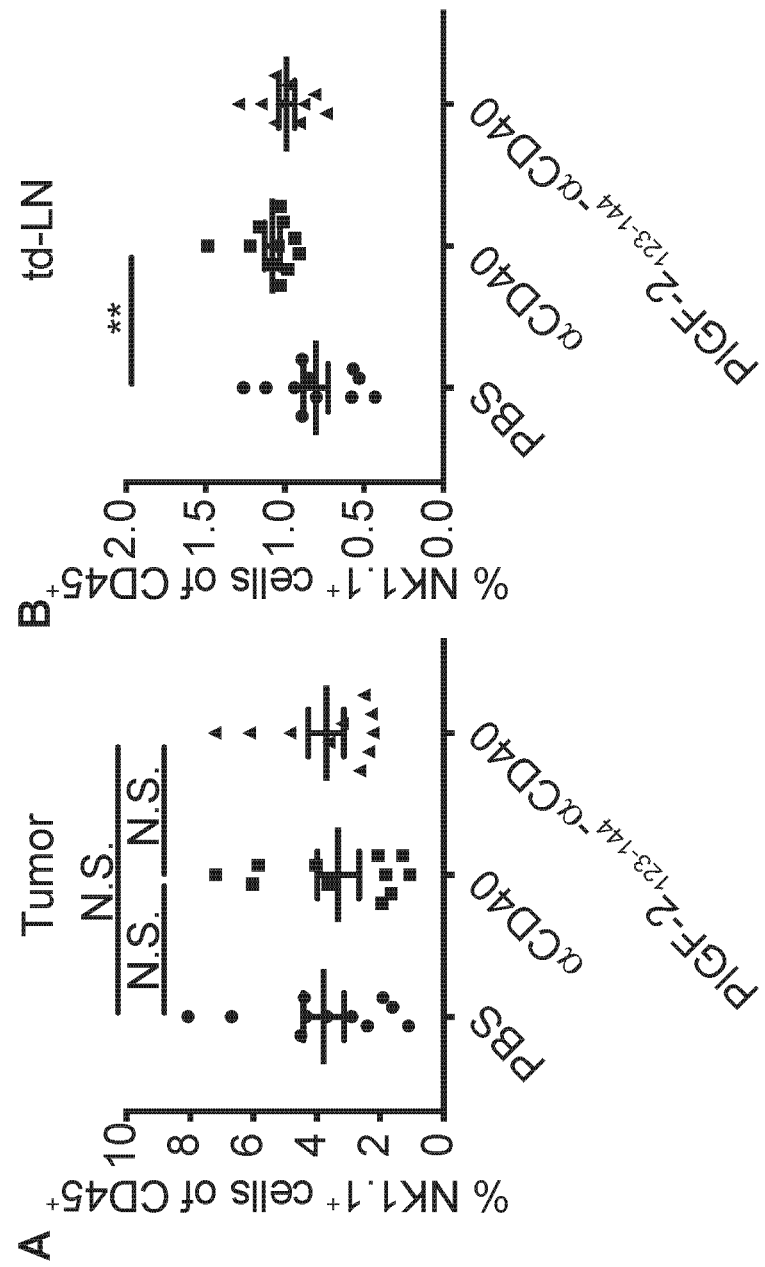
FIG. 39A-B

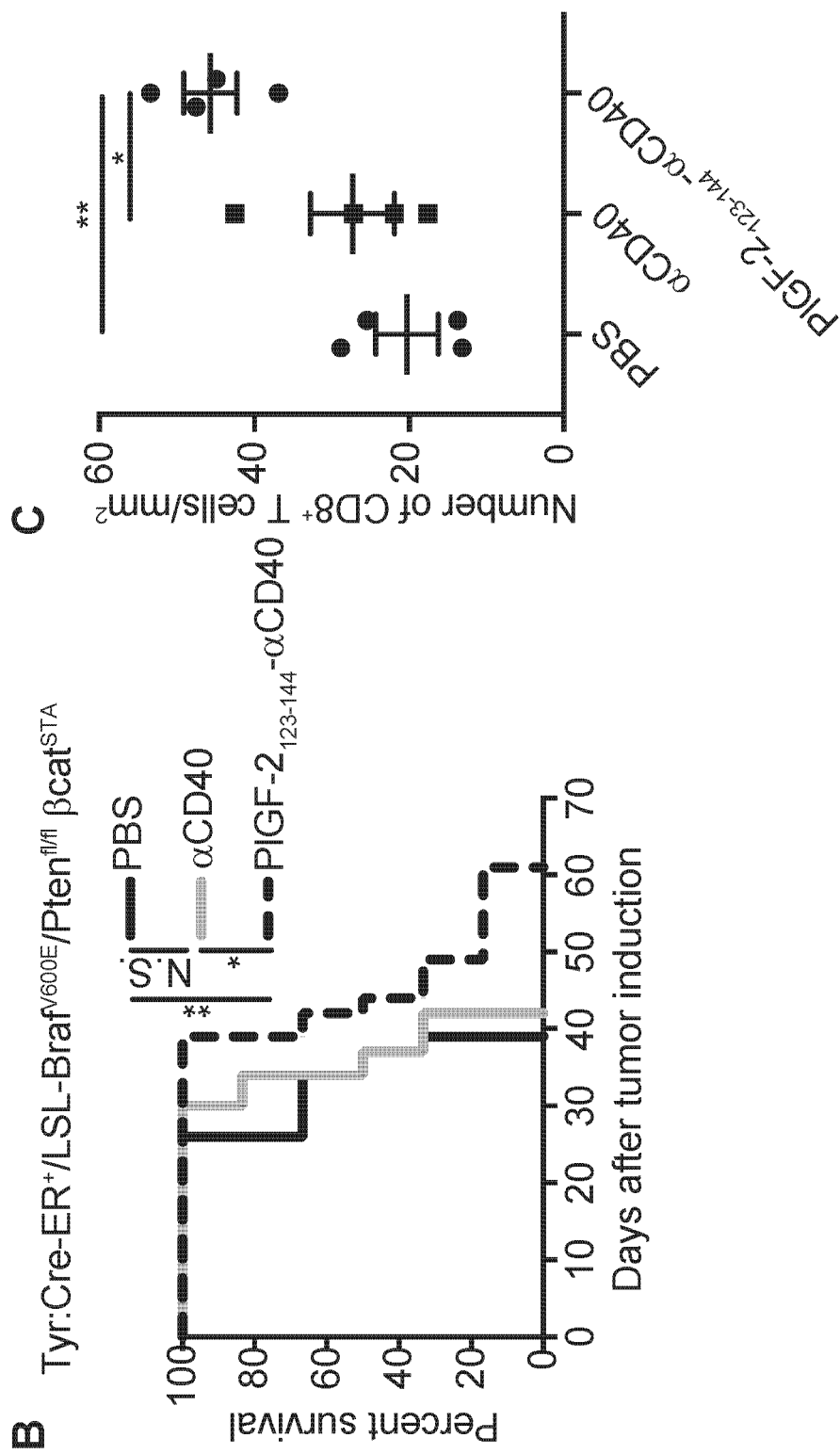
FIG. 41B-C

SEQUENCE LISTING

<160> NUMBER OF SEQ ID NOS: 16

<210> SEQ ID NO 1
<211> LENGTH: 22
<212> TYPE: PRT
<213> ORGANISM: Artificial Sequence
<220> FEATURE:
<223> OTHER INFORMATION: PlGF-2 ECM affinity peptide

<400> SEQUENCE: 1

Arg Arg Arg Pro Lys Gly Arg Gly Lys Arg Arg Arg Glu Lys Gln Arg
1               5                   10                  15

Pro Thr Asp Cys His Leu
            20

<210> SEQ ID NO 2
<211> LENGTH: 30
<212> TYPE: PRT
<213> ORGANISM: Artificial Sequence
<220> FEATURE:
<223> OTHER INFORMATION: ECM-affinity peptide from CXCL-12

<400> SEQUENCE: 2

Gly Arg Arg Glu Glu Lys Val Gly Lys Lys Glu Lys Ile Gly Lys Lys
1               5                   10                  15

Lys Arg Gln Lys Lys Arg Lys Ala Ala Gln Lys Arg Lys Asn
            20                  25                  30

<210> SEQ ID NO 3
<211> LENGTH: 205
<212> TYPE: PRT
<213> ORGANISM: Artificial Sequence
<220> FEATURE:
<223> OTHER INFORMATION: ECM affinity peptide is from the VWF A3 domain

<400> SEQUENCE: 3

Cys Ser Gly Glu Gly Leu Gln Ile Pro Thr Leu Ser Pro Ala Pro Asp
1               5                   10                  15

Cys Ser Gln Pro Leu Asp Val Ile Leu Leu Leu Asp Gly Ser Ser Ser
            20                  25                  30

Phe Pro Ala Ser Tyr Phe Asp Glu Met Lys Ser Phe Ala Lys Ala Phe
        35                  40                  45

Ile Ser Lys Ala Asn Ile Gly Pro Arg Leu Thr Gln Val Ser Val Leu
    50                  55                  60

Gln Tyr Gly Ser Ile Thr Thr Ile Asp Val Pro Trp Asn Val Val Pro
65                  70                  75                  80

Glu Lys Ala His Leu Leu Ser Leu Val Asp Val Met Gln Arg Glu Gly
                85                  90                  95

Gly Pro Ser Gln Ile Gly Asp Ala Leu Gly Phe Ala Val Arg Tyr Leu
            100                 105                 110

Thr Ser Glu Met His Gly Ala Arg Pro Gly Ala Ser Lys Ala Val Val
        115                 120                 125

Ile Leu Val Thr Asp Val Ser Val Asp Ser Val Asp Ala Ala Ala Asp
    130                 135                 140

Ala Ala Arg Ser Asn Arg Val Thr Val Phe Pro Ile Gly Ile Gly Asp
145                 150                 155                 160

Arg Tyr Asp Ala Ala Gln Leu Arg Ile Leu Ala Gly Pro Ala Gly Asp
                165                 170                 175

Ser Asn Val Val Lys Leu Gln Arg Ile Glu Asp Leu Pro Thr Met Val
            180                 185                 190

```
Thr Leu Gly Asn Ser Phe Leu His Lys Leu Cys Ser Gly
        195                 200                 205

<210> SEQ ID NO 4
<211> LENGTH: 170
<212> TYPE: PRT
<213> ORGANISM: Artificial Sequence
<220> FEATURE:
<223> OTHER INFORMATION: PlFG-2 peptide

<400> SEQUENCE: 4

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Arg Arg Pro
    130                 135                 140

Lys Gly Arg Gly Lys Arg Arg Glu Lys Gln Arg Pro Thr Asp Cys
145                 150                 155                 160

His Leu Cys Gly Asp Ala Val Pro Arg Arg
                165                 170

<210> SEQ ID NO 5
<211> LENGTH: 30
<212> TYPE: PRT
<213> ORGANISM: Artificial Sequence
<220> FEATURE:
<223> OTHER INFORMATION: PlGF-2 ECM affinity peptide

<400> SEQUENCE: 5

Arg Arg Arg Pro Lys Gly Arg Gly Lys Arg Arg Glu Lys Gln Arg
1               5                   10                  15

Pro Thr Asp Cys His Leu Cys Gly Asp Ala Val Pro Arg Arg
            20                  25                  30

<210> SEQ ID NO 6
<211> LENGTH: 18
<212> TYPE: PRT
<213> ORGANISM: Artificial Sequence
<220> FEATURE:
<223> OTHER INFORMATION: PlGF-2 ECM affinity peptide

<400> SEQUENCE: 6

Arg Arg Pro Lys Gly Arg Gly Lys Arg Arg Glu Lys Gln Arg Pro
1               5                   10                  15

Thr Asp
```

-continued

```
<210> SEQ ID NO 7
<211> LENGTH: 15
<212> TYPE: PRT
<213> ORGANISM: Artificial Sequence
<220> FEATURE:
<223> OTHER INFORMATION: ECM affinity peptide

<400> SEQUENCE: 7

Arg Arg Arg Pro Lys Gly Arg Gly Lys Arg Arg Arg Glu Lys Gln
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: ECM affinity peptide

<400> SEQUENCE: 8

Gly Lys Arg Arg Arg Glu Lys Gln
1               5

<210> SEQ ID NO 9
<211> LENGTH: 8
<212> TYPE: PRT
<213> ORGANISM: Artificial Sequence
<220> FEATURE:
<223> OTHER INFORMATION: ECM affinity peptide

<400> SEQUENCE: 9

Arg Arg Arg Pro Lys Gly Arg Gly
1               5

<210> SEQ ID NO 10
<211> LENGTH: 21
<212> TYPE: PRT
<213> ORGANISM: Artificial Sequence
<220> FEATURE:
<223> OTHER INFORMATION: ECM affinity peptide

<400> SEQUENCE: 10

Arg Arg Lys Thr Lys Gly Lys Arg Lys Arg Ser Arg Asn Ser Gln Thr
1               5                   10                  15

Glu Glu Pro His Pro
            20

<210> SEQ ID NO 11
<211> LENGTH: 222
<212> TYPE: PRT
<213> ORGANISM: Artificial Sequence
<220> FEATURE:
<223> OTHER INFORMATION: ECM affinity peptide from the VWF A1 domain

<400> SEQUENCE: 11

Cys Gln Glu Pro Gly Gly Leu Val Val Pro Thr Asp Ala Pro Val
1               5                   10                  15

Ser Pro Thr Thr Leu Tyr Val Glu Asp Ile Ser Glu Pro Pro Leu His
            20                  25                  30

Asp Phe Tyr Cys Ser Arg Leu Leu Asp Leu Val Phe Leu Leu Asp Gly
        35                  40                  45

Ser Ser Arg Leu Ser Glu Ala Glu Phe Glu Val Leu Lys Ala Phe Val
    50                  55                  60

Val Asp Met Met Glu Arg Leu Arg Ile Ser Gln Lys Trp Val Arg Val
65                  70                  75                  80
```

-continued

Ala Val Val Glu Tyr His Asp Gly Ser His Ala Tyr Ile Gly Leu Lys
                85                  90                  95

Asp Arg Lys Arg Pro Ser Glu Leu Arg Arg Ile Ala Ser Gln Val Lys
            100                 105                 110

Tyr Ala Gly Ser Gln Val Ala Ser Thr Ser Glu Val Leu Lys Tyr Thr
        115                 120                 125

Leu Phe Gln Ile Phe Ser Lys Ile Asp Arg Pro Glu Ala Ser Arg Ile
    130                 135                 140

Thr Leu Leu Leu Met Ala Ser Gln Glu Pro Gln Arg Met Ser Arg Asn
145                 150                 155                 160

Phe Val Arg Tyr Val Gln Gly Leu Lys Lys Lys Val Ile Val
                165                 170                 175

Pro Val Gly Ile Gly Pro His Ala Asn Leu Lys Gln Ile Arg Leu Ile
            180                 185                 190

Glu Lys Gln Ala Pro Glu Asn Lys Ala Phe Val Leu Ser Ser Val Asp
        195                 200                 205

Glu Leu Glu Gln Gln Arg Asp Glu Ile Val Ser Tyr Leu Cys
    210                 215                 220

<210> SEQ ID NO 12
<211> LENGTH: 98
<212> TYPE: PRT
<213> ORGANISM: Artificial Sequence
<220> FEATURE:
<223> OTHER INFORMATION: ECM affinity peptide from CXCL-12

<400> SEQUENCE: 12

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Gly Arg Arg Glu Glu Lys Val Gly Lys Lys Glu Lys
65                  70                  75                  80

Ile Gly Lys Lys Lys Arg Gln Lys Lys Arg Lys Ala Ala Gln Lys Arg
                85                  90                  95

Lys Asn

<210> SEQ ID NO 13
<211> LENGTH: 2813
<212> TYPE: PRT
<213> ORGANISM: Artificial Sequence
<220> FEATURE:
<223> OTHER INFORMATION: ECM affinity peptide from human von Willebrand
      factor

<400> SEQUENCE: 13

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

```
Cys Gln Lys Arg Ser Phe Ser Ile Ile Gly Asp Phe Gln Asn Gly Lys
 65                  70                  75                  80

Arg Val Ser Leu Ser Val Tyr Leu Gly Glu Phe Phe Asp Ile His Leu
                 85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
            130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
            290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
            370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Val Gln Leu Pro Leu Leu Lys Gly Asp Leu
465                 470                 475                 480
```

```
Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
            690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
            770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
```

-continued

```
                900             905             910
Gly Cys Ser His Pro Ser Val Lys Cys Lys Arg Val Thr Ile Leu
            915             920             925
Val Glu Gly Gly Glu Ile Glu Leu Phe Asp Gly Val Asn Val Lys
            930             935             940
Arg Pro Met Lys Asp Glu Thr His Phe Glu Val Glu Ser Gly Arg
945             950             955             960
Tyr Ile Ile Leu Leu Leu Gly Lys Ala Leu Ser Val Val Trp Asp Arg
            965             970             975
His Leu Ser Ile Ser Val Val Leu Lys Gln Thr Tyr Gln Glu Lys Val
            980             985             990
Cys Gly Leu Cys Gly Asn Phe Asp Gly Ile Gln Asn Asn Asp Leu Thr
            995            1000            1005
Ser Ser Asn Leu Gln Val Glu Asp Pro Val Asp Phe Gly Asn
            1010            1015            1020
Ser Trp Lys Val Ser Ser Gln Cys Ala Asp Thr Arg Lys Val Pro
            1025            1030            1035
Leu Asp Ser Ser Pro Ala Thr Cys His Asn Asn Ile Met Lys Gln
            1040            1045            1050
Thr Met Val Asp Ser Ser Cys Arg Ile Leu Thr Ser Asp Val Phe
            1055            1060            1065
Gln Asp Cys Asn Lys Leu Val Asp Pro Glu Pro Tyr Leu Asp Val
            1070            1075            1080
Cys Ile Tyr Asp Thr Cys Ser Cys Glu Ser Ile Gly Asp Cys Ala
            1085            1090            1095
Cys Phe Cys Asp Thr Ile Ala Ala Tyr Ala His Val Cys Ala Gln
            1100            1105            1110
His Gly Lys Val Val Thr Trp Arg Thr Ala Thr Leu Cys Pro Gln
            1115            1120            1125
Ser Cys Glu Glu Arg Asn Leu Arg Glu Asn Gly Tyr Glu Cys Glu
            1130            1135            1140
Trp Arg Tyr Asn Ser Cys Ala Pro Ala Cys Gln Val Thr Cys Gln
            1145            1150            1155
His Pro Glu Pro Leu Ala Cys Pro Val Gln Cys Val Glu Gly Cys
            1160            1165            1170
His Ala His Cys Pro Pro Gly Lys Ile Leu Asp Glu Leu Leu Gln
            1175            1180            1185
Thr Cys Val Asp Pro Glu Asp Cys Pro Val Cys Glu Val Ala Gly
            1190            1195            1200
Arg Arg Phe Ala Ser Gly Lys Lys Val Thr Leu Asn Pro Ser Asp
            1205            1210            1215
Pro Glu His Cys Gln Ile Cys His Cys Asp Val Val Asn Leu Thr
            1220            1225            1230
Cys Glu Ala Cys Gln Glu Pro Gly Gly Leu Val Val Pro Pro Thr
            1235            1240            1245
Asp Ala Pro Val Ser Pro Thr Thr Leu Tyr Val Glu Asp Ile Ser
            1250            1255            1260
Glu Pro Pro Leu His Asp Phe Tyr Cys Ser Arg Leu Leu Asp Leu
            1265            1270            1275
Val Phe Leu Leu Asp Gly Ser Ser Arg Leu Ser Glu Ala Glu Phe
            1280            1285            1290
Glu Val Leu Lys Ala Phe Val Val Asp Met Met Glu Arg Leu Arg
            1295            1300            1305
```

```
Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695
```

```
Ser Ser Ser Phe Pro Ala Ser     Tyr Phe Asp Glu Met     Lys Ser Phe
    1700            1705                    1710

Ala Lys Ala Phe Ile Ser Lys     Ala Asn Ile Gly Pro     Arg Leu Thr
    1715            1720                    1725

Gln Val Ser Val Leu Gln Tyr     Gly Ser Ile Thr Thr     Ile Asp Val
    1730            1735                    1740

Pro Trp Asn Val Val Pro Glu     Lys Ala His Leu Leu     Ser Leu Val
    1745            1750                    1755

Asp Val Met Gln Arg Glu Gly     Gly Pro Ser Gln Ile     Gly Asp Ala
    1760            1765                    1770

Leu Gly Phe Ala Val Arg Tyr     Leu Thr Ser Glu Met     His Gly Ala
    1775            1780                    1785

Arg Pro Gly Ala Ser Lys Ala     Val Val Ile Leu Val     Thr Asp Val
    1790            1795                    1800

Ser Val Asp Ser Val Asp Ala     Ala Asp Ala Ala Arg     Ser Asn
    1805            1810                    1815

Arg Val Thr Val Phe Pro Ile     Gly Ile Gly Asp Arg     Tyr Asp Ala
    1820            1825                    1830

Ala Gln Leu Arg Ile Leu Ala     Gly Pro Ala Gly Asp     Ser Asn Val
    1835            1840                    1845

Val Lys Leu Gln Arg Ile Glu     Asp Leu Pro Thr Met     Val Thr Leu
    1850            1855                    1860

Gly Asn Ser Phe Leu His Lys     Leu Cys Ser Gly Phe     Val Arg Ile
    1865            1870                    1875

Cys Met Asp Glu Asp Gly Asn     Glu Lys Arg Pro Gly     Asp Val Trp
    1880            1885                    1890

Thr Leu Pro Asp Gln Cys His     Thr Val Thr Cys Gln     Pro Asp Gly
    1895            1900                    1905

Gln Thr Leu Leu Lys Ser His     Arg Val Asn Cys Asp     Arg Gly Leu
    1910            1915                    1920

Arg Pro Ser Cys Pro Asn Ser     Gln Ser Pro Val Lys     Val Glu Glu
    1925            1930                    1935

Thr Cys Gly Cys Arg Trp Thr     Cys Pro Cys Val Cys     Thr Gly Ser
    1940            1945                    1950

Ser Thr Arg His Ile Val Thr     Phe Asp Gly Gln Asn     Phe Lys Leu
    1955            1960                    1965

Thr Gly Ser Cys Ser Tyr Val     Leu Phe Gln Asn Lys     Glu Gln Asp
    1970            1975                    1980

Leu Glu Val Ile Leu His Asn     Gly Ala Cys Ser Pro     Gly Ala Arg
    1985            1990                    1995

Gln Gly Cys Met Lys Ser Ile     Glu Val Lys His Ser     Ala Leu Ser
    2000            2005                    2010

Val Glu Leu His Ser Asp Met     Glu Val Thr Val Asn     Gly Arg Leu
    2015            2020                    2025

Val Ser Val Pro Tyr Val Gly     Gly Asn Met Glu Val     Asn Val Tyr
    2030            2035                    2040

Gly Ala Ile Met His Glu Val     Arg Phe Asn His Leu     Gly His Ile
    2045            2050                    2055

Phe Thr Phe Thr Pro Gln Asn     Asn Glu Phe Gln Leu     Gln Leu Ser
    2060            2065                    2070

Pro Lys Thr Phe Ala Ser Lys     Thr Tyr Gly Leu Cys     Gly Ile Cys
    2075            2080                    2085

Asp Glu Asn Gly Ala Asn Asp     Phe Met Leu Arg Asp     Gly Thr Val
```

```
                    2090                2095                2100
Thr Thr Asp Trp Lys Thr Leu Val Gln Glu Trp Thr Val Gln Arg
        2105                2110                2115
Pro Gly Gln Thr Cys Gln Pro Ile Leu Glu Glu Gln Cys Leu Val
        2120                2125                2130
Pro Asp Ser Ser His Cys Gln Val Leu Leu Leu Pro Leu Phe Ala
        2135                2140                2145
Glu Cys His Lys Val Leu Ala Pro Ala Thr Phe Tyr Ala Ile Cys
        2150                2155                2160
Gln Gln Asp Ser Cys His Gln Glu Gln Val Cys Glu Val Ile Ala
        2165                2170                2175
Ser Tyr Ala His Leu Cys Arg Thr Asn Gly Val Cys Val Asp Trp
        2180                2185                2190
Arg Thr Pro Asp Phe Cys Ala Met Ser Cys Pro Pro Ser Leu Val
        2195                2200                2205
Tyr Asn His Cys Glu His Gly Cys Pro Arg His Cys Asp Gly Asn
        2210                2215                2220
Val Ser Ser Cys Gly Asp His Pro Ser Glu Gly Cys Phe Cys Pro
        2225                2230                2235
Pro Asp Lys Val Met Leu Glu Gly Ser Cys Val Pro Glu Glu Ala
        2240                2245                2250
Cys Thr Gln Cys Ile Gly Glu Asp Gly Val Gln His Gln Phe Leu
        2255                2260                2265
Glu Ala Trp Val Pro Asp His Gln Pro Cys Gln Ile Cys Thr Cys
        2270                2275                2280
Leu Ser Gly Arg Lys Val Asn Cys Thr Thr Gln Pro Cys Pro Thr
        2285                2290                2295
Ala Lys Ala Pro Thr Cys Gly Leu Cys Glu Val Ala Arg Leu Arg
        2300                2305                2310
Gln Asn Ala Asp Gln Cys Cys Pro Glu Tyr Glu Cys Val Cys Asp
        2315                2320                2325
Pro Val Ser Cys Asp Leu Pro Pro Val Pro His Cys Glu Arg Gly
        2330                2335                2340
Leu Gln Pro Thr Leu Thr Asn Pro Gly Glu Cys Arg Pro Asn Phe
        2345                2350                2355
Thr Cys Ala Cys Arg Lys Glu Glu Cys Lys Arg Val Ser Pro Pro
        2360                2365                2370
Ser Cys Pro Pro His Arg Leu Pro Thr Leu Arg Lys Thr Gln Cys
        2375                2380                2385
Cys Asp Glu Tyr Glu Cys Ala Cys Asn Cys Val Asn Ser Thr Val
        2390                2395                2400
Ser Cys Pro Leu Gly Tyr Leu Ala Ser Thr Ala Thr Asn Asp Cys
        2405                2410                2415
Gly Cys Thr Thr Thr Thr Cys Leu Pro Asp Lys Val Cys Val His
        2420                2425                2430
Arg Ser Thr Ile Tyr Pro Val Gly Gln Phe Trp Glu Glu Gly Cys
        2435                2440                2445
Asp Val Cys Thr Cys Thr Asp Met Glu Asp Ala Val Met Gly Leu
        2450                2455                2460
Arg Val Ala Gln Cys Ser Gln Lys Pro Cys Glu Asp Ser Cys Arg
        2465                2470                2475
Ser Gly Phe Thr Tyr Val Leu His Glu Gly Glu Cys Cys Gly Arg
        2480                2485                2490
```

```
Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 14
<211> LENGTH: 196
<212> TYPE: PRT
<213> ORGANISM: Artificial Sequence
<220> FEATURE:
<223> OTHER INFORMATION: ECM affinity peptide from human von Willebrand
      factor comprising residues 1686-1881

<400> SEQUENCE: 14

Cys Ser Gln Pro Leu Asp Val Ile Leu Leu Leu Asp Gly Ser Ser Ser
```

```
            1               5                  10                 15
          Phe Pro Ala Ser Tyr Phe Asp Glu Met Lys Ser Phe Ala Lys Ala Phe
                          20                  25                  30

Ile Ser Lys Ala Asn Ile Gly Pro Arg Leu Thr Gln Val Ser Val Leu
                          35                  40                  45

Gln Tyr Gly Ser Ile Thr Thr Ile Asp Val Pro Trp Asn Val Val Pro
                          50                  55                  60

Glu Lys Ala His Leu Leu Ser Leu Val Asp Val Met Gln Arg Glu Gly
           65                 70                  75                  80

Gly Pro Ser Gln Ile Gly Asp Ala Leu Gly Phe Ala Val Arg Tyr Leu
                          85                  90                  95

Thr Ser Glu Met His Gly Ala Arg Pro Gly Ala Ser Lys Ala Val Val
                          100                 105                 110

Ile Leu Val Thr Asp Val Ser Val Asp Ser Val Asp Ala Ala Ala Asp
                          115                 120                 125

Ala Ala Arg Ser Asn Arg Val Thr Val Phe Pro Ile Gly Ile Gly Asp
                          130                 135                 140

Arg Tyr Asp Ala Ala Gln Leu Arg Ile Leu Ala Gly Pro Ala Gly Asp
          145                 150                 155                 160

Ser Asn Val Val Lys Leu Gln Arg Ile Glu Asp Leu Pro Thr Met Val
                          165                 170                 175

Thr Leu Gly Asn Ser Phe Leu His Lys Leu Cys Ser Gly Phe Val Arg
                          180                 185                 190

Ile Cys Thr Gly
                          195

<210> SEQ ID NO 15
<211> LENGTH: 202
<212> TYPE: PRT
<213> ORGANISM: Artificial Sequence
<220> FEATURE:
<223> OTHER INFORMATION: vonWillebrand A3 domain protein

<400> SEQUENCE: 15

Cys Ser Gln Pro Leu Asp Val Ile Leu Leu Leu Asp Gly Ser Ser Ser
           1               5                  10                  15

Phe Pro Ala Ser Tyr Phe Asp Glu Met Lys Ser Phe Ala Lys Ala Phe
                          20                  25                  30

Ile Ser Lys Ala Asn Ile Gly Pro Arg Leu Thr Gln Val Ser Val Leu
                          35                  40                  45

Gln Tyr Gly Ser Ile Thr Thr Ile Asp Val Pro Trp Asn Val Val Pro
                          50                  55                  60

Glu Lys Ala His Leu Leu Ser Leu Val Asp Val Met Gln Arg Glu Gly
           65                 70                  75                  80

Gly Pro Ser Gln Ile Gly Asp Ala Leu Gly Phe Ala Val Arg Tyr Leu
                          85                  90                  95

Thr Ser Glu Met His Gly Ala Arg Pro Gly Ala Ser Lys Ala Val Val
                          100                 105                 110

Ile Leu Val Thr Asp Val Ser Val Asp Ser Val Asp Ala Ala Ala Asp
                          115                 120                 125

Ala Ala Arg Ser Asn Arg Val Thr Val Phe Pro Ile Gly Ile Gly Asp
                          130                 135                 140

Arg Tyr Asp Ala Ala Gln Leu Arg Ile Leu Ala Gly Pro Ala Gly Asp
          145                 150                 155                 160

Ser Asn Val Val Lys Leu Gln Arg Ile Glu Asp Leu Pro Thr Met Val
```

```
                     165                 170                 175
Thr Leu Gly Asn Ser Phe Leu His Lys Leu Cys Ser Gly Phe Val Arg
            180                 185                 190

Ile Cys Thr Gly His His His His His His
        195                 200

<210> SEQ ID NO 16
<211> LENGTH: 343
<212> TYPE: PRT
<213> ORGANISM: Artificial Sequence
<220> FEATURE:
<223> OTHER INFORMATION: ECM affinity peptide from decorin

<400> SEQUENCE: 16

Gly Pro Phe Gln Gln Arg Gly Leu Phe Asp Phe Met Leu Glu Asp Glu
1               5                   10                  15

Ala Ser Gly Ile Gly Pro Glu Val Pro Asp Asp Arg Asp Phe Glu Pro
            20                  25                  30

Ser Leu Gly Pro Val Cys Pro Phe Arg Cys Gln Cys His Leu Arg Val
        35                  40                  45

Val Gln Cys Ser Asp Leu Gly Leu Asp Lys Val Pro Lys Asp Leu Pro
50                  55                  60

Pro Asp Thr Thr Leu Leu Asp Leu Gln Asn Asn Lys Ile Thr Glu Ile
65                  70                  75                  80

Lys Asp Gly Asp Phe Lys Asn Leu Lys Asn Leu His Ala Leu Ile Leu
                85                  90                  95

Val Asn Asn Lys Ile Ser Lys Val Ser Pro Gly Ala Phe Thr Pro Leu
            100                 105                 110

Val Lys Leu Glu Arg Leu Tyr Leu Ser Lys Asn Gln Leu Lys Glu Leu
        115                 120                 125

Pro Glu Lys Met Pro Lys Thr Leu Gln Glu Leu Arg Ala His Glu Asn
130                 135                 140

Glu Ile Thr Lys Val Arg Lys Val Thr Phe Asn Gly Leu Asn Gln Met
145                 150                 155                 160

Ile Val Ile Glu Leu Gly Thr Asn Pro Leu Lys Ser Ser Gly Ile Glu
                165                 170                 175

Asn Gly Ala Phe Gln Gly Met Lys Lys Leu Ser Tyr Ile Arg Ile Ala
            180                 185                 190

Asp Thr Asn Ile Thr Ser Ile Pro Gln Gly Leu Pro Pro Ser Leu Thr
        195                 200                 205

Glu Leu His Leu Asp Gly Asn Lys Ile Ser Arg Val Asp Ala Ala Ser
210                 215                 220

Leu Lys Gly Leu Asn Asn Leu Ala Lys Leu Gly Leu Ser Phe Asn Ser
225                 230                 235                 240

Ile Ser Ala Val Asp Asn Gly Ser Leu Ala Asn Thr Pro His Leu Arg
                245                 250                 255

Glu Leu His Leu Asp Asn Asn Lys Leu Thr Arg Val Pro Gly Gly Leu
            260                 265                 270

Ala Glu His Lys Tyr Ile Gln Val Val Tyr Leu His Asn Asn Asn Ile
        275                 280                 285

Ser Val Val Gly Ser Ser Asp Phe Cys Pro Pro Gly His Asn Thr Lys
290                 295                 300

Lys Ala Ser Tyr Ser Gly Val Ser Leu Phe Ser Asn Pro Val Gln Tyr
305                 310                 315                 320
```

```
Trp Glu Ile Gln Pro Ser Thr Phe Arg Cys Val Tyr Val Arg Ser Ala
            325                 330                 335
Ile Gln Leu Gly Asn Tyr Lys
            340
```

METHODS OF TREATING CANCER WITH PLACENTA GROWTH FACTOR PEPTIDE LINKED TO IMMUNOTHERAPEUTIC ANTIBODIES

CROSS-REFERENCE TO RELATED APPLICATIONS

This application is a national phase application under 35 U.S.C. § 371 of International Application No. PCT/US2018/028505 filed Apr. 20, 2018, which claims the benefit of priority of U.S. Provisional Patent Application No. 62/487,823 filed Apr. 20, 2017, all of which are hereby incorporated by reference in their entirety.

BACKGROUND

I. Field of the Invention

The invention generally relates to the field of medicine. More particularly, it concerns compositions and methods involving nucleotide constructs, proteins—including antibodies, and immunotherapy for treating cancers.

II. Background

Much like infectious agents, tumor cells express specific antigens that differentiate them from normal cells, and T cell infiltration within tumors is associated with overall survival (OS) in patients with different cancers. However, cancer cells evade immune responses through a variety of mechanisms, enabling malignant cells to grow and spread. In fact, patients with a compromised immune system may have an increased incidence of cancer and are more likely to develop malignant tumors. There is a dynamic relationship between a patient's immune system and tumor cells. Normally, the immune system is capable of eliminating tumor cells. However, the more compromised or suppressed a patient's immune system is, the more likely it is that tumor cells will use evasive techniques to avoid the immune system.

Although considerable progress has been made in understanding how cancer evade destructive immunity, measures to counteract tumor escape have not kept pace. Tumors exploit several immunological processes to evade immunity and therapeutics targeted at just one process of immune evasion may not be enough to offset cancer growth, especially aggressive cancer growth. There is a need in the art for therapies that target multiple aspects of immune evasion. For example, the immune system depends on multiple checkpoints or "immunological brakes" to avoid overactivation of the immune system on healthy cells. Tumor cells often take advantage of these checkpoints to escape detection by the immune system. Checkpoint inhibitors have been described in the art. However, many of these therapies come with side-effects that prohibit administration of a non-toxic effective amount. There is a need in the art for therapies that can deliver an effective amount of these compositions without toxicity.

SUMMARY OF INVENTION

The methods and compositions described herein address the need in the art by providing compositions and methods for a therapy with an antibody that is specifically targeted to and/or retained intra- or peri-tumorally, limiting systemic exposure and reducing side-effects. Accordingly, aspects of the disclosure relate to a composition comprising an immunotherapeutic antibody operatively linked to an extracellular matrix (ECM)-affinity peptide. An ECM-affinity peptide is one that has affinity for an extracellular matrix protein.

In one embodiment, the ECM-affinity peptide comprises a peptide from placenta growth factor-2 (PlGF-2). In one embodiment, the ECM-affinity peptide comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) contiguous amino acids of one of the ECM-affinity peptides disclosed herein, including SEQ ID NOS: 1-13. It is specifically contemplated that 1, 2, 3, 4, 5, 6, 7, 8, 9, 10, 11, 12, 13, 14, 15, 16, 17, 18, 19, or 20 contiguous amino acids (or any range derivable therein) from any of the ECM-affinity peptides disclosed herein may be excluded in the peptide in some embodiments. In one embodiment, the ECM-affinity peptide comprises a peptide that has at least or at most 70, 72, 74, 76, 78, 80, 82, 84, 86, 88, 90, 92, 94, 96, 98, 99, or 100% identity (or any range derivable therein) to one of SEQ ID NOS:1-16 or to a peptide from within SEQ ID NOS:1-16. In some embodiments, the peptide is at least 85% identical to SEQ ID NO:1. In some embodiments, the peptide comprises or consists of SEQ ID NO:1. In some embodiments, the ECM-affinity peptide comprises a CXCL-12 peptide. In some embodiments, the CXCL-12 peptide comprises a CXCL-12γ peptide. In some embodiments, the peptide is at least 85% identical to SEQ ID NO:2 (CXCL-12-$\gamma_{69-98}$). In some embodiments, the ECM-affinity peptide comprises a decorin peptide. In some embodiments, the decorin peptide is at least 85% identical to SEQ ID NO:16 or comprises SEQ ID NO:16. In one embodiment, the ECM-affinity peptide comprises a von Willebrand factor (VWF) peptide. In some embodiments, the VWF peptide is a VWF A1 or A3 peptide. In some embodiments, the VWF peptide comprises a peptide that is at least 85% identical to SEQ ID NO:3, SEQ ID NO:11, SEQ ID NO:14, SEQ ID NO:15, or fragments thereof. In some embodiments, the VWF peptide comprises SEQ ID NO:3, SEQ ID NO:11, or SEQ ID NO:14, or is a fragment thereof.

In some embodiments, the peptide is covalently linked to the antibody. In some embodiments, the peptide is cross-linked to the antibody through a bifunctional linker. Linkers, such as amino acid or peptidimimetic sequences may be inserted between the peptide and/or antibody sequence. In an embodiment, a fynomer domain is joined to a Heavy (H) chain or Light (L) chain immediately after the last amino acid at the amino(NH$_2$)-terminus or the carboxy(C)-terminus of the Heavy (H) chain or the Light (L) chain. Linkers may have one or more properties that include a flexible conformation, an inability to form an ordered secondary structure or a hydrophobic or charged character which could promote or interact with either domain. Examples of amino acids typically found in flexible protein regions may include Gly, Asn and Ser. Other near neutral amino acids, such as Thr and Ala, may also be used in the linker sequence. The length of the linker sequence may vary without significantly affecting the function or activity of the fusion protein (see, e.g., U.S. Pat. No. 6,087,329). In a particular aspect, a peptide and an antibody heavy or light chain are joined by a peptide sequence having from about 1 to 25 amino acid residues. Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Examples of linkers further comprise a linear carbon chain, such as CN (where N=1-100 carbon atoms, e.g., C, CC, CCC, CCCC, CCCCC, CCCCCC, CCCCCCC, CCCCCCCC). In some embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In some embodiments, the linker is sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its sulfo-NHS ester is reactive toward primary amines (as found in lysine and the protein or peptide N-terminus). Further, the linker may be maleimidocaproyl (mc).

In some embodiments, the immunotherapeutic antibody comprises an immune checkpoint inhibitory antibody. In some embodiments, the checkpoint inhibitory antibody comprises an anti-CTLA4, PD-L1, PD-1, TIM3, ICOS, CD39, BTLA, KIR, LAG3, VISTA, LAG-3, TIGIT, or CD47 antibody. In some embodiments, the checkpoint inhibitory antibody comprises pembrolizumab, nivolumab, atezolizumab, ipilimumab, tremelimumab, avelumab, or durvalumab. In some embodiments, the immunotherapeutic antibody comprises a CD-40 agonistic antibody. In some embodiments, the immunotherapeutic antibody comprises a GITR, CD134, CD137, CD27, CD28, or CD122 agonistic antibody. In some embodiments, the immunotherapeutic antibody comprises an antibody described herein. In some embodiments, the antibody is a humanized antibody, a fully human antibody, a chimeric antibody, and/or a recombinant antibody.

In some embodiments, the ratio of peptide to antibody is about 1:1 to 10:1. In some embodiments, the ratio of peptide to antibody is at least, at most, or exactly about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 30:1, 35:1, 40:1, 45:1, 50:1, or 100:1 (or any derivable range therein).

In some embodiments, the composition further comprises a second immunotherapeutic antibody operatively linked to an extracellular matrix (ECM)-affinity peptide. In some embodiments, the composition comprises a CTLA4 antibody operatively linked to an ECM-affinity peptide and a PD-L1 antibody operatively linked to an ECM-affinity peptide. In some embodiments, the composition comprises a CTLA4 antibody operatively linked to an ECM-affinity peptide and a PD-1 antibody operatively linked to an ECM-affinity peptide. In some embodiments, the composition further comprises a third immunotherapeutic antibody operatively linked to an ECM-affinity peptide. In some embodiments, the composition comprises a GITR antibody operatively linked to an ECM-affinity peptide, a CD134 antibody operatively linked to an ECM-affinity peptide, and a CD137 antibody operatively linked to an ECM-affinity peptide.

Further aspects relate to a method for treating cancer in a subject comprising administering a composition of the disclosure to a subject. In some embodiments, the composition is administered systemically or by intra-tumoral, peri-tumoral, intraarterial, or transcatheter injection. In some embodiments, the PlGF-2 or CXCL-12γ peptides (i.e. SEQ ID NO: 1, 2, 4-10, or 12) described herein are administered intra-tumorally or peri-tumorally. In some embodiments, the VWF peptides described herein (i.e. SEQ ID NO: 3, 11, 13, 14, or 15) are administered systemically. The systemic administration may be parenteral or intravenous, for example. In some embodiments, the method for treating cancer comprises administering multiple compositions of the disclosure to a subject. In embodiments in which two or more immunotherapeutic antibodies operatively linked to ECM-affinity peptides are administered, the antibodies can be administered together as part of the same composition or separately as part of different compositions.

In some embodiments, the administered dose of the antibody operatively linked to the peptide is less than the minimum effective dose of the antibody administered without the peptide. In some embodiments, the administered dose of the antibody operatively linked to the peptide is at least 10% less than the minimum effective dose of the antibody administered without the peptide. In some embodiments, the administered dose of the antibody operatively linked to the peptide is at least 5, 10, 15, 20, 25, 30, 35, 40, 45, 50, 55, 60, 65, 70, 75, or 80% less (or any derivable range therein) than the minimum effective dose of the antibody administered without the peptide.

In some embodiments, the patient has been previously treated with a cancer immunotherapeutic. In some embodiments, the previous cancer therapeutic comprised a checkpoint inhibitory antibody. In some embodiments, the subject experienced grade two, three, or four side effects from the previous cancer therapeutic. In some embodiments, the subject has been diagnosed with a cancer. In some embodiments, the cancer comprises lung cancer, prostate cancer, ovarian cancer, testicular cancer, brain cancer, glioblastoma, pediatric tumors, germ cell tumors, melanoma, colon cancer, rectal cancer, gastric cancer, esophageal cancer, tracheal cancer, head and neck cancer, pancreatic cancer, liver cancer, breast cancer, cervical cancer, and vulvar cancer. In some embodiments, the cancer comprises melanoma or breast cancer. In some embodiments, the cancer is non-hemological. In some embodiments, the cancer comprises a solid tumor. In some embodiments, the cancer comprises distant metastasis. In some embodiments, the cancer is a metastatic cancer. In some embodiments, the metastatic cancer comprises at least a first tumor and a second tumor, either of which may be a metastasis of a primary tumor. In some embodiments, the second tumor is at a site that is remote from the first tumor. In some embodiments, the second tumor is in a different organ or a different body part than the first tumor or is at least 10, 20, 30, 40, 50, 60, 70, 80, 90, or 100 cm away from the first tumor. In some embodiments, administering the composition locally to the first tumor, such as by peri-tumoral or intra-tumoral injection, may effectively treat the second tumor, such as by reducing its size, halting its growth, or decreasing the rate of its growth, despite the immunotherapeutic antibody not making contact with the second tumor at all, or despite the concentration of the immunotherapeutic antibody in the vicinity of the second tumor being insufficient on its own to effectively treat the second tumor. Thus, in some embodiments, the composition is administered peri-tumorally or intra-tumorally to the first tumor and is not administered peri-tumorally or intra-tumorally to the second tumor or systemically. In some embodiments, the second tumor is effectively treated by the local administration to the first tumor.

In some embodiments, the method further comprises administration of an additional cancer therapy. In some embodiments, the additional cancer therapy comprises radiation, vaccination, chemotherapy, adoptive T-cell therapy, cytokine therapy, anti-CD47 antibodies, anti-GD2 antibodies, or immunologic adjuvants. In some embodiments, the additional cancer therapy comprises one or more of MUC-1 inhibitors, CD40 activators, IDO inhibitors, and OX86 agonists. In some embodiments, the additional cancer therapy comprises one or more of indoximod, GDC-0919, 1-methyl-D-tryptophan, norharmane hydrochloride, norharmane, CAY10581, INCB024360, and 2-benzyl-2-thiopseudourea hydrochloride. In some embodiments, the efficacy of the additional cancer therapy is increased relative to administering the additional cancer therapy without the composition. Administering the composition may make a tumor more susceptible to certain treatments than it would be without the composition, so an additional cancer therapy may be effective when used in combination with the composition even though it would be relatively ineffective when used alone.

In some embodiments, the method further comprises administration of a second immunotherapeutic antibody operatively linked to an extracellular matrix (ECM)-affinity peptide. In some embodiments, the method comprises administration of a CTLA4 antibody operatively linked to an ECM-affinity peptide and administration of a PD-L1 antibody operatively linked to an ECM-affinity peptide. In some embodiments, the method comprises administration of a CTLA4 antibody operatively linked to an ECM-affinity peptide and administration of a PD-1 antibody operatively linked to an ECM-affinity peptide. In some embodiments, administering the compositions disclosed herein induces system tumor immunity.

Further aspects relate to a method of treating cancer in a patient comprising administering a CD40 agonistic antibody operatively linked to an ECM-affinity peptide, wherein the patient has a cancer that is resistant to immune checkpoint therapy. Any of the ECM-affinity peptides or proteins disclosed herein may be used in combination with the CD40 agonistic antibody in this method. In addition, the features of the methods of treatment described above may be used with this method of treatment. In some embodiments, the patient has been diagnosed with a cancer known to be resistant to immune checkpoint therapy. In some embodiments, the patient has previously received an immune checkpoint therapy. In some embodiments, the cancer was resistant to the immune checkpoint therapy. In some embodiments, the patient was determined to be a poor responder to the immune checkpoint therapy.

Any embodiment disclosed herein can be implemented or combined with any other embodiment disclosed herein, including aspects of embodiments for compounds can be combined and/or substituted and any and all compounds can be implemented in the context of any method described herein. Similarly, aspects of any method embodiment can be combined and/or substituted with any other method embodiment disclosed herein. Moreover, any method disclosed herein may be recited in the form of "use of a composition" for achieving the method. It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

In some embodiments, there are methods that are provided. The method comprises administering any composition as disclosed herein.

The terms "protein", "polypeptide" and "peptide" are used interchangeably herein when referring to a gene product.

The terms "subject," "mammal," and "patient" are used interchangeably. In some embodiments, the subject is a mammal. In some embodiments, the subject is a human. In some embodiments, the subject is a mouse, rat, rabbit, dog, donkey, or a laboratory test animal such as fruit fly, zebrafish, etc.

In some embodiments, the patient has been previously treated for the cancer. In some embodiments, the subject was resistant to the previous cancer treatment. In some embodiments, the subject was determined to be a poor responder to the cancer treatment.

It is contemplated that the methods and compositions include exclusion of any of the embodiments described herein.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb. A composition "consisting essentially of" the recited elements excludes any further active ingredients but does not exclude pharmaceutical excipients, buffers, structural components, etc.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-F. PlGF-$2_{123\text{-}144}$ peptide-conjugated IgG (PlGF-$2_{123\text{-}144}$-IgG) binds promiscuously to ECM proteins with high affinity and is released by plasmin. (A) Schematic of conjugation of PlGF-$2_{123\text{-}144}$ peptide (PlGF-$2_{123\text{-}144}$) to IgG Ab, resulting in binding to ECM proteins. (B) PlGF-$2_{123\text{-}144}$- and wt-rat IgG2a were analyzed by SDS-PAGE under reducing conditions with coomassie blue staining. (C)

Figure 2H:
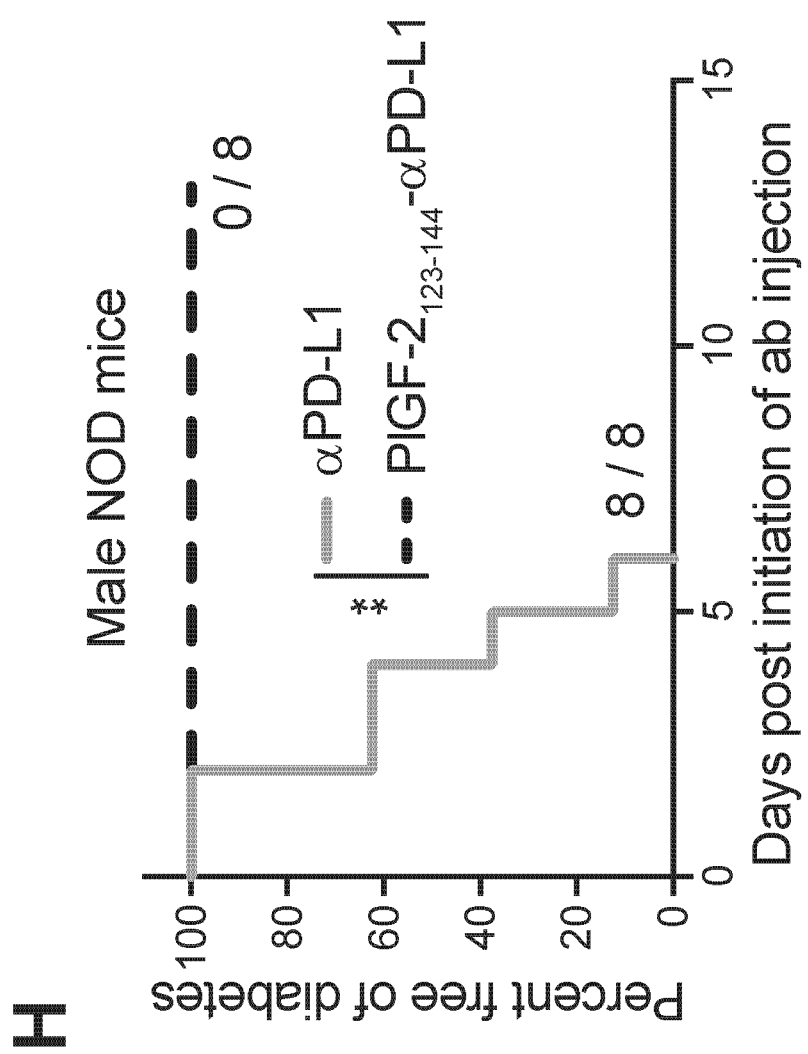

PlGF-2$_{123-144}$-αCTLA4 (clone UC10-4F10-11: 4F10) and (D) PlGF-2$_{123-144}$-αPD-L1 binding to ECM proteins, measured by ELISA. A450 nm represents absorbance at 450 nm. Bovine serum albumin (BSA) served as a negative control (n=6, mean±SD). (E) Affinities (Kd values are shown) of PlGF-2$_{123-144}$- and wt-, αCTLA4 (2 clones: 4F10 and 9H10) and αPD-L1 against fibronectin, collagen type I, rmCTLA4, and/or rmPD-L1 were measured by ELISA (n=4). N.D.=not determined because of low signals. (F) PlGF-2$_{123-144}$-rat IgG2a lost fibronectin and collagen I binding capacity after 0.1 U/mL plasmin cleavage, measured by ELISA (n=4, mean±SD). Statistical analyses were done using ANOVA with Tukey's test **p<0.01.

FIG. 2A-G. PlGF-2$_{123-144}$-conjugation reduces systemic exposure to Abs and potential treatment-related tissue damage. 5×10$^5$ B16F10 cells were inoculated on day 0. (A, B) PlGF-2$_{123-144}$-αCTLA4 and PlGF-2$_{123-144}$-αPD-L1 (100 μg each), αCTLA4 and αPD-L1 (100 μg each), or PBS was administered on day 4. PlGF-2$_{123-144}$-Abs and PBS were injected p.t., and wt Abs were injected either i.p. or p.t. Blood plasma was collected on day 5, 7, 9 and 11. Concentrations of (A) αCTLA4 and (B) αPD-L1 in blood plasma, determined by ELISA (n=8, mean±SEM). (C-G) PlGF-2$_{123-144}$- or wt-αCTLA4 and αPD-L1 (500 μg each/injection) were injected p.t. on day 4 and 7. On day 9, blood serum was collected and concentrations of (C) TNFα, (D) IFNγ, (E) IL2, (F) ALT levels in serum were measured (mean±SEM). (G) On day 8, the number of lymphocytes infiltration spots in liver tissue was counted and normalized with area (mean±SEM). Statistical analyses were done using ANOVA with Tukey's test. *p<0.05; **p<0.01.

FIG. 2H. 16 weeks old male NOD/ShiLtJ mice were given 100 μg of αPD-L1 on day 0 and 2. All Ab injections were intradermally at the back skin. Clinical diabetes was defined as a blood glucose reading of 250 mg/dL for three consecutive days. The number of mice that developed diabetes by the end of the experiment/total mice are described in the figure. Statistical analyses were done using Log-rank (Mantel-Cox) test. **p<0.01.

FIG. 3A-H. PlGF-2$_{123-144}$-αCTLA4+PlGF-2$_{123-144}$-αPD-L1 reduces B16F10 melanoma growth rate. (A, B) 1×10$^6$ B16F10-OVA cells or (C-H) 5×10$^5$ B16F10 cells were inoculated on day 0. PlGF-2$_{123-144}$-αCTLA4+PlGF-2$_{123-144}$-αPD-L1 (PlGF-2$_{123-144}$-Abs), αCTLA4+αPD-L1 (Abs), Abs+non-crosslinked PlGF-2$_{123-144}$ peptide, or PBS was administered on (A-F) day 4, 7, 10 or (G, H) 300 μg for day 4, 6 and 100 μg for 9, 12. Abs were injected either i.p. or p.t. Ab doses per administration are indicated on the figure. As αCTLA4 clones, 4F10 in (A-D) and 9H10 in (E-H) were used. Graphs depict (A, C, E, G) tumor volume until the first mouse died, and (B, D, F, H) survival rates. Tumor volumes are presented in mean±SEM. (A, B, C, D) n>6, (E, F) n>9, (G, H) n>5. Statistical analyses were done using ANOVA with Tukey's test for tumor size and Log-rank (Mantel-Cox) test for survival curves. *p<0.05; **p<0.01.

FIG. 4A-P. PlGF-2$_{123-144}$-αCTLA4+PlGF-2$_{123-144}$-αPD-L1 treatment evokes T cell activation resulting in increased B16F10 melanoma-infiltrating CD8$^+$ T cells. 5×10$^5$ B16F10 cells were inoculated on day 0. PlGF-2$_{123-144}$-αCTLA4+PlGF-2$_{123-144}$-αPD-L1 (PlGF-2$_{123-144}$-Abs), αCTLA4+αPD-L1 (Abs), or PBS was administered on day 4 and 7. Abs were injected at 100 μg each/injection either i.p. or p.t. Clone 9H10 was used as αCTLA4. Tumor and td-LN were taken on day 8, followed by FACS analysis. (A) Number and (B) frequency of CD8$^+$ CD3$^+$ tumor-infiltrating T cells. (C) The frequencies of CD62L$^+$ CD44$^+$ effector cells and (D) PD-1$^+$ cells of CD8$^+$ CD3$^+$ tumor-infiltrating T cells. (E) Number and (F) frequency of CD4$^+$ CD3$^+$ tumor-infiltrating T cells. (G) The frequencies of CD62L$^+$ CD44$^+$ effector cells and (H) Foxp3$^+$ CD25$^+$ Treg cells of CD4$^+$ CD3$^+$ tumor-infiltrating T cells. (I-L) T cells were extracted from tumor and stimulated with αCD28 and αCD3 for 6 h. Graphs depict the % of (I) Gzmb$^+$, (J) IL2$^+$, (K) TNFα$^+$, and (L) IFNγ$^+$ of CD8$^+$ CD3$^+$ T cells. (M-P) Graphs depict the % of (M) CD62L$^+$ CD44$^+$ effector cells of CD8$^+$ CD3$^+$ T cells, (N) Foxp3$^+$ CD25$^+$ Treg cells of CD4$^+$ CD3$^+$ T cells, (O) CD62L$^+$ CD44$^+$ memory, and (P) PD-1$^+$ cells of CD8$^+$ CD3$^+$ T cells in td-LN. Statistical analyses were done using ANOVA with Tukey's test *p<0.05; **p<0.01.

FIG. 5A-C. PlGF-2$_{123-144}$-αCTLA4+PlGF-2$_{123-144}$-αPD-L1 treatment induces systemic anti-tumor immunity. (A) Schedule of tumor inoculation and Ab administration throughout the experiment. 5×10$^5$ B16F10 cells were inoculated intradermally on day 0 in the left side of mouse back skin, and then repeated on day 2 in the right side. PlGF-2$_{123-144}$-αCTLA4+PlGF-2$_{123-144}$-αPD-L1 (PlGF-2$_{123-144}$-Abs), αCTLA4+αPD-L1 (Abs) or PBS was administered on day 4, 7, and 10. Abs were injected at 100 μg each/injection either i.p. or p.t. P.t. injections were performed only beside the left tumor, but not the right tumor. (B) Tumor volumes of 1$^{st}$ tumor on the left back and (C) 2$^{nd}$ tumor on the right back were measured (n=9, mean±SEM). Statistical analyses were done using ANOVA with Tukey's test **p<0.01.

FIG. 6A-D. PlGF-2$_{123-144}$-αCTLA4+PlGF-2$_{123-144}$-αPD-L1 exhibits anti-tumor activity in clinically relevant cancer models. (A) Tyr:Cre-ER$^+$/LSL-Braf$^{V600}$/Pten$^{fl/fl}$ mice received 50 μg of 4-OH-tamoxifen on their back skin to induce melanoma development. PlGF-2$_{123-144}$-αCTLA4+PlGF-2$_{123-144}$-αPD-L1 (PlGF-2$_{123-144}$-Abs), αCTLA4+αPD-L1 (Abs) or PBS were injected p.t. at day 0, 3 and 6 after tumors were visible. Abs were injected at 100 μg each/injection. (BC) MMTV-PyMT cells were obtained from spontaneously developed breast cancer in FVB-Tg (MMTV-PyVT) transgenic mice and cultured in vitro. 8×10$^5$ MMTV-PyMT cells were inoculated into the right mammary gland fat pad. After 7, 10, and 13 days, Abs were injected at 100 μg each/injection p.t. (D) 30 days after the first tumor inoculation, 8×10$^5$ MMTV-PyMT cells were again inoculated into the left mammary gland fat pad in PlGF-2$_{123-144}$-Abs treated tumor-free survivors or in naïve mice. Numbers indicate how many mice remain tumor-free among total mice at the end of the experiment. Graphs depict (A, B, D) tumor volume until the first mouse died, and (C) survival rates. αCTLA4 clone 9H10 was used. Tumor volumes are presented as mean±SEM. (A) n>6, (BC) n>12, (C) n>6. Statistical analyses were done using ANOVA with Tukey's test for tumor size and Log-rank (Mantel-Cox) test for survival curves. *p<0.05; **p<0.01.

FIG. 7A-C. MALDI-TOF MS analysis confirmed that molecular weights are increased by PlGF-2$_{123-144}$ conjugation to αCTLA4 (4F10) and αPD-L1. (A) wt 4F10, (B) PlGF-2$_{123-144}$-4F10, (C) αPD-L1 and (D) PlGF-2$_{123-144}$-αPD-L1. The X-axis is mass to charge ratio (m/z) and the Y-axis is % intensity of doubly charged ions. The average molecular weight shifts are calculated by comparison of PlGF-2$_{123-144}$-conjugated forms vs its wt forms.

FIG. 8A-B. Binding of (A) wt-αCTLA4 (4F10) and (B) αPD-L1 for ECM proteins, measured by ELISA. Absorbance 450 nm (A450 nm) were measured. Bovine serum albumin (BSA) served as a control (n=6, mean±SD).

FIG. 9A-F. Affinities of PlGF-2$_{123-144}$-αCTLA4 (two clones: (AB) 4F10 and (CD) 9H10) and (EF) PlGF-2$_{123-144}$-αPD-L1 for fibronectin and collagen I. The graphs show the binding curves obtained by ELISA (n=4, mean±SEM). The signals were fitted by non-linear regression to obtain the Kd using absorbance A450 nm=Bmax*[ECM protein]/(Kd+[ECM protein]). The Kd values are shown in FIG. 1E.

FIG. 10A-C. Affinities of PlGF-2$_{123-144}$- or wt-, αCTLA4 (two clones: (A) 4F10 and (B) 9H10) and (C) αPD-L1 for their antigens. The graphs show the binding curves obtained by ELISA (n=4, mean±SEM). The signals were fitted by non-linear regression to obtain the Kd using A450 nm=Bmax*[antigen]/(Kd+[antigen]). The Kd values are shown in FIG. 1E.

FIG. 11A-B. PlGF-2$_{123-144}$- and wt-αCTLA4 binds to T33.1 cell line, and PlGF-2$_{123-144}$- and wt-αPD-L1 binds to B16F10 cells with similar levels. (A) 1×10$^5$ T cell hybridoma (T33.1 cell) were incubated with PlGF-2$_{123-144}$- or wt-, αCTLA4. (B) 1×10$^5$ B16F10 cells were incubated with PlGF-2$_{123-144}$- or wt-, αPD-L1. Then, cells were stained with secondary antibodies. Bound antibodies were detected by flow cytometry. As αCTLA4, 4F10 was used. To avoid the influence of remaining ECM proteins on the cell surface, B16F10 cells were treated with 10 μM heparin for 30 min while incubating with PlGF-2$_{123-144}$- or wt-αPD-L1. Gray, Isotype control antibody. Black, αCTLA4 or αPD-L1.

Figure 12:
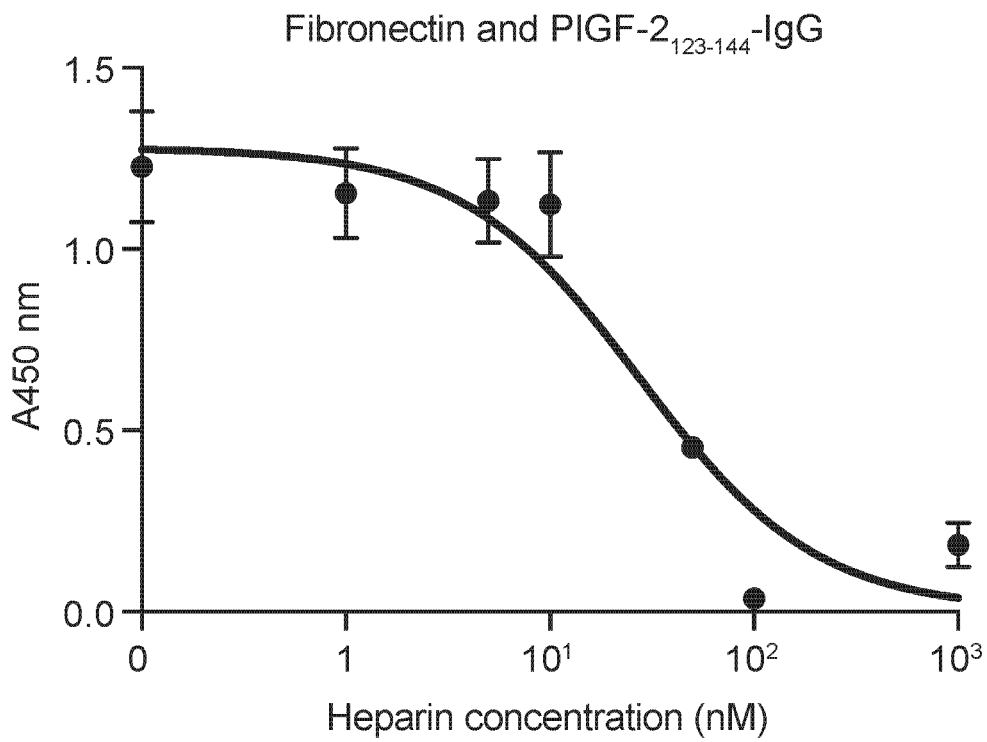

FIG. 12. Heparin inhibits fibronectin binding of PlGF-2$_{123-144}$-Abs. Affinities of PlGF-2$_{123-144}$-rat IgG2a for fibronectin in the presence of several concentrations of heparin. The graph shows the binding curves obtained by ELISA (n=4, mean±SEM).

Figure 13:
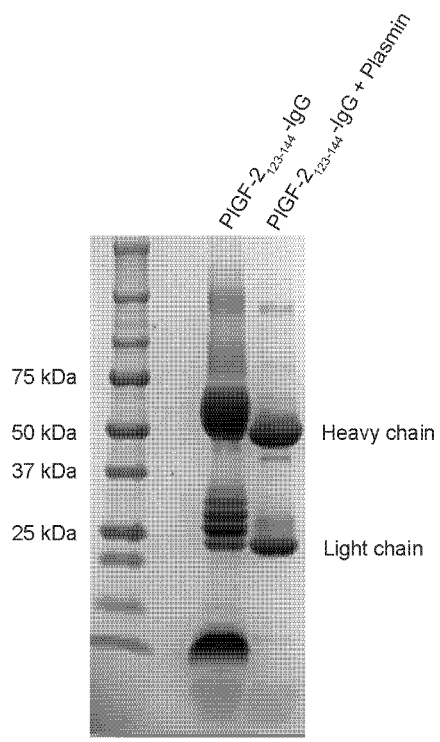

FIG. 13. Plasmin-cleaved PlGF-2$_{123-144}$ observed by SDS-PAGE gel. 10 μg/mL PlGF-2$_{123-144}$-rat IgG2a were incubated with 0.1 U/mL plasmin overnight at 37° C. The solution was subjected to SDS-PAGE under reducing conditions, and analyzed by coomassie blue staining.

Figure 14:
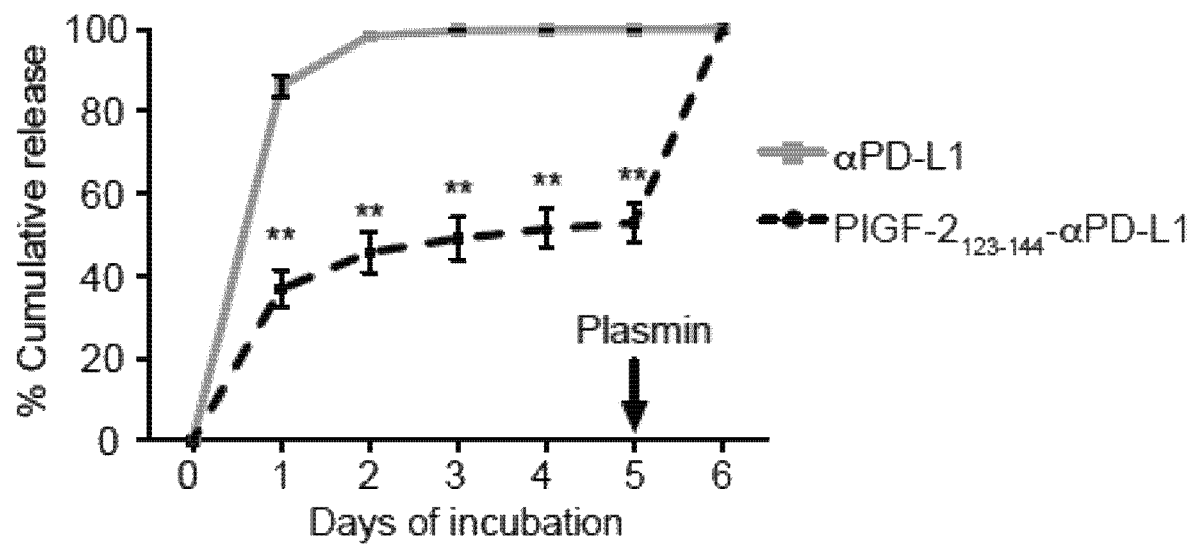

FIG. 14. PlGF-2$_{123-144}$-Abs are retained in the collagen tissue in vitro. Retention of PlGF-2$_{123-144}$- versus wt-αPD-L1 onto a polymerized collagen sheet. Collagen matrices were incubated in the presence of 10 μg/mL antibody for 3 h and further incubated in 2 mL of physiological buffer for 5 days. The buffer was changed every day, and antibody was released with 0.1 U/mL plasmin on day 5. αPD-L1 levels were quantified for each day by ELISA. (n=4, mean±SEM). Statistical analyses were done using ANOVA with Tukey's test **p<0.01.

Figure 15:
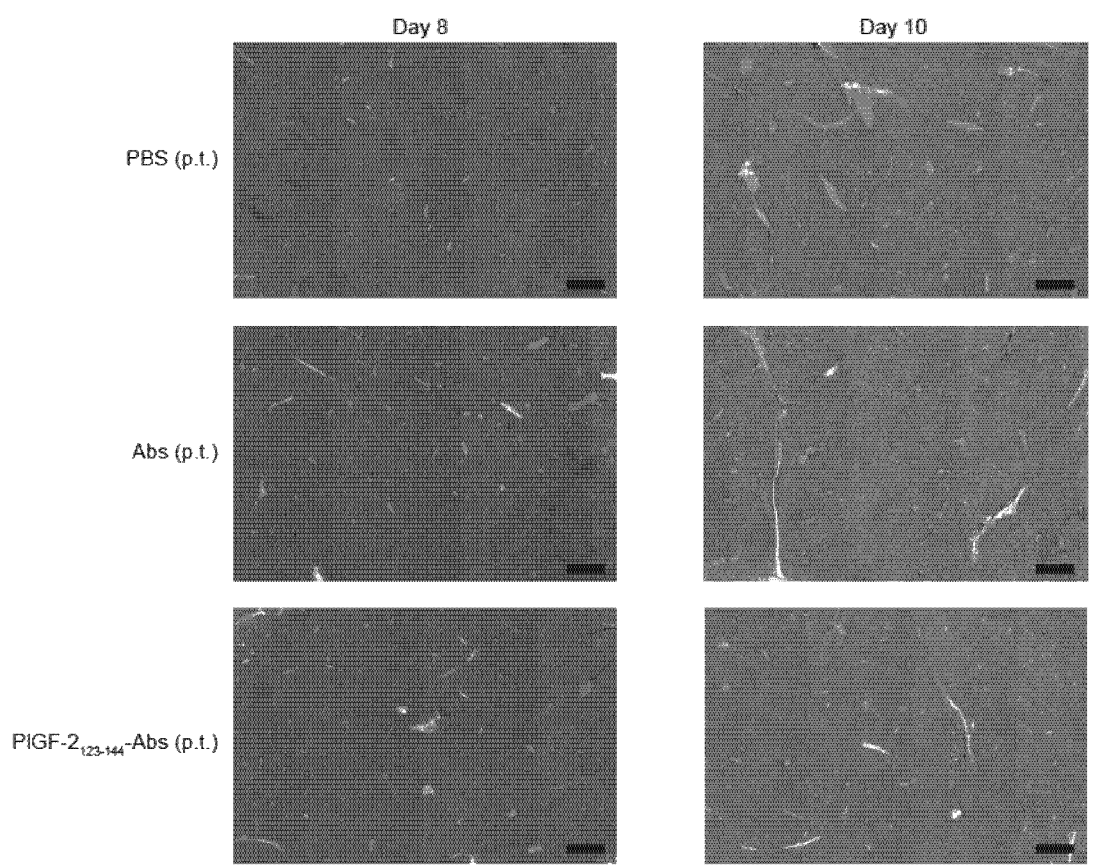

FIG. 15. PlGF-2$_{123-144}$-conjugation reduces liver damage induced by αCTLA4+αPD-L1 injection. 5×10$^5$ B16F10 cells were inoculated on day 0. PlGF-2$_{123-144}$-αCTLA4+ PlGF-2$_{123-144}$-αPD-L1, αCTLA4+αPD-L1 (500 μg each), or PBS was injected on day 4 and day 7. Histologic liver sections on day 8 and day 10. Scale bar=400 μm. Representative sections of groups of 5 mice.

Figure 16:
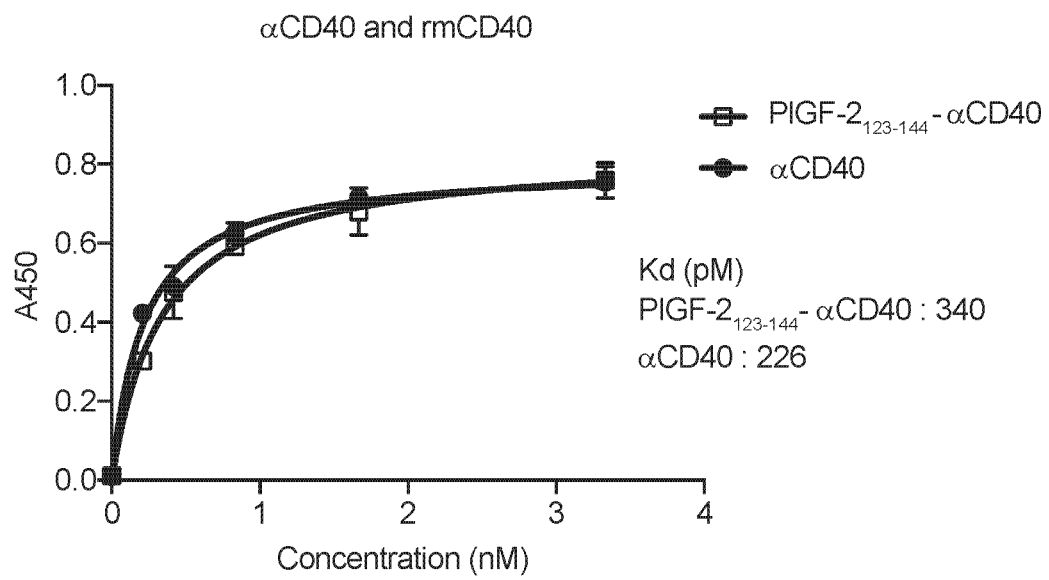

FIG. 16. Affinities of PlGF-2$_{123-144}$- or wt-, αCD40 for recombinant mouse CD40 protein. The graphs show the binding curves obtained by ELISA (n=4, mean±SEM). The signals were fitted by non-linear regression to obtain the Kd using A450 nm=Bmax*[antigen]/(Kd+[antigen]). The Kd values are shown in the figure.

Figure 17:
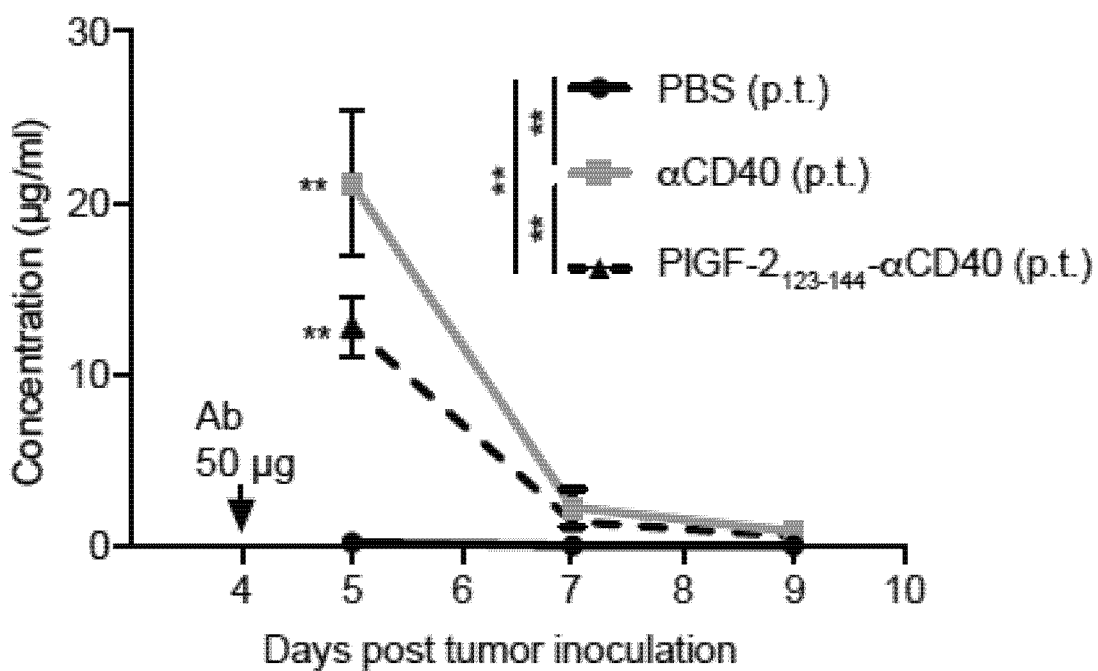

FIG. 17. PlGF-2$_{123-144}$-conjugation reduces concentration of αCD40 in blood plasma after p.t. injection. 5×10$^5$ B16F10 cells were inoculated on day 0. 50 μg of PlGF-2$_{123-144}$-αCD40, αCD40 or PBS was injected p.t. on day 4. Blood plasma was collected on day 5, 7 and 9. Concentrations of αCD40 in blood plasma was determined by ELISA (n=5, mean±SEM). Statistical analyses were done using ANOVA with Tukey's test using the values of each day. **p<0.01.

Figure 18:
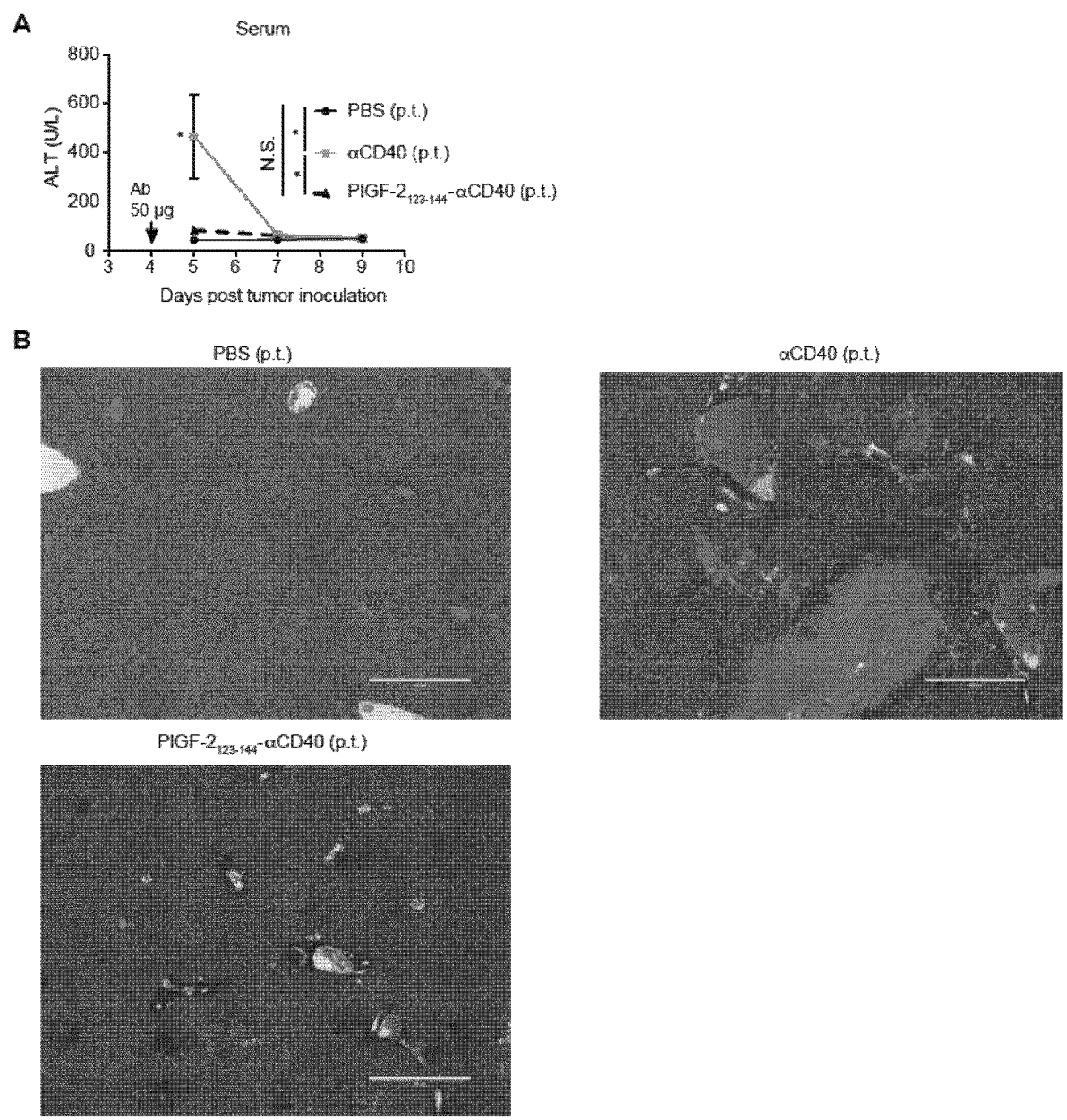

FIG. 18A-B. PlGF-2$_{123-144}$-conjugation reduces liver damage induced by αCD40 injection. 5×10$^5$ B16F10 cells were inoculated on day 0. 50 μg of PlGF-2$_{123-144}$-αCD40 or αCD40 was injected on day 4. (A) Alanine aminotransferase (ALT) levels in serum were measured on indicated days (n>8, mean±SEM). (B) Histologic liver sections 3 days after p.t. injection of 50 μg PlGF-2$_{123-144}$-αCD40, αCD40, or PBS. Scale bar=400 μm. Representative sections of groups of 3 mice. Statistical analyses were done using ANOVA with Tukey's test using the values of each day. *p<0.05; N.S.=not significant.

Figure 19:
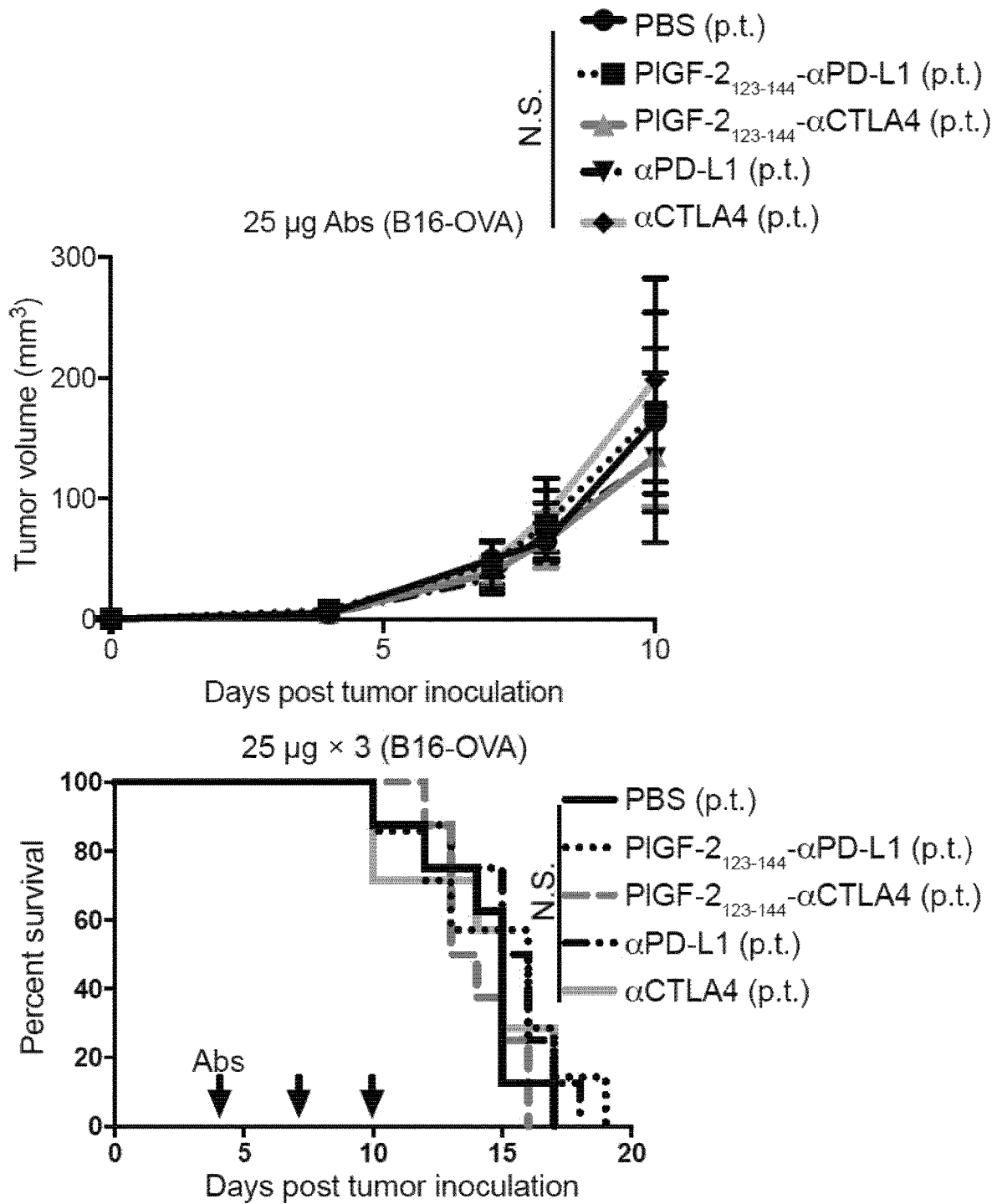

FIG. 19. Neither single agent treatment of PlGF-2$_{123-144}$-αCTLA4 nor PlGF-2$_{123-144}$-αPD-L1 affects tumor growth. C57BL/6 mice were injected intradermally with 1×10$^6$ B16F10-OVA cells on day 0. On day 4, 7, and 10, mice were treated with 50 μg/dose of PlGF-2$_{123-144}$-αCTLA4, PlGF-2$_{123-144}$-αPD-L1, αCTLA4, αPD-L1, or PBS. Graphs depict tumor volume until the first mouse died and survival rates. As αCTLA4 clone, 4F10 was used. Tumor volumes are presented in mean±SEM. Statistical analyses were done using ANOVA with Tukey's test for tumor size and Log-rank (Mantel-Cox) test for survival curve. N.S.=not significant.

Figure 20:
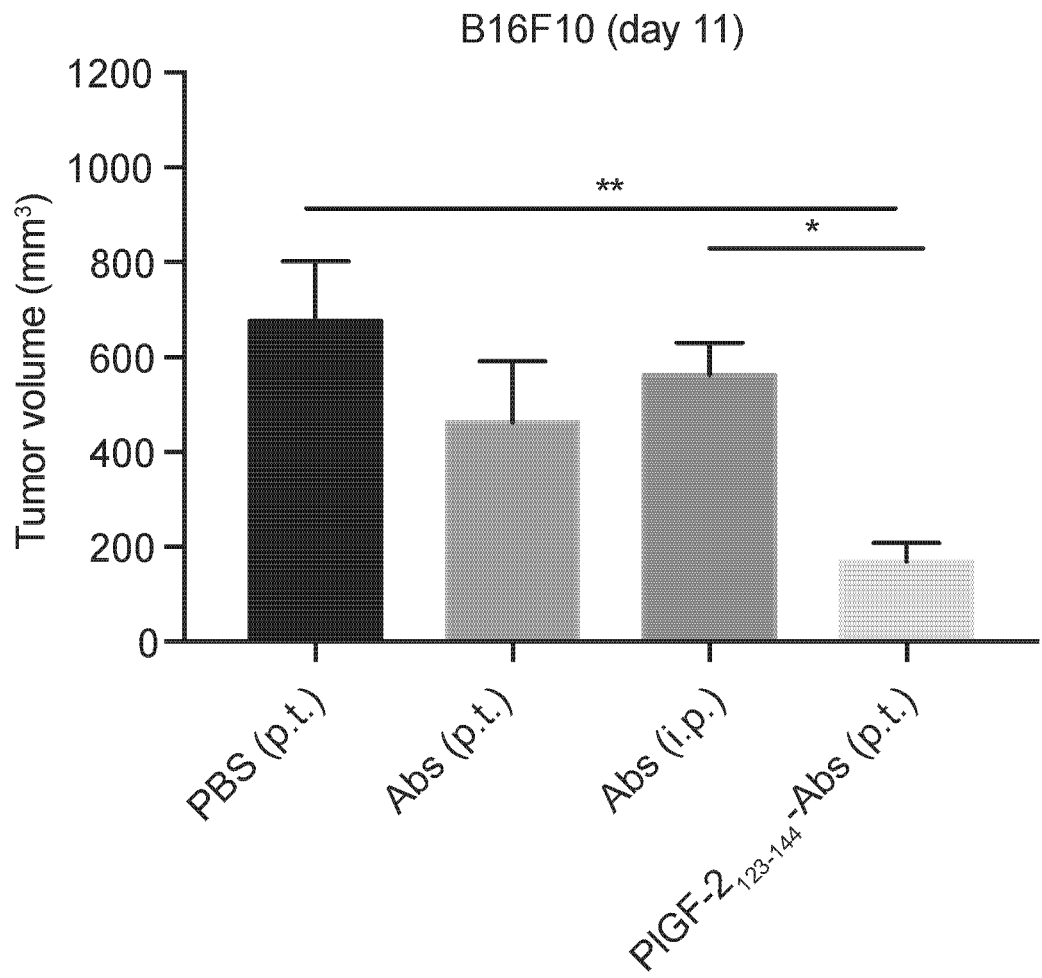
Figure 21:
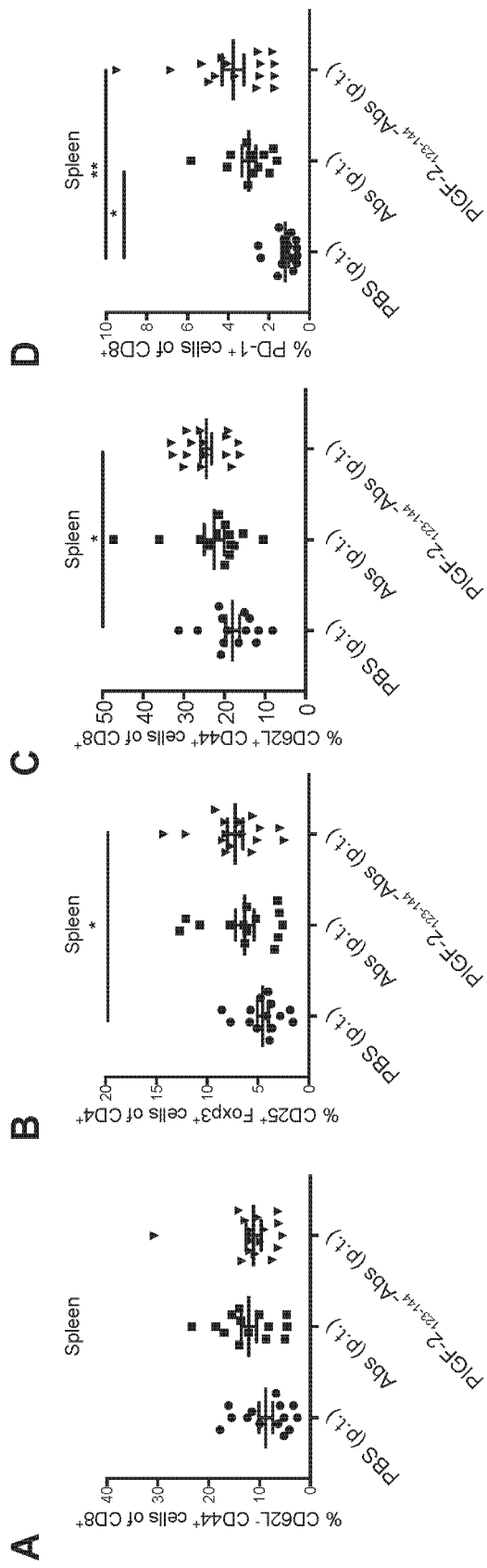

FIG. 20. Single injections of PlGF-2$_{123-144}$-Abs suppress tumor growth. C57BL/6 mice were injected intradermally with 5×10$^5$ B16F10 cells on day 0. On day 4, mice were treated with PlGF-2$_{123-144}$-αCTLA4 and PlGF-2$_{123-144}$-αPD-L1 (PlGF-2$_{123-144}$-Abs), αCTLA4 and αPD-L1 (Abs) (100 μg each), or PBS. Tumor size was measured on day 11. As αCTLA4 clone, 9H10 was used. Data are presented in mean±SEM. Statistical analyses were done using ANOVA with Tukey's test for tumor size. *p<0.05; **p<0.01.

FIG. 21A-D. PlGF-2$_{123-144}$-Abs activate T cells in the spleen. 5×10$^5$ B16F10 cells were inoculated on day 0. PlGF-2$_{123-144}$-αCTLA4 and PlGF-2$_{123-144}$-αPD-L1 (PlGF-2$_{123-144}$-Abs), αCTLA4 and αPD-L1 (Abs), or PBS was administered on day 4 and 7. Abs were injected 100 μg each/injection p.t. Clone 9H10 was used as αCTLA4. The spleen was taken on day 8, followed by FACS analysis. (A-D) Graphs depict the % of (A) CD62L$^-$ CD44$^+$ effector cells of CD8$^+$ T cells, (B) Foxp3$^+$ CD25$^+$ Treg cells of CD4$^+$ T cells (C) CD62L$^+$ CD44$^+$ memory and (D) PD-1$^+$ cells of CD8$^+$ T cells in the spleen. Bars represent mean±SEM. Statistical analyses were done using ANOVA with Tukey's test *p<0.05; **p<0.01.

FIG. 22A-D. PlGF-2$_{123-144}$-Abs activates tumor antigen-specific T cells in td-LN, tested in the B16F10-OVA model. 1×10$^6$ B16F10-OVA cells were inoculated on day 0. PlGF-2$_{123-144}$-αCTLA4 and PlGF-2$_{123-144}$-αPD-L1 (PlGF-2$_{123-144}$-Abs), αCTLA4 and αPD-L1 (Abs), or PBS was administered on day 4 and 7. Abs were injected 100 μg each/injection p.t. Clone 9H10 was used as αCTLA4. Tumor, td-LN, non-td-LN (LN from another side), and spleen were taken on day 8, followed by FACS analysis. (A-D) Graphs depict the % of OVA$_{257-264}$ (SIINFEKL)-specific CD8$^+$ T cells in (A) td-LN, (B) non-td-LN, (C) spleen, and (D) tumor, determined by SIINFEKL-MHCI pentamer staining. Bars represent mean±SEM. Statistical analyses were done using ANOVA with Tukey's test **p<0.01.

FIG. 23A-B. Individual tumor growth curves of FIG. 5. 5×10$^5$ B16F10 cells were inoculated intradermally on day 0 in the left back, and then repeated on day 2 in the right back. PlGF-2$_{123-144}$-αCTLA4+PlGF-2$_{123-144}$-αPD-L1 (PlGF-2$_{123-144}$-Abs), αCTLA4+αPD-L1 (Abs) or PBS was administered on day 4, 7, and 10. Abs were injected at 100 μg each/injection either i.p. or p.t. P.t. injection was performed only beside the left tumor, but not the right tumor. Graphs depict individual growth of (A) left and (B) right tumors. αCTLA4 clone 9H10 was used.

Figure 24:
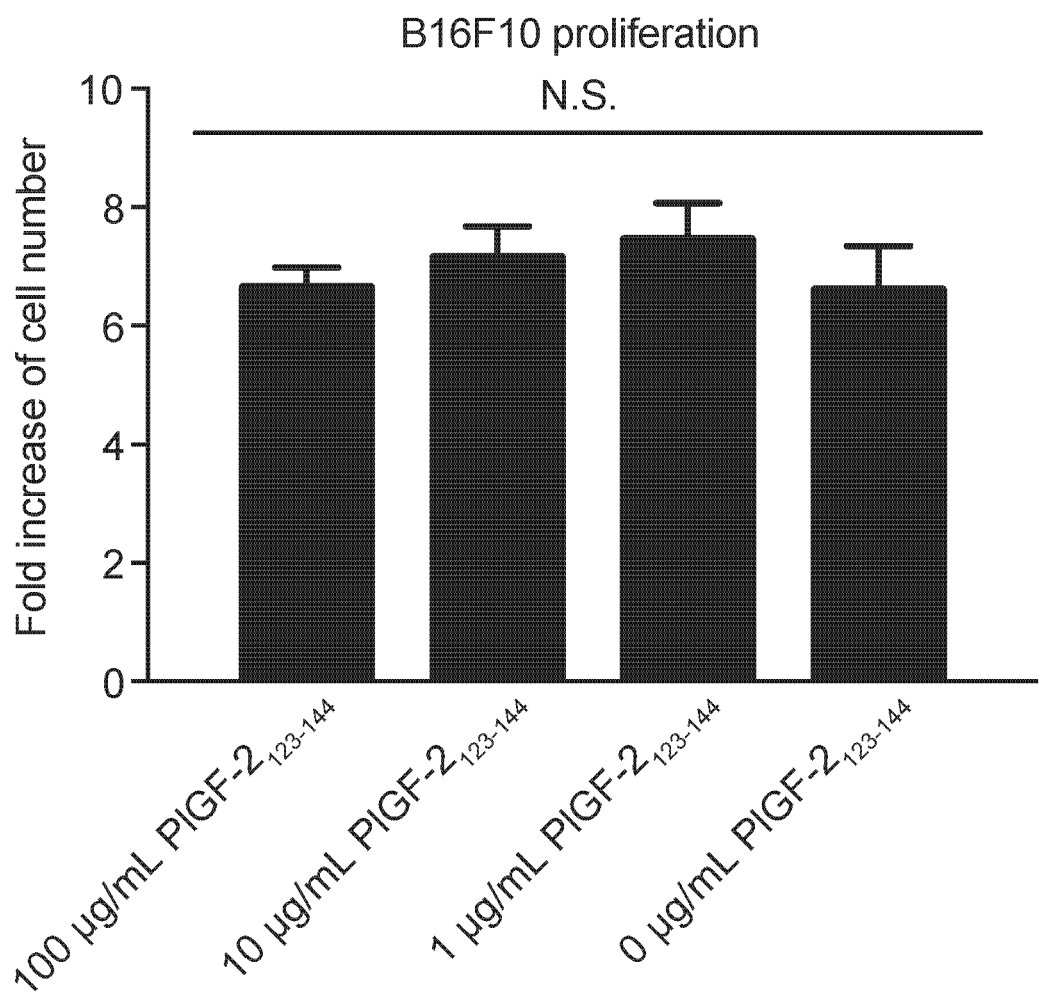

FIG. 24. PlGF-2$_{123-144}$ peptide does not affect B16F10 cells proliferation. 5×10$^4$ B16F10 melanoma cells were cultured in the presence or absence of indicated concentrations of PlGF-2$_{123-144}$ peptide in 24-well plates. After 3 days of incubation, cell numbers were counted. (n=4, mean±SD.) Statistical analyses were done using ANOVA with Tukey's test. N.S.=not significant.

Figure 25:
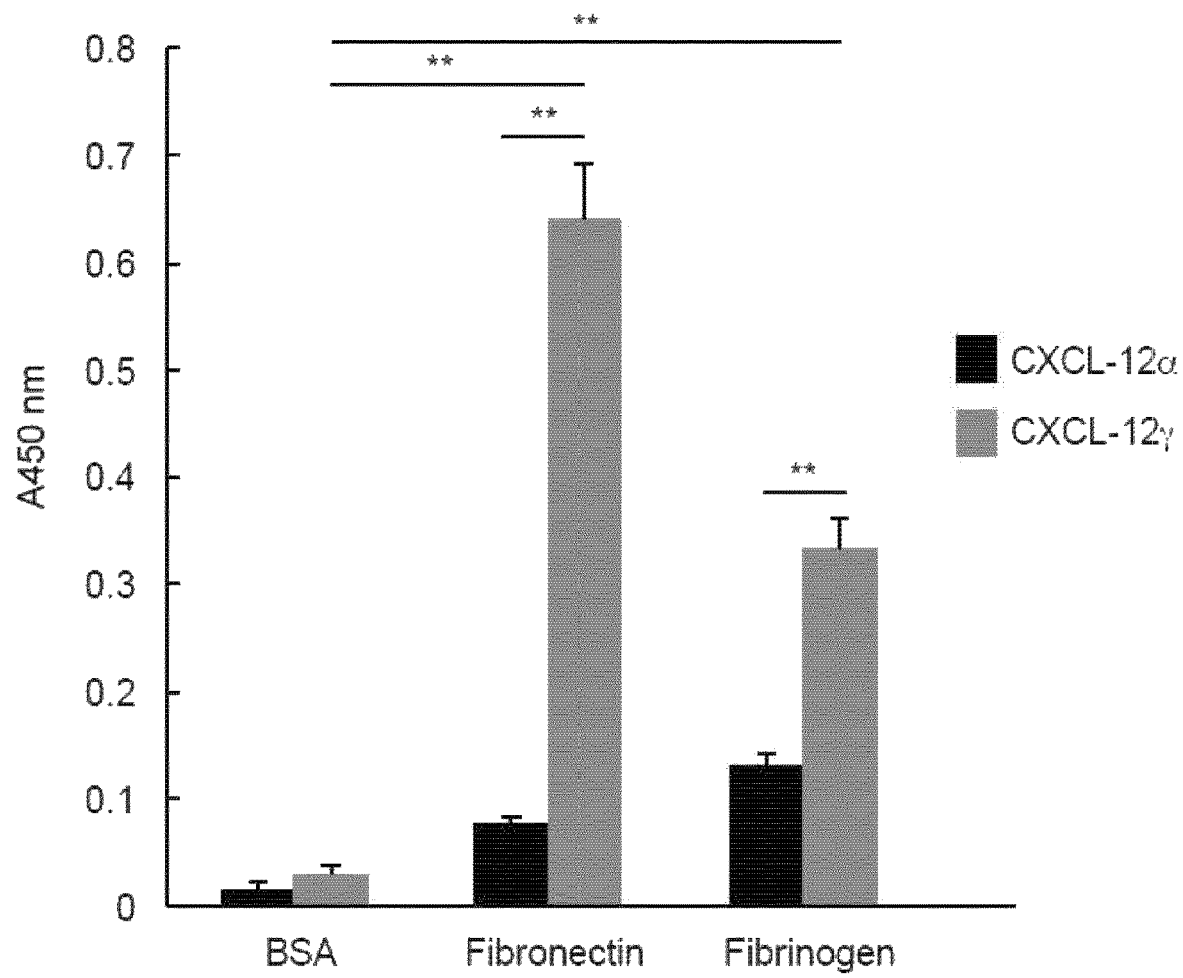

FIG. 25. CXCL-12γ binds to ECM proteins strongly compared to CXCL-12α. CXCL-12γ binding to ECM proteins, measured by ELISA. ELISA plates were coated with 10 µg/mL ECM proteins (fibronectin and fibrinogen) and further incubated with 1 µg/mL recombinant human CXCL-12γ or CXCL-12α. Bound CXCL-12 was detected using a specific antibody for CXCL-12. A450 nm represents absorbance at 450 nm. Bovine serum albumin (BSA) served as a negative control (n=3, mean±SD). Statistical analyses were done using ANOVA with Tukey's test **$p<0.01$.

Figure 26:
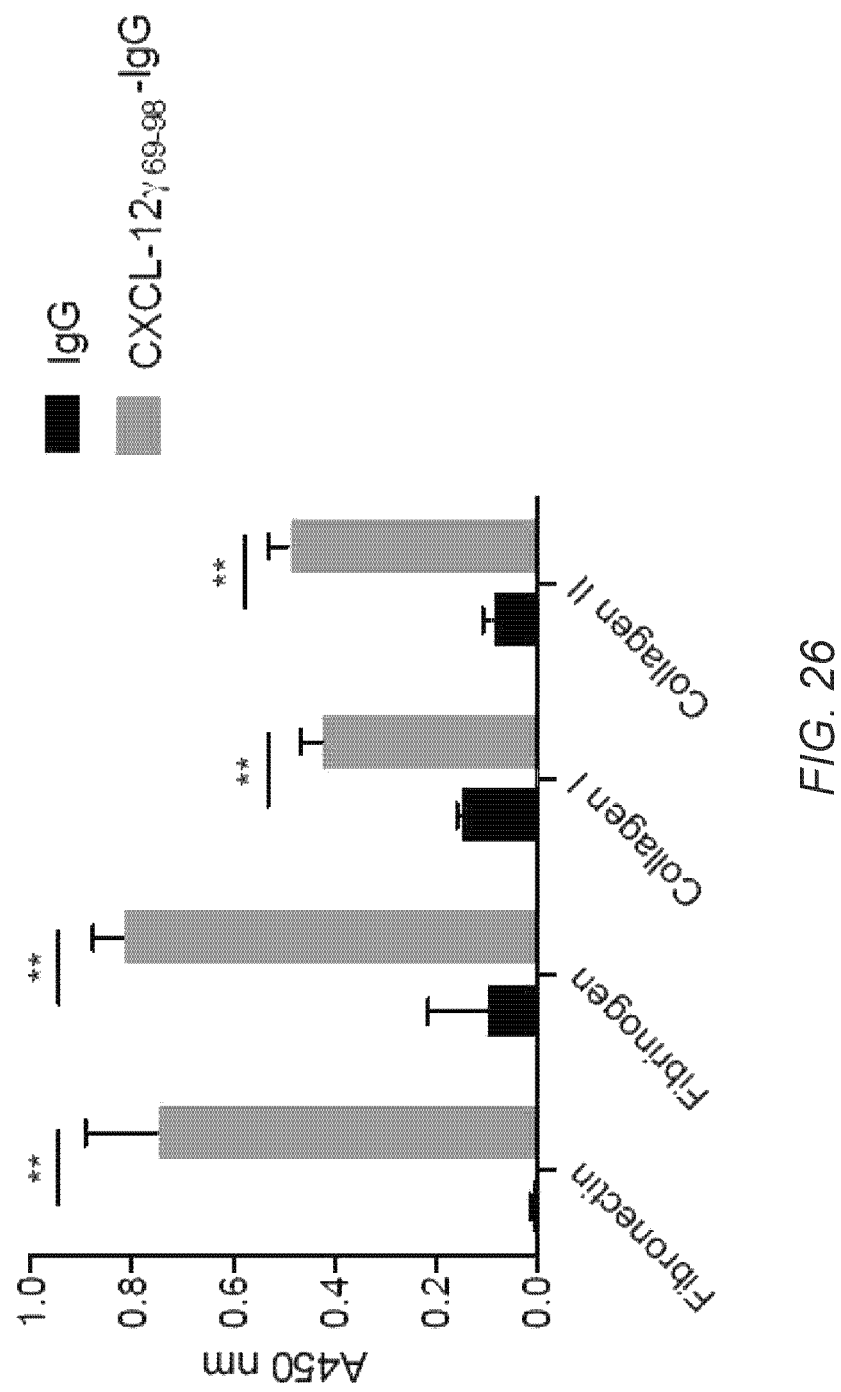

FIG. 26. CXCL-12γ$_{6-98}$ peptide-conjugated IgG (CXCL-12γ$_{6-98}$-IgG) binds to ECM proteins. CXCL-12γ$_{6-98}$-IgG binding to ECM proteins, measured by ELISA. ELISA plates were coated with 10 µg/mL ECM proteins (fibronectin, fibrinogen, collagen type I, and collagen type II) and further incubated with 10 µg/mL recombinant human CXCL-12γ$_{6-98}$ peptide-conjugated IgG (CXCL-12γ$_{6-98}$-IgG) or wild-type IgG. Bound IgG was detected using a specific antibody for IgG. A450 nm represents absorbance at 450 nm. (n=3, mean±SD). Statistical analyses were done using ANOVA with Tukey's test **$p<0.01$.

Figure 27:
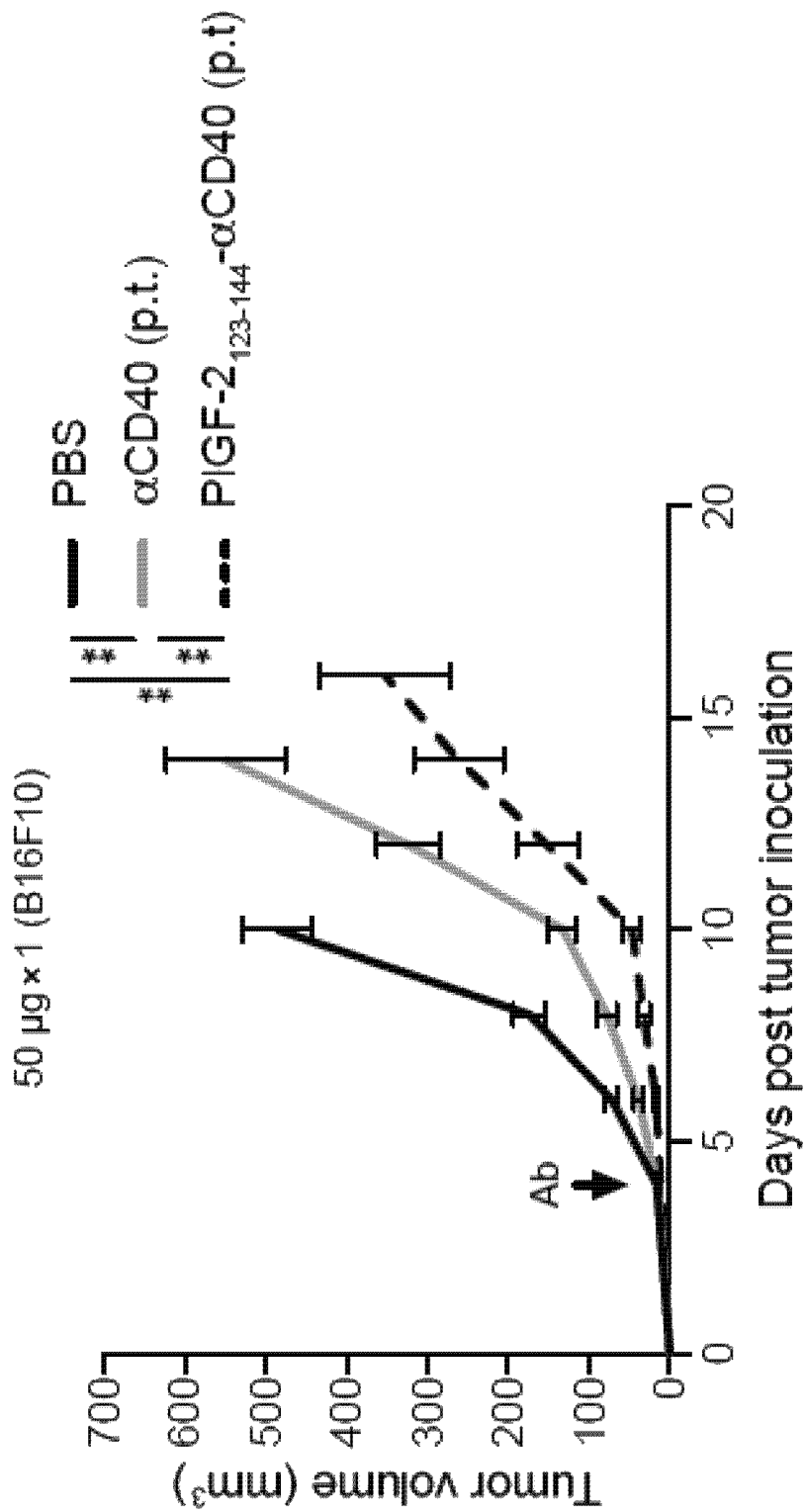

FIG. 27. PlGF-2$_{123-144}$-αCD40 treatment further reduces B16F10 melanoma growth rate, compared to αCD40 treatment. CD40 is a tumor necrosis factor receptor superfamily member expressed on antigen-presenting cell (APC) including dendritic cells (DC), monocytes, and B cells. Ligand ligation to CD40 on DC induces increased cell surface expression of co-stimulatory and major histocompatibility complex (MHC) molecules and production of pro-inflammatory cytokines. This leads to enhanced T cell activation. Here, the inventors used an anti-CD40 agonistic antibody (αCD40), which has been shown to suppress tumor growth, to test if PlGF-2$_{123-144}$ peptide conjugation enhance its therapeutic effect on tumor. 5×10$^5$ B16F10 cells were inoculated on day 0. 50 µg of PlGF-2$_{123-144}$-αCD40, αCD40, or PBS was administered on day 4. Abs were injected p.t. Graph depicts tumor volume until the first mouse in each group died. Tumor volumes are presented in mean±SEM. n>8. Statistical analyses were done using ANOVA with Tukey's test or student's t-test. **$p<0.01$.

FIG. 28A-B. CBD protein-conjugated antibody binds to collagen I and III with high affinity and retain binding to their targets. (A) Schematic of conjugation of the vWF A3 recombinant protein to IgG antibody, resulting in binding to collagen. (B) Affinities (K$_D$ values are shown) of CBD- and unmodified αPD-L1 and αCTLA4 against collagen type I and collagen type III, rmCTLA4, and/or rmPD-L1 were measured by ELISA. N.D.=not determined because of low signals.

Figure 29B:
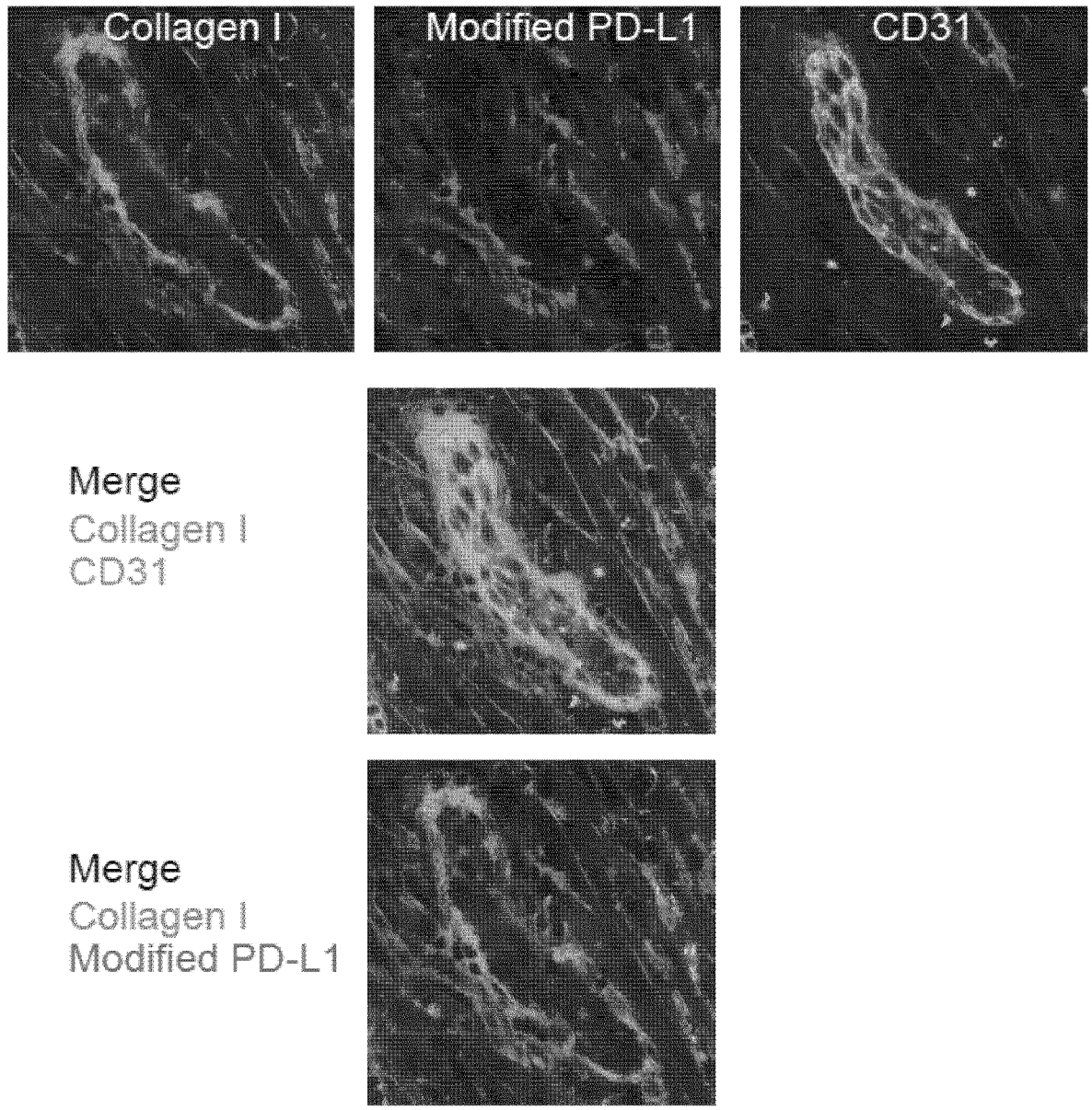

FIG. 29A-B. CBD protein localizes tumor after i.v. injection through collagen affinity. 5×10$^5$ MMTV-PyMT cells were inoculated. (A) 50 µg of DyLight 800-labeled CBD was injected i.v. when tumor volume reached 500 mm$^3$. Fluorescence analysis of each organ revealed the bio-distribution of CBD protein after 48 hrs of injection. % distribution of the CBD protein was calculated as radiant intensity of organ interested/total radiant intensity of tested organs and normalized by organ weight. (B) 100 µg of DyLight 594-labeled CBD-αPD-L1 and 100 µg of DyLight 488-labeled αCollagen I were injected i.v. when tumor volume reached 100 mm$^3$. 30 min after injection, tumor was harvested and analyzed.

FIG. 30A-G. CBD fusion reduces systemic exposure to immune drugs and treatment-related toxicity. 5×10$^5$ B16F10 cells were inoculated on day 0. (A, B) CBD-αCTLA4 and CBD-αPD-L1 (100 µg each), αCTLA4 and αPD-L1 (100 µg each), or PBS was injected i.v. on day 4. Blood serum was collected on day 5, 6, 8 and 10. Concentrations of (A) αCTLA4 and (B) αPD-L1 were determined by ELISA (n=8, mean±SEM). (C-G) CBD- or unmodified-αCTLA4 and αPD-L1 (100 µg each/injection) were injected i.v. on day 4 and 7. (C-D) On day 8, cytokine concentration, (C) TNFα and (D) IL-6 in blood plasma were measured (mean±SEM). (E-F) On day 10, the number of lymphocytic infiltration spots in histologic (E) lung and (F) liver sections were counted and divided by area (mean±SEM). (G) On day 10, blood serum was collected and ALT levels were measured (mean±SEM). Statistical analyses were done using ANOVA with Tukey's test. Two experimental replicates. *$p<0.05$; **$p<0.01$; N.S.=not significant.

FIG. 31A-E. CBD-CPI treatment reduce tumor growth rate in 3 murine tumor models. (A) 5×10$^5$ B16F10 cells, (B) 5×10$^5$ CT26 cells, (C-D) 5×10$^5$ MMTV-PyMT cells were inoculated on day 0. CBD-αCTLA4+CBD-αPD-L1 (CBD-CPI), αCTLA4+αPD-L1 (CPI) or PBS was administered on (A) day 4, (B) day 5, (C-D) day 7. CBD- and unmodified CPI were injected i.v. and PlGF-2$_{123-144}$-CPI were injected peri-tumorally (p.t.). Antibody doses per administration are indicated on the figure. (A-C) Graphs depict tumor volume until the first mouse died and (D) survival rate. (E) 30 days after the first tumor inoculation, 5×10$^5$ MMTV-PyMT cells were again inoculated into the right mammary gland fat pad in CBD-CPI treated tumor-free survivors or in naïve mice. Numbers indicate how many mice remain tumor-free among total mice after 40 days of tumor re-challenge. (A) n=9. (B) PBS, n=11; CPI 25 µg, n=11; CPI 100 µg, n=10; CBD-CPI 25 µg, n=10; CBD-CPI 100 µg, n=9. (C) n=8. (D) CBD-CPI, n=12; other treatment groups, n=11. (E) n=6. Tumor volumes are presented as mean±SEM. Three experimental replicates. Statistical analyses were done using ANOVA with Tukey's test for tumor size and Log-rank (Mantel-Cox) test for survival curves. *$p<0.05$; **$p<0.01$.

Figure 32:
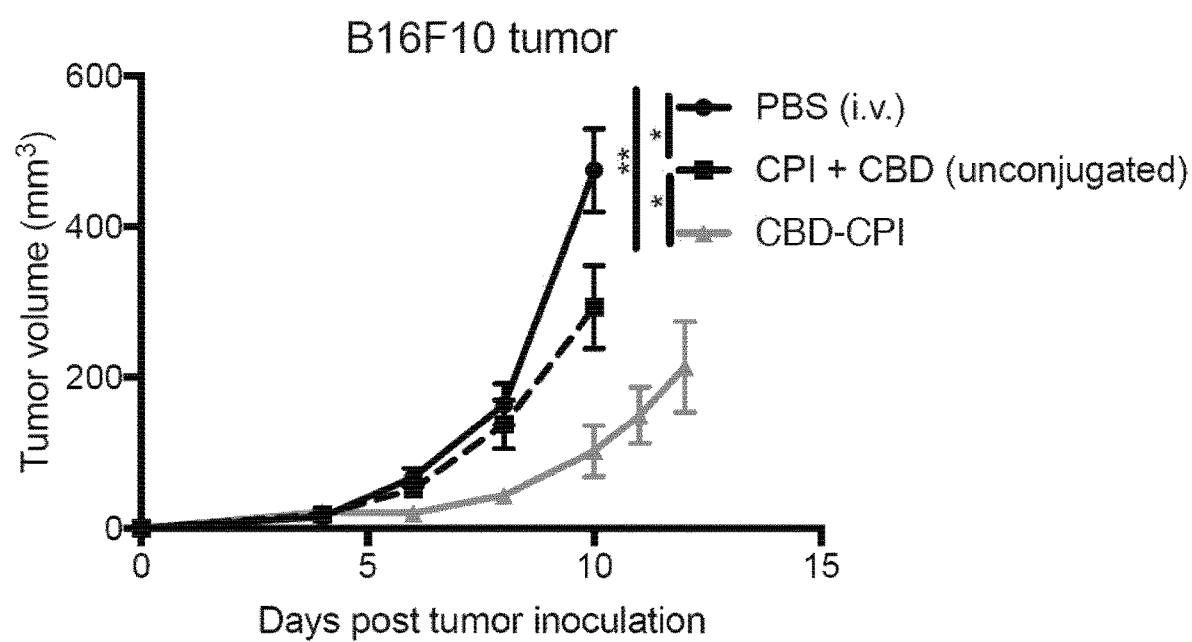

FIG. 32. Conjugation of CBD to CPI are indispensable for B16F10 tumor growth suppression. 5×10$^5$ B16F10 melanoma cells were inoculated in the back skin on day 0. Combination of 100 µg of CBD-αPD-L1+100 µg of CBD-αPD-L1, or 100 µg of αPD-L1+100 µg of αPD-L1+CBD protein (without conjugation), or PBS was administered on day 4 (n=4-5). Antibody was injected i.v. The graph depicts tumor volume until the first mouse died. Tumor volumes are presented as mean±SEM. Statistical analyses were done using ANOVA with Tukey's test. **$p<0.01$, *$p<0.05$.

FIG. 33. CBD-CPI treatment increase B16F10 melanoma-infiltrating cytotoxic CD8$^+$ T cells. 5×10$^5$ B16F10 cells were inoculated on day 0. CBD-αCTLA4+CBD-αPD-L1 (CBD-CPI), αCTLA4+αPD-L1 (CPI), or PBS was administered on day 4. CPI were injected i.v. at 100 µg each. Tumors were taken on day 8, followed by flow cytometric analysis. Frequency of (A) CD8$^+$CD3$^+$ and (B) CD4$^+$CD3$^+$ tumor-infiltrating T cells within CD45$^+$ lymphocytes. (C) Foxp3$^+$CD25$^+$ Treg of CD4$^+$CD3$^+$ tumor-infiltrating T cells. (D) The ratio of CD62L$^-$CD44$^+$CD8$^+$ CD3$^+$ effector T cells versus Foxp3$^+$CD25$^+$ Treg. (E-G) T cells were extracted from tumor and stimulated with αCD28 and αCD3 for 6 h. Graphs depict the % of (E) (F) TNFα$^+$, (G) IFNγ$^+$ of CD8$^+$ CD3$^+$ T cells. Bars represents mean±SEM. Two experimental replicates. Statistical analyses were done using ANOVA with Tukey's test. *p<0.05; **p<0.01.

FIG. 34A-D. PlGF-2$_{123\text{-}144}$ conjugated αCD40 binds to ECM proteins and shows prolonged injection-site tissue retention. (A) PlGF-2$_{123\text{-}144}$- and unmodified αCD40 were analyzed by SDS-PAGE under reducing conditions with coomassie blue staining. (B) PlGF-2$_{123\text{-}144}$- and unmodified αCD40 binding affinities to fibronectin, vitronectin and collagen I were measured by ELISA. A450 nm represents absorbance at 450 nm. BSA served as a negative control (n=6, mean±SD). (C) PlGF-2$_{123\text{-}144}$- and unmodified αCD40 binding affinities to recombinant mouse CD40 was measured by ELISA. A450 nm represents absorbance at 450 nm (n=4, mean±SD). (D) Skin tissue retention of PlGF-2$_{123\text{-}144}$-αCD40 was tested in the in vivo imaging system. Cyanine 7-labeled PlGF-2$_{123\text{-}144}$- and unmodified αCD40 were injected in the back skin of athymic nude mice, followed by imaging every 24 hr. The graph represents a time profile of quantification of signal intensity by performing a region-of-interest (ROI) analysis. Fluorescence intensity by measuring the ROI was normalized by initial fluorescence intensity (n=5, mean±SEM). Two experimental replicates. Statistical analyses were done using a two-tailed Student's t-test. **p<0.01.

FIG. 35A-E. PlGF-2$_{123\text{-}144}$ conjugation reduces systemic exposure to αCD40 and treatment-related toxicity. $10^5$ B16F10 cells were inoculated on day 0. PlGF-2$_{123\text{-}144}$-αCD40 (50 μg), αCD40, or PBS was administered on day 4 p.t. (A) Blood serum was collected on day 4 (4 hr after injection), 6, and 8. The concentration of αCD40 in blood serum was determined by ELISA (n=6, mean±SEM). (B-C) Concentrations of IL-6 and TNFα in blood serum were measured by ELISA (n=6, mean±SEM). (D) ALT levels in serum were measured (n=9-14, mean±SEM). (E) Histologic liver sections 3 days after p.t. injection of 50 μg PlGF-2$_{123\text{-}144}$-αCD40, αCD40, or PBS. Scale bar=400 μm. Representative sections of groups of 3 mice. Statistical analyses were done using ANOVA with Tukey's test using the values of each day. Two experimental replicates. *p<0.05; **p<0.01; N.S.=not significant.

Figure 36:
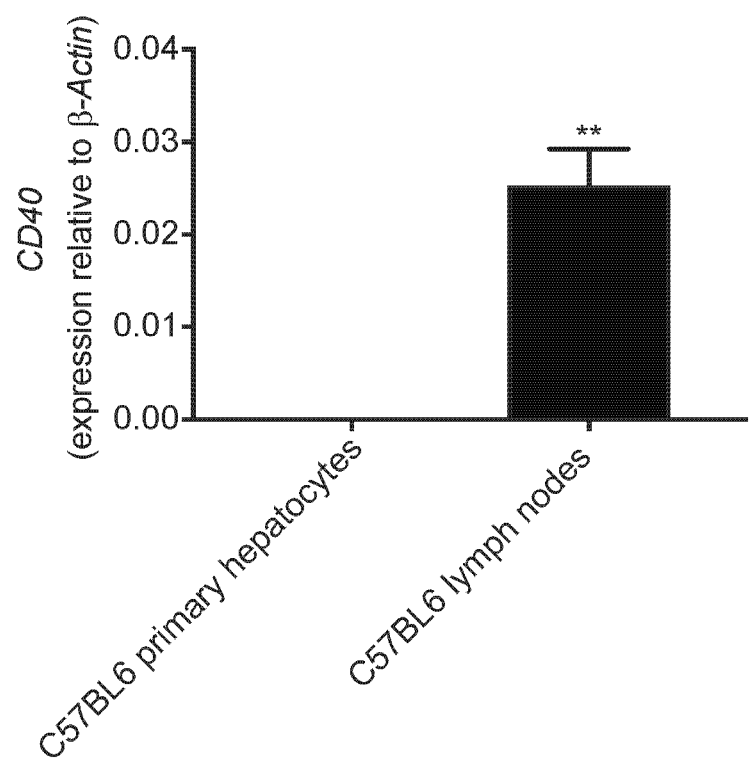

FIG. 36. Hepatocytes barely express CD40. The expression of CD40 was measured in primary hepatocytes and total LN cells from naïve C57BL/6 mice by qPCR. Gene expression levels relative to β-Actin are indicated (n=3, mean±SEM).

FIG. 37A-D. PlGF-2$_{123\text{-}144}$-αCD40 suppresses growth of multiple tumors compared to unmodified αCD40. (A-B) $5\times10^5$ B16F10 melanoma cells were inoculated in the back skin on day 0. (A) 10 μg or (B) 50 μg of PlGF-2$_{123\text{-}144}$-αCD40, αCD40, or PBS was administered on day 4 (A; n=8-9, B; n=8-9). (C) $5\times10^5$ CT26 colon carcinoma cells were inoculated in the back skin on day 0. 10 μg of PlGF-2$_{123\text{-}144}$-αCD40, αCD40, or PBS was administered on day 5 (n=6-7). (D) $8\times10^5$ MMTV-PyMT breast cancer cells were inoculated into the right mammary fat pad. 50 μg of PlGF-2$_{123\text{-}144}$-αCD40, αCD40, or PBS was administered on day 7 (n=7-9). Antibody was injected p.t. The graph depicts tumor volume until the first mouse in each group died. Tumor volumes are presented as mean±SEM. Statistical analyses were done using ANOVA with Tukey's test or Student's t-test. **p<0.01, *p<0.05.

Figure 38O:
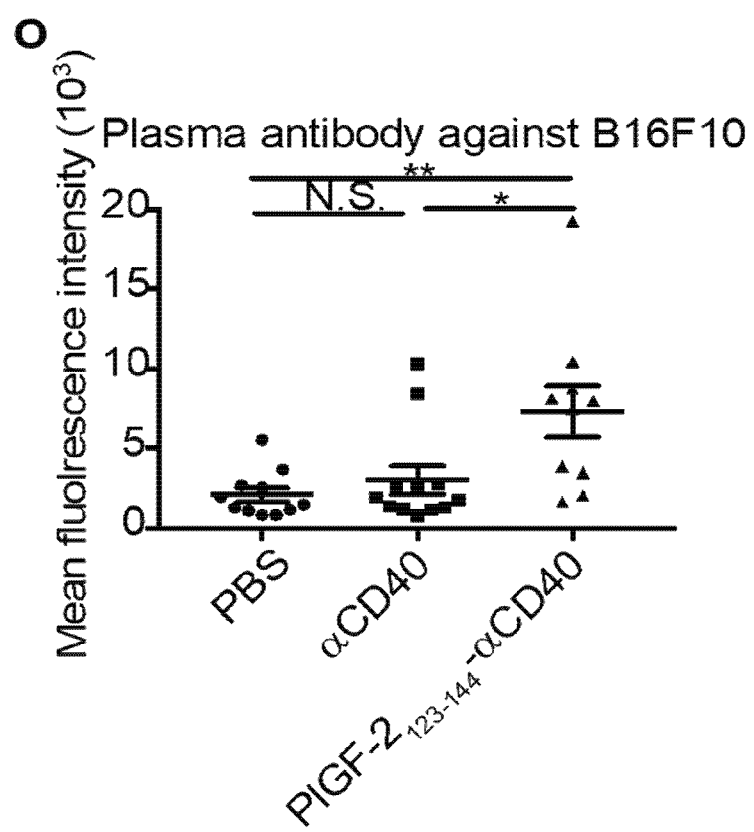

FIG. 38A-O. PlGF-2$_{123\text{-}144}$-αCD40 treatment activates T cells, B cells, DCs, and macrophages within tumor. $5\times10^5$ B16F10 cells were inoculated on day 0. 50 μg of PlGF-2$_{123\text{-}144}$-αCD40, αCD40, or PBS was administered on day 4. αCD40 was injected p.t. A-L, Tumor and td-LN were taken on day 9, followed by flow cytometric analysis. Graphs depict the % of (A) CD11c$^+$ DCs of CD45$^+$ lymphocytes within tumor. (B) CD11c$^+$ DCs of CD45$^+$ lymphocytes within td-LN. (C) MHCII$^{High}$CD86$^+$ cells of CD11c$^+$ DCs within tumor. (D) MHCII$^{High}$CD86$^+$ cells of CD11c$^+$ DCs within td-LN. (E) MHCII$^{High}$CD86$^+$ cells of F4/80$^+$ macrophages within tumor. (F) MHCII$^{High}$CD86$^+$ cells of F4/80$^+$ macrophages within td-LN. (G) CD8$^+$CD3$^+$ T cells of CD45$^+$ lymphocytes within tumor. (H) CD62L$^-$CD44$^+$ effector cells of CD8$^+$CD3$^+$ T cells within tumor. (I) CD4$^+$CD3$^+$ T cells of CD45$^+$ lymphocytes within tumor. (J) CD25$^+$Foxp3$^+$ Treg cells of CD4$^+$CD3$^+$ T cells within tumor. (K) The cell number ratio of CD62L$^-$CD44$^+$CD8$^+$CD3$^+$ effector T cells/CD25$^+$Foxp3$^+$ CD4$^+$CD3$^+$ Treg cells within tumor. (L) PD-1$^+$ cells of CD8$^+$CD3$^+$ T cells within tumor. (M-O) Tumor, td-LN, and blood plasma were taken on day 11. (M) MHCII$^{High}$CD86$^+$ cells of B220$^+$ B cells within tumor. (N) MHCII$^{High}$CD86$^+$ cells of B220$^+$ B cells within td-LN. (O) Mean fluorescence intensity by flow cytometry of endogenous anti-B16F10 cells antibodies. Bars represent mean±SEM. Two experimental replicates. Statistical analyses were done using ANOVA with Tukey's test. *p<0.05; **p<0.01.

FIG. 39A-B. αCD40 treatment did not alter frequency of NK cells. $5\times10^5$ B16F10 cells were inoculated on day 0. 50 μg of PlGF-2$_{123\text{-}144}$-αCD40, αCD40, or PBS was administered on day 4. αCD40 was injected p.t. Tumor and td-LN were taken on day 9, followed by flow cytometric analysis. Graphs depict the % of NK1.1$^+$ cells of CD45$^+$ cells (A) in the tumor and (B) in the td-LN (mean±SEM). Statistical analyses were done using ANOVA with Tukey's test.

Figure 40A:
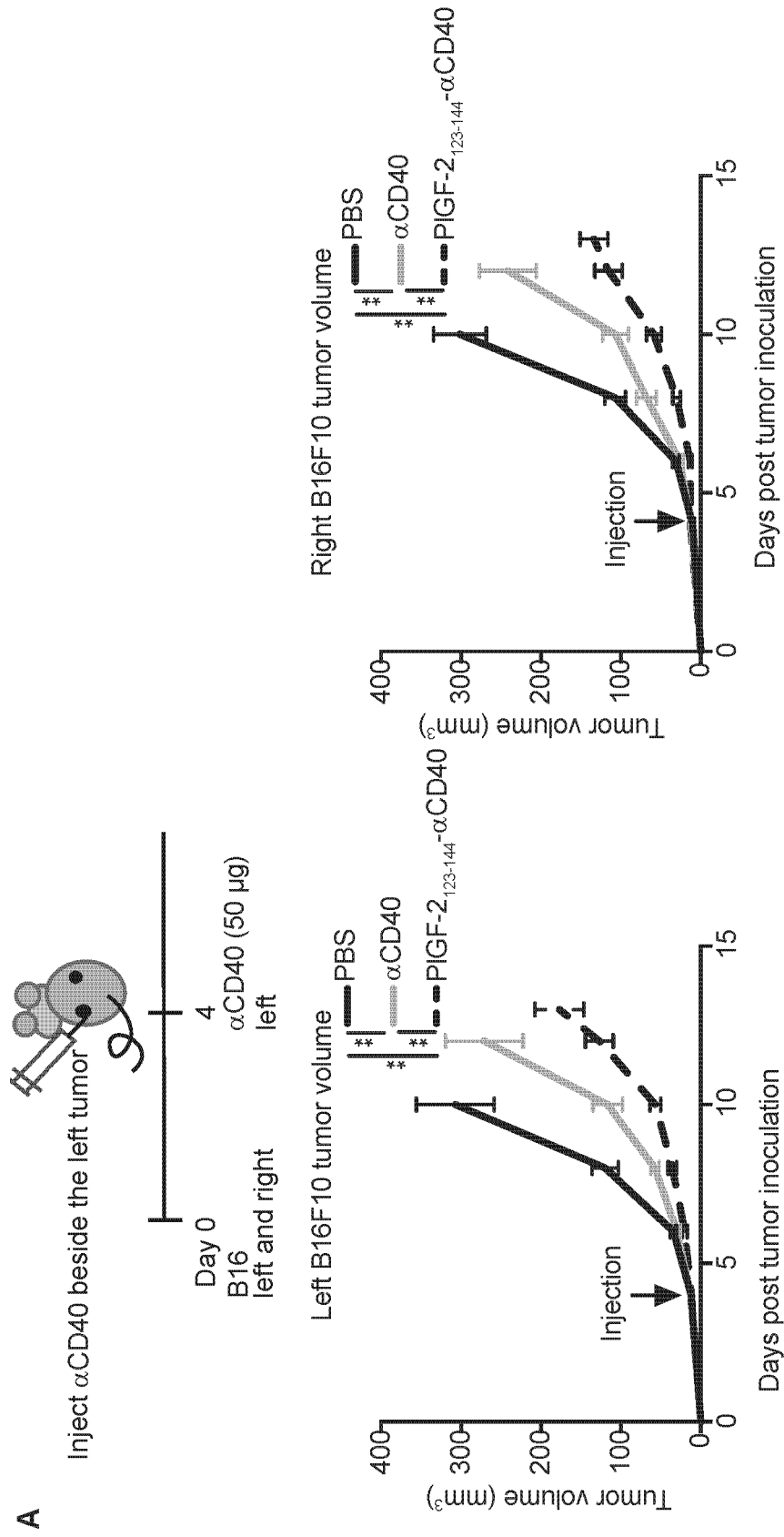
Figure 40B:
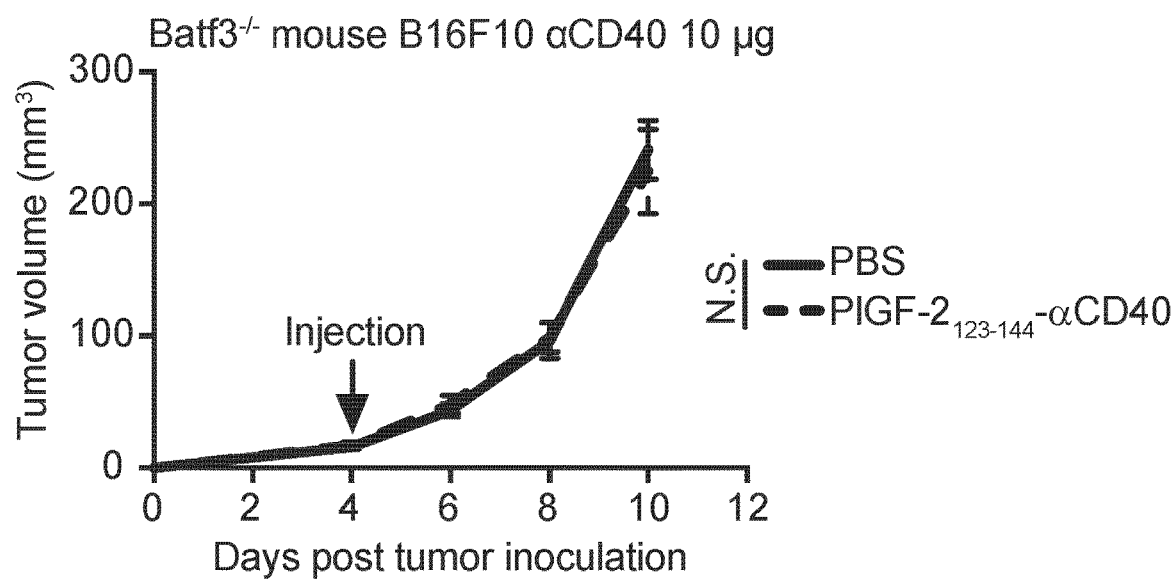

FIG. 40A-B. PlGF-2$_{123\text{-}144}$-αCD40 treatment induces systemic antitumor immunity. (A) $5\times10^5$ B16F10 cells were inoculated intradermally on day 0 both in the left and right sides of mouse back skin. 50 μg of PlGF-2$_{123\text{-}144}$-αCD40, αCD40 or PBS was administered on day 4. P.t. injections were performed only beside the left tumor, but not the right tumor. Tumor volumes of the tumor on the left back and the tumor on the right back were measured (n=9, mean±SEM). (B) $5\times10^5$ B16F10 melanoma cells were inoculated in the back skin of Batf3$^{-/-}$ mice on day 0. 10 μg of PlGF-2$_{123\text{-}144}$-αCD40 or PBS was administered on day 4. Tumor volumes are presented as mean±SEM (n=9). Two experimental replicates. Statistical analyses were done using ANOVA with Tukey's test *p<0.05; **p<0.01.

Figure 41A:
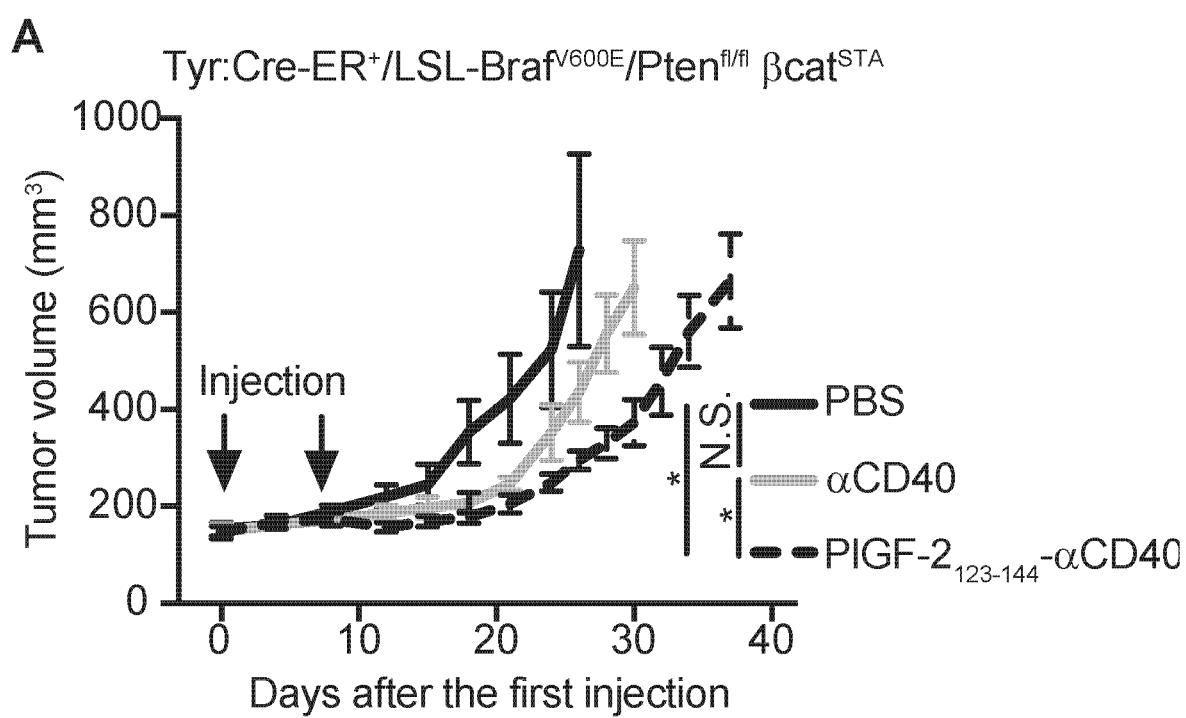

FIG. 41A-C. PlGF-2$_{123\text{-}144}$-αCD40 treatment shows antitumor activity against β-catenin-expressing genetically engineered primary melanomas. Tyr: Cre-ER$^+$/LSL-Braf$^{V600E}$/Pten$^{fl/fl}$ βcat$^{STA}$ mice received 50 μg of 4-OH-tamoxifen on their back skin to induce melanoma development. Day 0 is defined as the time point when tumors first become visible. PlGF-2$_{123\text{-}144}$-αCD40, αCD40, or PBS was injected p.t. on days 0 and 7. αCD40 was injected at 10 μg of each/injection. (A) Tumor sizes are shown (n=6, mean±SEM). (B) Survival rates are shown (n=6). (C) The density of CD8$^+$ CD3$^+$ T cells in the Tyr:Cre-ER$^+$/LSL-Braf$^{V600E}$/Pten$^{fl/fl}$ βCat$^{STA}$ tumor is shown (mean±SEM). 3-4 fields of images per tumor were taken, and the average T cell density was calculated. Two experimental replicates. Statistical analyses were done using ANOVA with Tukey's test. For single comparisons, a two-tailed Student's t-test was used. Log-rank (Mantel-Cox) test for survival curves. *p<0.05; **p<0.01.

Figure 42:
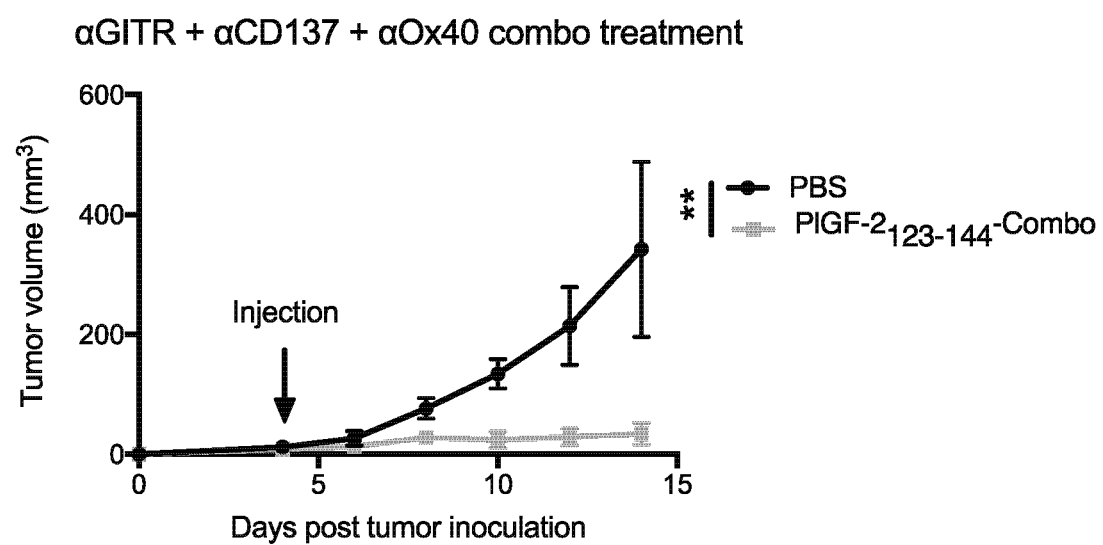

FIG. 42. Peri-tumoral injection of PlGF-2$_{123\text{-}144}$-αOx40, PlGF-2$_{123\text{-}144}$-αCD137, and PlGF-2$_{123\text{-}144}$-αGITR in combination suppressed B16F10 tumor growth.

Figure 43:
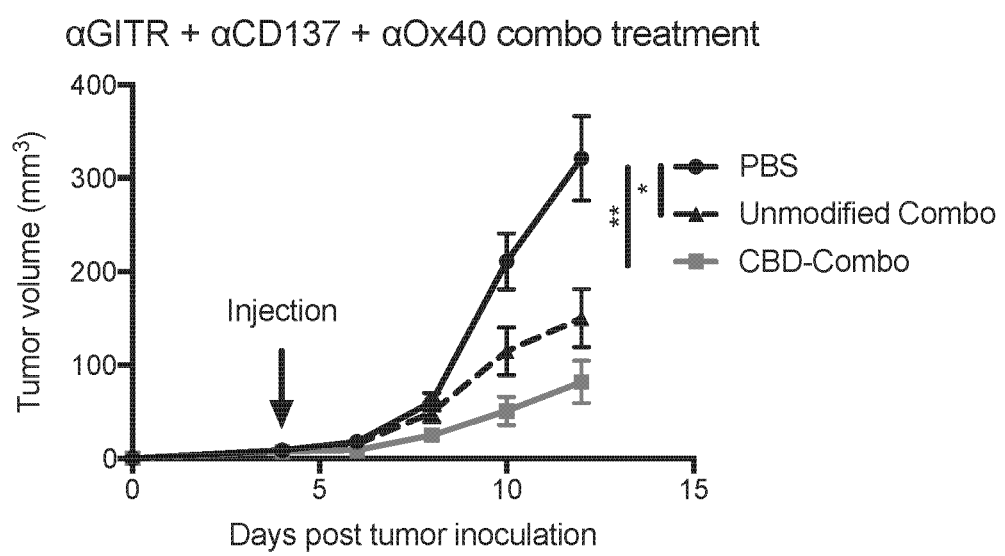

FIG. 43. Intravenous injection of CBD-αOx40, CBD-αCD137, and CBD-αGITR in combination suppressed B16F10 tumor growth.

Figure 44:
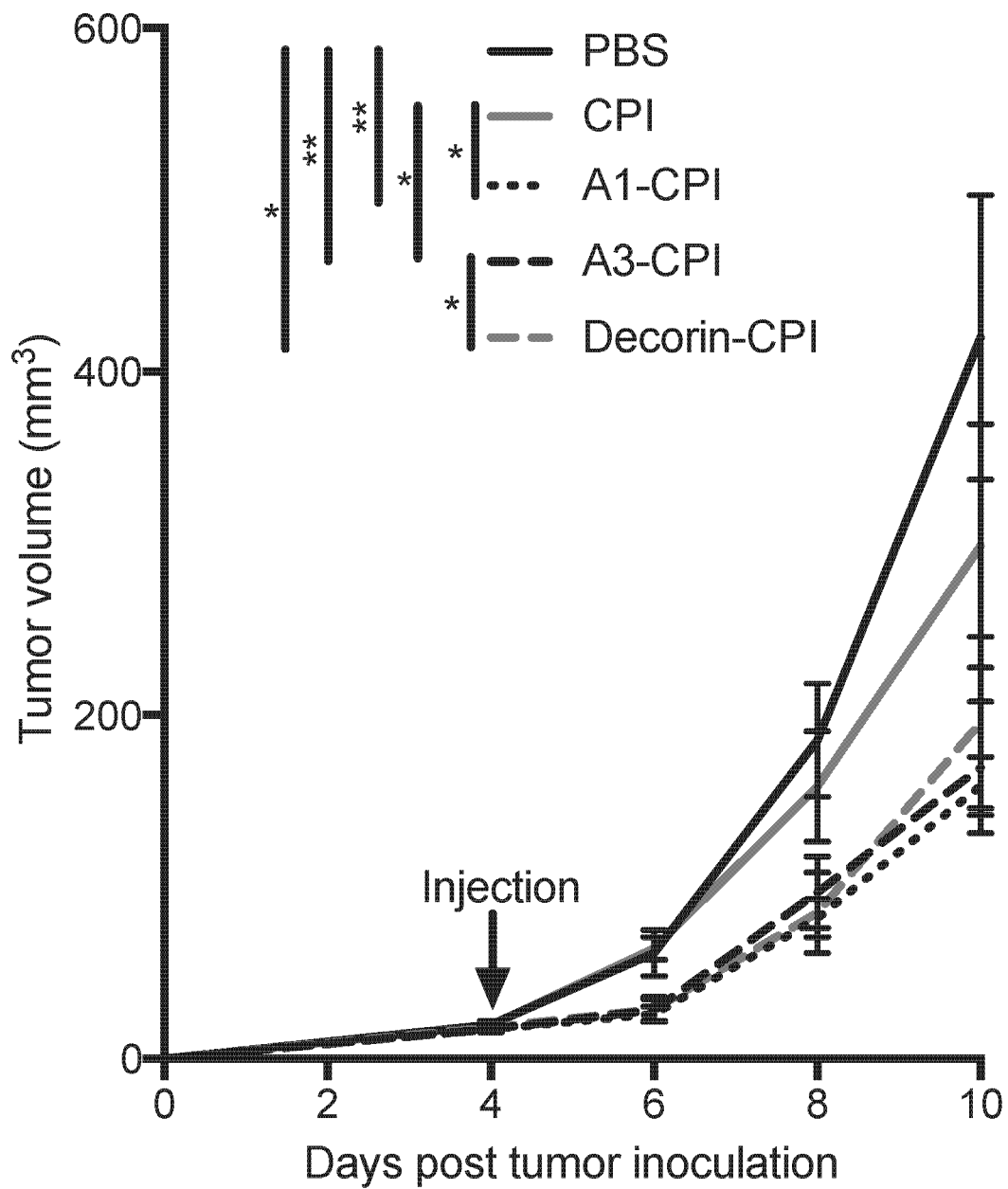

FIG. 44. Decorin and vWF A1 peptides conjugated to CPI have enhanced antitumor activity. PBS or one of four treatments were administered i.v.: (1) vWF A1-αCTLA4 and vWF A1-αPD-L1 (25 µg each); (2) vWF A3-αCTLA4 and vWF A3-αPD-L1 (25 µg each); (3) decorin-αCTLA4 and decorin-αPD-L1 (25 µg each); and (4) αCTLA4 and αPD-L1 (100 µg each). Tumor volume (mean±SEM) until the first mouse died is shown. Two experimental replicates. *p<0.05; **p<0.01.

DETAILED DESCRIPTION

Immunotherapeutic antibodies have been shown to exhibit considerable anti-tumor activity, but previous studies have reported instances of severe treatment-related adverse events. The methods and compositions described herein provide for localized therapy with an antibody that is retained intra- or peri-tumorally, limiting systemic exposure and reducing side-effects that, in some cases, can be so severe that either the therapy has to be discontinued or an effective dose that is also tolerable is not achieved. The examples provided herein demonstrate enhanced tissue retention and lower antibody concentrations in blood plasma following ECM-affinity peptide conjugation, reducing systemic side effects such as liver damage. Peri-tumoral (p.t.) injections of the compositions described herein significantly delayed tumor growth, prolonging survival compared to controls in mouse models for melanoma and breast cancer. This translatable approach of engineered ECM-binding antibodies represent a novel approach in immunotherapy.

A. Immunotherapeutic Antibodies

The immunotherapeutic antibodies of the disclosure include CD40 and immune checkpoint inhibitor antibodies. As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the term antibody includes a heavy and light chain of an antibody and immunological portions thereof. The phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

An "immune checkpoint inhibitor" is any molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation, such as with chronic viral infection, for example, immune checkpoint pathways can suppress the immune response and lead to immune exhaustion. Examples of immune checkpoint pathways include, without limitation, PD-1/PD-L1, CTLA4/B7-1, TIM-3, LAG3, By-He, H4, HAVCR2, ID01, CD276, VISTA, VTCN1, ICOS, CD39, TIGIT, CD47, KIR, and BTLA. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Examples of immune checkpoint inhibitors can be found, for example, in WO2014/144885. Such immune checkpoint inhibitors are incorporated by reference herein.

PD-1 (also known as CD279) is a cell surface receptor from the Ig superfamily that is expressed on T cells and pro-B cells. PD-1 acts as an immune checkpoint, which upon binding of one of its ligands, PD-L1 or PD-L2, inhibits the activation of T cells. Therefore, overexpression of PD-L1 or PD-L2 in the tumoral microenvironment leads to the inhibition of the intratumoral immune responses. Anti-PD-1/PD-L1 antibodies interfere with ligand binding and thus inhibit the deactivation of T cells.

CTLA-4, also known as CD152, is a protein receptor on the surface of T cells. When bound to CD80 (B7-1) and CD86 (B7-2) present on the surface of antigen presenting cells, CTLA-4 deactivates the T cells. Blocking CTLA-4 by means of an antagonistic antibody interferes with this mechanism and thus preserves the activity of the T cells.

Further immune checkpoint inhibitors are inhibitors to indoleamine 2,3-dioxygenase (IDO), TIM3, Lymphocyte-activation gene 3 (LAG3), Tigit, B- and T-lymphocyte attenuator (BTLA), VISTA, ICOS, CD39, KIRs, and CD47.

In some embodiments of any one of the methods, compositions or kits provided, the immune checkpoint inhibitor is a polypeptide that inhibits an immune checkpoint pathway. In some embodiments of any one of the methods, compositions or kits provided, the inhibitor is a fusion protein. In some embodiments of any one of the methods, compositions or kits provided, the immune checkpoint inhibitor is a humanized monoclonal antibody. In some embodiments, the checkpoint inhibitor is a human antibody.

Non-limiting examples of immune checkpoint inhibitors include fully human monoclonal antibodies, such as RG7446, BMS-936558/MDX-1106, BMS-936559 (anti-PDL1 antibody), Yervoy/ipilimumab (anti-CTLA-4 checkpoint inhibitor), and Tremelimumab (CTLA-4 blocking antibody); humanized antibodies, such as pidilizumab (CT-011, CureTech Ltd.) and Keytruda/Pembrolizumab (MK-3475, Merck, PD-1 blocker); and fusion proteins, such as AMP-224 (Merck). Other examples of checkpoint inhibitors include PD-L1 monoclonal antibody Anti-B7-H1 (MEDI4736/durvalumab), Nivolumab (BMS-936558, Bristol-Myers Squibb, anti-PD1 antibody), CT-011 (anti-PD1 antibody), BY55 monoclonal antibody, MPLDL3280A/atezolizumab (anti-PDL1 antibody), and MSB0010718C/avelumab (anti-PDL1 antibody), MDX-1105 (Medarex), MPDL3280A (Genentech), Anti-KIR antibodies such as lirlumab (Innate Pharma) and IPH2101 (Innate Pharma) may perform similar functions in NK cells. Further examples of immune checkpoint inhibitors include an IDO inhibitor (epacadostat), a TIM3 antibody (MBG453), an anti-LAG3 monoclonal antibody (LAG525), BMS-986016 (a further anti-LAG3 antibody), JNJ-61610588 (a fully human IgG1 Kappa anti-VISTA), MEDI-570 (a monoclonal antibody for ICOS), and OREG-103/BY40 (a CD39-blocking antibody). Further immune checkpoint inhibitors are described in WO2010027423, WO2010027828, WO2012145493, WO2014179664, WO2011159877, WO2015112900, WO2010029434, WO2010029435, WO2012135408, WO2010089411, WO2015200119, WO2015036394, WO2015112800, WO2015058573, WO2011110604, WO2015195163, WO2015112805, WO2015181342, WO2014100079, WO2014055897, WO2010036959, WO2016011160, WO2015155738, WO2015119930, WO2015119923, WO2013019906, WO2013181452, WO2015119944, WO2015088847, WO2015009856, WO2015103602, WO2015095404, WO2015095423, WO2015095410, WO2012120125, WO2014207064, WO2010097597, WO2012142237, WO2014150677, WO2014150646, WO2015031295, WO2015006520, WO2015002918, and WO2011045340.

Non-limiting examples of immunotherapeutic antibodies that may be included in the compositions disclosed herein, used in the methods disclosed herein, and/or linked or conjugated to an ECM-affinity peptide include Abciximab Adalimumab, Alemtuzumab, Alirocumab, Atezolizumab, Avelumab, Basiliximab, Belimumab, Bevacizumab, Bezlotoxumab, Blinatumomab, Brentuximab vedotin, Brodalumab, Canakinumab, Capromab pendetide, Catumaxomab, Certolizumab pegol, Cetuximab, Cixutumumab, Daclizumab, Daratumumab, Denosumab, Dinutuximab, Dupilumab, Durvalumab, Eculizumab, Elotuzumab, Ertumaxomab, Etaracizumab, Evolocumab, Gemtuzumab ozogamicin, Girentuximab, Golimumab, Guselkumab, Ibritumomab tiuxetan, Idarucizumab, Imciromab, Infliximab, Ipilimumab, Ixekizumab, Mepolizumab, Natalizumab, Necitumumab, Nivolumab, Obiltoxaximab, Obinutuzumab, Ocrelizumab, Ofatumumab, Olaratumab, Omalizumab, Palivizumab, Panitumumab, Pembrolizumab, Pertuzumab, Ramucirumab, Ranibizumab, Raxibacumab, Reslizumab, Rituximab, Rovelizumab, Ruplizumab, Secukinumab, Siltuximab, Tocilizumab, Tositumomab, Trastuzumab, Trastuzumab emtansine, Ustekinumab, Vedolizumab, Etanercept, and MK-3475.

B. ECM-Affinity Peptides

Embodiments of the disclosure relate to ECM-affinity peptides. In some embodiments, the ECM-affinity peptide comprises a peptide from PlGF-2. PlGF-2 has the following sequence:

PlGF2:

(SEQ ID NO: 4)
MPVMRLFPCFLQLLAGLALPAVPPQQWALSAGNGSSEVEVVPFQEVWGRSY

CRALERLVDVVSEYPSEVEHMFSPSCVSLLRCTGCCGDENLHCVPVETANV

TMQLLKIRSGDRPSYVELTFSQHVRCECRPLREKMKPERRRPKGRGKRRRE

KQRPTDCHLCGDAVPRR.

Exemplary PlGF-2 ECM affinity peptides include:

(SEQ ID NO: 5)
RRRPKGRGKRRREKQRPTDCHLCGDAVPRR;

(SEQ ID NO: 1)
RRRPKGRGKRRREKQRPTDCHL;

(SEQ ID NO: 6)
RRPKGRGKRRREKQRPTD;

(SEQ ID NO: 7)
RRRPKGRGKRRREKQ;

(SEQ ID NO: 8)
GKRRREKQ;

(SEQ ID NO: 9)
RRRPKGRG;
and (SEQ ID NO: 10)
RRKTKGKRKRSRNSQTEEPHP.

In some embodiments, the ECM-affinity peptide is a peptide from CXCL-12γ. The sequence of CXCL-12γ is the following: CXCL-12γ: KPVSLSYRCPCRFFESH-VARANVKHLKILNTPNCALQIVARLKNNNRQV-CIDPKLKW IQEYLEKALNKGR-REEKVGKKEKIGKKKRQKKRKAAQKRKN (SEQ ID NO:12). An exemplary peptide includes all or part of SEQ ID NO:12 and the following peptide:

(SEQ ID NO: 2)
GRREEKVGKKEKIGKKKRQKKRKAAQKRKN.

In some embodiments, the ECM-affinity peptide is a peptide from von Willebrand factor (VWF). The sequence of human VWF comprises the following: MIPARFAGVL LALALILPGT LCAEGTRGRS STARCSLFGS DFVNTFDGSM YSFAGYCSYL LAGGCQKRSF SIIGDFQNGK RVSLSVYLGE FFDIHLFVNG TVTQGDQRVS MPYASKGLYL ETEAGYYKLS GEAYGFVARI DGSGNFQVLL SDRYFNKTCG LCGNFNIFAE DDFMTQEGTL TSDPYDFANS WALSSGEQWC ERASPPSSSC NISSGEMQKG LWEQCQLLKS TSVFARCHPL VDPEPFVALC EKTLCECAGG LECACPALLE YARTCAQEGM VLYGWTDHSA CSPVCPAGME YRQCVSPCAR TCQSLHINEM CQERCVDGCS CPEGQLLDEG LCVESTECPC VHSGKRYPPG TSLSRDCNTC ICRNSQWICS NEECPGECLV TGQSHFKSFD NRYFTFSGIC QYLLARDCQD HSFSIVIETV QCADDRDAVC TRSVTVRLPG LHNSLVKLKH GAGVAMDGQD VQLPLLKGDL RIQHTVTASV RLSYGEDLQM DWDGRGRLLV KLSPVYAGKT CGLCGNYNGN QGDDFLTPSG LAEPRVEDFG NAWKLHGDCQ DLQKQHSDPC ALNPRMTRFS EEACAVLTSP TFEACHRAVS PLPYLRNCRY DVCSCSDGRE CLCGALASYA AACAGRGVRV AWREPGRCEL NCPKGQVYLQ CGTPCNLTCR SLSYPDEECN EACLEGCFCP PGLYMDERGD CVPKAQCPCY YDGEIFQPED IFSDHHTMCY CEDGFMHCTM SGVPGSLLPD AVLSSPLSHR SKRSLSCRPP MVKLVCPADN LRAEGLECTK TCQNYDLECM SMGCVSGCLC PPGMVRHENR CVALERCPCF HQGKEYAPGE TVKIGCNTCV CRDRKWNCTD HVCDATCSTI GMAHYLTFDG LKYLFPGECQ YVLVQDYCGS NPGTFRILVG NKGCSHPSVK CKKRVTILVE GGEIELFDGE VNVKRPMKDE THFEVVESGR YIILLLGKAL SVVWDRHLSI SVVLKQTYQE KVCGLCGNFD GIQNNDLTSS NLQVEEDPVD FGNSWKVSSQ CADTRKVPLD SSPATCHNNI MKQTMVDSSC RILTSDVFQD CNKLVDPEPY LDVCIYDTCS CESIGDCACF CDTIAAYAHV CAQHGKVVTW RTATLCPQSC EERNLRENGY ECEWRYNSCA PACQVTCQHP EPLACPVQCV EGCHAHCPPG KILDELLQTC VDPEDCPVCE VAGRRFASGK KVTLNPSDPE HCQICHCDVV NLTCEACQEP GGLVVPPTDA PVSPTTLYVE DISEPPLHDF YCSRLLDLVF LLDGSSRLSE AEFEVLKAFV VDMMERLRIS QKWVRVAVVE YHDGSHAYIG LKDRKRPSEL RRIASQVKYA GSQVASTSEV LKYTLFQIFS KIDRPEASRI TLLLMASQEP QRMSRNFVRY VQGLKKKKVI VIPVGIGPHA NLKQIRLIEK QAPENKAFVL SSVDELEQQR DEIVSYLCDL APEAPPPTLP PDMAQVTVGP GLLGVSTLGP KRNSMVLDVA FVLEGSDKIG EADFNRSKEF MEEVIQRMDV GQDSIHVTVL QYSYMVTVEY PFSEAQSKGD ILQRVREIRY QGGNRTNTGL ALRYLSDHSF LVSQGDREQA PNLVYMVTGN PASDEIKRLP GDIQVVPIGV GPNANVQELE RIGWPNAPIL IQDFETLPRE APDLVLQRCC SGEGLQIPTL SPAPDCSQPL DVILLLDGSS SFPASYFDEM KSFAKAFISK ANIGPRLTQV SVLQYGSITT IDVPWNVVPE KAHLLSLVDV MQREGGPSQI GDALGFAVRY LTSEMHGARP GASKAVVILV TDVSVDSVDA AADAARSNRV TVFPIGIGDR YDAAQLRILA GPAGDSNVVK LQRIEDLPTM VTLGNSFLHK LCSGFVRICM DEDGNEKRPG DVWTLPDQCH TVTCQPDGQT LLKSHRVNCD RGLRPSCPNS QSPVKVEETC GCRWTCPCVC TGSSTRHIVT FDGQNFKLTG SCSYVLFQNK EQDLEVILHN GACSPGARQG CMKSIEVKHS ALSVELHSDM EVTVNGRLVS VPYVGGNMEV NVYGAIMHEV RFNHLGHIFT FTPQNNEFQL QLSPKTFASK TYGLCGICDE NGANDFMLRD GTVTTDWKTL VQEWTVQRPG QTCQPILEEQ CLVPDSSHCQ VLLLPLFAEC HKVLAPATFY AICQQDSCHQ EQVCEVIASY AHLCRTNGVC VDWRTPDFCA MSCPPSLVYN HCEHGCPRHC DGNVSSCGDH PSEGCFCPPD KVMLEGSCVP EEACTQCIGE DGVQHQFLEA WVPDHQPCQI CTCLSGRKVN CTTQPCPTAK APTCGLCEVA RLRQNADQCC PEYECVCDPV SCDLPPVPHC ERGLQPTLTN PGECRPNFTC ACRKEECKRV SPPSCPPHRL PTLRKTQCCD EYECACNCVN STVSCPLGYL ASTATNDCGC TTTTCLPDKV CVHRSTIYPV GQFWEEGCDV CTCTDMEDAV MGLRVAQCSQ KPCEDSCRSG FTYVLHEGEC CGRCLPSACE VVTGSPRGDS QSSWKSVGSQ WASPENPCLI NECVRVKEEV FIQQRNVSCP QLEVPVCPSG FQLSCKTSAC CPSCRCERME ACMLNGTVIG PGKTVMIDVC TTCRCMVQVG VISGFKLECR KTTCNPCPLG YKEENNTGEC CGRCLPTACT IQLRGGQIMT LKRDETLQDG CDTHFCKVNE RGEYFWEKRV TGCPPFDEHK CLAEGGKIMK IPGTCCDTCE EPECNDITAR LQYVKVGSCK SEVEVDIHYC QGKCASKAMY SIDINDVQDQ CSCCSPTRTE PMQVALHCTN GSVVYHEVLN AMECKCSPRK CSK (SEQ ID NO:13). In some embodiments, the peptide is from the VWF A3 domain. The VWF A3 domain is derived from the human sequence, residues 1670-1874 (907-1111 of mature VWF) and has the following sequence: CSGEGLQIPTLSPAPDCSQPLDVILLLDGSSSFPASYFDEMKSFAKAFISKANIGPRLTQVSVLQYGSITTIDVPWNVVPEKAHLLSLVDVMQREGGPSQIGDALGFAVRYLTSEMHGARPGASKAVVILVTDVSVDSVDAAADAARSNRVTVFPIGIGDRYDAAQLRILAGPAGDSNVVKLQRIEDLPTMVTLGNSFLHKLCSG (SEQ ID NO:3). In some embodiments, the peptide comprises residues 1686-1881 (923-1118 of mature VWF), which has the following sequence: CSQPLDVILLLDGSSSFPASYFDEMKSFAKAFISKANIGPRLTQVSVLQYGSITTIDVPWNVVPEKAHLLSLVDVMQREGGPSQIGDALGFAVRYLTSEMHGARPGASKAVVILVTDVSVDSVDAAADAARSNRVTVFPIGIGDRYDAAQLRILAGPAGDSNVVKLQRIEDLPTMVTLGNSFLHKLCSGFVRICTG (SEQ ID NO:14). Exemplary peptides include all or part of SEQ ID NO:13, all or part of SEQ ID NO:3, or all or part of SEQ ID NO:14. In some embodiments, the peptide is from the VWF A1 domain. The VWF A1 domain is derived from the human sequence, residues 1237-1458 (474-695 of mature VWF) and has the following sequence:

(SEQ ID NO: 11)

```
CQEPGGLVVPPTDAPVSPTTLYVEDISEPPLHDFYCSRLLDLVFLLDGSSR

LSEAEFEVLKAFVVDMMERLRISQKWVRVAVVEYHDGSHAYIGLKDRKRPS

ELRRIASQVKYAGSQVASTSEVLKYTLFQIFSKIDRPEASRITLLLMASQE

PQRMSRNFVRYVQGLKKKKVIVIPVGIGPHANLKQIRLIEKQAPENKAFVL

SSVDELEQQRDEIVSYLC.
```

In some embodiments, the ECM-affinity peptide is from decorin. The decorin peptide may comprise residues 17-359, which has the following sequence: GPFQQRGLFDFMLEDEASGIGPEVPDDRDFEPSLGPVCPFRCQCHLRVVQCSDLGLDKVPKDLPPDTTLLDLQNNKITEIKDGDFKNLKNLHALILVNNKISKVSPGAFTPLVKLERLYLSKNQLKELPEKMPKTLQELRAHENEITKVRKVTFNGLNQMIVIELGTNPLKSSGIENGAFQGMKKLSYIRIADTNITSIPQGLPPSLTELHLDGNKISRVDAASLKGLNNLAKLGLSFNSISAVDNGSLANTPHLRELHLDNNKLTRVPGGLAEHKYIQVVYLHNNNISVVGSSDFCPPGHNTKKASYSGVSLFSNPVQYWEIQP- STFRCVYVRSAIQLGNYK (SEQ ID NO:16). Exemplary peptides include all or part of SEQ ID NO:16.

The ECM-affinity peptide may be a peptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to a peptide of the disclosure. The peptide or polypeptide may have one or more conservative or non-conservative substitutions. Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The polypeptides described herein may include 1, 2, 3, 4, 5, 6, 7, 8, 9, 10, 11, 12, 13, 14, 15, or more (or any derivable range therein) variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of a peptide or polypeptide of the disclosure.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein of a peptide or polypeptide of the disclosure.

The polypeptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein).

A linker sequence may be included in the antibody-peptide construction. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate that antibody and the peptide.

The ECM-affinity peptides of the disclosure may have affinity to one or more components of the extracellular matrix such as fibronectin, collagen, (collagen type I, collagen type III, and/or collagen type IV), tenascin C, fibrinogen, and fibrin.

C. Nucleic Acids

In certain embodiments, the current disclosure concerns recombinant polynucleotides encoding the proteins, polypeptides, and peptides of the invention, such as ECM-affinity peptide operatively linked to immunotherapeutic antibodies. Therefore, certain embodiments relate to nucleotides encoding for an ECM-affinity polypeptide and/or an ECM-affinity polypeptide fused to an immunotherapeutic antibody, or fragment thereof, such as the heavy or light chain.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences.

Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode a polypeptide or peptide of the disclosure. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a polypeptide or peptide of the disclosure.

The nucleic acid segments used in the current disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, the current disclosure provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

The disclosure also contemplates the use of polynucleotides which are complementary to all the above described polynucleotides.

1. Vectors

Polypeptides of the disclosure may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a polypeptide of the disclosure, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

2. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI)×/poly(rc) (Tavernier et al., 1983); Adenovirus 5 E2—E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MEW Class I Gene H-2κb—Interferon (Blanar et al., 1989); HSP70—E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone a Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

3. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

4. Selectable and Screenable Markers

In certain embodiments of the invention, cells containing a nucleic acid construct of the current disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

5. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

6. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name Bac-to-Bac® Baculovirus Expression System from ThermoFisher and BacPAK™ Baculovirus Expression System from Takara®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from ThermoFisher®, which carries the T-REx™ (tetracycline-regulated expression) System, an inducible mammalian expression system that uses the full-length CMV promoter. ThermoFisher® also provides a yeast expression system designed for high-level production of recombinant proteins in the yeast genus Pichia. One of skill in the art would know how to express a vector, such as an expression construct, to produce a nucleic acid sequence or its cognate polypeptide, protein, or peptide.

D. Combination Therapy

The compositions and related methods of the present disclosure, particularly administration of and ECM-affinity peptide operatively linked to an immunotherapeutic antibody may also be used in combination with the administration of additional therapies such as the additional therapeutics described herein or in combination with other traditional therapeutics known in the art.

The therapeutic compositions and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent, chemotherapeutic, or checkpoint inhibitor described herein or known in the art is "B".

| | | | | | |
|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In some embodiments, more than one course of therapy may be employed. It is contemplated that multiple courses may be implemented.

1. Chemotherapeutics

The term "chemotherapeutic agent," refers to a therapeutic compound and/or drug which may be used to, among other things, treat cancer. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication.

Suitable classes of chemotherapeutic agents include (a) alkylating agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) natural products, such as *vinca* alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) miscellaneous agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some embodiments, cisplatin is a particularly suitable chemotherapeutic agent.

Other suitable chemotherapeutic agents include antimicrotubule agents, e.g., Paclitaxel ("Taxol") and doxorubicin hydrochloride ("doxorubicin").

Nitrogen mustards are another suitable chemotherapeutic agent useful in the methods of the disclosure. A nitrogen mustard may include, but is not limited to, mechlorethamine ($HN_2$), cyclophosphamide and/or ifosfamide, melphalan (L-sarcolysin), and chlorambucil. Cyclophosphamide, available from West-Ward, is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

Actual dosage levels of the active ingredients in the methods of this disclosure may be varied so as to obtain an amount of the active ingredient which is effective to achieve the desired therapeutic response for a particular patient, composition and mode of administration, without being toxic to the patient. The selected dosage level will depend upon a variety of factors, including the activity of the chemotherapeutic agent selected, the route of administration, the time of administration, the rate of excretion of the chemotherapeutic agent, the duration of the treatment, other drugs, compounds and/or materials used in combination with the particular chemotherapeutic agent, the age, sex, weight, condition, general health and prior medical history of the patient being treated, and like factors well known in the medical arts.

It is envisioned that combining the effects of chemotherapy and the expression of the therapeutic polypeptide may enhance the antitumor effect of each of these agents if used alone (i.e., if the therapeutic polypeptide is administered directly, and not induced by the presence of the chemotherapeutic agent). A physician having ordinary skill in the art can readily determine and prescribe the effective amount of the construct and the chemotherapeutic agent required. For example, the physician could start doses of the construct and/or chemotherapy at levels lower than that required in order to achieve the desired therapeutic effect and gradually increase the dosage until the desired effect is achieved.

2. Ionizing Radiation

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Gray and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein). In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

In some embodiments, an IR regimen and/or total IR dose is prescribed by a doctor or attending medical professional. The medical professional may monitor and/or access the progress of the patient throughout the administration of the IR and/or the medical professional may access the patient at the completion of the administration of the prescribed IR dose and prescribe a new dose/regimen of IR based on the assessment.

3. Additional Agents

In some embodiments, the method further comprises administration of an additional agent. In some embodiments, the additional agent is an immunostimulator. The term "immunostimulator" as used herein refers to a compound that can stimulate an immune response in a subject, and may include an adjuvant. In some embodiments, an immunostimulator is an agent that does not constitute a specific antigen, but can boost the strength and longevity of an immune response to an antigen. Such immunostimulators may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherichia coli, Salmonella minnesota, Salmonella typhimurium*, or *Shigella flexneri* or specifically with MPL® (ASO4), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+squalene+MPL.), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the additional agent comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9; preferably the recited immunostimulators comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the additional agents also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, additional agents may be proinflammatory stimuli released from necrotic cells (e.g., urate crystals). In some embodiments, additional agents may be activated components of the complement cascade (e.g., CD21, CD35, etc.). In some embodiments, additional agents may be activated components of immune complexes. Additional agents also include complement receptor agonists, such as a molecule that binds to CD21 or CD35. In some embodiments, the complement receptor agonist induces endogenous complement opsonization of the synthetic nanocarrier. In some embodiments, immunostimulators are cytokines, which are small proteins or biological factors (in the range of 5 kDa-20 kDa) that are released by cells and have specific effects on cell-cell interaction, communication and behavior of other cells. In some embodiments, the cytokine receptor agonist is a small molecule, antibody, fusion protein, or aptamer.

In some embodiments, the additional agent is an antibody-drug conjugate. In some embodiments, the antibody-drug conjugate is selected from gemtuzumab ozogamicin, brentuximab vedotin, and trastuzumab emtansine.

In some embodiments, the additional agent is a chimeric antigen receptor (CAR). CARs are artificial T cell receptors which graft a specificity onto an immune effector cell. The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal.

E. Therapeutic Methods

The current methods and compositions relate to methods for treating cancer. In some embodiments, the cancer comprises a solid tumor. In some embodiments, the cancer is non-lymphatic. In some embodiments, the cancer is breast cancer or melanoma.

The compositions of the disclosure may be used for in vivo, in vitro, or ex vivo administration. The route of administration of the composition may be, for example, intratumoral, intracutaneous, subcutaneous, intravenous, intralymphatic, and intraperitoneal administrations. In some embodiments, the administration is intratumoral or intralymphatic or peri-tumoral. In some embodiments, the compositions are administered directly into a cancer tissue or a lymph node.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The cancers amenable for treatment include, but are not limited to, tumors of all types, locations, sizes, and characteristics. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, specific breast cancers such as ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, Paget's disease of the nipple, phyllodes tumors of the breast, recurrent and/or metastatic breast, cancer, luminal A or B breast cancer, triple-negative/basal-like breast cancer, and HER2-enriched breast cancer, lymphoid cancer, bronchial adenomas/carcinoids, tracheal cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal germ cell tumor, extrahepatic bile duct cancer, eye cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood salivary gland cancer sarcoma, Ewing family of tumors, Kaposi sarcoma, soft tissue sarcoma, uterine Sézary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

F. Pharmaceutical Compositions and Methods

In some embodiments, pharmaceutical compositions are administered to a subject. Different aspects involve administering an effective amount of a composition to a subject. In some embodiments, a composition comprising an inhibitor may be administered to the subject or patient to treat cancer or reduce the size of a tumor. Additionally, such compounds can be administered in combination with an additional cancer therapy.

Compositions can be formulated for parenteral administration, e.g., formulated for injection via the intravenous, transcatheter injection, intraarterial injection, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The preparation of such formulations will be known to those of skill in the art in light of the present disclosure. Other routes of administration include intratumoral, peri-tumoral, intralymphatic, injection into cancer tissue, and injection into lymph nodes. In some embodiments, the administration is systemic.

Other routes of administration are also contemplated. For example, the constructs and agents may be administered in association with a carrier. In some embodiments, the carrier is a nanoparticle or microparticle. In some embodiments, the nanoparticle or microparticle is a tumor directed nanoparticle or microparticle. For example, the carrier may further comprise a targeting moiety that directs the carrier to the tumor. The targeting moiety may be a binding agent (e.g. antibody, including scFv, etc. or other antigen binding agent) that specifically recognizes tumor cells. In some embodiments, the construct is enclosed within the carrier. In some embodiments, the construct is covalently or non-covalently attached to the surface of the carrier. In some embodiments, the carrier is a liposome.

Particles can have a structure of variable dimension and known variously as a microsphere, microparticle, nanoparticle, nanosphere, or liposome. Such particulate formulations can be formed by covalent or non-covalent coupling of the construct to the particle.

By "particle," "microparticle," "bead," "microsphere," and grammatical equivalents herein is meant small discrete particles that are administrable to a subject. In certain embodiments, the particles are substantially spherical in shape. The term "substantially spherical," as used herein, means that the shape of the particles does not deviate from a sphere by more than about 10%.

The particles typically consist of a substantially spherical core and optionally one or more layers. The core may vary in size and composition. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired particle diameter), these layers typically being applied on the outer surface of the particle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference in its entirety.

As previously stated, the particle may, in addition to the core, include one or more layers. The purposes for including layers in the microparticle may vary. Alternatively, the surface of the particle may be functionalized directly. A layer may provide suitable surfaces for attaching chemical functionalities for chemical binding or coupling sites.

Layers can be produced on the microparticles in a variety of ways known to those skilled in the art. Examples include sol-gel chemistry techniques such as described in Iler (1979); Brinker and Scherer (1990). Additional approaches to producing layers on particles include surface chemistry and encapsulation techniques such as described in Partch and Brown (1998); Pekarek et al. (1994); Hanprasopwattana (1996); Davies (1998); and references therein. Vapor deposition techniques may also be used; see for example Golman and Shinohara (2000); and U.S. Pat. No. 6,387,498. Still other approaches include layer-by-layer self-assembly techniques such as described in Sukhorukov et al. (1998); Caruso et al. (1998); Caruso et al. (1999); U.S. Pat. No. 6,103,379 and references cited therein.

Particles may be formed by contacting an aqueous phase containing the construct and a polymer and a nonaqueous phase followed by evaporation of the nonaqueous phase to cause the coalescence of particles from the aqueous phase as taught in U.S. Pat. No. 4,589,330 or 4,818,542. Preferred polymers for such preparations are natural or synthetic copolymers or polymers selected from the group consisting of gleatin agar, starch, arabinogalactan, albumin, collagen, polyglycolic acid, polylactic acid, glycolide-L(-) lactide poly(epsilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic acid, glycolide-L(-) lactide poly(epsilon-caprolactone, poly(epsilon-caprolactone-CO-lactic acid), and poly(epsilon-caprolactone-CO-glycolic acid. Solvents useful for dissolving the polymer include: water, hexafluoroisopropanol, methylenechloride, tetrahydrofuran, hexane, benzene, or hexafluoroacetone sesquihydrate.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms of an infection have disappeared or been reduced.

II. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Extracellular Matrix-Binding Peptide Conjugation to Immune Checkpoint Blockade Antibodies Enhances Efficacy of Anti-Tumor Therapy Immune checkpoint blockade exhibits considerable anti-tumor activity, but previous studies have reported instances of severe treatment-related adverse events. The inventors sought to explore local immune checkpoint blockade, with an antibody (Ab) form that would be retained intra- or peri-tumorally, limiting systemic exposure. To accomplish this, an extracellular matrix (ECM)-super affinity peptide derived from placenta growth factor-2 ($PlGF-2_{123-144}$) was conjugated to checkpoint blockade Abs. This example demonstrates enhanced tissue retention and lower Ab concentrations in blood plasma following $PlGF-2_{123-144}$ conjugation, reducing systemic side effects such as liver damage. Peri-tumoral (p.t.) injections of $PlGF-2_{123-144}$-anti-CTLA4 and $PlGF-2_{123-144}$-anti-PD-L1 Abs significantly delayed tumor growth, prolonging survival compared to wild-type (wt) forms in murine melanoma and breast cancer models. These $PlGF-2_{123-144}$-Abs increase tumor-infiltrating activated $CD8^+$ and $CD4^+$ T cells, resulting in a delay of distant tumor growth as well. This translatable approach of engineered ECM-binding Abs presents a novel approach in checkpoint blockade.

Immune checkpoints are inhibitory pathways used by the immune system to protect host tissues from damage, particularly when the immune system is activated. Recently, malignant tumors have been shown to utilize these mechanisms to evade immune-mediated rejection. Based on this, immune checkpoint blockade has been demonstrated to be a promising approach for cancer therapy.

Cytotoxic T-lymphocyte antigen 4 (CTLA4, CD152) is a transmembrane protein expressed on regulatory T cells (Tregs) and activated $CD8^+$ T cells. It functions as an inducer of immune suppressive signals by binding to CD80 or CD86 on antigen-presenting cells (APCs). Thus, CTLA4 blocking antibodies (Abs) (αCTLA4) inhibit the inactivation of T cells. In the clinic, αCTLA4 (ipilimumab) treatment resulted in improved survival of melanoma patients. Some tumor cells express programmed death-ligand 1 (PD-L1, CD274, B7-H1), a key molecule in the pathway to evade immune response via binding to PD-1 on activated T cells. PD-L1 and PD-1 association results in decreased cytokine production, inhibition of proliferation, and apoptosis of T cells. Anti-PD-L1 (αPD-L1: atezolizumab, avelumab and durvalumab) blocking antibodies have shown antitumor efficacy against several types of cancer. Moreover, combination therapy using nivolumab (αPD-1) and ipilimumab showed significant prolongation of survival and has been approved by the US Food and Drug Administration (FDA) for treatment of advanced melanoma.

Clinical trials using multiple checkpoint blockage antibodies have been approved. However, 68.7% of patients showed grade 3 or 4 side effects. In particular, 36.4% of these patients could not continue with the therapy due to treatment-related adverse events. In terms of treatment efficacy, the objective response rate was 57.6%. Also, studies using an aggressive murine tumor model, B16F10 melanoma, reported that treatment with these Abs did not induce complete regression, suggesting room to improve their therapeutic effects.

Heparin binding domains (HBDs) that exist in several growth factors (GF) bind to a variety of extracellular matrix (ECM) proteins. By screening binding of GFs to a variety of ECM proteins, the inventors have discovered that the HBD of placenta growth factor-2 ($PlGF-2_{123-144}$) has exceptionally high affinities towards multiple ECM proteins. The inventors have shown that fusion of the $PlGF-2_{123-144}$-domain to GFs enhanced their tissue retention and therapeutic efficacy in mouse models of skin and bone regeneration. This example describes immune checkpoint blockade antibodies (or "Abs") conjugated with $PlGF-2_{123-144}$ peptide for cancer immunotherapy. It is hypothesized that the enhanced retention of checkpoint blockade Abs surrounding the tumor tissue would improve their anti-tumor efficacy by enhancing T cell activation and decreasing the side effects of therapy by lowering systemic exposure.

A. Results

1. $PlGF-2_{123-144}$ Peptide-Conjugated Abs Bind to ECM Proteins and their Targets.

First, the capacity of $PlGF-2_{123-144}$-conjugated Abs to bind ECM proteins in vitro was examined. After mixing IgG Abs with sulfo-sulfosuccinimidyl 4-(N-maleimidomethyl) cyclohexane-1-carboxylate (sulfo-SMCC), $PlGF-2_{123-144}$ peptide was crosslinked covalently to the Ab (FIG. 1A). SDS-PAGE revealed that molecular weights of both light and heavy chains of IgG were increased (FIG. 1B). An average of 6.3 and 6 $PlGF-2_{123-144}$ peptides were bound to monoclonal αCTLA4 (4F10) and monoclonal αPD-L1 respectively, as calculated by MALDI-TOF MS (FIG. 7). Both $PlGF-2_{123-144}$-αCTLA4 and $PlGF-2_{123-144}$-αPD-L1 bound to 8 different ECM proteins: fibronectin, fibrinogen, vitronectin, osteopontin, collagen type I, collagen type II, collagen type III, and collagen type IV. In comparison, neither wt αCTLA4 nor αPD-L1 bound to the tested ECM proteins (FIG. 1CD and FIG. 8). Strong binding affinities (nM range dissociation constant (Kd) values) of $PlGF-2_{123-144}$-αCTLA4 (9H10 and 4F10), and of $PlGF-2_{123-144}$-αPD-L1 against fibronectin and collagen type I, main components of skin ECM, were observed (FIG. 1E and FIG. 9). Importantly, $PlGF-2_{123-144}$-αCTLA4 and $PlGF-2_{123-144}$-αPD-L1 recognized their target antigens with similar Kd values to the wild-type (wt) forms (FIG. 1E and FIG. 10). FACS analysis also showed that $PlGF-2_{123-144}$-4F10 bound to a T cell hybridoma, and $PlGF-2_{123-144}$-αPD-L1 bound to B16F10 cells as well as their wt counterparts (FIG. 11). Taken together, these data showed that $PlGF-2_{123-144}$-Abs bind ECM proteins without impairment of their antigen recognition capacities.

2. $PlGF-2_{123-144}$-Abs Lose Affinities for ECM Proteins by Competition with Heparin or by Plasmin Cleavage.

Next, the release of $PlGF-2_{123-144}$-Abs from ECM proteins was examined. Addition of excess heparin reduces $PlGF-2_{123-144}$-IgG binding to fibronectin in a dose-dependent manner, consistent with previous observations (FIG. 12). Addition of plasmin deprived PlGF-2$_{123-144}$-IgG of its ECM binding activity accompanied by mobility sifts in SDS-PAGE (FIG. 1F and FIG. 13). These data suggest that PlGF-2$_{123-144}$-Abs can be released from ECM proteins either by heparin or by plasmin-mediated cleavage of a site within the PlGF-2$_{123-144}$ peptide.

3. PlGF-2$_{123-144}$-Abs are Retained Peri-Tumorally.

The tissue retention capacities of PlGF-2$_{123-144}$-Abs was then examined. Dense bovine collagen sheet was used as an in vitro tissue mimicking model and incubated with PlGF-2$_{123-144}$- or wt-αPD-L1. After 4 times of buffer changes, plasmin digestion released 47.1% of bound PlGF-2$_{123-144}$-αPD-L1, whereas <0.1% wt αPD-L1 was released, suggesting that PlGF-2$_{123-144}$-αPD-L1 was retained in the collagen matrix (FIG. 14). Next, histological analysis was performed to determine if PlGF-2$_{123-144}$-Abs remain at the injection site long-term after peri-tumoral (p.t.) injection through binding to endogenous ECMs in vivo. As a result, both PlGF-2$_{123-144}$-αCTLA4 and PlGF-2$_{123-144}$-αPD-L1 were detected within the tumor tissue 6 days after injection. In comparison, both wt αCTLA4 and wt αPD-L1 were not detected at this time point. Taken together, PlGF-2$_{123-144}$ conjugation enhanced tumor tissue retention of both αCTLA4 and αPD-L1 when injected p.t.

4. PlGF-2$_{123-144}$ Conjugation Decreases Treatment-Related Adverse Events.

Since PlGF-2$_{123-144}$-Abs displayed prolonged retention near the injection site, it was hypothesized that the concentrations of Abs in plasma would be lower compared to wt Abs. To test this hypothesis, the Ab concentrations in blood plasma over time were measured (FIG. 2A-B). After inoculation with B16F10 cells, mice were given a single administration (100 μg each) of αCTLA4 and αPD-L1 on day 4. Concentrations were highest in all groups on the first day after injection. Furthermore, injection of wt Abs via p.t. and intra-peritoneal (i.p.) administration routes showed similar blood plasma concentrations. The concentrations of both PlGF-2$_{123-144}$-Abs in blood plasma were significantly lower compared to their wt forms, and were barely detected 3 days after injection, suggesting that PlGF-2$_{123-144}$ conjugation may reduce systemic toxicity of αCTLA$^4$/αPD-L1. Next, side-effects were examined. αCTLA4 and αPD-L1 were administrated 4 and 7 days after tumor inoculation, then cytokine concentrations in serum and clinically used liver damage marker (i.e. alanine aminotransferase (ALT) activity) were examined. Wt Abs administration increased both TNFα and IFNγ concentrations in serum 2 days after the second injection, whereas PlGF-2$_{123-144}$-Abs did not (FIG. 2CD). Interestingly, IL2 serum concentration was maintained after both wt- and PlGF-2$_{123-144}$-Abs treatment (FIG. 2E). Additionally, Wt Abs, but not PlGF-2$_{123-144}$-Abs treatment, increased ALT activity in serum 2 days after the second injection (FIG. 2F). Additionally, histologic analysis showed that wt Abs induced lymphocytes infiltration and necrotic structures in the liver (FIG. 2G and FIG. 15). In contrast, the tissue structure was maintained following PlGF-2$_{123-144}$-conjugated Abs treatment. To further confirm the reduced systemic toxicity by PlGF-2$_{123-144}$ conjugation, we employed non-obese diabetic (NOD) mice, which reportedly develop auto-immune diabetes following αPD-L1 administration via αPD-L1 binding to islets cells. Wt αPD-L1 administration induced diabetes to all of 16 weeks old NOD male mice until day 6, whereas PlGF-2$_{123-144}$-αPD-L1 was 0% on 15 days after the initiation of Ab treatment (FIG. 2H). Taken together, these results indicated that PlGF-2$_{123-144}$ conjugation decreases systemic toxicity of checkpoint blockade Abs.

As another model to examine the influence of PlGF-2$_{123-144}$ conjugation on the reduction of toxicity, an anti-CD40 agonistic antibody (αCD40), known as an accelerator of APC maturation was used. Importantly, PlGF-2$_{123-144}$ conjugation to αCD40 did not impair its antigen recognition capacity and decreased concentration in blood plasma after p.t. injection (FIGS. 16-17). Wt αCD40 significantly increased ALT level compared to PBS-treated group, but PlGF-2$_{123-144}$-αCD40 did not (FIG. 18A). Histologic analysis of the liver showed that αCD40 induced marked morphological changes, as evidenced by hepatocyte necrosis and leukocyte infiltration (FIG. 18B). In contrast, the tissue structure was maintained following PlGF-2$_{123-144}$-αCD40 treatment. These results indicated that PlGF-2$_{123-144}$ conjugation decreases systemic toxicity of immune checkpoint Abs.

5. PlGF-2$_{123-144}$-Abs Significantly Suppress Growth of B16F10 Tumors Compared to Wt Abs.

The anti-tumor activity of PlGF-2$_{123-144}$-αCTLA4+PlGF-2$_{123-144}$-αPD-L1 combination therapy was examined. Four days after ovalbumin (OVA)-expressing B16F10 cell inoculation, αCTLA4+αPD-L1 (25 μg each/injection) were administered every 3 days for 3 doses. Neither i.p. nor p.t. injections of wt Abs exhibited anti-tumor effects at this dose and treatment regime. In contrast, p.t. administration of PlGF-2$_{123-144}$-αCTLA4+PlGF-2$_{123-144}$-αPD-L1 displayed a therapeutic effect, slowing tumor growth and prolonging survival (FIG. 3A-B). Importantly, administration of αCTLA4+αPD-L1+PlGF-2$_{123-144}$ peptide (without conjugation) did not display an anti-tumor effect, indicating that the conjugation of PlGF-2$_{123-144}$ to Abs is indispensable for this action. All single agent treatments of PlGF-2$_{123-144}$- or wt-, αCTLA4 or αPD-L1 exhibited similar growth curves as PBS-treatment controls (FIG. 19), suggesting that combination of PlGF-2$_{123-144}$-αCTLA4+PlGF-2$_{123-144}$-αPD-L1 administration is crucial. We repeated administration of both Abs using mice inoculated with wt B16F10 cells, i.e., lacking the OVA transgene. PlGF-2$_{123-144}$ combination Abs again extended survival and slowed tumor progression, whereas wt Abs did not (FIG. 3C-D). Higher doses (100 μg each/injection) combined with αCTLA4 clone 9H10, which induces Treg depletion, further suppressed tumor growth and extended survival (FIG. 3E-F). Even a single p.t. injection of PlGF-2$_{123-144}$-αCTLA4+PlGF-2$_{123-144}$-αPD-L1 led to significantly smaller tumor size (FIG. 20). Further increasing the dose (300 μg each, twice, then 100 μg each, twice) again slowed tumor growth in PlGF-2$_{123-144}$-Abs-treated group (FIG. 3G-H). Taken together, these data indicated that local treatment with PlGF-2$_{123-144}$-αCTLA4+PlGF-2$_{123-144}$-αPD-L1 mediate robust anti-tumor effects compared to their wt forms.

6. The numbers of tumor-infiltrating and activated CD8$^+$ T cells are increased by PlGF-2$_{123-144}$-αCTLA4+PlGF-2$_{123-144}$-αPD-L1 treatment.

Figure 22:
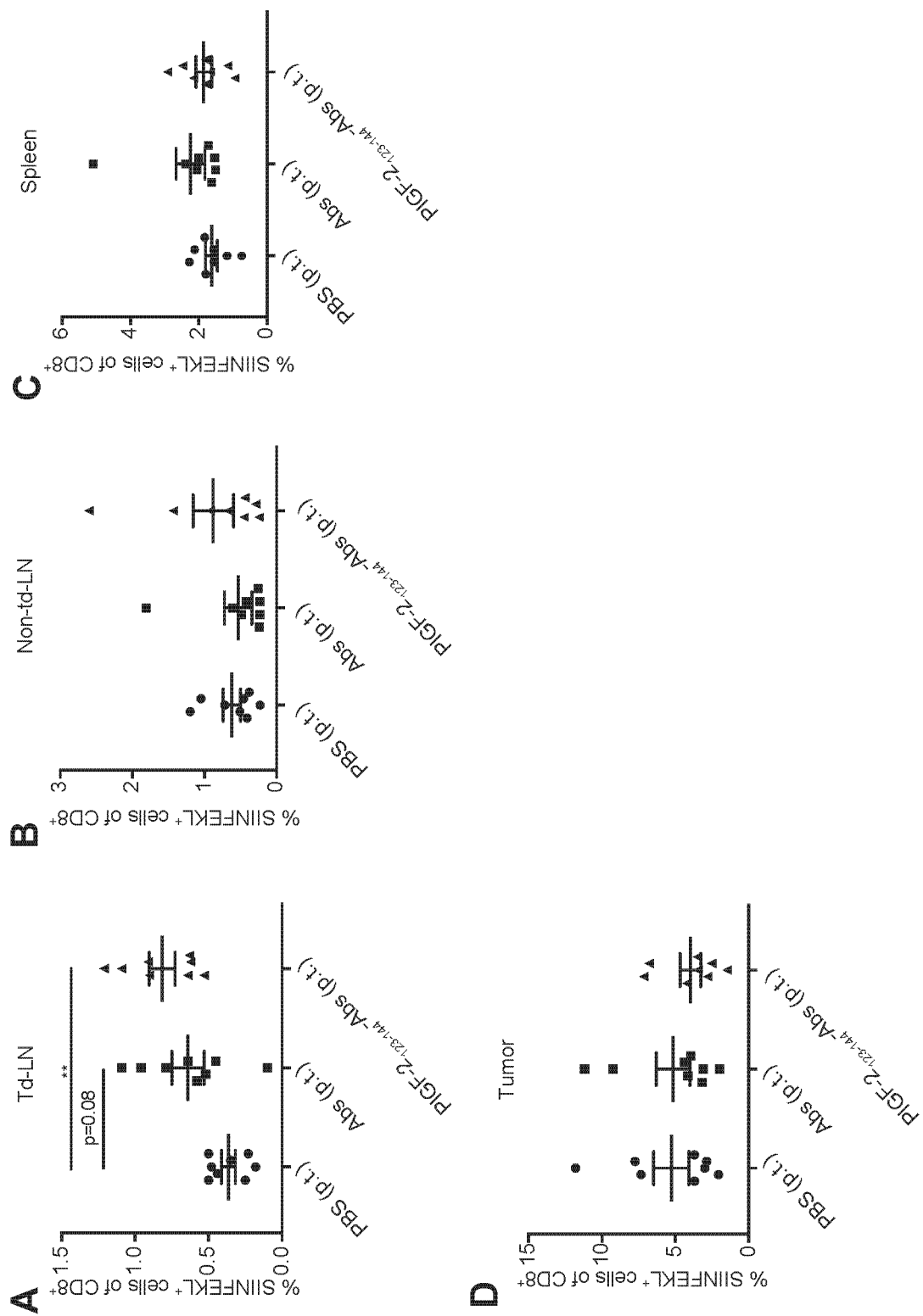

To determine the mechanism behind the therapeutic action of PlGF-2$_{123-144}$-Abs treatment, T cell responses were characterized in wt B16F10 tumor-bearing mice. Abs were injected twice p.t. or i.p., on day 4 and 7 after tumor inoculation. On day 8, leucocytes were extracted from the tumor, tumor-draining lymph node (td-LN), and spleen. PlGF-2$_{123-144}$-αCTLA4+PlGF-2$_{123-144}$-αPD-L1 significantly increased the number and the frequency of CD8$^+$ CD3$^+$ T cells within the tumor compared to wt Abs and PBS injections (FIG. 4AB). The percentages of the effector population (defined as CD62L$^+$ CD44$^+$) and PD-1$^+$ cells in CD8$^+$ T cells were increased compared to PBS treatment, indicating activation of CD8$^+$ T cells (FIG. 4CD). PlGF-2$_{123-144}$-combination Abs also increased the number of CD4$^+$ T cells in the tumor (FIG. 4EF). The percentage of effector CD4$^+$ T cells was also increased (FIG. 4G). Concurrently, the percentage of CD25$^+$ Foxp3$^+$ Tregs in the CD4$^+$ T cell population was maintained (FIG. 4H). To test whether tumor-infiltrating CD8$^+$ T cells could be activated to produce tumor suppressive cytokines, CD8$^+$ T cells were extracted and stimulated ex vivo using αCD3 and αCD28. Consequently, the PlGF-2$_{123-144}$-αCTLA4+PlGF-2$_{123-144}$-αPD-L1 treated group showed increased % of IFNγ$^+$, IL2$^+$, TNFα$^+$ and Gzmb$^+$ cells in CD8$^+$ tumor-infiltrating T cells compared to PBS treatment group (FIG. 4I-L). PlGF-2$_{123-144}$-αCTLA4+PlGF-2$_{123-144}$-αPD-L1 did not affect the percentages of Tregs and effector CD8$^+$ T cells in the td-LN and spleen, whereas central memory and PD-1$^+$ CD8$^+$ T cells were increased. This suggests that these PlGF-2$_{123-144}$-Ab treatments increased tumor-antigen-experienced T cells systemically (FIGS. 4M-P and FIG. 21). Finally, PlGF-2$_{123-144}$-αCTLA4+PlGF-2$_{123-144}$-αPD-L1 treatment increased OVA$_{257-264}$ antigen-specific CD8$^+$ T cells in td-LN, tested in the B16F10-OVA model (FIG. 22). Collectively, PlGF-2$_{123-144}$-αCTLA4+PlGF-2$_{123-144}$-αPD-L1 treatment effectively activates tumor-infiltrating T cells effectively, leading to the therapeutic effects observed in FIG. 3.

7. PlGF-2$_{123-144}$-Abs Treatment Induces Systemic Anti-Tumor Immunity.

Figure 23:
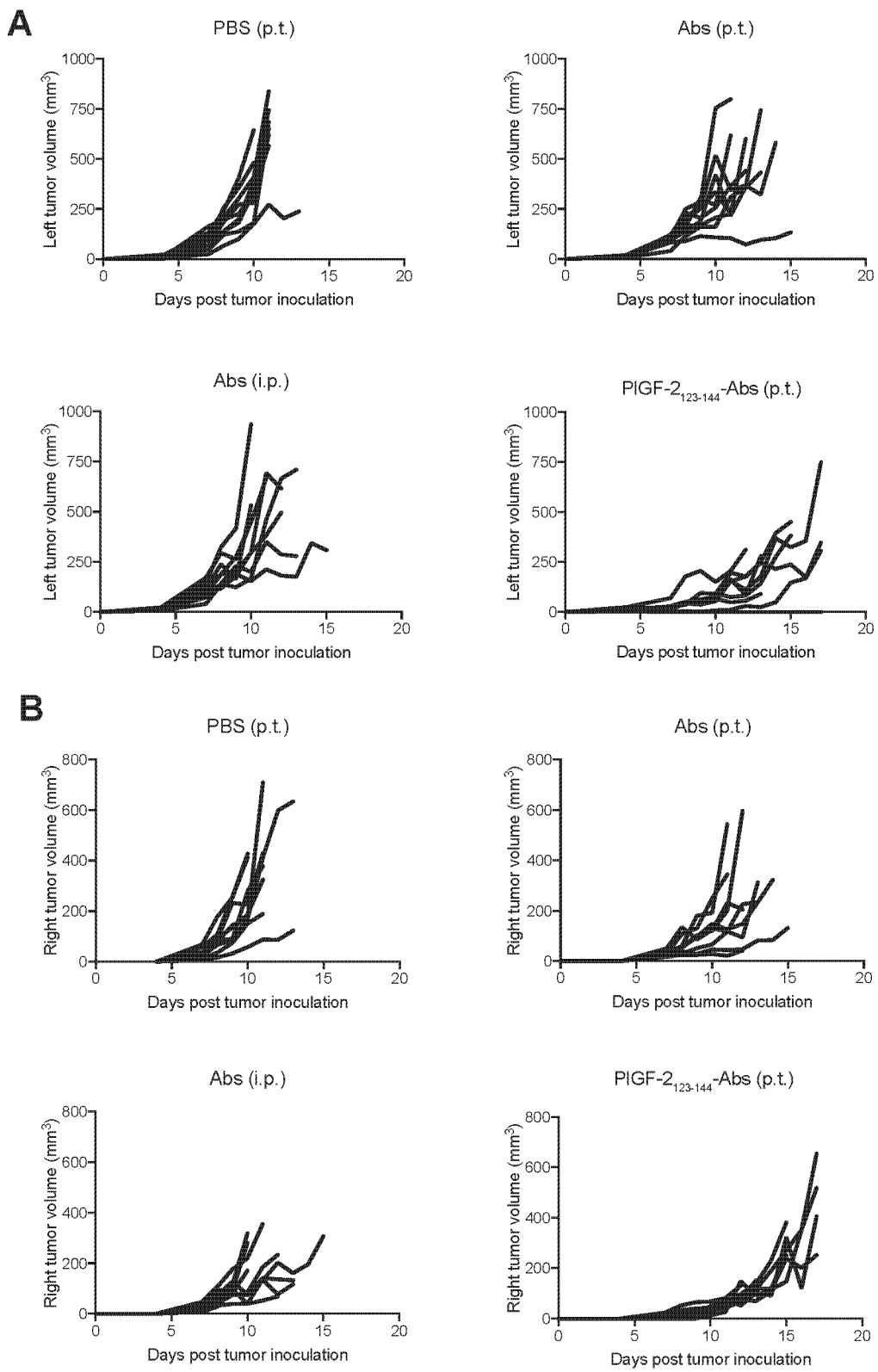

The increase of systemic central memory and PD-1$^+$ CD8$^+$ T cells, as well as stimuli-responsive cytokine producing CD8$^+$ T cells in the tumor following PlGF-2$_{123-144}$-αCTLA4+PlGF-2$_{123-144}$-αPD-L1 treatment led the inventors to investigate whether PlGF-2$_{123-144}$-Abs could mediate anti-tumor responses in a distant tumor. B16F10 cells were inoculated in the left back of the mouse on day 0 and in the right back of the mouse on day 2 (FIG. 5A). Subsequently, the Abs were injected p.t. beside the left tumor or i.p. on day 4, 7, and 10. As a result, the p.t. injection of PlGF-2$_{123-144}$-αCTLA4+PlGF-2$_{123-144}$-αPD-L1 slowed the outgrowth of both the left (ipsilateral) and right (contralateral) tumors (FIGS. 5B-C and FIG. 23). To the contrary, wt Abs had little therapeutic effect on either tumor when injected via p.t. or i.p. These data indicate that PlGF-2$_{123-144}$-αCTLA4+PlGF-2$_{123-144}$-αPD-L1 treatment near one tumor enhances a systemic anti-tumor action.

8. PlGF-2$_{123-144}$-Abs Treatment have Therapeutic Effects on Clinically Relevant Melanoma and Breast Cancer Models.

Figure 6D:
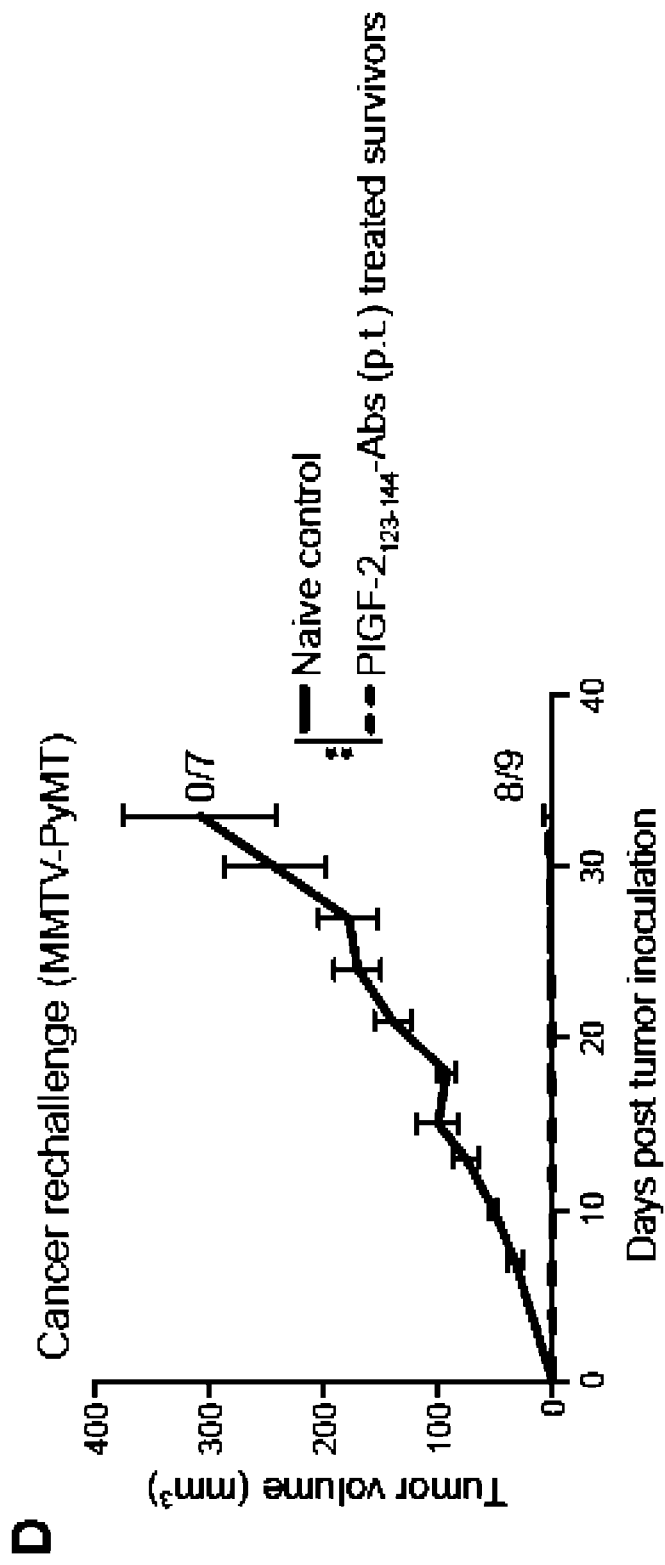

As a clinically relevant melanoma model, Tyr:Cre-ER$^+$/SL-Braf$^{V600E}$/Pten$^{fl/fl}$ mice, which carry mutations commonly observed in melanoma patients were employed. Three doses of p.t. injections of PlGF-2$_{123-144}$-αCTLA4+PlGF-2$_{123-144}$-αPD-L1 given via p.t. administration led to a reduction in tumor size compared to PBS or wt Abs treated groups (FIG. 6A). The PlGF-2$_{123-144}$-combination Abs also significantly suppressed the growth of MMTV-PyMT, epithelial-like breast cancer cells, and prolonged survival (FIG. 6B-C). PlGF-2$_{123-144}$-Abs administration induced eradication of cancer in 11 out of 17 mice, whereas wt Abs treatment eradicated tumors in 5 of 15 mice. To validate long-term anti-cancer immune protection, mice whose tumors were eradicated by PlGF-2$_{123-144}$-combination Abs treatment were re-challenged with MMTV-PyMT cells. Consequently, only 1 of 9 mice developed palpable tumors, whereas all naïve mice grew detectable tumors, confirming that PlGF-2$_{123-144}$-combination Abs induced immunologic memory (FIG. 6D). These data indicate that the PlGF-2$_{123-144}$-αCTLA4+PlGF-2$_{123-144}$-αPD-L1 therapeutic effect is applicable to multiple cancer types.

B. Discussion

Despite their efficacy, the side effects of ipilimumab (an αCTLA4) and atezolizumab (an αPD-L1) have been identified as serious problems. The inventors sought to explore, in cases where tumoriregional therapy would be feasible, whether such local therapy with matrix-binding forms of these Abs would be beneficial. In this study, the side effects of PlGF-2$_{123-144}$-conjugated Abs were reduced compared to wt Abs treatments. PlGF-2$_{123-144}$-Abs, which remain localized near the tumor tissue and thus reduce the concentration in the blood circulation, should maintain the systemic immune homeostasis by avoiding influence on non-tumor antigen specific T cells (FIG. 2). Also, PlGF-2$_{123-144}$ conjugation may allow a decrease the administered dose, as tumor growth delay was shown at low dosages where wt Abs had no effect (FIG. 3). These data are encouraging with regard to treatment of patients who have discontinued checkpoint blockade therapy due to the associated side effects, as well as who are not amenable to systemic chemotherapy.

The inventors have shown that B16F10 growth is difficult to slow using conventional αCTLA4 and αPD-L1 therapy, even when high doses are administered (FIGS. 3 and 5). It is thus remarkable that local anti-tumor activity with PlGF-2$_{123-144}$-αCTLA4+PlGF-2$_{123-144}$-αPD-L1 so substantially delayed B16F10 growth, an effect achieved solely through a peptide conjugation approach, as reported in this Example. Since PlGF-2$_{123-144}$ itself does not bind to the VEGF receptor and did not affect tumor growth in vitro or in vivo (FIG. 3 and FIG. 24), slow- and local-release are indicated to dramatically improve the therapeutic effect of αCTLA4 and αPD-L1 through efficient activation of endogenous T cells. To more efficiently eradicate immune-suppressed tumors, PlGF-2$_{123-144}$-αCTLA4+PlGF-2$_{123-144}$-αPD-L1 in combination with other therapies (e.g. radiation, vaccination or other proteins) may be used. In the case of MMTV-PyMT breast cancer, PlGF-2$_{123-144}$-combination Abs eradicated cancers in 65% of mice and provided protection from cancer re-challenge. These data suggest that PlGF-2$_{123-144}$-αCTLA4+PlGF-2$_{123-144}$-αPD-L1 effectively suppresses growth of multiple cancer types.

The localized therapy also suppressed growth of a tumor contralateral from the injection site, which is consistent with earlier observations (FIG. 5). This data highlights the feasibility to treat patients with metastatic tumors by administration of PlGF-2$_{123-144}$-αCTLA4+PlGF-2$_{123-144}$-αPD-L1. With the low concentration of PlGF-2$_{123-144}$-conjugated Abs in the blood combined with the increase in activated CD8$^+$ T cells, the mechanism of a distant tumor treatment is likely due to effective tumor-antigen specific CD8$^+$ T cell activation (FIGS. 2, 4, and 5). Wild-type (wt) antibodies (Abs) distributed systemically via i.p. or p.t. administration did not significantly suppress B16F10 tumor growth at the dosages used in this study. P.t. injections of wt Abs resulted in increased Gzmb$^+$ and IFNγ$^+$ of CD8$^+$ T cells in tumor, and in increased central memory and PD-1$^+$ of CD8$^+$ T cells in tdLN. However, the number of tumor-infiltrating CD8$^+$ and CD4$^+$ T cells did not increase compared to PBS treatment. Importantly, the percentage of CD8$^+$ T cells producing IL2 in response to stimulation was higher for PlGF-2$_{123-144}$-conjugated Abs compared to wt Abs. Since IL2$^+$ CD8$^+$ T cells have been reported to play a crucial role in anti-tumor immune responses, it is theorized that these are the reasons why p.t. injection of PlGF-2$_{123-144}$-αCTLA4+PlGF-2$_{123-144}$-αPD-L1, but not wt Abs suppressed tumor outgrowth both ipsilateral and contralateral tumors.

PlGF-2$_{123-144}$-IgG binds to a variety of ECM proteins, which should contribute to their prolonged tissue retention at the injection site (FIG. 1). Bound PlGF-2$_{123-144}$-Abs can be released by plasmin or by heparin. Cancer cells reportedly secrete proteases more than normal cells. For example, B16F10 cells express tissue plasmin activator, which activates plasminogen into plasmin. Therefore, it is theorized that cancer-derived proteases may contribute to PlGF-2$_{123-144}$-Abs release from ECM also in vivo.

Two αCTLA4 clones (9H10 and 4F10) were utilized to investigate if Treg depletion contributes to tumor suppression. Because both clones suppressed tumor growth, it appears that ligand blocking, as opposed to Treg depletion, by αCTLA4 primarily contributed to the anti-tumor activity observed in this study (FIG. 3).

A main advantage of synthesizing PlGF-2$_{123-144}$-Abs is in production simplicity, as reactions can be done under aqueous conditions in only 90 minutes. A limitation of this scheme is the lack of control for the site of peptide conjugation. However, this example demonstrates that PlGF-2$_{123-144}$ conjugation did not alter the affinities of the conjugated Abs against their antigens, a result that could not have been predicted (FIG. 1).

In conclusion, it was found that αCTLA4 and αPD-L1 were enhanced in their anti-tumor activities when ECM-binding properties were installed. Conjugation of PlGF-2$_{123-144}$ enhanced injection-site tissue retention of the conjugated Abs. A reduction in systemic side effects was demonstrated, associated with lower Abs concentrations in plasma and less observed damage to liver tissue. P.t. injections of PlGF-2$_{123-144}$-αCTLA4+PlGF-2$_{123-144}$-αPD-L1 significantly activated tumor-infiltrating T cells, resulting in delayed tumor growth and prolonged survival. Importantly, this localized therapy suppressed growth in a distant tumor and in a tumor re-challenge model. This approach of engineered ECM-binding Abs is useful for clinical immune checkpoint blockade for cancer therapy.

C. Materials and Methods

1. Synthesis of PlGF-2$_{123-144}$-Abs

Rat anti-mouse PD-L1 (clone: 10F.9G2, Bio X Cell), hamster anti-mouse CTLA4 (clone: UC10-4F10-11 or 9H10, Bio X Cell), rat anti-mouse CD40 (clone: FGK45, Bio X Cell), or rat IgG2a control antibody (BioLegend) was incubated with 15 eq. of sulfo-SMCC for 30 min at RT. Excess sulfo-SMCC was removed using a Zeba spin desalting column (Thermo Fisher Scientific). 15 eq. of PlGF-2$_{123-144}$ peptide (RRRPKGRGKRRREKQRPTDCHL) was then added and reacted for 1 h at 4° C. The peptide was synthesized with >95% purity by GenScript.

2. Sodium Dodecyl Sulfate Acrylamide Gel Electrophoresis (SDS-PAGE)

SDS-PAGE was performed on 4-20% gradient gels (Bio-Rad) after Abs were reduced with 10 mM DTT. After electrophoresis, gels were stained with SimplyBlue SafeStain (Thermo Fisher Scientific) according to manufacturer's instruction. Gel images were acquired with the ChemiDoc XRS+ system (Bio-Rad).

3. MALDI-TOF MS

MALDI-TOF MS analyses were done by the proteomics core facility at EPFL. Antibody solutions were dialyzed to exchange the buffer to 50 mM ammonium bicarbonate. The antibody samples (5-10 µg) were desalted with a C4 filter pipette tip (home-made 250 µg capacity), and then eluted using 85% acetonitrile, 0.1% trifluoroacetic acid in water. The cleaned Abs were dried in speed-vac for 10 min, and re-solubilized in 5 µL 2% acetonitrile, 0.1% trifluoroacetic acid in water. Analyses by MALDI-TOF were conducted on Applied Biosystems 4800 MALDI TOF/TOF mass spectrometer using high mass linear positive mode. Typically, spectra from 1000 to 1500 laser shots were summed to obtain the final spectrum. MALDI Matrix 2,5-dihydroxybenzoic acid (Applied Biosystems) at 70 mg/mL in methanol was used for all experiments. 0.5 µL of analyte and 1 µL of the matrix solution were deposited on the stainless steel target, mixed with a micropipette, and allowed to air-dry, forming a cocrystalline sample/matrix complex. The measurements were externally calibrated at three points with a mix of carbonic anhydrase, enolase, and bovine serum albumin (BSA, Sigma-Aldrich).

4. Detection of Antibody Binding to ECM Proteins 96-well ELISA plates (Greiner Bio One) were coated with 10 µg/mL recombinant human ECM proteins, fibronectin (Sigma-Aldrich), fibrinogen (VWF and fibronectin depleted, Enzyme Research Laboratories), osteopontin (Sigma-Aldrich), vitronectin (Sigma-Aldrich), collagen I (EMD Millipore), collagen II (EMD Millipore), collagen III (EMD Millipore), or collagen IV (EMD Millipore) in PBS for 1 h at 37° C., followed by blocking with 2% BSA in PBS with 0.05% Tween 20 (PBS-T) for 1 h at RT. Then, wells were washed with PBS-T and further incubated with 10 µg/mL PlGF-2$_{123-144}$- or wt-Abs for 1 h at RT. After 3 washes with PBS-T, wells were incubated for 1 h at RT with HRP-conjugated Abs against rat IgG or hamster IgG (Jackson ImmunoResearch). After washes, bound Abs were detected with tetramethylbenzidine substrate by measurement of the absorbance at 450 nm with subtraction of 570 nm.

5. Binding Affinity Assay 96-well ELISA plates (Greiner Bio One) were coated with 10 µg/mL fibronectin, collagen I, recombinant mouse (rm) CTLA4 (Sino Biological), rmCD40 (Sino Biological) or rmPD-L1 (Sino Biological) in PBS for 1 h at 37° C., followed by blocking with 2% BSA in PBS-T for 1 h at RT. Then, wells were washed with PBS-T and further incubated with PlGF-2$_{123-144}$- or wt-Abs at increasing concentration for 1 h at RT. After 3 washes with PBS-T, wells were incubated for 1 h at RT with HRP-conjugated Abs against hamster IgG or rat IgG. After washes, bound Abs were detected with tetramethylbenzidine substrate by measurement of the absorbance at 450 nm with subtractions of 570 nm. The apparent dissociation constant (Kd) values were obtained by nonlinear regression analysis in Prism software (v7, GraphPad Software) assuming one-site specific binding.

6. Recognition of Antigens on Cell Surfaces $1 \times 10^5$ B16F10 or T33.1 cells were incubated with 1 µg/mL PlGF-2$_{123-144}$ Abs, unconjugated Abs or isotype control in PBS containing 2% FBS for 30 min at 4° C. After wash, Alexa Fluor 488-conjugated anti-hamster or anti-rat antibody (Jackson ImmunoResearch) was added and incubated for 30 min at 4° C. Cells were then stained with propidium iodide and analyzed by flow cytometry.

7. Inhibition of PlGF-2$_{123-144}$-Abs Binding to Fibronectin by Heparin 96-well ELISA plates were coated with 10 µg/mL of fibronectin in PBS at 37° C. for 1 h, and further blocked with 2% BSA in PBS-T for 1 h at RT. Then, wells were washed with PBS-T and incubated with 10 µg/mL of PlGF-2$_{123-144}$-conjugated rat IgG2a control antibody (in PBS-T with 0.1% BSA) with increasing concentration of heparin for 1 h at RT.

After 3 washes with PBS-T, bound Abs were detected using HRP-conjugated goat anti-rat secondary antibody (Jackson ImmunoResearch).

8. PlGF-$2_{123-144}$ Cleavage by Plasmin 1 mg/mL PlGF-$2_{123-144}$-Abs were incubated with 0.1 U/mL plasmin overnight at 37° C. Cleavage of PlGF-$2_{123-144}$ by plasmin was detected by SDS-PAGE. ECM-binding affinity of plasmin-treated antibody was obtained by ELISA as described above.

9. Release Profiles of PlGF-$2_{123-144}$-αPD-L1 and αPD-L1 from Collagen Gels

Collagen gels were prepared by mixing 8.5 mL of bovine collagen (5 mg/mL, Symatese) with 800 µL of 10×MEM (Life Technologies) followed by 1.8 mL of NaOH (0.1 M). 500 µL of neutralized collagen solution were allowed to gel in 1.5 mL protein low-binding tubes (Thermo Fisher Scientific). After 15 min of gelation, 10 µg/mL of PlGF-$2_{123-144}$-αPD-L1 or αPD-L1 was incubated for 3 h in 800 µL of release buffer (0.1% BSA in PBS), followed by wash with release buffer. Thereafter, 800 µL of release buffer was added to each collagen gel and incubated at 37° C. (5% $CO_2$). Every 24 h, release buffer aliquots were taken and frozen down, followed by the addition of new release buffer to the collagen gels. This release buffer steps were repeated 5 times. After the fifth buffer change, the collagen gels were incubated with plasmin for 12 h (0.1 U/mL, Roche). To get release profile of the Abs from collagen gel, all the collected release samples were thawed and the concentrations were obtained by ELISA as described above.

10. Mice and Cell Lines

C57BL/6 mice and FVB mice, ages 8 to 12 weeks, were obtained from Charles River (France or USA), unless otherwise noted. Non-obese diabetic (NOD)/ShiLtJ mice were obtained from The Jackson Laboratory and bred in the animal facility at University of Chicago. $Braf^{V600E}/Pten^{-/-}$, ages 6 to 12 weeks were provided by Prof. T. Gajewski (University of Chicago). Experiments were performed with approval from the Veterinary Authority of the Canton de Vaud, Switzerland and the Institutional Animal Care and Use Committee of the University of Chicago (IACUC). B16F10 cells and B16F10-OVA cells were obtained from the American Type Culture Collection and cultured according to the instructions. T33.1 cells were provided from Prof. J. Blum (Indiana University). MMTV-PyMT cells were obtained from spontaneously developed breast cancer in FVB-Tg(MMTV-PyVT) transgenic mice (polyoma middle T antigen oncogene expression was induced by mouse mammary tumor virus promotor) and cultured in vitro. All cell lines were checked for mycoplasma contamination.

11. Abs Retention Analysis and Immunohistochemistry of Skin Tissue Sections

C57BL/6 mice were anesthetized with isoflurane (4% for induction and 1.5% for maintenance) and their backs were shaved. A total of $5 \times 10^5$ B16F10 cells re-suspended in 50 µL of PBS were injected intradermally on the left side of the back of each mouse. After 4 days, mice were injected with 10 µg of αCTLA4 (4F10) and αPD-L1 (p.t.). Histological analysis was performed on serial sections (10 µm frozen sections) until reaching the central portion of the melanoma. Cryosections, fixed with 4% paraformaldehyde (PFA) and blocked with 2% BSA, were incubated with Alexa Fluor 488-conjugated anti-hamster or anti-rat antibody (both from Jackson ImmunoResearch) and biotinylated anti-S100 antibody (Invitrogen) for 1 h RT, followed by staining with Alexa Fluor 647-conjugated streptavidin (BioLegend). Images were taken with DMi8 microscope (Leica).

12. Antibody Concentration Analysis $5 \times 10^5$ B16F10 melanoma cells were injected intradermally on left side of the back of each mouse. After 4 days, mice were injected with 100 µg of αCTLA4 (9H10), 100 µg of αPD-L1 (p.t. or i.p.) or, 50 µg of αCD40. Blood samples were collected in heparinized tubes from the submandibular vein of the cheek pouch with a 4-mm lancet on 5, 7, and 9 days after tumor inoculation. Concentrations of αCTLA4, αPD-L1, and αCD40 in plasma were measured by ELISA as described above.

13. Serum Cytokine Concentration Analysis $5 \times 10^5$ B16F10 melanoma cells were injected intradermally on left side of the back of each 12 weeks old C57BL/6 mouse (The Jackson Laboratory). After 4 and 7 days, mice received two doses of 500 µg αCTLA4 and αPD-L1. Blood samples were collected in tubes, followed by overnight incubation at 4° C. Cytokine concentrations in serum were measured by Ready-SET-Go! ELISA kits for mouse TNFα and mouse IFNγ (eBioscience) and mouse IL2 DuoSet ELISA kit (R & D Systems) according to the manufacture's protocol.

14. ALT Assays $5 \times 10^5$ B16F10 melanoma cells were injected intradermally on left side of the back of each mouse. After 4 days, mice were received two doses of 500 µg αCTLA4 and αPD-L1, or single injection of 50 µg αCD40 (p.t.). Blood samples were collected in tubes, followed by >4 h incubation at 4° C. ALT activity in serum was measured by ALT assay kit (Sigma-Aldrich) according to the manufacture's protocol.

15. Liver Histology $5 \times 10^5$ B16F10 melanoma cells were injected intradermally on left side of the back of each mouse (day 0). After 4 days, mice received a single injection of 50 µg PlGF-$2_{123-144}$- or wt-αCD40 (p.t.). 7 days after tumor inoculation, livers were collected and fixed with 4% PFA. After embedding in paraffin, blocks were cut into 5 µm sections, followed by staining with hematoxylin and eosin. Images were captured with an EVOS FL Auto microscope (Life Technologies). Diabetes monitoring of NOD mice after αPD-L1 treatment.

16 weeks old male NOD mice were given 100 µg of αPD-L1 on day 0 and 2. All Ab injections were intradermal in the back skin. Clinical diabetes was defined as a blood glucose reading of 250 mg/dL for three consecutive days. Blood glucose was measured by Alpha TRAK 2 Glucose Meter (Abbott Animal Health). Blood glucose levels were monitored daily from 2 days after initiation of the treatment until the mice were sacrificed.

16. B16F10 Tumor Inoculation and Abs Injection

A total of $1 \times 10^6$ B16F10-OVA or $5 \times 10^5$ B16F10 cells re-suspended in 50 µL of PBS were inoculated intradermally on the left side of the back of each C57BL/6 mouse. After 4, 7, or 10 days, mice were injected with 25, 50, 100, or 300 µg of αCTLA4 and/or αPD-L1 intradermally beside the tumor p.t. or i.p. For distant tumor experiments, $5 \times 10^5$ B16F10 cells were injected intradermally on the left side of the back of each mouse on day 0 and on the right side on day 2. On day 4, 7, and 10, mice were injected with 100 µg of αCTLA4 and αPD-L1 (p.t.). Tumors were measured with a digital caliper starting 4 days after first tumor inoculation, and volumes were calculated as ellipsoids, where V=4/3× 3.14×depth/2×width/2×height/2. Mice were sacrificed at the point when either tumor volume had reached over 500 $mm^3$.

17. Tissue and Cell Preparation and T Cell Subset Analysis $2 \times 10^5$ B16F10 melanoma cells were injected intradermally on the left side of the back of each C57BL/6 mouse.

After 4 and 7 days, mice were injected with 100 μg of αCTLA4 and αPD-L1 (p.t. or i.p.). Mice were sacrificed on day 8. Spleens, LNs, and tumors were harvested. Tumors were digested in Dulbecco's Modified Eagle Medium (DMEM) supplemented with 2% FBS, 2 mg/mL collagenase D and 40 μg/mL DNase I (Roche) for 30 min at 37° C. Single-cell suspensions were obtained by gently disrupting the organs through a 70-mm cell strainer. Red blood cells were lysed with ACK lysing buffer (Quality Biological). Cells were counted and re-suspended in Iscove's Modified Dulbecco's Medium (IMDM) supplemented with 10% FBS and 1% penicillin/streptomycin (full medium; all from Life Technologies) and used for flow cytometry staining and ex vivo T cell stimulation.

18. Flow Cytometry and Abs

Single cell suspensions from spleens, LNs, and tumors were prepared as described above. Following a washing step, approximately $2 \times 10^6$ cells were used for antibody staining. Abs against the following molecules were used throughout the paper if not otherwise indicated: CD3 (145-2C11, BD Biosciences), CD4 (RM4-5, BD Biosciences), CD8a (53-6.7, BD Biosciences), CD25 (PC61, BD Biosciences), CD45 (30-F11, BD Biosciences), CD44 (IM7, BD Biosciences), CD62L (MEL-14, BD Biosciences), PD-1 (29F.1A12, BioLegend), Foxp3 (MF23, BD Biosciences), IL2 (JES6-5H4, BD Biosciences), IFNγ (XMG1.2, BD Biosciences), TNFα (MP6-XT22, eBioscience), and Grzb (NGZB, eBioscience). Fixable live/dead cell discrimination was performed using Fixable Viability Dye eFluor 455 (eBioscience) according to the manufacturer's instructions. Staining was carried out on ice for 20 min if not indicated otherwise, and intracellular staining was performed using the Foxp3-staining kit according to manufacturer's instructions (BioLegend). Staining of OVA-specific cells was performed using the SIINFEKL-MHCI pentamer (Proimmune), conjugated with Phycoerythrin (PE). For staining, pentamers were diluted 1:10 in PBS containing 2% FBS and incubated for 20 minutes at RT. Following a washing step, cells were stained with specific Abs for 20 minutes on ice prior to fixation. All flow cytometric analyses were done using a Gallios (Beckman Coulter) or a Fortessa (BD Biosciences) flow cytometer and analyzed using Kaluza (Beckman Coulter) or FlowJo software (Tree Star).

19. Ex Vivo T Cell Stimulation

Single cell suspensions from tumor, spleen, and LN were prepared as described above. For tumor samples, CD8⁺ T cells were isolated using EasySep kits (STEMCELL Technologies) following the manufacturer's instructions. 96-well cell culture plates (BD Falcon) were coated with 10 μg/mL αCD3 (145-2C11, BioLegend) in PBS overnight at 37° C. A total of $2 \times 10^6$ spleen, tumor cells or $5 \times 10^5$ LN cells were plated in 96-well plates and cultured in full medium for 6 h at 37° C. in the presence of 2 μg/mL αCD28 (EL-4, BioLegend) and 5 μg/mL brefeldin A for the last 3 h (Sigma-Aldrich). Cells were harvested, stained, and analyzed by flow cytometry as described above.

20. Tyr:Cre-ER⁺/LSL-Braf$^{V600E}$/Pten$^{fl/fl}$ Melanoma Induction and Abs Injection 8-12-week-old Tyr: Cre-ER⁺/LSL-Braf$^{V600}$/Pten$^{fl/fl}$ mice were shaved on the back and 5 μL of 4-OH-tamoxifen (Sigma-Aldrich) at 10 mg/mL was applied topically, as previously described (see, for example, Spranger, S. et al., Nature 523, 231-235 (2015)). 0, 3, and 6 days after the visible tumor development, mice were injected with 100 μg of αCTLA4 and αPD-L1 p.t. for a total of 3 injections. Volume was computed as Volume=Surface*Z, where Surface is computed through ImageJ analysis and Z is the thickness of the tumor, measured with a digital caliper. Mice were sacrificed at the point when tumor volume had reached over 1000 mm³.

21. MMTV-PyMT Tumor Inoculation and Abs Injection

FVB Mice were anesthetized with isoflurane (4% for induction and 1.5% for maintenance) and the hair surrounding the mammary glands of FVB Mice was shaved. A total of $8 \times 10^5$ MMTV-PyMT cells re-suspended in 50 μL of PBS were injected subcutaneously into the mammary gland on the right side of each mouse. After 7, 10, or 13 days, mice were injected with 100 μg of αCTLA4 and αPD-L1 (p.t.). Tumors were measured with a digital caliper as described above. Mice were sacrificed when tumor volume reached over 500 mm³.

22. Cell Proliferation Assay

B16F10 melanoma cells were plated in 24-well plates at a density of $5 \times 10^4$ cells/well and incubated overnight at 37° C. in DMEM supplemented with 10% FBS. 1, 10, and 100 μg/mL PlGF-2$_{123-144}$ peptide was then added. After 3 days of incubation, cell numbers were counted using a hemocytometer.

23. Statistical Analysis

Statistically significant differences between experimental groups were determined by one-way ANOVA followed by Tukey's HSD post hoc test with Prism software (v7, GraphPad). The symbols * and ** indicate P values less than 0.05 and 0.01, respectively; N.S., not significant.

Example 2—CXCL12 Peptides, ECM-Affinity Peptides, Linked to Antibodies Binds to ECM Proteins Using the methods below, it was found that CXCL-12 peptides linked to antibodies bound to ECM proteins, indicating their effectiveness for being retained locally for cancer therapeutic applications.

Detection of CXCL-12 Binding to Human ECM Proteins:

96-well ELISA plates (med binding: Greiner Bio-One) were coated with 10 μg/mL recombinant human ECM proteins, fibronectin (Sigma-Aldrich), fibrinogen (VWF and fibronectin depleted, Enzyme Research Laboratories). After blocking with 2% BSA solution containing PBS-T, 1 μg/mL of recombinant human CXCL-12 α (Peprotech) or CXCL-12γ (R and D systems) was added. Bound CXCL-12 was detected with 1 μg/mL of mouse anti-human CXCL-12 antibody (R and D systems). After 1 h of incubation, horseradish peroxidase (HRP) conjugated goat anti-mouse antibody (1:2000 dilution, Dako) was added and incubated for another 1 h. Then, 50 μL tetramethylbenzidine substrate (Sigma) was added. The reactions were stopped by adding 25 μL of 2N H2SO4. Subsequently, the absorbance at 450 nm were measured with references of 570 nm.

Synthesis of CXCL-12$_{γ69-98}$-Abs:

Rat IgG2a control antibody (BioLegend) was incubated with 15 eq. of sulfo-SMCC for 30 min at RT. Excess sulfo-SMCC was removed using a Zeba spin desalting column (Thermo Fisher Scientific). 15 eq. of CXCL-12γ$_{6-98}$ with C-terminus Cysteine (GR-REEKVGKKEKIGKKKRQKKRKAAQKRKNC) peptide was then added and reacted for 1 h at 4° C. The peptide was synthesized with >95% purity by GenScript.

Detection of Antibody Binding to ECM Proteins:

96-well ELISA plates (Greiner Bio One) were coated with 10 μg/mL recombinant human ECM proteins, fibronectin (Sigma-Aldrich), fibrinogen (VWF and fibronectin depleted, Enzyme Research Laboratories), collagen I (EMD Millipore), or collagen II (EMD Millipore) in PBS for 1 h at 37°

C., followed by blocking with 2% BSA in PBS with 0.05% Tween 20 (PBS-T) for 1 h at RT. Then, wells were washed with PBS-T and further incubated with 10 μg/mL CXCL-12$\gamma_{6-98}$- or wt-Abs for 1 h at RT. After 3 washes with PBS-T, wells were incubated for 1 h at RT with HRP-conjugated Abs against rat IgG (Jackson ImmunoResearch). After washes, bound Abs were detected with tetramethylbenzidine substrate by measurement of the absorbance at 450 nm with subtraction of 570 nm.

Example 3—Tumor Collagen Targeting of Immunomodulatory Antibodies

One focus is to enhance binding of immunomodulatory antibodies such as checkpoint blockade antibodies to the ECM located in the tumor microenvironment. The inventors are designing and producing conjugates of immunomodulatory antibodies that bind to collagen, which is abundant in the tumor microenvironment.

Collagen is an ECM protein, located in the various connective tissues. 27 types of collagens have been identified, and collagen type I is reported as the most abundant collagen in the human body. Collagen regulates a variety of cellular biological functions such as proliferation, differentiation, and adhesion. von Willebrand factor (VWF) A domain has specific affinity against collagen among non-bacterial origin proteins/peptides. Within these proteins/peptides, the VWF A1-A3 domain (especially the A3 domain) has exceptionally high affinity against several types of collagens such as collagen type I, collagen type III, and collagen type IV. VWF binds to collagen in vivo when blood vessels are damaged and collagen is exposed. This binding results in the initiation of the thrombosis cascade.

Here, the inventors hypothesize that chemical conjugation or recombinant fusion of the VWF A3 or A1 domain recombinant protein (VWF A3 or A1) or decorin with the immunomodulatory antibodies will improve localization and retention of antibodies within the tumor microenvironment. Subsequently, VWF A3-conjugation may enhance anti-tumor efficacy and decrease systemic side-effects, as the inventors have proposed above in the ECM-binding peptide conjugated antibodies. Although these VWF A3-conjugated immunomodulatory antibodies (VWF A3-antibodies) would be expected to have anti-tumor effects after intra/peri-tumoral injection as well, it is contemplated that its even greater usefulness will be to function after systemic administration (i.e. intravenously (i.v.) or i.p.), which is more generally clinically applicable. Inventors focus on the VWF A3 (human VWF$_{1670-1874}$, sequence is described above) as a ECM-affinity peptide; however, inventors also teach the A1 domain (human VWF$_{1237-1458}$, sequence is described below) and decorin as well, because of their binding to collagen.

Production and Purification of VWF A3:

The sequence encoding for VWF A3 will be cloned and subcloned into the bacterial expression vector pGEX6P-1. The GST-VWF A3 recombinant protein will be expressed in *E. coli* BL21. The GST-fusion VWF A3 recombinant protein will be purified using a GST column. The GST tag will be removed by a specific enzyme for GST tag.

Synthesis of VWF A3-Conjugated Antibodies:

Anti-mouse PD-L1, anti-mouse CTLA4, anti-mouse CD40 or rat IgG2a control antibody will be incubated with sulfo-SMCC. Excess sulfo-SMCC will be removed using a desalting column. Recombinant VWF A3 protein will be then added and be incubated. Other checkpoint blockade antibodies can also be used.

Tumor Inoculation and Immunomodulatory Antibody Treatment Through Local Administration (p.t. Injection):

Tumor cells (e.g. B16F10) will be inoculated intradermally (i.d.). After tumors become visible, mice will receive p.t. injection of VWF A3- or wt-αCTLA4, αPD-L1 and/or αCD40. Tumor size will be monitored until it reaches the euthanasian criteria. Here, inventors expect that VWF A3 conjugation enhances tumor tissue localization and retention of antibody, and decreases antibody concentrations in blood plasma, when injected locally through binding to collagen in the tumor microenvironment. This will reduce the incidence of side-effects caused by immunomodulatory antibody treatment. VWF A3-antibodies should maintain the systemic immune homeostasis by avoiding influence on non-tumor antigen specific T cells as inventors have observed in PlGF-2$_{123-144}$-conjugated antibodies. As for anti-tumor efficacy, an increase in antibody concentration near the tumor microenvironment will lead to effective tumor-antigen specific CD8$^+$ T cell activation. In contrast, wt antibodies distributed systemically via p.t. administration will not efficiently suppress tumor growth.

Tumor Inoculation and Immunomodulatory Antibody Treatment Through Systemic Administration (i.v. Injection):

Tumor cells (e.g. B16F10) will be inoculated i.d. After tumors become visible, mice will receive i.v. injections of VWF A3- or wt-αCTLA4, αPD-L1 and/or αCD40 from tail vein. Tumor size will be monitored until it reaches the euthanasian criteria. Here, the inventors expect that i.v. injection of VWF A3-antibodies will show enhanced tumor tissue localization and retention and decreased antibody concentrations in blood plasma, even when injected i.v. through binding to collagen in the tumor microenvironment. Through a similar mechanism to what is described above with p.t. injection, VWF-A3 conjugation will increase antibody concentration within the tumor microenvironment, leading to reduced incidence of side-effects and enhance the anti-tumor efficacy of immunomodulatory antibodies. In contrast, wt antibodies administered via i.v. injection will not significantly concentrate at the tumor microenvironment, will not suppress tumor growth as efficiently and will show more incidents of side-effects compared to VWF A3-antibodies.

Example 4—Targeted Antibody Cancer Immunotherapies Through Collagen Affinity

Immunotherapy with immune checkpoint inhibitors (CPI) is frequently accompanied with adverse events. The inventors addressed this by targeting these immunotherapeutic molecules to tumors via conjugation or fusion to a collagen-binding domain (CBD) derived from von Willebrand factor, harnessing the exposure of tumor stroma collagen to blood components due to the leakiness of the tumor vasculature. This Example shows that intravenously administered CBD protein accumulated mainly in tumors, with lesser exposure in the liver and kidney where endothelia are fenestrated. In melanoma-bearing animals, CBD conjugation or fusion decreased the systemic toxicity of CPI. CBD-CPI significantly suppressed tumor growth compared to their unmodified forms in multiple murine cancer models. CBD-CPI increased tumor-infiltrating CD8$^+$ T cells.

While CPI therapies have shown good promise, they also show severe side-effects in some instances, including immune-related adverse events (48-58). In combination therapy, 96% of patients experienced adverse events and 36% of patients discontinued therapy due to adverse events (55). As such immunotherapeutics serve to activate immune responses, their side-effects caused by immune activation typically result from off tumor-target drug action (59-63). One strategy to address this problem is through drug targeting approaches, which seek to deliver drugs only where they are needed, thereby focusing their actions on the disease site. In Example 1 above, the inventors demonstrated that peritumoral (p.t.) administration of CPI antibodies conjugated to a matrix binding peptide enhances anti-tumor efficacy and reduces off-target effects. While injection near the tumor leads to improved outcomes as demonstrated above, it could also be advantageous in many situations to administer the drug systemically and have it target to the tumor sites from the blood.

Collagen is the most abundant protein in the mammalian body and exists in almost all tissues (65). Collagen, an ECM protein, is richly present in the subendothelial space of the blood vessel as well as the tumor stroma. Because of its insolubility under physiological conditions, collagen barely exists within the blood (66, 67). The vasculature of tumors is hyperpermeable compared to the normal blood vessel, due to an abnormal structure (68). Thus, with this leakiness, collagen in the tumor can be exposed to molecules carried in the bloodstream preferentially to other tissues (69-73). Moreover, many tumor tissues contain increased amounts of collagen compared to normal tissues (74, 75).

von Willebrand factor (vWF), a hemostasis factor, binds to both types I and III collagen (76, 77). When a blood vessel is injured, collagen beneath the endothelial cells is exposed to proteins in the blood, and vWF-collagen binding initiates the thrombosis cascade (77, 78). The vWF A domain has the highest affinity for collagen among reported non-bacterial origin proteins/peptides (79). Particularly within the A domain, the A3 domain of vWF has been reported as a collagen binding domain (CBD, using this abbreviation to refer specifically to the vWF A3 collagen-binding domain) (80).

A. Results

1. CBD-Fused CPI Bind to Collagen and their Targets

The inventors first examined the capacities of CBD-conjugated CPI (CBD-CPI) to bind collagen in vitro. After mixing CPI antibodies with sulfo-succinimidyl 4-(N-maleimidomethyl) cyclohexane-1-carboxylate (sulfo-SMCC) to functionalize the antibodies at lysine amine sites via reaction with the succinimidyl groups, vWF A3 domain recombinant protein with an intrinsic cysteine residue was crosslinked covalently to the functionalized antibody by reaction with the maleimide groups (FIG. 28A). Strong binding affinities (nM range dissociation constant ($K_D$) values) of CBD-αCTLA4, and of CBD-αPD-L1 against collagen type I and III were observed (FIG. 28B). Importantly, CBD-αCTLA4 and CBD-αPD-L1 recognized their target antigens with similar $K_D$ values to the unmodified form (FIG. 28B). These data thus show that CBD-CPI antibodies bind to collagens without impairment of their binding capacities to their targets.

2. CBD Protein Localizes in the Tumor

An in vivo bio-distribution analysis was performed to determine if CBD localizes in the tumor microenvironment after intravenous (i.v.) injection through binding to endogenous collagen. MMTV-PyMT breast cancer was inoculated in the FVB mouse. When the tumor volume reached 500 mm$^3$, DyLight 800-labeled CBD protein was injected. 2 days after injection, the tumor and organs including heart, lung, kidney, liver, spleen, and stomach were harvested. Fluorescence detection revealed that the CBD protein preferentially localized in the tumor, with minor localization in the liver and kidney, where the endothelium is fenestrated (FIG. 29A). We then analyzed the localization of the injected CBD-αPD-L1 within the MMTV-PyMT breast cancer (FIG. 29B). 100 µg of DyLight 594 labeled CBD-αPD-L1 and 100 µg of DyLight 488 labeled αCollagen I were injected i.v. Thirty min after injection, CBD-αPD-L1 and αCollagen I was co-localized around the tumor blood vessel. CBD-αPD-L1, but not αCollagen I localized the sub-endothelial space, suggesting greater penetration of the CBD-αPD-L1, compared to αCollagen I. These data demonstrate tumor vasculature targeting of CBD after i.v. injection.

3. CBD Conjugation Decreases Treatment-Related Adverse Events

Figure 30G:
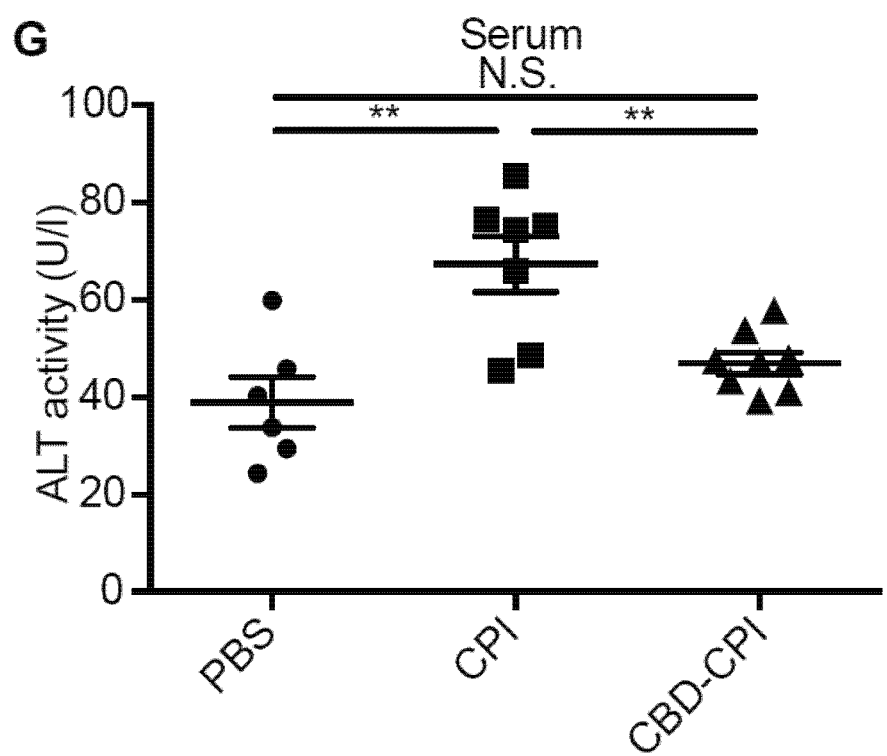

The injected CPI and CBD-CPI concentrations in blood plasma in B16F10 tumor-bearing mice over time were measured (FIG. 30A-B). The concentrations of both CBD-αCTLA4 and CBD-αPD-L1 in blood plasma were significantly lower compared to their unmodified forms. Next, side-effects were examined. After αCTLA4 and αPD-L1 administration to B16F10 tumor-bearing mice, blood serum, lung and liver were collected. Unmodified CPI administration significantly increased both TNFα and IL-6 concentrations in serum, whereas CBD-CPI did not (FIG. 30C-D). Histologic analysis showed that unmodified CPI induced marked morphological changes and lymphocyte infiltration in the lung and the liver (FIG. 30E-F), whereas tissue structure was relatively maintained following CBD-CPI treatment. Additionally, unmodified CPI, but not CBD-CPI treatment, increased alanine aminotransferase (ALT) activity, a clinically used liver damage marker, in serum (FIG. 30G). Taken together, these results show that CBD conjugation decreases systemic toxicity of CPI immunotherapy.

4. CBD-CPI Significantly Suppresses Growth of Multiple Tumors Compared to their Unmodified Forms The antitumor efficacy of CBD-αCTLA4+CBD-αPD-L1 combination therapy using B16F10 melanoma, CT26 colon carcinoma and MMTV-PyMT breast cancer models was examined. In B16F10 melanoma, unmodified CPI treatment did not exhibit antitumor effects under this regimen. In contrast, CBD-CPI displayed a therapeutic effect, significantly slowing tumor growth (FIG. 31A) at both 25 µg and 100 µg single doses. Importantly, administration of CPI+CBD protein without conjugation did not show an antitumor effect, indicating that the conjugation of CBD to CPI is indispensable for this action (FIG. 32). CBD-CPI was also compared to local (p.t.) administration of ECM-binding PlGF-$2_{123-144}$-CTLA4 and PlGF-$2_{123-144}$-PD-L1. Systemic targeting of the CBD-CPI molecules achieved similar efficacy as the local administration of the PlGF-$2_{123-144}$-CPI molecules (FIG. 31A). In the case of CT26 tumor, a single dose of unmodified CPI slowed tumor progression; CBD-CPI treatment significantly further suppressed tumor growth (FIG. 31B). CBD-CPI also has shown higher antitumor efficacy against MMTV-PyMT breast cancer and extended survival of mice compared to unmodified CPI (FIG. 31C-D). Remarkably, CBD-CPI led to complete remission in 6 mice out of 12, and no mice re-challenged with MMTV-PyMT cells developed palpable tumors, whereas all naïve mice grew detectable tumors, demonstrating that CBD-CPI induced immunologic memory (FIG. 31E).

Figure 33G:
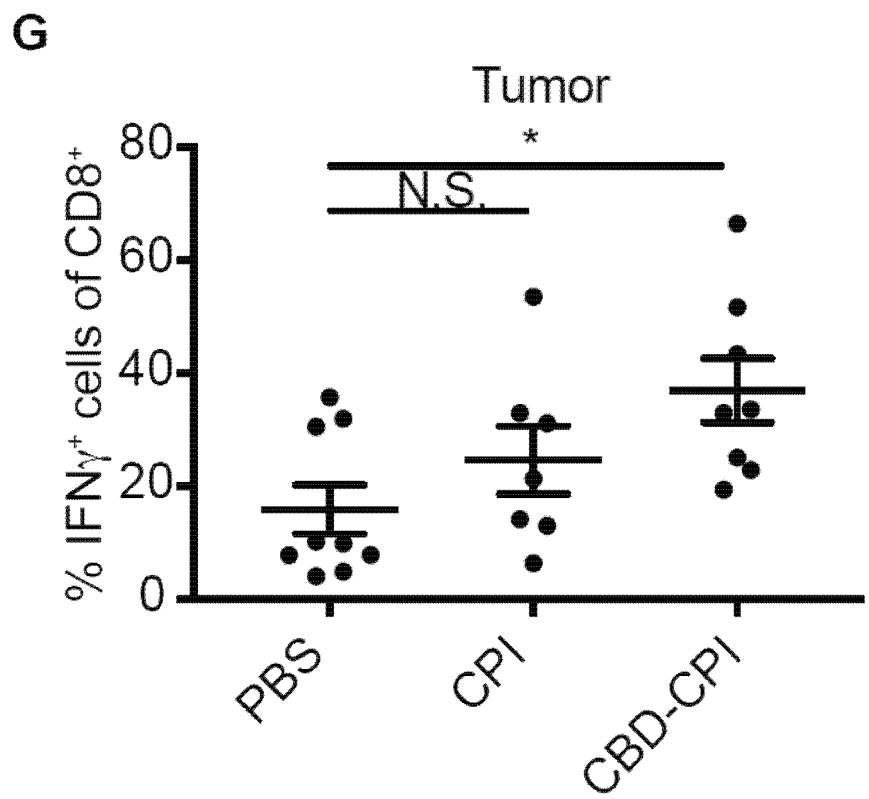

5. The Numbers of Activated Tumor-Infiltrating CD8+ T Cells are Increased by CBD-CPI Treatment To determine the mechanism behind the therapeutic action of CBD-CPI treatment, T cell responses were characterized in B16F10 tumor-bearing mice. CBD-CPI significantly increased the frequency of CD8$^+$CD3$^+$ T cells of CD45+ cells within the tumor compared to unmodified CPI and PBS injection (FIG. 33A), whereas the frequency of CD4+CD3+ T cells were maintained in all groups (FIG. 33B). CBD-CPI treatment, but not CPI treatment, significantly decreased the percentage of CD25+Foxp3+ Tregs within the CD4+ T cell population, supporting the tumor targeting ability of CBD-αCTLA4, because we utilized αCTLA4 with Treg depletion capacity (81) (FIG. 33C). As a consequence, CBD-CPI treatment significantly enhanced effector (CD62L−CD44+) CD8+ T-cell-to-Treg ratios within the tumor, a predictive of therapeutic efficacy (82), compared to unmodified CPI and PBS treatment (FIG. 33D). To test whether tumor-infiltrating CD8+ T cells produced higher levels of effector cytokines, CD8+ T cells were stimulated ex vivo using αCD3 and αCD28. CBD-CPI treatment significantly increased the percentage of IFNγ+, IL2+, and TNFα+ cells in CD8+ tumor-infiltrating T cells compared to PBS treatment group, whereas unmodified CPI treatment did not (FIG. 33E-G). Collectively, CBD-αCTLA4+CBD-αPD-L1 combination treatment effectively activated tumor-infiltrating T cells, corresponding to the therapeutic effects observed in FIG. 31A-E.

6. Conjugation of CPI to vWF A1 Domain and Decorin Polypeptides Also Enhance Antitumor Activity The antitumor effect of CPI (combination of αCTLA4 and αPD-L1) conjugates with other collagen binding domains, namely the vWF A1 domain and decorin, were tested. The vWF A1 domain and decorin also have high affinity towards collagen, specifically binding to type VI collagen, which the vWF A3 domain does not bind. These 3 CBD proteins have different binding sites on collagen. Decorin protein and vWF A1 domain protein were produced and purified, following the same procedure as with the vWF A3 domain. The vWF A1 domain and decorin were conjugated to the CPI antibodies following the same procedure as for conjugation of the vWF A3 domain protein to CPI.

$5 \times 10^5$ B16F10 cells were inoculated on day 0. The vWF A1 domain, the vWF A3 domain, and decorin were used as CBD in CBD-CPI antibody conjugates. PBS or one of four treatments were administered i.v. on day 4: (1) vWF A1-αCTLA4 and vWF A1-αPD-L1 (25 each); (2) vWF A3-αCTLA4 and vWF A3-αPD-L1 (25 µg each); (3) decorin-αCTLA4 and decorin-αPD-L1 (25 µg each); and (4) αCTLA4 and αPD-L1 (100 µg each). FIG. 44 depicts tumor volume (mean±SEM) until the first mouse died. Statistical analyses were done using ANOVA with Tukey's test. Two experimental replicates. *p<0.05; **p<0.01. FIG. 44 shows that the antitumor activities of the vWF A1 domain-CPI conjugates and decorin-CPI conjugates are as high as the vWF A3 domain-CPI conjugates, but higher than unmodified CPI.

B. Discussion

Strategies of targeted cancer therapy can be classified as active targeting or passive targeting (83). Antibody-drug conjugates are an example of active targeting. Targeting is based on the attachment of drugs to specific ligands (e.g., antibodies) that are tumor or tumor cell-specific (84), facilitating delivery of cancer drugs specifically to tumor cell surfaces. An example of passive targeting is a drug embedded in a nanoparticle carrier. Nanoparticles are expected to have a prolonged half-life in the blood, leading to accumulation in tumor where the vasculature is leaky via the enhanced permeability and retention effect (85, 86). Therefore, passive targeting is based on the longevity of the pharmaceutical carrier in the blood and its accumulation in pathological sites with irregular vasculature and thus enhanced accumulation.

The CBD-based drug targeting approach is a hybrid of active and passive targeting. It is similar to active targeting in terms of tumor collagen targeting based on molecular affinity, but it also exploits the leaky structure of tumor vessels as in passive targeting (68). The CBD-drugs are tumor microenvironment-specific, yet not via targeting a molecule that is specifically located in the tumor, but rather via exploiting tumor-specific accessibility. Thus, the CBD may be usable without prior investigation of tumor antigens. Moreover, since the CBD does not bind to a tumor cell-specific target, it is not subject to clearance by endocytosis. As such, the CBD approach turns the tumor subendothelium and stroma into both a drug target and a drug reservoir.

There are only a few proteins that reportedly bind to types I and III collagen among natural ligands of non-bacterial origin (79). vWF exhibits especially high affinity against these collagens (79). Association of the vWF A3 domain and collagen is an initiator of the thrombosis cascade, thus this binding commonly occurs in the human body. In this example, the tumor microenvironment was targeted using the vWF A3 domain as a collagen binding domain. Previously, a tumor matrix targeting approach that fuses a single chain antibody fragment against a tumor-specific fibronectin splice variant domain and cytokines has been tested in animal models and clinical trials (87-89). Specifically, single chain antibodies against the fibronectin extra-domain A (EDA) and EDB domains localize within tumor tissue, and a fusion protein of the single chain antibody and IL-2 showed enhanced antitumor efficacy compared to unmodified IL-2 in a mouse model (87, 90). Using collagen affinity instead, as demonstrated in this Example, can be advantageous, in that there is likely more collagen than EDA or EDB fibronectin in the tumor, and in that the vWF A3 domain binds to multiple collagen types (79), unlike more specific ligands such as peptides, antibodies or antibody fragments. Moreover, the ligand utilized in this Example is a human protein rather than an engineered protein with potential immunogenicity. Targeting collagen addresses a binding site that is ubiquitous but only accessible in the tumor tissue due to its leaky vasculature. The inventors also observed the deeper penetration of CBD-αPD-L1 around the subendothelium compared to αcollagen I, which may suggest the advantages of the use of the vWF A3 domain over αcollagen to target tumor vasculature. Thus, the approach taken in this Example is innovative both in the methodology (high affinity protein domains derived from a protein that naturally exists in the body) and in the biological approach (targeting the protein that is abundant in the body but that is only exposed in the tumor via its leaky vasculature).

C. Materials and Methods

1. Production and Purification of Recombinant vWF A3 Domain

The sequences encoding the human vWF A3 domain residues 1686-1881 (923-1118 of mature VWF) (SEQ ID NO:14) was synthesized and sub cloned into the mammalian expression vector pcDNA3.1(+) by Genscript. A sequence encoding 6 His was added at the N-terminus for further purification of the recombinant protein. The sequence of the expressed A3 domain protein was as follows (SEQ ID NO:15):

```
CSQPLDVILLLDGSSSFPASYFDEMKSFAKAFISKANIGPRLTQVSVLQYG

SITTIDVPWNVVPEKAHLLSLVDVMQREGGPSQIGDALGFAVRYLTSEMHG

ARPGASKAVVILVTDVSVDSVDAAADAARSNRVTVFPIGIGDRYDAAQLRI

LAGPAGDSNVVKLQRIEDLPTMVTLGNSFLHKLCSGFVRICTGHHHHHH
```

Suspension-adapted HEK-293F cells were routinely maintained in serum-free FreeStyle 293 Expression Medium (Gibco). On the day of transfection, cells were inoculated into fresh medium at a density of $1\times10^6$ cells/ml. 2 μg/ml plasmid DNA, 2 μg/ml linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. 6 days after transfection, the cell culture medium was collected by centrifugation and filtered through a 0.22 μm filter. Culture media was loaded into a HisTrap HP 5 ml column (GE Healthcare), using an ÄKTA pure 25 (GE Healthcare). After washing of the column with wash buffer (20 mM imidazole, 20 mM $NaH_2PO_4$, 0.5 M NaCl, pH 7.4), protein was eluted with a gradient of 500 mM imidazole (in 20 mM $NaH_2PO_4$, 0.5 M NaCl, pH 7.4). The eluate was further purified with size exclusion chromatography using a HiLoad Superdex 200PG column (GE Healthcare). All purification steps were carried out at 4° C. The expression of vWF A3 domain was determined by western blotting using anti-His tag antibody (BioLegend) and the proteins were verified as >90% pure by SDS-PAGE.

2. Synthesis of CBD-CPI Antibody

Rat anti-mouse PD-L1 (clone: 10F.9G2, Bio X Cell), hamster anti-mouse CTLA4 (clone: 9H10, Bio X Cell) was incubated with 15 eq. of sulfo-SMCC for 30 min at RT. Excess sulfo-SMCC was removed using a Zeba spin desalting column (Thermo Fisher Scientific). 5 eq. of CBD protein (the vWF A3 domain, with an N-terminal cysteine residue) was then added and reacted for 1 hr at RT.

3. Detection of CPI Antibody Binding to Collagen and their Target Proteins 96-well ELISA plates (Greiner Bio One) were coated with 10 μg/mL collagen I (EMD Millipore), collagen III (EMD Millipore), recombinant mouse (rm) CTLA4 (Sino Biological), or rmPD-L1 (Sino Biological) in PBS for 1 h at 37° C., followed by blocking with 2% BSA in PBS with 0.05% Tween 20 (PBS-T) for 1 hr at RT. Then, wells were washed with PBS-T and further incubated with 10 μg/mL CBD- or unmodified CPI for 1 hr at RT. After 3 washes with PBS-T, wells were incubated for 1 hr at RT with HRP-conjugated antibody against rat IgG or Syrian hamster IgG (Jackson ImmunoResearch). After washes, bound CPI were detected with tetramethylbenzidine substrate by measurement of the absorbance at 450 nm with subtraction of the measurement at 570 nm. The apparent dissociation constant ($K_D$) values were obtained by nonlinear regression analysis in Prism software (v7, GraphPad Software) assuming one-site specific binding.

4. Mice and Cell Lines

C57BL/6 and Balb/c, age 8 to 12 wk, were obtained from the Jackson Laboratories. FVB mice, age 8 to 12 wk, were obtained from the Charles River. Tyr:Cre-ER$^+$/LSL-Braf$^{V600}$/Pten$^{fl/fl}$ mice, age 6 to 12 wk were generated as reported previously (91) and bred at the animal facility of the University of Chicago according to the institutional guidance (91) and were provided by Prof. T. Gajewski (University of Chicago). Experiments were performed with approval from the Institutional Animal Care and Use Committee of the University of Chicago. B16F10 cells and CT26 cells were obtained from the American Type Culture Collection and cultured according to the instructions. MMTV-PyMT cells were obtained from spontaneously developed breast cancer in FVB-Tg(MMTV-PyVT) transgenic mice (polyoma middle T antigen oncogene expression was induced by mouse mammary tumor virus promotor) and cultured in vitro. All cell lines were checked for *mycoplasma* contamination by a pathogen test IMPACT I (IDEXX BioResearch).

5. In Vivo Bio-Distribution Study

The vWF A3 domain protein was fluorescently labeled using DyLight 800 NHS ester (Thermo Fisher) and unreacted dye was removed by a Zebaspin spin column (Thermo Fisher) according to the manufacture's instruction. A total of $5\times10^5$ MMTV-PyMT cells re-suspended in 50 μL of PBS were injected subcutaneously into the mammary fat pad on the right side of each FVB mouse. When the tumor reached 500 mm$^3$, 50 μg of DyLight 800 labeled CBD was injected i.v. Organs were extracted and imaged 48 hr after injection with the Xenogen IVIS Imaging System 100 (Xenogen) under the following conditions: f/stop: 2; optical filter excitation 740 nm; excitation 800 nm; exposure time: 5 sec; small binning.

6. Histological Analysis of Injected CBD-αPD-L1 within Tumor

A total of $5\times10^5$ MMTV-PyMT cells re-suspended in 50 μL of PBS were injected subcutaneously into the mammary fat pad on the right side of each FVB mouse. When the tumor reached 100 mm$^3$, 100 μg of DyLight 594 labeled CBD-αPD-L1 and 100 μg of DyLight 488 labeled αCollagen I (Abcam) was injected i.v. After 30 min, tumors were harvested, washed in cold PBS, fixed with 2% PFA for 10 min at room temperature, and washed in PBS. Then, tumors were cast in 2% agarose gel (LE Quick Dissolve Agarose, GeneMate) in 12 well plates. The gel plugs containing tumors were marked for orientation and mounted on a vibrating microtome (VT1200S, Leica) equipped with a buffer tray. Sections were collected in order in cold PBS, and fixed with 2% paraformaldehyde in PBS for 5 min at room temperature. Staining of tumor with DyLight 633-anti-mouse CD31 antibody and microscopic imaging was performed using a Leica SP5 AOBS II tandem scanner spectral confocal microscope as described previously (92).

7. Antibody Concentration Analysis $5\times10^5$ B16F10 melanoma cells were injected intradermally on left side of the back of each mouse. After 4 days, mice were injected with 100 μg each of CPI i.v. Blood samples were collected in tubes on 5, 6, and 8 days after tumor inoculation. Concentrations of CPI in serum were measured by ELISA as described above.

8. Serum Cytokine Concentration Analysis $5\times10^5$ B16F10 melanoma cells were injected intradermally on left side of the back of each 15 wk old C57BL/6 mouse. After 4 days, mice received two doses of 100 μg each CPI. On day 5, 6, and 8, blood samples were collected in tubes, followed by overnight incubation at 4° C. Cytokine concentrations in serum were measured by Ready-SET-Go! ELISA kits (eBioscience) according to the manufacture's protocol.

9. ALT Activity Analysis

B16F10 tumor bearing mice received 100 μg CPI injection, 4 and 7 days after tumor inoculation. On day 10, blood samples were collected in tubes, followed by >4 h incubation at 4° C. On the same day, serum was collected and ALT activity was measured by ALT assay kit (Sigma-Aldrich) according to the manufacture's protocol.

10. Histology

B16F10 tumor bearing mice received CPI injection (αPD-L1 and αCTLA4 100 μg, each), 4 and 7 days after tumor inoculation. 10 days after tumor inoculation, liver and lung were collected and fixed with 2% PFA. After embedding in paraffin, blocks were cut into 5 μm sections, followed by staining with hematoxylin and eosin. Images were captured with an EVOS FL Auto microscope (Life Technologies). For quantification of lymphocytic infiltration, the number of lymphocyte infiltration foci in 10 high-power fields (×400) was counted with light microscopy (BX53, Olympus). Slides were evaluated independently by two pathologists (H. A. and M. Y.) who were blinded to the treatment. Microscopic images were captured with color CCD camera (DP27, Olympus).

11. Antitumor Efficacy of CPI on B16F10 Tumor

A total of $5 \times 10^5$ B16F10 cells re-suspended in 50 μL of PBS were inoculated intradermally on the left side of the back of each C57BL/6 mouse. After 4 days, mice were injected with CPI (αPD-L1 and αCTLA4 25 μg or 100 each) i.v. Tumors were measured with a digital caliper starting 4 days after tumor inoculation, and volumes were calculated as ellipsoids, where V=4/3×3.14×depth/2×width/2×height/2. Mice were sacrificed at the point when either tumor volume had reached over 500 mm$^3$.

12. Antitumor Efficacy of CPI on CT26 Tumor

A total of $5 \times 10^5$ CT26 cells re-suspended in 50 μL of PBS were inoculated intradermally on the left side of the back of each Balb/c mouse. After 5 days, mice were injected i.v. with CPI (αPD-L1 and αCTLA4 25 μg or 100 each). Tumors were measured with a digital caliper starting 5 days after tumor inoculation as described above. Mice were sacrificed at the point when either tumor volume had reached over 500 mm$^3$.

13. Tissue and Cell Preparation and T Cell Subset Analysis $5 \times 10^5$ B16F10 melanoma cells were injected intradermally on the left side of the back of each C57BL/6 mouse. Mice were injected i.v. with CPI (αPD-L1 and αCTLA4 100 μg, each) on day 4. Mice were sacrificed on day 8. Tumors were harvested and were digested in Dulbecco's Modified Eagle Medium (DMEM) supplemented with 2% FBS, 2 mg/mL collagenase D and 40 μg/mL DNase I (Roche) for 30 min at 37° C. Single-cell suspensions were obtained by gently disrupting the organs through a 70-mm cell strainer. Red blood cells were lysed with ACK lysing buffer (Quality Biological). Cells were counted and re-suspended in Iscove's Modified Dulbecco's Medium (IMDM) supplemented with 10% FBS and 1% penicillin/streptomycin (full medium; all from Life Technologies) and used for flow cytometry staining.

14. Flow Cytometry and Antibodies

Single cell suspensions from tumors were prepared as described above. Following a washing step, approximately $2 \times 10^6$ cells were used for antibody staining. Antibodies against the following molecules were used throughout the paper if not otherwise indicated: CD3 (145-2C11, BD Biosciences), CD4 (RM4-5, BD Biosciences), CD8a (53-6.7, BD Biosciences), CD25 (PC61, BD Biosciences), CD45 (30-F11, BD Biosciences), CD44 (IM7, BD Biosciences), CD62L (MEL-14, BD Biosciences), PD-1 (29F.1A12, BioLegend), Foxp3 (MF23, BD Biosciences). Fixable live/dead cell discrimination was performed using Fixable Viability Dye eFluor 455 (eBioscience) according to the manufacturer's instructions. Staining was carried out on ice for 20 min if not indicated otherwise, and intracellular staining was performed using the Foxp3-staining kit according to manufacturer's instructions (BioLegend). Following a washing step, cells were stained with specific antibodies for 20 min on ice prior to fixation. All flow cytometric analyses were done using a Fortessa (BD Biosciences) flow cytometer and analyzed using FlowJo software (Tree Star).

15. Ex Vivo T Cell Stimulation

Single cell suspensions from tumor were prepared as described above. CD8$^+$ T cells were isolated using EasySep kits (STEMCELL Technologies) following the manufacturer's instructions, except that biotinylated αCD105 (12403, BioLegend) was added to the EasySep CD8$^+$ T cell Isolation Cocktail to remove B16F10 melanoma cells. 96-well cell culture plates (BD Falcon) were coated with 10 μg/mL αCD3 (145-2C11, BioLegend) in PBS overnight at 37° C. Extracted T cells from tumor were plated in 96-well plates and cultured in full medium for 6 h at 37° C. in the presence of 2 μg/mL αCD28 (EL-4, BioLegend) and 5 μg/mL brefeldin A (Sigma-Aldrich). Cells were harvested, stained, and analyzed by flow cytometry as described above.

16. Statistical Analysis

Statistical methods were not used to predetermine necessary sample size, but sample sizes were chosen based on estimates from pilot experiments and previously published results such that appropriate statistical tests could yield significant results. Synthesis of CBD-CPI and tumor treatments were performed by multiple individuals to ensure reproducibility. All experiments are replicated at least twice in the laboratory. For animal studies, mice were randomized into treatment groups within a cage immediately before the first CPI injection and treated in the same way. The survival endpoint was reached when the tumor size became over 500 mm$^3$ for B16F10, CT26 and MMTV-PyMT tumors, and 1000 mm$^3$ for Tyr:Cre-ER$^+$/LSL-Braf$^{V600}$/Pten$^{fl/fl}$ βCat$^{STA}$ tumor. The n values used to calculate statistics are indicated in figure legends. Experiments were not performed in a blinded fashion. Statistically significant differences between experimental groups were determined using Prism software (v7, GraphPad). Where one-way ANOVA followed by Tukey's HSD post hoc test was used, variance between groups was found to be similar by Brown-Forsythe test. For non-parametric data, Kruskal-Wallis test followed by Dunn's multiple comparison test was used. For single comparisons, a two-tailed Student's t-test was used. Survival curves were analyzed by using the log-rank (Mantel-Cox) test. The symbols * and ** indicate P values less than 0.05 and 0.01, respectively; N.S., not significant.

Example 5—Improving Efficacy and Safety of Agonistic Anti-CD40 Antibody Through Extracellular Matrix Affinity CD40 (tumor necrosis factor receptor superfamily 5: TNFRSF5) is a 48 kDa type I transmembrane protein expressed by antigen-presenting cells (APCs) (1). CD40 mediates an activation signal on APCs when ligated by CD40L (CD154), expressed predominantly by activated helper T cells.

Agonistic antibodies against CD40 (αCD40) have been shown to suppress tumor growth in both mouse models and clinical trials (2-11). On DCs, αCD40 increases cell-surface expression of co-stimulatory and major histocompatibility complex (MHC) molecules and induces pro-inflammatory cytokines, leading to enhanced B and T cell activation (2, 12-14). αCD40 binding on follicular B cells induces proliferation, immunoglobulin class switching, and secretion of antitumor antibodies (4,15). B cell depletion partially impairs the antitumor efficacy of αCD40 treatment in murine malignant mesothelioma (4). On tumor-associated macrophages, αCD40 treatment drives phenotype switching from M2 to M1 type, which is accompanied by induction of cytotoxic T cell and natural killer (NK) cell responses against tumors (6,7). Thus, αCD40 treatment can induce anti-tumor effects through activation of several cell types, both directly (APCs, including B cells) and indirectly (T cells, NK cells).

Several agonistic αCD40 antibodies have been developed for human cancer immunotherapy (e.g., CP-870,893, dacetuzumumab, ADC-1013, and Chi Lob 7/4) and have shown favorable antitumor responses in melanoma, pancreatic carcinoma, mesothelioma, and lymphoma (1,8,9). However, much remains to be improved with αCD40 therapy; for example, treatment-related adverse events such as interleukin-6 (IL-6) and tumor necrosis factor-α (TNF-α) cytokine release syndrome and hepatotoxicity have been reported after αCD40 treatment in the clinic (11), limiting the dosage of αCD40 treatment (1). To address these issues, local injection of αCD40 such as intra-tumoral or peritumoral (p.t.) injection has been tested and has shown higher antitumor efficacy compared to systemic injection (e.g. intra-venous or intra-peritoneal injection) in several mouse tumor models (2, 16-19).

Immune checkpoint inhibitor (CPI) therapy such as cytotoxic T-lymphocyte-associated protein 4/programmed cell death 1 (CTLA4/PD-1) inhibition exhibits considerable antitumor activity in the clinic (20-22). Because the main mechanism of CTLA4/PD-1 inhibition therapy is antitumor T cell activation, the success of CPI therapy is largely dependent on T cell infiltration into the tumor (23,24). However, partially due to poor T cell infiltration, a substantial number of patients do not respond to CPI therapy. The response rates against advanced melanoma for monotherapies range from 19% for αCTLA4 (ipilimumab) to 44% for αPD-1 (nivolumab) (25). Therefore, the development of alternative strategies as mono- or adjunctive therapies to enhance T cell infiltration into tumors is needed for tumor immunotherapy.

This Example describes an αCD40 variant that binds extracellular matrix through a super-affinity peptide derived from placenta growth factor (PlGF-$2_{123-144}$) to enhance αCD40's effects when administered locally. Peri-tumoral injection of PlGF-$2_{123-144}$-αCD40 antibody showed prolonged tissue retention at the injection site and substantially decreased systemic exposure, resulting in decreased liver toxicity. In four mouse tumor models, PlGF-$2_{123-144}$-αCD40 antibody demonstrated enhanced antitumor efficacy compared to its unmodified form and correlated with activated dendritic cells, B cells, and T cells in the tumor and in the tumor-draining lymph node. Moreover, in a genetically engineered Braf$^{V600E}$ βcat$^{STA}$ melanoma model that does not respond to checkpoint inhibitors, PlGF-$2_{123-144}$-αCD40 antibody treatment enhanced T cell infiltration into the tumors and slowed tumor growth. Together, these results demonstrate the marked therapeutic advantages of engineering matrix binding domains onto agonistic anti-CD40 antibody as a therapeutic for cancer immunotherapy.

A. Results

1. PlGF-$2_{123-144}$ Peptide Conjugation Enhances ECM Binding and Prolongs Tissue Retention of αCD40

Figure 34A:
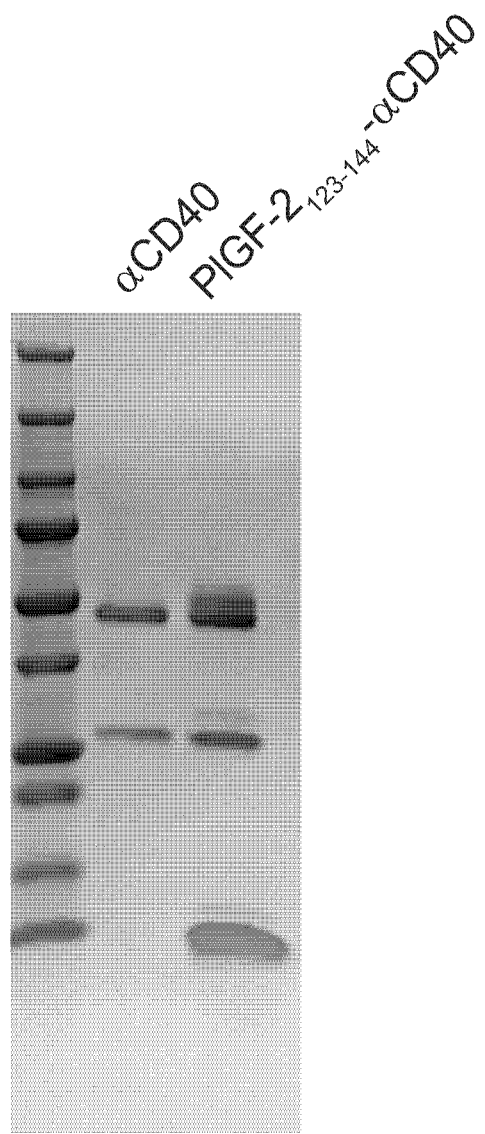
Figure 34B:
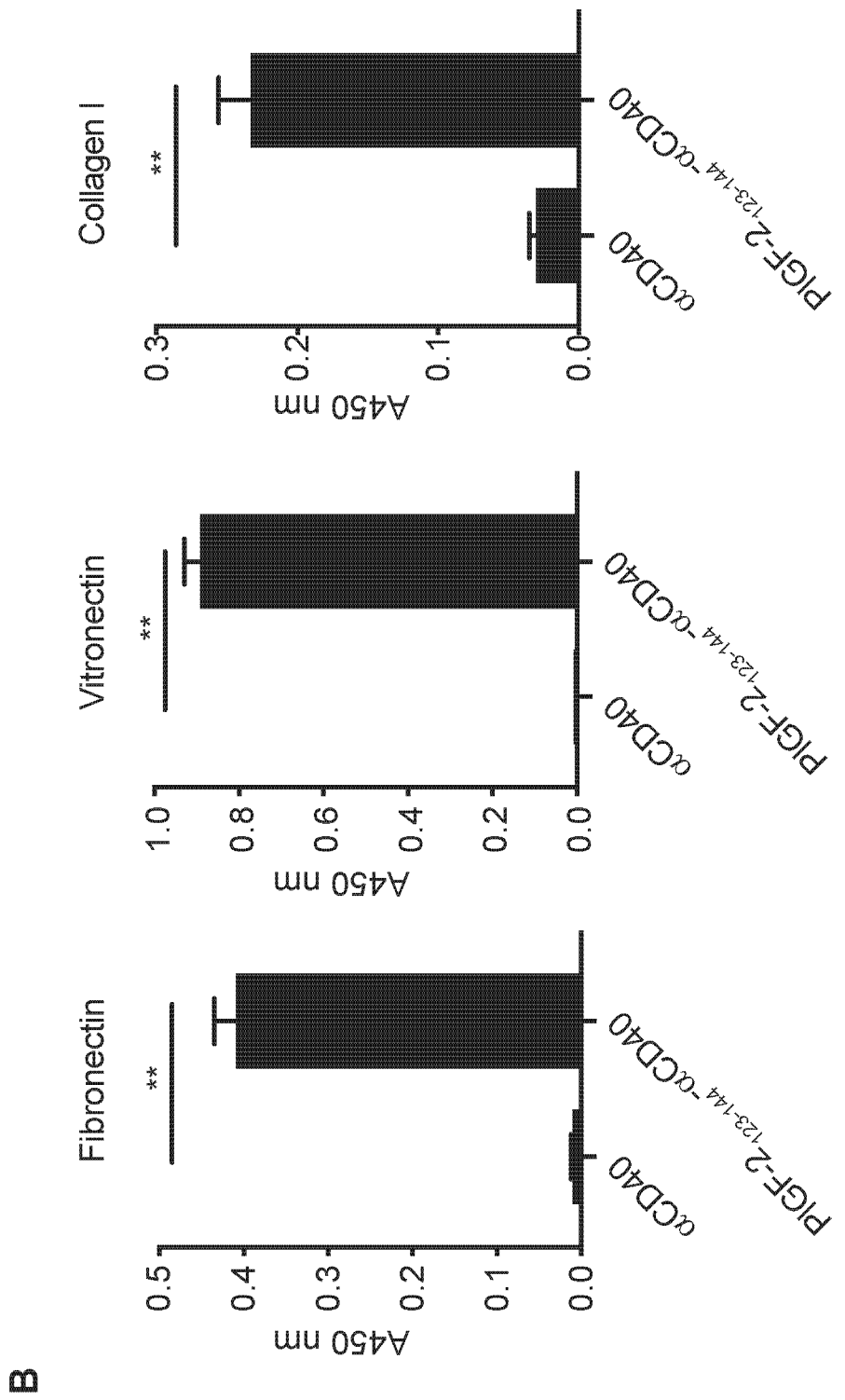
Figure 34C:
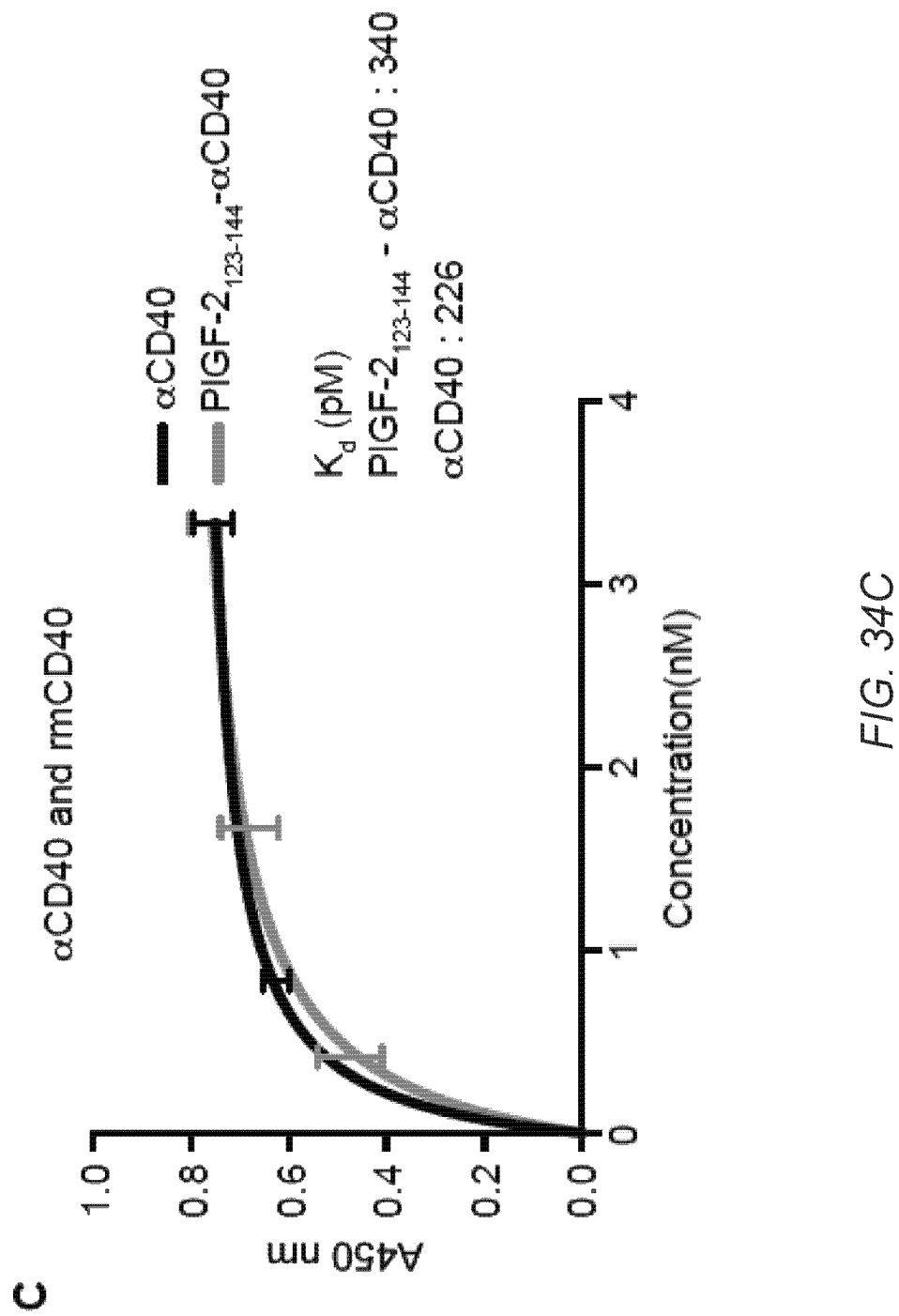

The ECM-binding properties of PlGF-$2_{123-144}$-αCD40 were characterized in vitro. SDS-PAGE revealed that the molecular weights of both the light and heavy chains of αCD40 were increased (FIG. 34A). PlGF-$2_{123-144}$-αCD40 bound to fibronectin, vitronectin, and collagen I, tested as major ECM proteins (FIG. 34B). In comparison, unmodified αCD40 did not bind to the tested ECM proteins. PlGF-$2_{123-144}$-αCD40 recognized recombinant mouse CD40 with a similar $K_d$ value as the unmodified antibody (FIG. 34C). These data show that PlGF-$2_{123-144}$-modification of αCD40 led to strong ECM binding without impairing its antigen recognition.

Figure 34D:
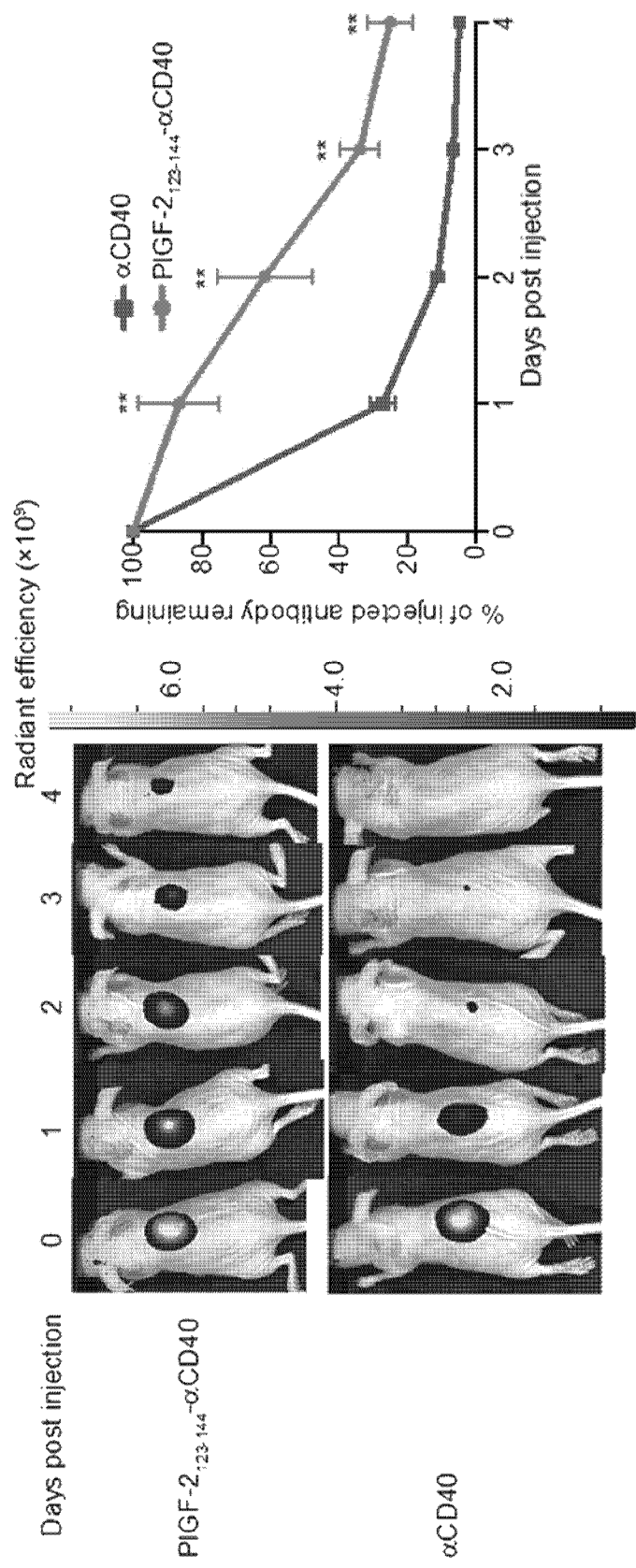

Next, the tissue retention capacity of PlGF-$2_{123-144}$-αCD40 was examined. Using in vivo imaging analysis, PlGF-$2_{123-144}$-αCD40 was shown to be retained at the injection site long-term through binding to endogenous ECM molecules. The signal of PlGF-$2_{123-144}$-αCD40 was detectable at the injection site for 96 hr after injection, whereas the signal of unmodified αCD40 became very low after 48 hr of injection. This data shows that PlGF-$2_{123-144}$ conjugation enhanced retention of αCD40 at the tissue injection site (FIG. 34D).

2. PlGF-$2_{123-144}$ Conjugation Lowers αCD40 Systemic Exposure and Prevents Treatment-Related Adverse Events Because PlGF-$2_{123-144}$-αCD40 showed prolonged retention at the injection site, the inventors hypothesized that the concentration of the injected PlGF-$2_{123-144}$-αCD40 in blood serum would be lower compared to unmodified αCD40, due to retention in the tumor injection site. αCD40 concentrations in blood serum over time were measured after a single peri-tumoral (p.t.) administration (50 µg) of αCD40 in B16F10 tumors 4 d after inoculation. The concentration of PlGF-$2_{123-144}$-αCD40 in blood serum was lower compared to αCD40 at all time points (FIG. 35A). This lower systemic exposure suggests that PlGF-$2_{123-144}$ conjugation might decrease systemic toxicity of αCD40.

Figure 35E:
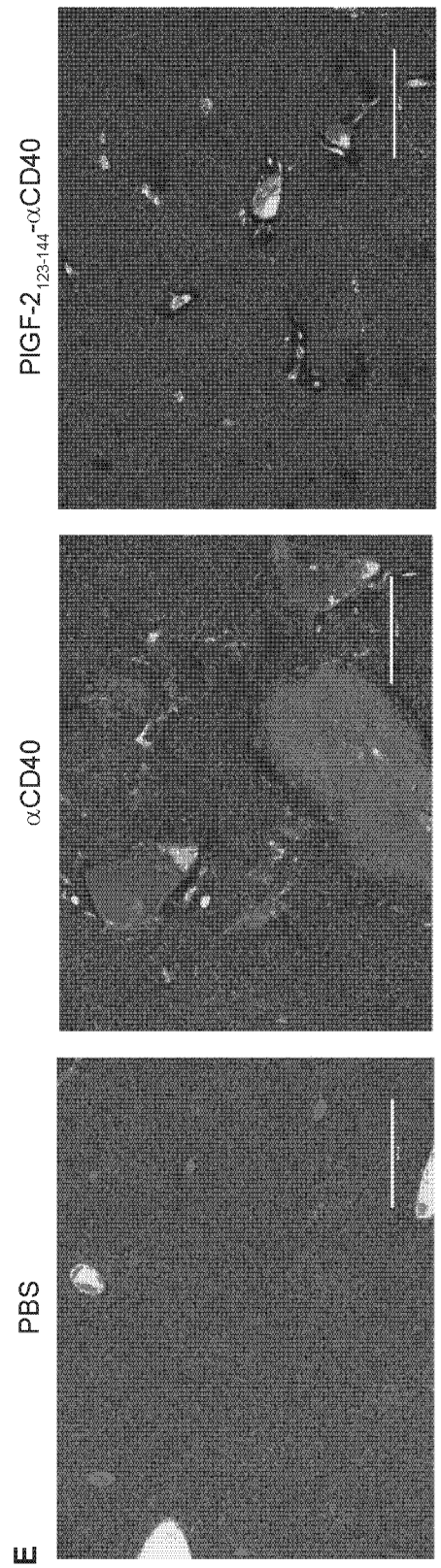

Next, treatment-related adverse events were examined. αCD40 was injected p.t. 4 days after B16F10 tumor inoculation, then blood serum was collected. Unmodified αCD40 administration significantly increased both IL-6 and TNFα concentrations in serum, whereas PlGF-$2_{123-144}$-αCD40 did not (FIG. 35B-C). Hepatotoxicity was investigated by measuring a clinically used liver damage marker, ALT activity. Unmodified αCD40 increased ALT activity levels compared to the PBS-treated group, but PlGF-$2_{123-144}$-αCD40 did not (FIG. 35D). In addition, histologic analysis of the liver showed that αCD40 induced marked morphological changes, as evidenced by hepatic necrosis and leukocyte infiltration (FIG. 35E). In contrast, no necrotic regions were observed after PlGF-$2_{123-144}$-αCD40 treatment, although some perivascular lymphocytic infiltration was still observed. mRNA of CD40 was not detected in hepatocytes (FIG. 36), consistent with an immunological rather than direct mechanism of hepatotoxicity (31). Taken together, these results indicate that PlGF-$2_{123-144}$ conjugation reduces the systemic toxicity of αCD40, likely through reduction of systemic exposure.

3. PlGF-$2_{123-144}$-αCD40 Showed Higher Antitumor Efficacy in Multiple Tumor Models Compared to Unmodified αCD40

The inventors tested the antitumor efficacy of PlGF-$2_{123-144}$-αCD40 treatment in mouse models that demonstrate T cell infiltration and thus are to an extent responsive to CPI. Four days after B16F10 cell inoculation, αCD40 (10 or 50 µg/injection) was administered p.t. At the dose of 10 µg/injection, PlGF-$2_{123-144}$-αCD40 treatment statistically significantly slowed tumor growth, whereas unmodified αCD40 did not show an antitumor effect (FIG. 37A). With an increased dose (50 µg/injection), unmodified αCD40 significantly slowed tumor growth and PlGF-$2_{123-144}$-αCD40 induced an even smaller tumor size, significantly more so than the unmodified antibody (FIG. 37B). Next, the inventors investigated antitumor efficacy against CT26 colon carcinoma (FIG. 37C). Five days after CT26 cells were inoculated, αCD40 was administered at 10 µg/injection p.t. PlGF-$2_{123-144}$-αCD40 treatment statistically significantly slowed tumor growth, whereas unmodified αCD40 did not show an antitumor effect (FIG. 37C). Similarly, the antitumor activity of PlGF-2$_{123\text{-}144}$-αCD40 in the MMTV-PyMT genetically engineered breast cancer model was examined (32) and it was found that p.t. administration of PlGF-2$_{123\text{-}144}$-αCD40 (50 µg/injection) again suppressed tumor growth significantly stronger than its unmodified form (FIG. 37D). PlGF-2$_{123\text{-}144}$-αCD40 administration induced eradication of tumors in 2 out of 9 mice; unmodified αCD40 treatment eradicated tumors in 1 of 8 mice. These data indicated that local treatment with PlGF-2$_{123\text{-}144}$-αCD40 exhibits superior antitumor efficacy compared to local treatment with its unmodified form in multiple tumor types.

4. PlGF-2$_{123\text{-}144}$-αCD40 Treatment Effectively Activates T Cells, B Cells, and DCs within the Tumor and Td-LN To investigate the mechanisms behind the therapeutic action of PlGF-2$_{123\text{-}144}$-αCD40 treatment, T cell and APC responses were analyzed in B16F10 tumor-bearing mice. 50 µg αCD40 was injected p.t. on day 4 after tumor inoculation. On day 9, leukocytes were extracted from the tumor and td-LN. The frequency of DCs as a percentage of CD45$^+$ cells within the tumor was slightly decreased by unmodified αCD40 treatment (FIG. 38A). Both PlGF-2$_{123\text{-}144}$-αCD40 and unmodified αCD40 significantly increased the frequency of CD11c$^+$ DCs in the td-LN (FIG. 38B). Both PlGF-2$_{123\text{-}144}$-αCD40 and unmodified αCD40 treatments significantly decreased the frequency of MHCII$^{High}$CD86$^+$ of CD11c$^+$ DCs in the tumor while increasing them in td-LN, indicating the maturation of CD11c$^+$ DCs (FIG. 38C). Similarly, the frequency of MHCII$^{High}$CD86$^+$ within F4/80$^+$ macrophages was significantly decreased in the tumor while being significantly increased in td-LN by both PlGF-2$_{123\text{-}144}$-αCD40 and unmodified αCD40 treatments, suggesting that αCD40 treatments induced activation of macrophages (FIG. 38E-F).

Regarding T cells, PlGF-2$_{123\text{-}144}$-αCD40 treatment significantly increased the frequency of CD8$^+$CD3$^+$ T cells of CD45$^+$ cells within the tumor compared to the PBS-treated group, while unmodified αCD40 treatment did not (FIG. 38G). PlGF-2$_{123\text{-}144}$-αCD40 treatment significantly increased the frequency of the effector population (defined as CD62L$^-$CD44$^+$) of CD8$^+$CD3$^+$ T cells within the tumor compared to the PBS-treated and unmodified αCD40-treated groups, indicating higher activation of CD8$^+$ T cells (FIG. 38H). Neither unmodified-nor PlGF-2$_{123\text{-}144}$-conjugated αCD40 treatments altered the frequency of CD4$^+$CD3$^+$ T cells of CD45$^+$ cells (FIG. 38I). The frequency of CD25$^+$Foxp3$^+$ Treg population of CD4$^+$CD3$^+$ T cells within the tumor was maintained in all treatment groups (FIG. 38J). Therefore, PlGF-2$_{123\text{-}144}$-αCD40 treatment significantly increased the ratio of effector CD8$^+$ T cell/Treg cell numbers within the tumor compared to PBS and unmodified αCD40 treatment groups (FIG. 38K). Unmodified αCD40 treatment slightly decreased the frequency of PD-1$^+$ of CD8$^+$CD3$^+$ T cells within the tumor compared to the PBS-treated group (FIG. 38L), consistent with previous research showing that αCD40 treatment reverses PD-1$^+$ exhausted tumor-infiltrated T cells into active cells (33).

In terms of B cell activation, the tumor and blood were analyzed on day 11. The frequency of MHCII$^{High}$CD86$^+$ within B cells was significantly enhanced by PlGF-2$_{123\text{-}144}$-αCD40 both in the tumor and td-LN, whereas αCD40 treatment increased the frequency of MHCII$^{High}$CD86$^+$ within B cells only in the td-LN (FIG. 38M-N). This data suggests that PlGF-2$_{123\text{-}144}$-αCD40 treatment induced activation of B cells. Crucially, PlGF-2$_{123\text{-}144}$-αCD40 treatment, but not unmodified αCD40 treatment, significantly increased induction of endogenous cell surface-binding antibodies against B16F10 cells (FIG. 38O), suggesting the B cell mediated antitumor mechanism as well.

The frequency of NK cells was maintained between all treatment groups within the tumor (FIG. 39). Unmodified αCD40 treatment slightly increased the frequency of NK cells in td-LN (FIG. 39).

Collectively, PlGF-2$_{123\text{-}144}$-αCD40 treatment effectively activated T cells, DCs, B cells, and macrophages in the tumor or td-LN, consistent with the increased therapeutic effects reported in FIG. 37.

5. PlGF-2$_{123\text{-}144}$-αCD40 Treatment Induces Systemic Antitumor Immunity Through CD8$^+$ T Cell Priming In light of the increase of mature APCs and activated CD8$^+$ T cells after PlGF-2$_{123\text{-}144}$-αCD40 treatment, it was investigated whether PlGF-2$_{123\text{-}144}$-αCD40 could mediate antitumor responses in a distant tumor when administered to one tumor locally. B16F10 cells were inoculated both in the left and in the right back of mice on day 0 (FIG. 40A). Subsequently, the αCD40 (50 µg/injection) forms were injected p.t. beside only the left tumor on day 4. The p.t. injection of PlGF-2$_{123\text{-}144}$-αCD40 slowed the outgrowth of both the left (ipsilateral) and right (contralateral) tumors; unmodified αCD40 did so as well, but to a significantly lesser extent. These data indicate that local PlGF-2$_{123\text{-}144}$-αCD40 treatment near one tumor enhances a systemic antitumor immunological activity capable of reducing tumor growth systemically.

To investigate if the anti-tumor effect of PlGF-2$_{123\text{-}144}$-αCD40 treatment is dependent on CD103$^+$ DCs or CD8α$^+$ DCs, Batf3 gene knockout mice were used. Batf3, a basic leucine zipper transcription factor, is essential for the development of cross-presenting DCs such as CD103$^+$ DCs and of CD8α$^+$ DCs (34-36). In Batf3$^-$ mice, the absence of these cross-presenting DCs severely compromises the cross-priming of CD8$^+$ T cells (37). Four days after B16F10 cell inoculation in Batf3$^{-/-}$ mice, PlGF-2$_{123\text{-}144}$-αCD40 (10 µg/injection) was administered p.t., as wild-type C57BL6 mice were treated in FIG. 37A. In contrast to wild-type mice, PlGF-2$_{123\text{-}144}$-αCD40 treatment did not slow B16F10 tumor growth in Batf3$^-$ mice (FIG. 40B). This data suggests that the CD103$^+$ DCs- or CD8α$^+$ DCs-mediated cross-priming of CD8$^+$ T cells plays a crucial role in the anti-tumor effect of PlGF-2$_{123\text{-}144}$-αCD40 treatment in B16F10 melanoma model.

6. PlGF-2$_{123\text{-}144}$-αCD40 Treatment Slows the Growth of β-Catenin-Expressing Genetically Engineered Primary Melanomas The above data demonstrated that PlGF-2$_{123\text{-}144}$-αCD40 treatment induces CD8$^+$ T cell infiltration in the B16F10 tumor (FIG. 38). To test whether PlGF-2$_{123\text{-}144}$-αCD40 treatment may show antitumor efficacy against tumors that have reduced T cell infiltration (and are therefore unresponsive to CPI therapy) through converting T cell non-inflamed tumors into inflamed tumors, Tyr:Cre-ER$^+$/LSL-Braf$^{V600E}$/Pten$^{fl/fl}$ βcat$^{STA}$ mice were used. These mice are genetically engineered with Cre-inducible expression of active B-Raf and biallelic deletion of PTEN, commonly altered molecular pathways in human melanoma, with inducible expression of stabilized β-catenin (28). β-catenin pathway expression has been shown to reduce infiltration of CD103$^+$ DCs, resulting in few T cells within the tumor microenvironment and unresponsiveness to CPI therapy (28). After tumor induction via local application of 4-OH-tamoxifen, unmodified or PlGF-2$_{123\text{-}144}$-αCD40 was administered via p.t. injection. Notably, p.t. administration of unmodified αCD40 slowed the growth of this tumor (FIG. 41A). More importantly, p.t. administration of PlGF-2$_{123\text{-}144}$-αCD40 treatment slowed tumor growth compared to PBS- and unmodified αCD40-treated groups (FIG. 41A). PlGF-2$_{123\text{-}144}$-αCD40 treatment but not αCD40 treatment prolonged survival (FIG. 41B).

Because PlGF-2$_{123\text{-}144}$-αCD40 treatment increased the frequency of CD8$^+$ T cells within B16F10 melanoma (FIG. 38G) and CD8$^+$ T cells are indispensable for antitumor effect by PlGF-2$_{123\text{-}144}$-αCD40 treatment (FIGS. 37A and 40B), the number of T cells in the Tyr:Cre-ER$^+$/LSL-Braf$^{V600E}$/ Pten$^{fl/fl}$ βcat$^{STA}$ tumors were analyzed (FIG. 41C). PlGF-2$_{123\text{-}144}$-αCD40 treatment statistically significantly increased the frequency of CD8$^+$ T cells within tumor microenvironment compared to PBS treatment and unmodified αCD40 treatment. These data demonstrate that PlGF-2$_{123\text{-}144}$-αCD40 treatment shows an antitumor effect even within a CPI-unresponsive tumor, more so than with the unmodified αCD40, consistent with the elevation of activated T cells observed in the B16F10 model.

B. Discussion

αCD40 as a cancer immunotherapeutic is associated with adverse events that limit the dosages of αCD40 that can be safely used in the clinic (11,38). In this Example, the incidence of such adverse events was reduced by PlGF-2$_{123\text{-}144}$ conjugation to αCD40 when it was administered p.t., similarly to PlGF-2$_{123\text{-}144}$-conjugated CPI antibodies (27). PlGF-2$_{123\text{-}144}$-αCD40, which remains localized near the tumor tissue injection site, should more closely maintain normal systemic immune homeostasis by avoiding influences on non-tumor antigen-specific T or B cells and reducing influences on myeloid cells resident in the liver (31). It is likely that the lower hepatotoxicity and systemic cytokine release observed after PlGF-2$_{123\text{-}144}$-αCD40 administration was due to this reduction in systemic exposure. Notably, PlGF-2$_{123\text{-}144}$ conjugation may even allow decreases in the administered dose, as tumor growth delay was shown at low local dosages, where unmodified αCD40 had no effect. These data suggest the possibility of treating patients who have discontinued therapy because of such adverse events, as well as who are not amenable to systemic therapy.

Of particular interest is the observation that αCD40 treatment suppressed the growth of Tyr:Cre-ER$^+$/LSL-Braf$^{V600E}$/Pten$^{fl/fl}$ βcat$^{STA}$ melanoma, a CPI therapy unresponsive tumor (28). There are considerable numbers of patients who do not respond to CPI therapy, mainly because of low T cell infiltration (22). In the clinic, 48% of non-T-cell-infiltrated melanomas reportedly show active β-catenin signaling (28). Development of a treatment strategy that shows efficacy in a corresponding genetically engineered mouse tumor model indicates that these patients would benefit from the treatment strategy. The above data show that PlGF-2$_{123\text{-}144}$-αCD40 treatment induced T cell infiltration into the Tyr:Cre-ER$^+$/LSL-Braf$^{V600E}$/Pten$^{fl/fl}$ TA melanoma tumor microenvironment. Given that there were statistically elevated CD8$^+$ T cell numbers in tumors of PlGF-2$_{123\text{-}144}$-αCD40-treated animals, and given the lack of response to therapy in CD103$^+$/CD8α$^+$ DC-negative Batf3$^{-/-}$ mice, it can be concluded that induction of antigen-specific CD8$^+$ T cell response through cross-presentation of tumor antigen drives the anti-tumor response more efficiently with PlGF-2$_{123\text{-}144}$-αCD40 treatment than with unmodified αCD40 treatment.

The localized therapy demonstrated above also suppressed growth of a tumor contralateral to the injection site, which is consistent with earlier observations of induction of systemic immunity (2,39-41). The above data indicate that injecting one accessible tumor site with PlGF-2$_{123\text{-}144}$-αCD40 would be effective in treating metastatic cancer. With the low concentration of PlGF-2$_{123\text{-}144}$-αCD40 in the blood combined with the increase in activated CD8$^+$ T cells in the tumor and the increase in induced anti-tumor cell antibody levels in the blood, the mechanism of action in a distant tumor is likely due to effective tumor antigen-specific immune cell activation, through which cytotoxic T lymphocytes and anti-tumor cell antibodies are disseminated systemically, rather than by leakage of PlGF-2$_{123\text{-}144}$-αCD40 from one tumor to the other. Unmodified αCD40 distributed systemically via p.t. administration did not significantly suppress B16F10 tumor growth as much as PlGF-2$_{123\text{-}144}$-αCD40. Because PlGF-2$_{123\text{-}144}$-αCD40 treatment activated CD1 DCs, macrophages and B cells in the td-LN, it is believed that effective activation of antitumor B cells and T cells through p.t. injection of αCD40 led to suppressed tumor outgrowth in both ipsilateral and contralateral tumors.

Local cancer immunotherapy has been tested in the clinic for melanoma, colorectal cancer, and lymphoma, exhibiting equivalent or higher antitumor efficacy compared to systemic administration of therapeutics (2,17,39-43). In a mouse model of colon carcinoma and thymoma, local administration of αCD40 with slow-release formulations (e.g., microparticle polymer, liposome and montanide oil emulsion) has enabled the use of lower doses of antibody, while maintaining or enhancing antitumor efficacy (2,17, 44). In this Example, the inventors have rather explored a molecular engineering approach to improve the antitumor effects of αCD40 even more, by PlGF-2$_{123\text{-}144}$ peptide conjugation, to thus employ the tumor stroma or the peritumoral stroma as a depot for antibody retention. This leads to favorable effects both on efficacy and safety when injected p.t. in multiple tumor models.

In summary, it was found that local injection of an ECM-binding variant of αCD40 has higher antitumor activity compared to its unmodified form, when administered p.t. Conjugation of PlGF-2$_{123\text{-}144}$ provided injection-site tissue retention of αCD40. A clear reduction in systemic side effects was demonstrated, associated with lower αCD40 concentrations in the systemic circulation, including reduced cytokine release syndrome and reduced hepatotoxicity. Peritumoral injection of PlGF-2$_{123\text{-}144}$-αCD40 alters the tumor microenvironment and significantly activates APCs (with CD103$^+$ and or CD8α$^+$ DCs being essential), resulting in delayed tumor growth and prolonged survival. This localized therapy also suppressed growth of a distant tumor. Importantly, favorable efficacy in a CPI-resistant melanoma model was observed; PlGF-2$_{123\text{-}144}$-αCD40 treatment enhanced T cell tumor-infiltration into this otherwise non-T cell inflamed tumor.

C. Materials and Methods

1. Synthesis of PlGF-2$_{123\text{-}144}$-αCD40

Rat anti-mouse CD40 (clone: FGK4.5, BioXCell) was incubated with 15 eq. of sulfo-succinimidyl 4-(N-maleimidomethyl) cyclohexane-1-carboxylate (sulfo-SMCC) for 30 min at room temperature. Excess sulfo-SMCC was removed using a Zeba spin desalting column (Thermo Fisher Scientific). 15 eq. of PlGF-2$_{123\text{-}144}$ peptide (RRRPKGRGKRR-REKQRPTDCHL) was then added and reacted for 1 hr at room temperature for conjugation to the thiol moiety on the C residue. The peptide had been synthesized with >95% purity by Genscript.

2. Sodium Dodecyl Sulfate Polyacrylamide Gel Electrophoresis (SDS-PAGE)

SDS-PAGE was performed on 4-20% gradient gels (Bio-Rad) after αCD40 was reduced with 10 mM DTT. After electrophoresis, gels were stained with SimplyBlue SafeStain (Thermo Fisher Scientific) according to the manufacturer's instruction. Gel images were acquired with the ChemiDoc XRS+ system (Bio-Rad).

3. Binding Assay 96-well ELISA plates (Greiner Bio One) were coated with 10 µg/mL recombinant human ECM proteins, fibronectin (Sigma-Aldrich), vitronectin (Sigma-Aldrich), collagen I (EMD Millipore), or with 1 µg/mL recombinant mouse (rm) CD40 (Sino Biological) in phosphate-buffered saline (PBS) for 1 hr at 37° C., followed by blocking with 2% bovine serum albumin (BSA) in PBS with 0.05% Tween 20 (PBS-T) for 1 hr at room temperature. Then, wells were washed with PBS-T and further incubated with PlGF-$2_{123-144}$- or unmodified αCD40 (10 µg/mL for ECM proteins) for 1 hr at room temperature. After 3 washes with PBS-T, wells were incubated for 1 hr at room temperature with horseradish peroxidase (HRP)-conjugated antibody against rat IgG (Jackson ImmunoResearch). After washes, bound αCD40 was detected with tetramethylbenzidine substrate by measurement of the absorbance at 450 nm with subtraction of the signal at 570 nm.

4. Mice and Cell Lines

Athymic nude (for imaging), C57BL/6 (for B16F10 melanoma model), Balb/c (for CT26 colon carcinoma model) and FVB (for MMTV-PyMT breast cancer model) mice, age 8-12 wk, were obtained from the Jackson Laboratories. Batf3$^{-/-}$ mice, age 8-12 wk, were a kind gift from Dr. Justin Kline (University of Chicago). Tyr:Cre-ER$^+$/LSL-Braf$^{V600E}$/Pten$^{fl/fl}$ βcat$^{STA}$ mice, age 6-12 wk, were generated as reported previously and bred at the animal facility of the University of Chicago according to the institutional guidance (28). Experiments were performed with approval from the Institutional Animal Care and Use Committee of the University of Chicago (protocol number 72470). B16F10 cells and CT26 cells were obtained from the American Type Culture Collection and cultured according to the instructions. MMTV-PyMT cells were obtained from spontaneously developed breast cancer in FVB-Tg (MMTV-PyVT) transgenic mice (polyoma middle T antigen oncogene expression was induced by mouse mammary tumor virus promotor) and cultured in vitro. All cell lines used in this study were checked for mycoplasma contamination by IMPACT I pathogen test (IDEXX BioResearch).

5. αCD40 Skin Retention Analysis

αCD40 was fluorescently labeled using sulfo-Cyanine 7 NHS ester (Lumiprobe) according to the manufacture's instruction. PlGF-$2_{123-144}$ peptide that is labeled with Cyanine 7 in its N-terminus was chemically synthesized with >90% purity by Thermo Fisher Scientific. Cyanine 7-labeled PlGF-$2_{123-144}$ was conjugated to αCD40 as described above. Athymic nude mice were injected with 40 µg of PlGF-$2_{123-144}$- or unmodified Cyanine 7 labeled αCD40 intradermally (i.d.). Mice were imaged every 24 hr after injection with a Xenogen IVIS Imaging System 100 (Xenogen) under the following conditions: f/stop: 2; optical filter excitation 710 nm; excitation 780 nm; exposure time: 1 sec; small binning.

6. Antibody Concentration Analysis

Measurement of antibody concentration in circulation was performed as described previously (27). 5×10$^5$ B16F10 melanoma cells were injected intradermally on the left side of the back of each 12 wk old C57BL/6 mouse. After 4 days, mice were injected with 50 µg of αCD40 peri-tumorally (p.t.). Blood samples were collected in tubes on days 4 (4 hr after αCD40 injection on this post-inoculation day), 6, and 8 days after tumor inoculation. Concentrations of αCD40 in serum were measured by ELISA as described above.

7. Serum Cytokine Concentration Analysis

5×10$^5$ B16F10 melanoma cells were injected intradermally on the left side of the back of each 12 wk old C57BL/6 mouse. After 4 days, mice received two doses of 50 µg αCD40. On day 4 (4 hr after αCD40 injection), 5, 6, and 8, blood samples were collected in tubes, followed by overnight incubation at 4° C. Cytokine concentrations in serum were measured by Ready-SET-Go! ELISA kits (eBioscience) according to the manufacturer's protocol.

8. ALT Activity Analysis

Serum alanine aminotransferase (ALT) activity was measured as described previously (27). B16F10 tumor bearing mice received 50 µg αCD40 injection, 4 days after tumor inoculation. On day 5, 7, and 9, blood samples were collected in tubes, followed by >4 hr incubation at 4° C. ALT activity in serum was measured by ALT assay kit (Sigma-Aldrich) according to the manufacturer's protocol.

9. Histology

Liver histology was performed as described previously (27). B16F10 tumor-bearing mice received 50 µg αCD40 injection, 4 days after tumor inoculation. 7 days after tumor inoculation, livers were collected and fixed with 2% paraformaldehyde. After embedding in paraffin, blocks were cut into 5 µm sections, followed by staining with hematoxylin and eosin. Images were captured with an EVOS FL Auto microscope (Life Technologies).

10. RNA Extraction and Gene Expression Analysis of CD40

Lymph node (LN) cells and hepatocytes were freshly isolated from C57BL/6 mice as previously described (29, 30). Total RNA was extracted from LN cells and hepatocytes using the RNeasy micro kit isolation protocol (Qiagen) according to manufacturer's instructions. cDNA was obtained by reverse transcription polymerase chain reaction (RT-PCR) of total RNA performed using the SuperScript III First Strand Synthesis SuperMix (Life Technologies) following manufacturer's instructions. Gene expression analysis was performed by TaqMan gene expression assays specific for CD40 (Mm00441891_m1) and β-Actin (Mm01268569_m1) (Life Technologies) in a LightCycler 96 System (Roche). Relative gene expression was quantified using the formula (gene expression fold change)=$2^{(c_qActin-c_qCD40)}$ with β-Actin as reference gene.

11. Antitumor Efficacy of αCD40 on B16F10 Melanoma

A total of 5×10$^5$ B16F10 cells re-suspended in 50 µL of PBS were inoculated intradermally on the left side of the back of each C57BL/6 mouse or Batf3$^{-/-}$ mouse. After 4 days, mice were injected with 10 µg or 50 µg of αCD40 p.t. For distant tumor experiments, 5×10$^5$ B16F10 cells were injected intradermally on the left and right sides of the back of each mouse on day 0. On day 4, mice were injected with 50 µg of αCD40 p.t. beside only the left tumor. Tumors were measured with a digital caliper starting 4 days after first tumor inoculation, and volumes were calculated as ellipsoids, where V=4/3×3.14×depth/2×width/2×height/2. Mice were sacrificed at the point when either tumor volume had reached over 500 mm$^3$.

12. Antitumor Efficacy of αCD40 on CT26 Colon Carcinoma

A total of 5×10$^5$ CT26 colon carcinoma cells re-suspended in 50 µL of PBS were inoculated intradermally on the left side of the back of each Balb/c mouse. After 5 days, mice were injected with 10 µg of αCD40 intradermally p.t. Tumors were measured with a digital caliper starting 5 days after tumor inoculation as described above. Mice were sacrificed at the point when either tumor volume had reached over 500 mm$^3$.

13. Antitumor Efficacy of αCD40 on MMTV-PyMT Breast Cancer

A total of $8 \times 10^5$ MMTV-PyMT cells re-suspended in 50 µL of PBS were injected subcutaneously into the mammary fat pad on the right side of each FVB mouse. After 7 days, mice were injected with 50 µg of αCD40 p.t. Tumors were measured with a digital caliper as described above. Mice were sacrificed when tumor volume reached over 500 $mm^3$.

14. Tissue and Cell Preparation and T Cell Subset Analysis $5 \times 10^5$ B16F10 melanoma cells were injected intradermally on the left side of the back of each C57BL/6 mouse. After 4 and 7 days, mice were injected with 50 µg of αCD40 p.t. Mice were sacrificed on day 8. Spleens, LNs, and tumors were harvested. Tumors were digested in Dulbecco's Modified Eagle Medium (DMEM) supplemented with 2% FBS, 2 mg/mL collagenase D and 40 µg/mL DNase I (Roche) for 30 min at 37° C. Single-cell suspensions were obtained by gently disrupting the tissues through a 70-mm cell strainer. Red blood cells were lysed with ACK lysing buffer (Quality Biological). Cells were counted and re-suspended in Iscove's Modified Dulbecco's Medium (IMDM) supplemented with 10% FBS and 1% penicillin/streptomycin (full medium; all from Life Technologies) and used for flow cytometry staining.

15. Flow Cytometry and Antibodies

Single cell suspensions from spleens, td-LNs, and tumors were prepared as described above. Following a washing step, approximately $2 \times 10^6$ cells were used for antibody staining. Antibodies were purchased from BD Biosciences if not otherwise indicated: CD3 (145-2C11), CD4 (RM4-5), CD8a (53-6.7), CD11c (HL3), CD25 (M-A251), CD44 (IM7), CD45 (30-F11), CD62L (MEL-14), CD86 (GL-1), F4/80 (T45-2342), Foxp3 (MF23), NK1.1 (PK136), MHCII (M5/114.15.2, BioLegend), PD-1 (29F.1A12, BioLegend). Fixable live/dead cell discrimination was performed using Fixable Viability Dye eFluor 455 (eBioscience) according to the manufacturer's instructions. Staining was carried out on ice for 20 min if not indicated otherwise, and intracellular staining was performed using the Foxp3-staining kit according to manufacturer's instructions (BioLegend). Following a washing step, cells were stained with specific antibodies for 20 min on ice prior to fixation. All flow cytometric analyses were done using a Fortessa (BD Biosciences) flow cytometer and analyzed using FlowJo software (FlowJo, LLC.).

16. Endogenous Antibody Detection

B16F10 tumor bearing mice received 10 µg αCD40 injection, 4 days after tumor inoculation. On day 11, blood plasma samples were collected in heparinized tubes. B16F10 cells were incubated with 10% plasma in PBS from treated mice (day 11) for 60 min at 4° C., washed twice with PBS, and then incubated with Alexa-Fluor-647-labeled rat anti-mouse-IgG (Jackson Immunoresearch) for 30 min at 4° C. After cells were washed in PBS, the mean fluorescence intensity was analyzed using a Fortessa cytometer.

17. Tyr:Cre$^+$/LSL-Braf$^{V600E}$/Pten$^{fl/fl}$) βCat$^{STA}$ Melanoma Induction and Antibody Injection 6-12 wk-old Tyr:Cre$^+$/LSL-Braf$^{V600E}$/Pten$^{fl/fl}$ βcat$^{STA}$ mice were shaved on the back and 5 µL of 4-OH-tamoxifen (Sigma-Aldrich) at 10 mg/mL was applied topically. Right after the visible tumor development (day 0) and again on day 7, mice were injected with 10 µg of αCD40 p.t. Volume was calculated as Volume=Surface*Z, where Surface is computed through ImageJ analysis and Z is the thickness of the tumor, measured with a digital caliper. Mice were sacrificed at the point when tumor volume had reached over 1000 $mm^3$.

18. Analysis of Tumor-Infiltrating T Cell Density

After euthanasia of a tumor-bearing mouse, part of the tumor was fixed with zinc fixative. Histological analysis was performed on serial sections (7 µm frozen sections) from the central portion of the melanoma. Cryosections blocked with 2% BSA in tris-buffered saline with TBS-T, were incubated with hamster anti-mouse anti-CD31 antibody (2H8, Abcam), rabbit anti-mouse anti-CD3 antibody (SP7, Abcam) and rat anti-mouse anti-CD8 antibody (53-6.7, BioLegend). After washing with TBS-T, sections were incubated with Alexa Fluor 488-conjugated anti-hamster antibody, Alexa Fluor 594-conjugated anti-rabbit antibody or Alexa Fluor 647-conjugated anti-rat antibody (Jackson ImmunoResearch) for 1 hr at room temperature. Images were taken with IX83 microscope (Olympus). After images were taken, the number of tumor-infiltrating CD8$^+$ T cells was counted using ImageJ software. Tumor-infiltrating CD8$^+$ T cells were defined as double-positive (co-localization) for CD8 and CD3, excluding the cells that are within the CD31$^+$ vessels. Intra-tumoral area was identified and calculated using bright field images.

19. Statistical Analysis

Multiple batches of PlGF-2$_{123-144}$-αCD40 were synthesized by multiple individuals, and tumor treatments were performed by multiple individuals to ensure reproducibility. For animal studies, mice were randomized into treatment groups within a cage immediately before the first αCD40 injection and treated in the same way. Statistically significant differences between experimental groups were determined using Prism software (v7, GraphPad). Where one-way ANOVA followed by Tukey's HSD post hoc test was used, variance between groups was found to be similar by Brown-Forsythe test. For single comparisons, a two-tailed Student's t-test was used. Survival curves were analyzed by using the log-rank (Mantel-Cox) test. All experiments are replicated at least twice. The symbols * and ** indicate P values less than 0.05 and 0.01, respectively; N.S., not significant.

Example 6—Additional ECM-Targeted Agonistic Antibody

In this Example, agonistic antibodies other than αCD40 are targeted to ECM and are shown to have enhanced antitumor activity. These agonistic antibodies include αCD134 (Ox40), αCD137 (4-1-BB), and αGITR and have alternative mechanism of action such as direct activation of T cells via co-stimulatory molecules. The αOx40 targets activated CD4$^+$ and CD8$^+$ T cells to enhance the generation of antigen-specific effector T cells and prevent the induction of T cell tolerance (45). The αCD137 increases the cytotoxicity of NK cells, causes CD8$^+$ T cell proliferation, and increases the antigen presentation of DCs (46). The αGITR activates T cells, enhances effector function activity including cytokine production and generates T cell memory (47).

1. Agonistic Antibodies Conjugated to PlGF-2 Peptide Inhibit Tumor Growth $5 \times 10^5$ B16F10 melanoma cells were inoculated in the back skin of mice on day 0. Combination of 50 µg of PlGF-2$_{123-144}$-αOx40, 50 µg of PlGF-2$_{123-144}$-αCD137, and 50 µg of PlGF-2$_{123-144}$-αGITR, or PBS was administered on day 4 (n=4-5). Antibodies were injected peritumorally (p.t.). FIG. 42 depicts tumor volume until the first mouse died and shows that the combination of antibodies significantly inhibited tumor growth. Tumor volumes are presented as mean±SEM. Statistical analyses were done using Student's t-test. **p<0.01.

2. Agonistic Antibodies Conjugated to CBD Inhibit Tumor Growth More than Unmodified Antibodies $5 \times 10^5$ B16F10 melanoma cells were inoculated in the back skin of mice on day 0. Combination of 50 µg of CBD-αOx40, 50 µg of CBD-αCD137, and 50 µg of CBD-αGITR, or of 50 µg of αOx40, 50 µg of αCD137, and 50 µg of αGITR, or PBS was administered on day 4 (n=4-5). Antibody was injected i.v. FIG. 43 depicts tumor volume until the first mouse died and shows that the combination of CBD-conjugated antibodies inhibited tumor growth more effectively than the combination of unmodified antibodies. Tumor volumes are presented as mean±SEM. Statistical analyses were done using ANOVA with Tukey's test. **$p<0.01$, *$p<0.05$.

Rat anti-mouse CD134 antibody (clone: OX-86, Bio X Cell), rat anti-mouse CD137 antibody (clone: 3H3, Bio X Cell), and rat anti-mouse GITR antibody (clone: DTA-1, Bio X Cell) were used. To conjugate PlGF-2$_{123-144}$ peptide to antibody, αCD134, αCD137, or αGITR was incubated with 15 eq. of sulfo-succinimidyl 4-(N-maleimidomethyl) cyclohexane-1-carboxylate (sulfo-SMCC) for 30 min at room temperature. Excess sulfo-SMCC was removed using a Zeba spin desalting column (Thermo Fisher Scientific). 15 eq. of PlGF-2$_{123-144}$ peptide (RRRPKGRGKRRREKQRPTD-CHL) was then added and reacted for 1 hr at room temperature for conjugation to the thiol moiety on the C residue. The peptide had been synthesized with >95% purity by Genscript. To conjugate CBD to antibody, αCD134, αCD137, or αGITR was incubated with 15 eq. of sulfo-SMCC for 30 min at RT. Excess sulfo-SMCC was removed using a Zeba spin desalting column (Thermo Fisher Scientific). 5 eq. of CBD protein (the vWF A3 domain, with an N-terminal cysteine residue) was then added and reacted for 1 hr at RT.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

REFERENCES

References for Example 5

1. Vonderheide R H, Glennie M J. Agonistic CD40 antibodies and cancer therapy. Clin Cancer Res 2013; 19:1035-43
2. Fransen M F, Sluijter M, Morreau H, Arens R, Melief C J. Local activation of CD8 T cells and systemic tumor eradication without toxicity via slow release and local delivery of agonistic CD40 antibody. Clin Cancer Res 2011; 17:2270-80
3. White A L, Chan H C, Roghanian A, French R R, Mockridge C I, Tutt A L, et al. Interaction with FcγRIIB is critical for the agonistic activity of anti-CD40 monoclonal antibody. J Immunol 2011; 187:1754-63
4. Jackaman C, Cornwall S, Graham P T, Nelson D J. CD40-activated B cells contribute to mesothelioma tumor regression. Immunol Cell Biol 2011; 89:255-67
5. Lum H D, Buhtoiarov I N, Schmidt B E, Berke G, Paulnock D M, Sondel P M, et al. In vivo CD40 ligation can induce T-cell-independent antitumor effects that involve macrophages. J Leukoc Biol 2006; 79:1181-92
6. Rakhmilevich A L, Alderson K L, Sondel P M. T-cell-independent antitumor effects of CD40 ligation. Int Rev Immunol 2012; 31:267-78 Rakhmilevich A L, Buhtoiarov I N, Malkovsky M, Sondel P M. CD40 ligation in vivo can induce T cell independent antitumor effects even against immunogenic tumors. Cancer Immunol Immunother: CII 2008; 57:1151-60
8. Hassan S B, Sorensen J F, Olsen B N, Pedersen A E. Anti-CD40-mediated cancer immunotherapy: an update of recent and ongoing clinical trials. Immunopharmacol Immunotoxicol 2014; 36:96-104
9. Johnson P, Challis R, Chowdhury F, Gao Y, Harvey M, Geldart T, et al. Clinical and biological effects of an agonist anti-CD40 antibody: a Cancer Research U K phase I study. Clin Cancer Res 2015; 21:1321-8
10. Beatty G L, Chiorean E G, Fishman M P, Saboury B, Teitelbaum U R, Sun W, et al. CD40 agonists alter tumor stroma and show efficacy against pancreatic carcinoma in mice and humans. Science 2011; 331:1612-6
11. Vonderheide R H, Flaherty K T, Khalil M, Stumacher M S, Baj or D L, Hutnick N A, et al. Clinical activity and immune modulation in cancer patients treated with C P-870,893, a novel CD40 agonist monoclonal antibody. J Clin Oncol 2007; 25:876-83
12. Gladue R P, Paradis T, Cole S H, Donovan C, Nelson R, Alpert R, et al. The CD40 agonist antibody CP-870,893 enhances dendritic cell and B-cell activity and promotes anti-tumor efficacy in SCID-hu mice. Cancer Immunol Immunother: CII 2011; 60:1009-17
13. Kikuchi T, Moore M A, Crystal R G. Dendritic cells modified to express CD40 ligand elicit therapeutic immunity against preexisting murine tumors. Blood 2000; 96:91-9
14. Nimanong S, Ostroumov D, Wingerath J, Knocke S, Woller N, Gurlevik E, et al. CD40 signaling drives potent cellular immune responses in heterologous cancer vaccinations. Cancer Res 2017; 77:1918-26
15. Hojer C, Frankenberger S, Strobl L J, Feicht S, Djermanovic K, Jagdhuber F, et al. B-cell expansion and lymphomagenesis induced by chronic CD40 signaling is strictly dependent on CD19. Cancer Res 2014; 74:4318-28
16. Mangsbo S M, Broos S, Fletcher E, Veitonmaki N, Furebring C, Dahlen E, et al. The human agonistic CD40 antibody ADC-1013 eradicates bladder tumors and generates T-cell-dependent tumor immunity. Clin Cancer Res 2015; 21:1115-26
17. Rahimian S, Fransen M F, Kleinovink J W, Amidi M, Ossendorp F, Hennink W E.
Polymeric microparticles for sustained and local delivery of antiCD40 and antiCTLA-4 in immunotherapy of cancer. Biomaterials 2015; 61:33-40
18. Sandin L C, Orlova A, Gustafsson E, Ellmark P, Tolmachev V, Totterman T H, et al. Locally delivered CD40 agonist antibody accumulates in secondary lymphoid organs and eradicates experimental disseminated bladder cancer. Cancer Immunol Res 2014; 2:80-90

19. 32nd annual meeting and pre-conference programs of the Society for Immunotherapy of Cancer (SITC 2017): part one National Harbor, Md., USA. 8-12 Nov. 2017 Abstracts. J Immunother Cancer 2017; 5:86
20. Allison J P. Immune checkpoint blockade in cancer therapy: The 2015 Lasker-DeBakey clinical medical research award. JAMA 2015; 314:1113-4
21. Sharma P, Allison J P. The future of immune checkpoint therapy. Science 2015; 348:56-61
22. Topalian S L, Drake C G, Pardoll D M. Immune checkpoint blockade: a common denominator approach to cancer therapy. Cancer Cell 2015; 27:450-61
23. Patel S P, Kurzrock R. P D-L1 expression as a predictive biomarker in cancer immunotherapy. Mol Cancer Ther 2015; 14:847-56
24. Wang X, Teng F, Kong L, Yu J. P D-L1 expression in human cancers and its association with clinical outcomes. Onco Targets Ther 2016; 9:5023-39
25. Larkin J, Chiarion-Sileni V, Gonzalez R, Grob J J, Cowey C L, Lao C D, et al. Combined nivolumab and ipilimumab or monotherapy in untreated melanoma. N Engl J Med 2015; 2015:23-34
26. Martino M M, Briquez P S, Guc E, Tortelli F, Kilarski W W, Metzger S, et al. Growth factors engineered for super-affinity to the extracellular matrix enhance tissue healing. Science 2014; 343:885-8
27. Ishihara J, Fukunaga K, Ishihara A, Larsson H M, Potin L, Hosseinchi P, et al. Matrix-binding checkpoint immunotherapies enhance antitumor efficacy and reduce adverse events. Sci Transl Med 2017; 9
28. Spranger S, Bao R, Gajewski T F. Melanoma-intrinsic beta-catenin signalling prevents anti-tumour immunity. Nature 2015; 523:231-5
29. Liu W, Hou Y, Chen H, Wei H, Lin W, Li J, et al. Sample preparation method for isolation of single-cell types from mouse liver for proteomic studies. Proteomics 2011; 11:3556-64
30. Broggi M A, Schmaler M, Lagarde N, Rossi S W. Isolation of murine lymph node stromal cells. Journal of visualized experiments: JoVE 2014:e51803
31. Byrne K T, Leisenring N H, Baj or D L, Vonderheide R H. CSF-1R-Dependent Lethal Hepatotoxicity When Agonistic CD40 Antibody Is Given before but Not after Chemotherapy. J Immunol 2016; 197:179-87
32. Guy C T, Cardiff R D, Muller W J. Induction of mammary tumors by expression of polyomavirus middle T oncogene: a transgenic mouse model for metastatic disease. Mol Cell Biol 1992; 12:954-61
33. Ngiow S F, Young A, Blake S J, Hill G R, Yagita H, Teng M W, et al. Agonistic CD40 mAb-driven IL12 reverses resistance to anti-PD1 in a T-cell-rich tumor. Cancer Res 2016; 76:6266-77
34. Martinez-Lopez M, Iborra S, Conde-Garrosa R, Sancho D. Batf3-dependent CD103+ dendritic cells are major producers of IL-12 that drive local Th1 immunity against *Leishmania major* infection in mice. Eur J Immunol 2015; 45:119-29
35. Edelson B T, Kc W, Juang R, Kohyama M, Benoit L A, Klekotka P A, et al. Peripheral CD103+ dendritic cells form a unified subset developmentally related to CD8alpha+ conventional dendritic cells. J Exp Med 2010; 207:823-36
36. Hildner K, Edelson B T, Purtha W E, Diamond M, Matsushita H, Kohyama M, et al. Batf3 deficiency reveals a critical role for CD8alpha+ dendritic cells in cytotoxic T cell immunity. Science 2008; 322:1097-100
37. Patel R, Sad S. Transcription factor Batf3 is important for development of CD8+ T-cell response against a phagosomal bacterium regardless of the location of antigen. Immunol Cell Biol 2016; 94:378-87
38. Vonderheide R H, Bajor D L, Winograd R, Evans R A, Bayne L J, Beatty G L. CD40 immunotherapy for pancreatic cancer. Cancer Immunol Immunother: CII 2013; 62:949-54
39. Fransen M F, van der Sluis T C, Ossendorp F, Arens R, Melief C J. Controlled local delivery of CTLA-4 blocking antibody induces CD8+ T-cell-dependent tumor eradication and decreases risk of toxic side effects. Clin Cancer Res 2013; 19:5381-9
40. Steiner M, Neri D. Antibody-radionuclide conjugates for cancer therapy: historical considerations and new trends. Clin Cancer Res 2011; 17:6406-16
41. Ellmark P, Mangsbo S M, Furebring C, Norlen P, Totterman T H. Tumor-directed immunotherapy can generate tumor-specific T cell responses through localized co-stimulation. Cancer Immunol Immunother: CII 2017; 66:1-7
42. Fransen M F, Ossendorp F, Arens R, Melief C J. Local immunomodulation for cancer therapy: Providing treatment where needed. Oncoimmunology 2013; 2:e26493
43. Marabelle A, Kohrt H, Caux C, Levy R. Intratumoral immunization: a new paradigm for cancer therapy. Clin Cancer Res 2014; 20:1747-56
44. Kwong B, Liu H, Irvine D J. Induction of potent anti-tumor responses while eliminating systemic side effects via liposome-anchored combinatorial immunotherapy. Biomaterials 2011; 32:5134-47
45. Aspeslagh, S., et al. Rationale for anti-OX40 cancer immunotherapy. *European journal of cancer* (Oxford, England: 1990) 52, 50-66 (2016).
46. Yonezawa, A., Dutt, S., Chester, C., Kim, J. & Kohrt, H. E. Boosting Cancer Immunotherapy with Anti-CD137 Antibody Therapy. *Clinical cancer research: an official journal of the American Association for Cancer Research* 21, 3113-3120 (2015).
47. Knee, D. A., Hewes, B. & Brogdon, J. L. Rationale for anti-GITR cancer immunotherapy. *European journal of cancer* (Oxford, England: 1990) 67, 1-10 (2016).
48. Allison, J. P. Immune checkpoint blockade in cancer therapy: The 2015 Lasker-DeBakey clinical medical research award. *JAMA* 314, 1113-1114 (2015).
49. Sharma, P. & Allison, J. P. The future of immune checkpoint therapy. *Science* 348, 56-61 (2015).
50. Topalian, S. L., Drake, C. G. & Pardoll, D. M. Immune checkpoint blockade: a common denominator approach to cancer therapy. *Cancer Cell* 27, 450-461 (2015).
51. Grosso, J. F. & Jure-Kunkel, M. N. CTLA-4 blockade in tumor models: an overview of preclinical and translational research. *Cancer Immun* 13, 5 (2013).
52. Hodi, F. S., et al. Improved survival with ipilimumab in patients with metastatic melanoma. *N Engl J Med* 363, 711-723 (2010).
53. Brahmer, J. R., et al. Safety and activity of anti-PD-L1 antibody in patients with advanced cancer. *N Engl J Med* 366, 2455-2465 (2012).
54. Alsaab, H. O., et al. PD-1 and PD-L1 Checkpoint Signaling Inhibition for Cancer Immunotherapy: Mechanism, Combinations, and Clinical Outcome. *Front Pharmacol* 8, 561 (2017).
55. Larkin, J., et al. Combined nivolumab and ipilimumab or monotherapy in untreated melanoma. *N Engl J Med* 2015, 23-34 (2015).

56. Boutros, C., et al. Safety profiles of anti-CTLA-4 and anti-PD-1 antibodies alone and in combination. *Nature reviews. Clinical oncology* 13, 473-486 (2016).
57. Miyoshi, Y., Ogawa, O. & Oyama, Y. Nivolumab, an anti-programmed cell death-1 antibody, induces fulminant type 1 diabetes. *Tohoku J Exp Med* 239, 155-158 (2016).
58. June, C. H., Warshauer, J. T. & Bluestone, J. A. Is autoimmunity the Achilles' heel of cancer immunotherapy? *Nature medicine* 23, 540-547 (2017).
59. The double edge of cancer immunotherapy. *Nature medicine* 23, 137 (2017).
60. Okamoto, M., et al. Fulminant type 1 diabetes mellitus with anti-programmed cell death-1 therapy. *J Diabetes Investig* 7, 915-918 (2016).
61. Mellati, M., et al. Anti-PD-1 and anti-PDL-1 monoclonal antibodies causing type 1 diabetes. *Diabetes Care* 38, e137-138 (2015).
62. Atkins, M. B., et al. High-dose recombinant interleukin 2 therapy for patients with metastatic melanoma: analysis of 270 patients treated between 1985 and 1993. *Journal of clinical oncology: official journal of the American Society of Clinical Oncology* 17, 2105-2116 (1999).
63. Klapper, J. A., et al. High-dose interleukin-2 for the treatment of metastatic renal cell carcinoma: a retrospective analysis of response and survival in patients treated in the surgery branch at the National Cancer Institute between 1986 and 2006. *Cancer* 113, 293-301 (2008).
64. Ishihara, J., et al. Matrix-binding checkpoint immunotherapies enhance antitumor efficacy and reduce adverse events. *Sci Transl Med* 9(2017).
65. Ricard-Blum, S. The collagen family. *Cold Spring Harb Perspect Biol* 3, a004978 (2011).
66. Dubois, C., Panicot-Dubois, L., Merrill-Skoloff, G., Furie, B. & Furie, B. C. Glycoprotein VI-dependent and -independent pathways of thrombus formation in vivo. *Blood* 107, 3902-3906 (2006).
67. Bergmeier, W. & Hynes, R. O. Extracellular matrix proteins in hemostasis and thrombosis. *Cold Spring Harb Perspect Biol* 4, a005132 (2012).
68. Nagy, J., Chang, S., Dvorak, A. & Dvorak, H. Why are tumour blood vessels abnormal and why is it important to know? *British journal of cancer* 100, 865 (2009).
69. Liang, H., et al. A collagen-binding EGFR single-chain Fv antibody fragment for the targeted cancer therapy. *J Control Release* 209, 101-109 (2015).
70. Liang, H., et al. A collagen-binding EGFR antibody fragment targeting tumors with a collagen-rich extracellular matrix. *Sci Rep* 6, 18205 (2016).
71. Yasunaga, M., Manabe, S., Tarin, D. & Matsumura, Y. Cancer-stroma targeting therapy by cytotoxic immunoconjugate bound to the collagen 4 network in the tumor tissue. *Bioconjugate chemistry* 22, 1776-1783 (2011).
72. Xu, J., et al. Proteolytic exposure of a cryptic site within collagen type IV is required for angiogenesis and tumor growth in vivo. *The Journal of cell biology* 154, 1069-1080 (2001).
73. Swartz, M. A. & Lund, A. W. Lymphatic and interstitial flow in the tumour microenvironment: linking mechanobiology with immunity. *Nat Rev Cancer* 12, 210-219 (2012).
74. Zhou, Z. H., et al. Reorganized collagen in the tumor microenvironment of gastric cancer and Its association with prognosis. *J Cancer* 8, 1466-1476 (2017).
75. Provenzano, P. P., et al. Collagen density promotes mammary tumor initiation and progression. *BMC Med* 6, 11 (2008).
76. Lenting, P. J., Casari, C., Christophe, O. D. & Denis, C. V. von Willebrand factor: the old, the new and the unknown. *Journal of thrombosis and haemostasis: JTH* 10, 2428-2437 (2012).
77. Shahidi, M. Thrombosis and von Willebrand Factor. *Advances in experimental medicine and biology* 906, 285-306 (2017).
78. Wu, D., et al. Inhibition of the von Willebrand (VWF)-collagen interaction by an antihuman VWF monoclonal antibody results in abolition of in vivo arterial platelet thrombus formation in baboons. *Blood* 99, 3623-3628 (2002).
79. Addi, C., Murschel, F. & De Crescenzo, G. Design and use of chimeric proteins containing a collagen-binding domain for wound healing and bone regeneration. *Tissue Engineering Part B: Reviews* (2016).
80. Ribba, A. S., et al. Ser968Thr mutation within the A3 domain of von Willebrand factor (VWF) in two related patients leads to a defective binding of VWF to collagen. *Thrombosis and haemostasis* 86, 848-854 (2001).
81. Simpson, T. R., et al. Fc-dependent depletion of tumor-infiltrating regulatory T cells co-defines the efficacy of anti-CTLA-4 therapy against melanoma. *J Exp Med* 210, 1695-1710 (2013).
82. Quezada, S. A., Peggs, K. S., Curran, M. A. & Allison, J. P. CTLA4 blockade and G M-CSF combination immunotherapy alters the intratumor balance of effector and regulatory T cells. *J Clin Invest* 116, 1935-1945 (2006).
83. Danhier, F., Feron, 0. & Preat, V. To exploit the tumor microenvironment: Passive and active tumor targeting of nanocarriers for anti-cancer drug delivery. *J Control Release* 148, 135-146 (2010).
84. Chari, R. V., Miller, M. L. & Widdison, W. C. Antibody-drug conjugates: an emerging concept in cancer therapy. *Angew Chem Int Ed Engl* 53, 3796-3827 (2014).
85. Maeda, H., Wu, J., Sawa, T., Matsumura, Y. & Hori, K. Tumor vascular permeability and the EPR effect in macromolecular therapeutics: a review. *J Control Release* 65, 271-284 (2000).
86. Swartz, M. A. & Fleury, M. E. Interstitial flow and its effects in soft tissues. *Annu Rev Biomed Eng* 9, 229-256 (2007).
87. Carnemolla, B., et al. Enhancement of the antitumor properties of interleukin-2 by its targeted delivery to the tumor blood vessel extracellular matrix. *Blood* 99, 1659-1665 (2002).
88. Eigentler, T. K., et al. A dose-escalation and signal-generating study of the immunocytokine L19-IL2 in combination with dacarbazine for the therapy of patients with metastatic melanoma. *Clinical cancer research: an official journal of the American Association for Cancer Research* 17, 7732-7742 (2011).
89. Ferrari, M., Onuoha, S. C. & Pitzalis, C. Going with the flow: harnessing the power of the vasculature for targeted therapy in rheumatoid arthritis. *Drug Discov Today* 21, 172-179 (2016).
90. Rybak, J. N., Roesli, C., Kaspar, M., Villa, A. & Neri, D. The extra-domain A of fibronectin is a vascular marker of solid tumors and metastases. *Cancer Res* 67, 10948-10957 (2007).
91. Spranger, S., Bao, R. & Gajewski, T. F. Melanoma-intrinsic beta-catenin signalling prevents anti-tumour immunity. *Nature* 523, 231-235 (2015).
92. Lee, S. S., Bindokas, V. P. & Kron, S. J. Multiplex three-dimensional optical mapping of tumor immune microenvironment. *Sci Rep* 7, 17031 (2017).

The invention claimed is:

1. A method for treating melanoma, colon or breast cancer in a subject comprising administering a composition comprising an immune checkpoint inhibitory anti-CTLA4 antibody covalently linked to a peptide comprising the amino acid sequence of SEQ ID NO: 1 to the subject.

2. The method of claim 1, wherein the method comprises:
   i) administration of an immune checkpoint inhibitory anti-CTLA4 antibody covalently linked to a peptide comprising the amino acid sequence of SEQ ID NO:1; and
   ii) (a) administration of an immune checkpoint inhibitory anti-PD-L1 antibody covalently linked to a second peptide comprising the amino acid sequence of SEQ ID NO:1 or (b) administration of an immune checkpoint inhibitory anti-PD-1 antibody covalently linked to a second peptide comprising the amino acid sequence of SEQ ID NO:1.

3. The method of claim 2, wherein the composition is administered systemically or by intra-tumoral, peri-tumoral, intraarterial, or transcatheter injection.

4. The method of claim 3, wherein the composition is administered by peri-tumoral injection.

5. The method of any claim 1, wherein the cancer is colon cancer.

6. The method of claim 1, wherein the cancer is breast cancer.

7. The method of claim 6, wherein the cancer is melanoma.

8. The method of claim 1, wherein the cancer is metastatic cancer.

9. The method of claim 8, wherein the composition is administered peri-tumorally or intra-tumorally.

10. The method of claim 1, wherein the peptide is crosslinked to the antibody through a bifunctional linker.

11. The method of claim 2, wherein the anti-CTLA4, anti-PD-1, or anti-PD-L1 antibody comprises pembrolizumab, nivolumab, atezolizumab, ipilimumab, tremelimumab, avelumab, or durvalumab.

12. The method of claim 1, wherein the ratio of peptide to antibody is 4:1 to 8:1.

13. A method for treating cancer in a subject comprising administering an immune checkpoint inhibitory anti-CTLA4 antibody covalently linked to a peptide comprising the amino acid sequence of SEQ ID NO:1 and either (i) an immune checkpoint inhibitory anti-PD-L1 antibody covalently linked to a second peptide comprising the amino acid sequence of SEQ ID NO:1 or (ii) an immune checkpoint inhibitory anti-PD-1 antibody covalently linked to a second peptide comprising the amino acid sequence of SEQ ID NO:1 to the subject, wherein the cancer comprises colon cancer, breast cancer, or melanoma.

* * * * *

UNITED STATES PATENT AND TRADEMARK OFFICE
CERTIFICATE OF CORRECTION

| | | |
|---|---|---|
| PATENT NO. | : 11,574,747 B2 | Page 1 of 1 |
| APPLICATION NO. | : 16/606539 | |
| DATED | : February 7, 2023 | |
| INVENTOR(S) | : Hubbell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 146 days.

Signed and Sealed this
Fourteenth Day of January, 2025

Derrick Brent
*Acting Director of the United States Patent and Trademark Office*